US012728003B2

(12) United States Patent
Spiegel et al.

(10) Patent No.: US 12,728,003 B2
(45) Date of Patent: Sep. 8, 2026

(54) DEVICES AND METHODS FOR AREA REDUCTION AND CLOSURE OF CARDIAC OPENINGS OR CAVITIES

(71) Applicant: Edwards Lifesciences Innovation (Israel) Ltd., Caesarea (IL)

(72) Inventors: Lauren Anne Spiegel, Irvine, CA (US); Hao Shang, Irvine, CA (US); Sam Shafigh, Irvine, CA (US); Steven Eric Decker, Anaheim, CA (US); Timothy Allen Dalton, Garden Grove, CA (US)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 43 days.

(21) Appl. No.: 18/137,012

(22) Filed: Apr. 20, 2023

(65) Prior Publication Data

US 2025/0161052 A1 May 22, 2025

Related U.S. Application Data

(63) Continuation of application No. PCT/IB2021/059851, filed on Oct. 26, 2021.

(Continued)

(51) Int. Cl.
*A61F 2/24* (2006.01)

(52) U.S. Cl.
CPC .......... *A61F 2/2487* (2013.01); *A61F 2/2454* (2013.01); *A61F 2220/0016* (2013.01); *A61F 2220/0075* (2013.01)

(58) Field of Classification Search
CPC .... A61F 2/2487; A61F 2/2442; A61F 2/2445; A61F 2/2466; A61F 2/2454; A61F 2/2457; A61B 17/0401
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 113331995 A 9/2021
EP 0611561 A1 8/1994
(Continued)

OTHER PUBLICATIONS

Agarwal et al. Interventional Cardiology Perspective Functional Tricuspid Regurgitation, Circ Cardiovasc Interv 2009;2;2;565-573 (2009).

(Continued)

*Primary Examiner* — Tuan V Nguyen
(74) *Attorney, Agent, or Firm* — Anya Adams

(57) ABSTRACT

Multiple anchors are transluminally slid distally over and along a first portion of a tether to a heart of a subject. The anchors are anchored to tissue of the heart, with the first portion of the tether extending transluminally to the heart. Within the heart, a bight of the tether is secured to the tissue by the anchors. A second portion of the tether extends from the bight to a second end of the tether. The first portion of the tether is subsequently slidably coupled to the second end of the tether such that the tether forms a closed loop. The tissue is subsequently reshaped by the loop being reduced in size by the first portion being slid through the slidable coupling. Other embodiments are also described.

20 Claims, 33 Drawing Sheets

Related U.S. Application Data

(60) Provisional application No. 63/106,324, filed on Oct. 27, 2020.

(56) References Cited

U.S. PATENT DOCUMENTS 3,840,018 A 10/1974 Heifetz
3,881,366 A 5/1975 Bradley et al.
3,898,701 A 8/1975 La Russa
4,042,979 A 8/1977 Angell
4,118,805 A 10/1978 Reimels
4,214,349 A 7/1980 Munch
4,261,342 A 4/1981 Aranguren Duo
4,290,151 A 9/1981 Massana
4,434,828 A 3/1984 Trincia
4,473,928 A 10/1984 Johnson
4,602,911 A 7/1986 Ahmadi et al.
4,625,727 A 12/1986 Leiboff
4,712,549 A 12/1987 Peters et al.
4,778,468 A 10/1988 Hunt et al.
4,917,698 A 4/1990 Carpentier et al.
4,935,027 A 6/1990 Yoon
4,961,738 A 10/1990 Mackin
5,042,707 A 8/1991 Taheri
5,061,277 A 10/1991 Carpentier et al.
5,064,431 A 11/1991 Gilbertson et al.
5,104,407 A 4/1992 Lam et al.
5,108,420 A 4/1992 Marks
5,201,880 A 4/1993 Wright et al.
5,258,008 A 11/1993 Wilk
5,300,034 A 4/1994 Behnke et al.
5,325,845 A 7/1994 Adair
5,346,498 A 9/1994 Greelis et al.
5,383,852 A 1/1995 Wright
5,449,368 A 9/1995 Kuzmak
5,450,860 A 9/1995 O'Connor
5,464,404 A 11/1995 Abela et al.
5,474,518 A 12/1995 Farrer Velazquez
5,477,856 A 12/1995 Lundquist
5,593,424 A 1/1997 Northrup, III
5,601,572 A 2/1997 Middleman et al.
5,626,609 A 5/1997 Zvenyatsky et al.
5,643,317 A 7/1997 Pavcnik et al.
5,669,919 A 9/1997 Sanders et al.
5,676,653 A 10/1997 Taylor et al.
5,683,402 A 11/1997 Cosgrove et al.
5,702,397 A 12/1997 Goble et al.
5,702,398 A 12/1997 Tarabishy
5,709,695 A 1/1998 Northrup
5,716,370 A 2/1998 Williamson et al.
5,716,397 A 2/1998 Myers
5,728,116 A 3/1998 Rosenman
5,730,150 A 3/1998 Peppel et al.
5,749,371 A 5/1998 Zadini et al.
5,752,963 A 5/1998 Allard et al.
5,782,844 A 7/1998 Yoon et al.
5,810,882 A 9/1998 Bolduc et al.
5,824,066 A 10/1998 Gross
5,830,221 A 11/1998 Stein et al.
5,843,120 A 12/1998 Israel et al.
5,855,614 A 1/1999 Stevens et al.
5,876,373 A 3/1999 Giba et al.
5,935,098 A 8/1999 Blaisdell et al.
5,957,953 A 9/1999 DiPoto et al.
5,961,440 A 10/1999 Schweich et al.
5,961,539 A 10/1999 Northrup et al.
5,984,959 A 11/1999 Robertson et al.
5,993,459 A 11/1999 Larsen et al.
6,042,554 A 3/2000 Rosenman et al.
6,045,497 A 4/2000 Schweich et al.
6,050,936 A 4/2000 Schweich et al.
6,059,715 A 5/2000 Schweich et al.
6,074,341 A 6/2000 Anderson et al.
6,074,401 A 6/2000 Gardiner et al.
6,074,417 A 6/2000 Peredo
6,086,582 A 7/2000 Altman et al.
6,102,945 A 8/2000 Campbell
6,106,550 A 8/2000 Magovern et al.
6,110,200 A 8/2000 Hinnenkamp
6,132,390 A 10/2000 Cookston et al.
6,143,024 A 11/2000 Campbell et al.
6,159,240 A 12/2000 Sparer et al.
6,165,119 A 12/2000 Schweich et al.
6,174,332 B1 1/2001 Loch et al.
6,183,411 B1 2/2001 Mortier et al.
6,187,040 B1 2/2001 Wright
6,210,347 B1 4/2001 Forsell
6,217,610 B1 4/2001 Carpentier et al.
6,228,032 B1 5/2001 Eaton et al.
6,231,561 B1 * 5/2001 Frazier ............... A61B 17/0401 604/500
6,231,602 B1 5/2001 Carpentier et al.
6,251,092 B1 6/2001 Qin et al.
6,296,656 B1 10/2001 Bolduc et al.
6,315,784 B1 11/2001 Djurovic
6,319,281 B1 11/2001 Patel
6,328,746 B1 12/2001 Gambale
6,332,893 B1 12/2001 Mortier et al.
6,355,030 B1 3/2002 Aldrich et al.
6,361,559 B1 3/2002 Houser et al.
6,368,348 B1 4/2002 Gabbay
6,402,780 B2 6/2002 Williamson et al.
6,406,420 B1 6/2002 McCarthy et al.
6,406,493 B1 6/2002 Tu et al.
6,419,696 B1 7/2002 Ortiz et al.
6,451,054 B1 9/2002 Stevens
6,458,076 B1 10/2002 Pruitt
6,461,336 B1 10/2002 Larré
6,461,366 B1 10/2002 Seguin
6,470,892 B1 10/2002 Forsell
6,503,274 B1 1/2003 Howanec et al.
6,524,338 B1 2/2003 Gundry
6,527,780 B1 3/2003 Wallace et al.
6,530,952 B2 3/2003 Vesely
6,533,772 B1 3/2003 Sherts et al.
6,537,314 B2 3/2003 Langberg et al.
6,547,801 B1 4/2003 Dargent et al.
6,554,845 B1 4/2003 Fleenor et al.
6,564,805 B2 5/2003 Garrison et al.
6,565,603 B2 5/2003 Cox
6,569,198 B1 5/2003 Wilson et al.
6,579,297 B2 6/2003 Bicek et al.
6,589,160 B2 7/2003 Schweich et al.
6,592,593 B1 7/2003 Parodi et al.
6,602,288 B1 8/2003 Cosgrove et al.
6,602,289 B1 8/2003 Colvin et al.
6,613,078 B1 9/2003 Barone
6,613,079 B1 9/2003 Wolinsky et al.
6,619,291 B2 9/2003 Hlavka et al.
6,626,899 B2 9/2003 Houser et al.
6,626,917 B1 9/2003 Craig
6,626,930 B1 9/2003 Allen et al.
6,629,534 B1 10/2003 St. Goar et al.
6,629,921 B1 10/2003 Schweich et al.
6,651,671 B1 11/2003 Donlon et al.
6,652,556 B1 11/2003 VanTassel et al.
6,682,558 B2 1/2004 Tu et al.
6,689,125 B1 2/2004 Keith et al.
6,689,164 B1 2/2004 Seguin
6,695,866 B1 2/2004 Kuehn et al.
6,702,826 B2 3/2004 Liddicoat et al.
6,702,846 B2 3/2004 Mikus et al.
6,706,065 B2 3/2004 Langberg et al.
6,709,385 B2 3/2004 Forsell
6,709,456 B2 3/2004 Langberg et al.
6,711,444 B2 3/2004 Koblish
6,719,786 B2 4/2004 Ryan et al.
6,723,038 B1 4/2004 Schroeder et al.
6,726,716 B2 4/2004 Marquez
6,726,717 B2 4/2004 Alfieri et al.
6,749,630 B2 6/2004 McCarthy et al.
6,752,813 B2 6/2004 Goldfarb et al.
6,764,310 B1 7/2004 Ichihashi et al.
6,764,510 B2 7/2004 Vidlund et al.
6,764,810 B2 7/2004 Ma et al.

(56) References Cited

U.S. PATENT DOCUMENTS

| | | | |
|---|---|---|---|
| 6,770,083 | B2 | 8/2004 | Seguin |
| 6,786,924 | B2 | 9/2004 | Ryan et al. |
| 6,786,925 | B1 | 9/2004 | Schoon et al. |
| 6,790,231 | B2 | 9/2004 | Liddicoat et al. |
| 6,797,001 | B2 | 9/2004 | Mathis et al. |
| 6,797,002 | B2 | 9/2004 | Spence et al. |
| 6,802,319 | B2 | 10/2004 | Stevens et al. |
| 6,805,710 | B2 | 10/2004 | Bolling et al. |
| 6,805,711 | B2 | 10/2004 | Quijano et al. |
| 6,855,126 | B2 | 2/2005 | Flinchbaugh |
| 6,858,039 | B2 | 2/2005 | McCarthy |
| 6,884,250 | B2 | 4/2005 | Monassevitch et al. |
| 6,893,459 | B1 | 5/2005 | Macoviak |
| 6,908,478 | B2 | 6/2005 | Alferness et al. |
| 6,908,482 | B2 | 6/2005 | McCarthy et al. |
| 6,918,917 | B1 | 7/2005 | Nguyen et al. |
| 6,926,730 | B1 | 8/2005 | Nguyen et al. |
| 6,960,217 | B2 | 11/2005 | Bolduc |
| 6,976,995 | B2 | 12/2005 | Mathis et al. |
| 6,986,775 | B2 | 1/2006 | Morales et al. |
| 6,989,028 | B2 | 1/2006 | Lashinski et al. |
| 6,997,951 | B2 | 2/2006 | Solem et al. |
| 7,004,176 | B2 | 2/2006 | Lau |
| 7,007,798 | B2 | 3/2006 | Happonen et al. |
| 7,011,669 | B2 | 3/2006 | Kimblad |
| 7,011,682 | B2 | 3/2006 | Lashinski et al. |
| 7,018,406 | B2 | 3/2006 | Seguin et al. |
| 7,037,334 | B1 | 5/2006 | Hlavka et al. |
| 7,077,850 | B2 | 7/2006 | Kortenbach |
| 7,077,862 | B2 | 7/2006 | Vidlund et al. |
| 7,087,064 | B1 | 8/2006 | Hyde |
| 7,101,395 | B2 | 9/2006 | Tremulis et al. |
| 7,101,396 | B2 | 9/2006 | Artof et al. |
| 7,112,207 | B2 | 9/2006 | Allen et al. |
| 7,118,595 | B2 | 10/2006 | Ryan et al. |
| 7,125,421 | B2 | 10/2006 | Tremulis et al. |
| 7,150,737 | B2 | 12/2006 | Purdy et al. |
| 7,159,593 | B2 | 1/2007 | McCarthy et al. |
| 7,166,127 | B2 | 1/2007 | Spence et al. |
| 7,169,187 | B2 | 1/2007 | Datta et al. |
| 7,172,625 | B2 | 2/2007 | Shu et al. |
| 7,175,660 | B2 | 2/2007 | Cartledge et al. |
| 7,186,262 | B2 | 3/2007 | Saadat |
| 7,186,264 | B2 | 3/2007 | Liddicoat et al. |
| 7,189,199 | B2 | 3/2007 | McCarthy et al. |
| 7,192,443 | B2 | 3/2007 | Solem et al. |
| 7,220,277 | B2 | 5/2007 | Arru et al. |
| 7,226,467 | B2 | 6/2007 | Lucatero et al. |
| 7,226,477 | B2 | 6/2007 | Cox |
| 7,226,647 | B2 | 6/2007 | Kasperchik et al. |
| 7,229,452 | B2 | 6/2007 | Kayan |
| 7,238,191 | B2 | 7/2007 | Bachmann |
| 7,288,097 | B2 | 10/2007 | Séguin |
| 7,294,148 | B2 | 11/2007 | McCarthy |
| 7,311,728 | B2 | 12/2007 | Solem et al. |
| 7,311,729 | B2 | 12/2007 | Mathis et al. |
| 7,314,485 | B2 | 1/2008 | Mathis |
| 7,316,710 | B1 | 1/2008 | Cheng et al. |
| 7,329,279 | B2 | 2/2008 | Haug et al. |
| 7,329,280 | B2 | 2/2008 | Bolling et al. |
| 7,335,213 | B1 | 2/2008 | Hyde et al. |
| 7,361,190 | B2 | 4/2008 | Shaoulian et al. |
| 7,364,588 | B2 | 4/2008 | Mathis et al. |
| 7,377,941 | B2 | 5/2008 | Rhee et al. |
| 7,390,329 | B2 | 6/2008 | Westra et al. |
| 7,404,824 | B1 | 7/2008 | Webler et al. |
| 7,431,692 | B2 | 10/2008 | Zollinger et al. |
| 7,442,207 | B2 | 10/2008 | Rafiee |
| 7,452,376 | B2 | 11/2008 | Lim et al. |
| 7,455,690 | B2 | 11/2008 | Cartledge et al. |
| 7,485,142 | B2 | 2/2009 | Milo |
| 7,485,143 | B2 | 2/2009 | Webler et al. |
| 7,500,989 | B2 | 3/2009 | Solem et al. |
| 7,507,252 | B2 | 3/2009 | Lashinski et al. |
| 7,510,575 | B2 | 3/2009 | Spenser et al. |
| 7,510,577 | B2 | 3/2009 | Moaddeb et al. |
| 7,527,647 | B2 | 5/2009 | Spence |
| 7,530,995 | B2 | 5/2009 | Quijano et al. |
| 7,549,983 | B2 | 6/2009 | Roue et al. |
| 7,559,936 | B2 | 7/2009 | Levine |
| 7,562,660 | B2 | 7/2009 | Saadat |
| 7,563,267 | B2 | 7/2009 | Goldfarb et al. |
| 7,563,273 | B2 | 7/2009 | Goldfarb et al. |
| 7,569,062 | B1 | 8/2009 | Kuehn et al. |
| 7,585,321 | B2 | 9/2009 | Cribier |
| 7,588,582 | B2 | 9/2009 | Starksen et al. |
| 7,591,826 | B2 | 9/2009 | Alferness et al. |
| 7,604,646 | B2 | 10/2009 | Goldfarb et al. |
| 7,608,091 | B2 | 10/2009 | Goldfarb et al. |
| 7,608,103 | B2 | 10/2009 | McCarthy |
| 7,618,449 | B2 | 11/2009 | Tremulis et al. |
| 7,625,403 | B2 | 12/2009 | Krivoruchko |
| 7,632,303 | B1 | 12/2009 | Stalker et al. |
| 7,635,329 | B2 | 12/2009 | Goldfarb et al. |
| 7,635,386 | B1 | 12/2009 | Gammie |
| 7,655,015 | B2 | 2/2010 | Goldfarb et al. |
| 7,666,204 | B2 | 2/2010 | Thornton et al. |
| 7,682,319 | B2 | 3/2010 | Martin et al. |
| 7,682,369 | B2 | 3/2010 | Séguin |
| 7,686,822 | B2 | 3/2010 | Shayani |
| 7,699,892 | B2 | 4/2010 | Rafiee et al. |
| 7,704,269 | B2 | 4/2010 | St. Goar et al. |
| 7,704,277 | B2 | 4/2010 | Zakay et al. |
| 7,722,666 | B2 | 5/2010 | Lafontaine |
| 7,736,388 | B2 | 6/2010 | Goldfarb et al. |
| 7,748,389 | B2 | 7/2010 | Salahieh et al. |
| 7,753,924 | B2 | 7/2010 | Starksen et al. |
| 7,758,632 | B2 | 7/2010 | Hojeibane et al. |
| 7,780,726 | B2 | 8/2010 | Seguin |
| 7,871,368 | B2 | 1/2011 | Zollinger et al. |
| 7,871,433 | B2 | 1/2011 | Lattouf |
| 7,883,475 | B2 | 2/2011 | Dupont et al. |
| 7,883,538 | B2 | 2/2011 | To et al. |
| 7,892,281 | B2 | 2/2011 | Seguin et al. |
| 7,927,370 | B2 | 4/2011 | Webler et al. |
| 7,927,371 | B2 | 4/2011 | Navia et al. |
| 7,942,927 | B2 | 5/2011 | Kaye et al. |
| 7,947,056 | B2 | 5/2011 | Griego et al. |
| 7,955,315 | B2 | 6/2011 | Feinberg et al. |
| 7,955,377 | B2 | 6/2011 | Melsheimer |
| 7,981,152 | B1 | 7/2011 | Webler et al. |
| 7,992,567 | B2 | 8/2011 | Hirotsuka et al. |
| 7,993,368 | B2 | 8/2011 | Gambale et al. |
| 7,993,397 | B2 | 8/2011 | Lashinski et al. |
| 8,012,201 | B2 | 9/2011 | Lashinski et al. |
| 8,034,103 | B2 | 10/2011 | Burriesci et al. |
| 8,052,592 | B2 | 11/2011 | Goldfarb et al. |
| 8,057,493 | B2 | 11/2011 | Goldfarb et al. |
| 8,062,355 | B2 | 11/2011 | Figulla et al. |
| 8,070,804 | B2 | 12/2011 | Hyde et al. |
| 8,070,805 | B2 | 12/2011 | Vidlund et al. |
| 8,075,616 | B2 | 12/2011 | Solem et al. |
| 8,100,964 | B2 | 1/2012 | Spence |
| 8,123,801 | B2 | 2/2012 | Milo |
| 8,142,493 | B2 | 3/2012 | Spence et al. |
| 8,142,495 | B2 | 3/2012 | Hasenkam et al. |
| 8,142,496 | B2 | 3/2012 | Berreklouw |
| 8,147,542 | B2 | 4/2012 | Maisano et al. |
| 8,152,844 | B2 | 4/2012 | Rao et al. |
| 8,163,013 | B2 | 4/2012 | Machold et al. |
| 8,187,299 | B2 | 5/2012 | Goldfarb et al. |
| 8,187,324 | B2 | 5/2012 | Webler et al. |
| 8,202,315 | B2 | 6/2012 | Hlavka et al. |
| 8,206,439 | B2 | 6/2012 | Gomez Duran |
| 8,216,302 | B2 | 7/2012 | Wilson et al. |
| 8,231,671 | B2 | 7/2012 | Kim |
| 8,262,725 | B2 | 9/2012 | Subramanian |
| 8,265,758 | B2 | 9/2012 | Policker et al. |
| 8,277,502 | B2 | 10/2012 | Miller et al. |
| 8,287,584 | B2 | 10/2012 | Salahieh et al. |
| 8,287,591 | B2 | 10/2012 | Keidar et al. |
| 8,292,884 | B2 | 10/2012 | Levine et al. |
| 8,303,608 | B2 | 11/2012 | Goldfarb et al. |
| 8,323,334 | B2 | 12/2012 | Deem et al. |

(56) References Cited

U.S. PATENT DOCUMENTS 8,328,868 B2 12/2012 Paul et al.
8,333,777 B2 12/2012 Schaller et al.
8,343,173 B2 1/2013 Starksen et al.
8,343,174 B2 1/2013 Goldfarb et al.
8,343,213 B2 1/2013 Salahieh et al.
8,349,002 B2 1/2013 Milo
8,353,956 B2 1/2013 Miller et al.
8,357,195 B2 1/2013 Kuehn
8,382,829 B1 2/2013 Call et al.
8,388,680 B2 3/2013 Starksen et al.
8,393,517 B2 3/2013 Milo
8,419,825 B2 4/2013 Bürgler et al.
8,430,926 B2 4/2013 Kirson
8,449,573 B2 5/2013 Chu
8,449,599 B2 5/2013 Chau et al.
8,454,686 B2 6/2013 Alkhatib
8,460,370 B2 6/2013 Zakay et al.
8,460,371 B2 6/2013 Hlavka et al.
8,475,491 B2 7/2013 Milo
8,475,525 B2 7/2013 Maisano et al.
8,480,732 B2 7/2013 Subramanian
8,518,107 B2 8/2013 Tsukashima et al.
8,523,940 B2 9/2013 Richardson et al.
8,551,161 B2 10/2013 Dolan
8,585,755 B2 11/2013 Chau et al.
8,591,576 B2 11/2013 Hasenkam et al.
8,608,797 B2 12/2013 Gross et al.
8,628,569 B2 1/2014 Benichou et al.
8,628,571 B1 1/2014 Hacohen et al.
8,641,727 B2 2/2014 Starksen et al.
8,652,202 B2 2/2014 Alon et al.
8,652,203 B2 2/2014 Quadri et al.
8,679,174 B2 3/2014 Ottma et al.
8,685,086 B2 4/2014 Navia et al.
8,728,097 B1 5/2014 Sugimoto et al.
8,728,155 B2 5/2014 Montorfano et al.
8,734,467 B2 5/2014 Miller et al.
8,734,699 B2 5/2014 Heideman et al.
8,740,920 B2 6/2014 Goldfarb et al.
8,747,463 B2 6/2014 Fogarty et al.
8,778,021 B2 7/2014 Cartledge
8,784,481 B2 7/2014 Alkhatib et al.
8,790,367 B2 7/2014 Nguyen et al.
8,790,394 B2 7/2014 Miller et al.
8,795,298 B2 8/2014 Hernlund et al.
8,795,355 B2 8/2014 Alkhatib
8,795,356 B2 8/2014 Quadri et al.
8,795,357 B2 8/2014 Yohanan et al.
8,808,366 B2 8/2014 Braido et al.
8,808,368 B2 8/2014 Maisano et al.
8,845,717 B2 9/2014 Khairkhahan et al.
8,845,723 B2 9/2014 Spence et al.
8,852,261 B2 10/2014 White
8,852,272 B2 10/2014 Gross et al.
8,858,623 B2 10/2014 Miller et al.
8,864,822 B2 10/2014 Spence et al.
8,870,948 B1 10/2014 Erzberger et al.
8,870,949 B2 10/2014 Rowe
8,888,843 B2 11/2014 Khairkhahan et al.
8,889,861 B2 11/2014 Skead et al.
8,894,702 B2 11/2014 Quadri et al.
8,911,461 B2 12/2014 Traynor et al.
8,911,494 B2 12/2014 Hammer et al.
8,926,696 B2 1/2015 Cabiri et al.
8,926,697 B2 1/2015 Gross et al.
8,932,343 B2 1/2015 Alkhatib et al.
8,932,348 B2 1/2015 Solem et al.
8,940,044 B2 1/2015 Hammer et al.
8,945,211 B2 2/2015 Sugimoto
8,951,285 B2 2/2015 Sugimoto et al.
8,951,286 B2 2/2015 Sugimoto et al.
8,961,595 B2 2/2015 Alkhatib
8,961,602 B2 2/2015 Kovach et al.
8,979,922 B2 3/2015 Jayasinghe et al.
8,992,604 B2 3/2015 Gross et al.
9,005,273 B2 4/2015 Salahieh et al.
9,011,520 B2 4/2015 Miller et al.
9,011,530 B2 4/2015 Reich et al.
9,023,100 B2 5/2015 Quadri et al.
9,072,603 B2 7/2015 Tuval et al.
9,107,749 B2 8/2015 Bobo et al.
9,119,719 B2 9/2015 Zipory et al.
9,125,632 B2 9/2015 Loulmet et al.
9,125,742 B2 9/2015 Yoganathan et al.
9,138,316 B2 9/2015 Bielefeld
9,173,646 B2 11/2015 Fabro
9,180,005 B1 11/2015 Lashinski et al.
9,180,007 B2 11/2015 Reich et al.
9,192,472 B2 11/2015 Gross et al.
9,198,756 B2 12/2015 Aklog et al.
9,226,825 B2 1/2016 Starksen et al.
9,265,608 B2 2/2016 Miller et al.
9,326,857 B2 5/2016 Cartledge et al.
9,414,921 B2 8/2016 Miller et al.
9,427,316 B2 8/2016 Schweich et al.
9,474,606 B2 10/2016 Zipory et al.
9,526,613 B2 12/2016 Gross et al.
9,561,104 B2 2/2017 Miller et al.
9,579,090 B1 2/2017 Simms et al.
9,693,865 B2 7/2017 Gilmore et al.
9,730,793 B2 8/2017 Reich et al.
9,788,941 B2 10/2017 Hacohen
9,801,720 B2 10/2017 Gilmore et al.
9,907,547 B2 3/2018 Gilmore et al.
10,368,852 B2 8/2019 Gerhardt et al.
2001/0021874 A1 9/2001 Carpentier et al.
2002/0022862 A1 2/2002 Grafton et al.
2002/0082525 A1 6/2002 Oslund et al.
2002/0087048 A1 7/2002 Brock et al.
2002/0103532 A1 8/2002 Langberg et al.
2002/0120292 A1 8/2002 Morgan
2002/0151916 A1 10/2002 Muramatsu et al.
2002/0151970 A1 10/2002 Garrison et al.
2002/0169358 A1 11/2002 Mortier et al.
2002/0177904 A1 11/2002 Huxel et al.
2002/0188301 A1 12/2002 Dallara et al.
2002/0188350 A1 12/2002 Arru et al.
2002/0198586 A1 12/2002 Inoue
2003/0050693 A1 3/2003 Quijano et al.
2003/0078465 A1 4/2003 Pai et al.
2003/0078653 A1 4/2003 Vesely et al.
2003/0083538 A1 5/2003 Adams et al.
2003/0093148 A1 5/2003 Bolling et al.
2003/0105519 A1 6/2003 Fasol et al.
2003/0114901 A1 6/2003 Loeb et al.
2003/0120340 A1 6/2003 Liska et al.
2003/0144657 A1 7/2003 Bowe et al.
2003/0167062 A1 9/2003 Gambale et al.
2003/0171760 A1 9/2003 Gambale
2003/0199974 A1 10/2003 Lee et al.
2003/0204193 A1 10/2003 Gabriel et al.
2003/0204195 A1 10/2003 Keane et al.
2003/0229350 A1 12/2003 Kay
2003/0229395 A1 12/2003 Cox
2004/0002735 A1 1/2004 Lizardi et al.
2004/0010287 A1 1/2004 Bonutti
2004/0019359 A1 1/2004 Worley et al.
2004/0019377 A1 1/2004 Taylor et al.
2004/0024451 A1 2/2004 Johnson et al.
2004/0039442 A1 2/2004 St. Goar et al.
2004/0044350 A1 3/2004 Martin et al.
2004/0049211 A1 3/2004 Tremulis et al.
2004/0059413 A1 3/2004 Argento
2004/0068273 A1 4/2004 Fariss et al.
2004/0106950 A1 6/2004 Grafton et al.
2004/0111095 A1 6/2004 Gordon et al.
2004/0122514 A1 6/2004 Fogarty et al.
2004/0127982 A1 7/2004 Machold et al.
2004/0133274 A1 7/2004 Webler et al.
2004/0133374 A1 7/2004 Kattan
2004/0138744 A1 7/2004 Lashinski et al.
2004/0138745 A1 7/2004 Macoviak et al.
2004/0148019 A1 7/2004 Vidlund et al.
2004/0148020 A1 7/2004 Vidlund et al.

(56) References Cited

U.S. PATENT DOCUMENTS

| | | | |
|---|---|---|---|
| 2004/0148021 | A1 | 7/2004 | Cartledge et al. |
| 2004/0176788 | A1 | 9/2004 | Opolski |
| 2004/0181287 | A1 | 9/2004 | Gellman |
| 2004/0186566 | A1 | 9/2004 | Hindrichs et al. |
| 2004/0193191 | A1 | 9/2004 | Starksen et al. |
| 2004/0243227 | A1 | 12/2004 | Starksen et al. |
| 2004/0260317 | A1 | 12/2004 | Bloom et al. |
| 2004/0260344 | A1 | 12/2004 | Lyons et al. |
| 2004/0260393 | A1 | 12/2004 | Rahdert et al. |
| 2004/0260394 | A1 | 12/2004 | Douk et al. |
| 2004/0267358 | A1 | 12/2004 | Reitan |
| 2005/0004668 | A1 | 1/2005 | Aklog et al. |
| 2005/0010287 | A1 | 1/2005 | Macoviak et al. |
| 2005/0010787 | A1 | 1/2005 | Tarbouriech |
| 2005/0016560 | A1 | 1/2005 | Voughlohn |
| 2005/0049692 | A1 | 3/2005 | Numamoto et al. |
| 2005/0055038 | A1 | 3/2005 | Kelleher et al. |
| 2005/0055087 | A1 | 3/2005 | Starksen |
| 2005/0060030 | A1 | 3/2005 | Lashinski et al. |
| 2005/0065601 | A1 | 3/2005 | Lee et al. |
| 2005/0070999 | A1 | 3/2005 | Spence |
| 2005/0075654 | A1 | 4/2005 | Kelleher |
| 2005/0075727 | A1 | 4/2005 | Wheatley |
| 2005/0090827 | A1 | 4/2005 | Gedebou |
| 2005/0090834 | A1 | 4/2005 | Chiang et al. |
| 2005/0096740 | A1 | 5/2005 | Langberg et al. |
| 2005/0107871 | A1 | 5/2005 | Realyvasquez et al. |
| 2005/0119734 | A1 | 6/2005 | Spence et al. |
| 2005/0125002 | A1 | 6/2005 | Baran et al. |
| 2005/0125011 | A1 | 6/2005 | Spence et al. |
| 2005/0131533 | A1 | 6/2005 | Alfieri et al. |
| 2005/0137686 | A1 | 6/2005 | Salahieh et al. |
| 2005/0137688 | A1 | 6/2005 | Salahieh et al. |
| 2005/0137695 | A1 | 6/2005 | Salahieh et al. |
| 2005/0159728 | A1 | 7/2005 | Armour et al. |
| 2005/0159810 | A1 | 7/2005 | Filsoufi |
| 2005/0171601 | A1 | 8/2005 | Cosgrove et al. |
| 2005/0177180 | A1 | 8/2005 | Kaganov et al. |
| 2005/0177228 | A1 | 8/2005 | Solem et al. |
| 2005/0187568 | A1 | 8/2005 | Klenk et al. |
| 2005/0192596 | A1 | 9/2005 | Jugenheimer et al. |
| 2005/0203549 | A1 | 9/2005 | Realyvasquez |
| 2005/0203606 | A1 | 9/2005 | VanCamp |
| 2005/0216039 | A1 | 9/2005 | Lederman |
| 2005/0216079 | A1 | 9/2005 | MaCoviak |
| 2005/0222665 | A1 | 10/2005 | Aranyi |
| 2005/0234481 | A1 | 10/2005 | Waller |
| 2005/0240199 | A1 | 10/2005 | Martinek et al. |
| 2005/0251177 | A1 | 11/2005 | Saadat et al. |
| 2005/0256532 | A1 | 11/2005 | Nayak et al. |
| 2005/0267478 | A1 | 12/2005 | Corradi et al. |
| 2005/0273138 | A1 | 12/2005 | To et al. |
| 2005/0288778 | A1 | 12/2005 | Shaoulian et al. |
| 2006/0004442 | A1 | 1/2006 | Spenser et al. |
| 2006/0004443 | A1 | 1/2006 | Liddicoat et al. |
| 2006/0020326 | A9 | 1/2006 | Bolduc et al. |
| 2006/0020327 | A1 | 1/2006 | Lashinski et al. |
| 2006/0020333 | A1 | 1/2006 | Lashinski et al. |
| 2006/0020336 | A1 | 1/2006 | Liddicoat |
| 2006/0025787 | A1 | 2/2006 | Morales et al. |
| 2006/0025858 | A1 | 2/2006 | Alameddine |
| 2006/0030885 | A1 | 2/2006 | Hyde |
| 2006/0041319 | A1 | 2/2006 | Taylor et al. |
| 2006/0069429 | A1 | 3/2006 | Spence et al. |
| 2006/0074486 | A1 | 4/2006 | Liddicoat et al. |
| 2006/0085012 | A1 | 4/2006 | Dolan |
| 2006/0095009 | A1 | 5/2006 | Lampropoulos et al. |
| 2006/0106423 | A1 | 5/2006 | Weisel et al. |
| 2006/0116757 | A1 | 6/2006 | Lashinski et al. |
| 2006/0122633 | A1 | 6/2006 | To et al. |
| 2006/0129166 | A1 | 6/2006 | Lavelle |
| 2006/0142694 | A1 | 6/2006 | Bednarek et al. |
| 2006/0149280 | A1 | 7/2006 | Harvie et al. |
| 2006/0149368 | A1 | 7/2006 | Spence |
| 2006/0161265 | A1 | 7/2006 | Levine et al. |
| 2006/0173251 | A1 | 8/2006 | Govari et al. |
| 2006/0184240 | A1 | 8/2006 | Jimenez et al. |
| 2006/0184242 | A1 | 8/2006 | Lichtenstein |
| 2006/0195134 | A1 | 8/2006 | Crittenden |
| 2006/0206203 | A1 | 9/2006 | Yang et al. |
| 2006/0212048 | A1 | 9/2006 | Crainich |
| 2006/0241622 | A1 | 10/2006 | Zergiebel |
| 2006/0241656 | A1 | 10/2006 | Starksen et al. |
| 2006/0241748 | A1 | 10/2006 | Lee et al. |
| 2006/0247763 | A1 | 11/2006 | Slater |
| 2006/0259135 | A1 | 11/2006 | Navia et al. |
| 2006/0271175 | A1 | 11/2006 | Woolfson et al. |
| 2006/0276871 | A1 | 12/2006 | Lamson et al. |
| 2006/0282161 | A1 | 12/2006 | Huynh et al. |
| 2006/0287661 | A1 | 12/2006 | Bolduc et al. |
| 2006/0287716 | A1 | 12/2006 | Banbury et al. |
| 2007/0001627 | A1 | 1/2007 | Lin et al. |
| 2007/0010800 | A1 | 1/2007 | Weitzner et al. |
| 2007/0016287 | A1 | 1/2007 | Cartledge et al. |
| 2007/0016288 | A1 | 1/2007 | Gurskis et al. |
| 2007/0021781 | A1 | 1/2007 | Jervis et al. |
| 2007/0027533 | A1 | 2/2007 | Douk |
| 2007/0027536 | A1 | 2/2007 | Mihaljevic et al. |
| 2007/0032823 | A1 | 2/2007 | Tegg |
| 2007/0038221 | A1 | 2/2007 | Fine et al. |
| 2007/0038293 | A1 | 2/2007 | St.Goar et al. |
| 2007/0038296 | A1 | 2/2007 | Navia et al. |
| 2007/0039425 | A1 | 2/2007 | Wang |
| 2007/0049942 | A1 | 3/2007 | Hindrichs et al. |
| 2007/0049970 | A1 | 3/2007 | Belef et al. |
| 2007/0051377 | A1 | 3/2007 | Douk et al. |
| 2007/0055206 | A1 | 3/2007 | To et al. |
| 2007/0060922 | A1 | 3/2007 | Dreyfuss |
| 2007/0061010 | A1 | 3/2007 | Hauser et al. |
| 2007/0066863 | A1 | 3/2007 | Rafiee et al. |
| 2007/0078297 | A1 | 4/2007 | Rafiee et al. |
| 2007/0080188 | A1 | 4/2007 | Spence et al. |
| 2007/0083168 | A1 | 4/2007 | Whiting et al. |
| 2007/0083235 | A1 | 4/2007 | Jervis et al. |
| 2007/0100427 | A1 | 5/2007 | Perouse |
| 2007/0106328 | A1 | 5/2007 | Wardle et al. |
| 2007/0112359 | A1 | 5/2007 | Kimura et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0118213 | A1 | 5/2007 | Loulmet |
| 2007/0118215 | A1 | 5/2007 | Moaddeb |
| 2007/0142907 | A1 | 6/2007 | Moaddeb et al. |
| 2007/0162111 | A1 | 7/2007 | Fukamachi et al. |
| 2007/0173931 | A1 | 7/2007 | Tremulis et al. |
| 2007/0198082 | A1 | 8/2007 | Kapadia et al. |
| 2007/0219558 | A1 | 9/2007 | Deutsch |
| 2007/0239208 | A1 | 10/2007 | Crawford |
| 2007/0244554 | A1 | 10/2007 | Rafiee et al. |
| 2007/0244556 | A1 | 10/2007 | Rafiee et al. |
| 2007/0255397 | A1 | 11/2007 | Ryan et al. |
| 2007/0255400 | A1 | 11/2007 | Parravicini et al. |
| 2007/0270755 | A1 | 11/2007 | Von Oepen et al. |
| 2007/0276437 | A1 | 11/2007 | Call et al. |
| 2007/0282375 | A1 | 12/2007 | Hindrichs et al. |
| 2007/0282429 | A1 | 12/2007 | Hauser et al. |
| 2007/0295172 | A1 | 12/2007 | Swartz |
| 2007/0299424 | A1 | 12/2007 | Cumming et al. |
| 2008/0004697 | A1 | 1/2008 | Lichtenstein et al. |
| 2008/0027483 | A1 | 1/2008 | Cartledge et al. |
| 2008/0027555 | A1 | 1/2008 | Hawkins |
| 2008/0033460 | A1 | 2/2008 | Ziniti et al. |
| 2008/0035160 | A1 | 2/2008 | Woodson et al. |
| 2008/0039935 | A1 | 2/2008 | Buch et al. |
| 2008/0051703 | A1 | 2/2008 | Thornton et al. |
| 2008/0058595 | A1 | 3/2008 | Snoke et al. |
| 2008/0065011 | A1 | 3/2008 | Marchand et al. |
| 2008/0065204 | A1 | 3/2008 | Macoviak et al. |
| 2008/0071366 | A1 | 3/2008 | Tuval et al. |
| 2008/0086138 | A1 | 4/2008 | Stone et al. |
| 2008/0086203 | A1 | 4/2008 | Roberts |
| 2008/0091169 | A1 | 4/2008 | Heideman et al. |
| 2008/0091257 | A1 | 4/2008 | Andreas et al. |

(56) References Cited

U.S. PATENT DOCUMENTS

2008/0097483 A1 4/2008 Ortiz et al.
2008/0097523 A1 4/2008 Bolduc et al.
2008/0103572 A1 5/2008 Gerber
2008/0140116 A1 6/2008 Bonutti
2008/0167713 A1 7/2008 Bolling
2008/0167714 A1 7/2008 St. Goar et al.
2008/0177380 A1 7/2008 Starksen et al.
2008/0195126 A1 8/2008 Solem
2008/0195200 A1 8/2008 Vidlund et al.
2008/0208265 A1 8/2008 Frazier et al.
2008/0221672 A1 9/2008 Lamphere et al.
2008/0228030 A1 9/2008 Godin
2008/0228223 A1 9/2008 Alkhatib
2008/0234729 A1 9/2008 Page et al.
2008/0262480 A1 10/2008 Stahler et al.
2008/0262609 A1 10/2008 Gross et al.
2008/0275300 A1 11/2008 Rothe et al.
2008/0275469 A1 11/2008 Fanton et al.
2008/0275551 A1 11/2008 Alfieri
2008/0281353 A1 11/2008 Aranyi et al.
2008/0281411 A1 11/2008 Berreklouw
2008/0287862 A1 11/2008 Weitzner et al.
2008/0288044 A1 11/2008 Osborne
2008/0288062 A1 11/2008 Andrieu et al.
2008/0294251 A1 11/2008 Annest et al.
2008/0300537 A1 12/2008 Bowman
2008/0300629 A1 12/2008 Surti
2008/0312506 A1 12/2008 Spivey et al.
2009/0024110 A1 1/2009 Heideman et al.
2009/0028670 A1 1/2009 Garcia et al.
2009/0043381 A1 2/2009 Macoviak et al.
2009/0054723 A1 2/2009 Khairkhahan et al.
2009/0054969 A1 2/2009 Salahieh et al.
2009/0062866 A1 3/2009 Jackson
2009/0076586 A1 3/2009 Hauser et al.
2009/0076600 A1 3/2009 Quinn
2009/0082797 A1 3/2009 Fung et al.
2009/0088837 A1 4/2009 Gillinov et al.
2009/0093877 A1 4/2009 Keidar et al.
2009/0099650 A1 4/2009 Bolduc et al.
2009/0105816 A1 4/2009 Olsen et al.
2009/0125102 A1 5/2009 Cartledge et al.
2009/0166913 A1 7/2009 Guo et al.
2009/0171439 A1 7/2009 Nissl
2009/0177266 A1 7/2009 Powell et al.
2009/0177274 A1 7/2009 Scorsin et al.
2009/0248148 A1 10/2009 Shaolian et al.
2009/0254103 A1 10/2009 Deutsch
2009/0264994 A1 10/2009 Saadat
2009/0287231 A1 11/2009 Brooks et al.
2009/0287304 A1 11/2009 Dahlgren et al.
2009/0299409 A1 12/2009 Coe et al.
2009/0326648 A1 12/2009 Machold et al.
2010/0001038 A1 1/2010 Levin et al.
2010/0010538 A1 1/2010 Juravic et al.
2010/0023056 A1 1/2010 Johansson et al.
2010/0023118 A1 1/2010 Medlock et al.
2010/0030014 A1 2/2010 Ferrazzi
2010/0030328 A1 2/2010 Seguin et al.
2010/0042147 A1 2/2010 Janovsky et al.
2010/0049213 A1 2/2010 Serina et al.
2010/0063542 A1 3/2010 van der Burg et al.
2010/0063550 A1 3/2010 Felix et al.
2010/0076499 A1 3/2010 McNamara et al.
2010/0094248 A1 4/2010 Nguyen et al.
2010/0094314 A1 4/2010 Hernlund et al.
2010/0106141 A1 4/2010 Osypka et al.
2010/0114180 A1 5/2010 Rock et al.
2010/0121349 A1 5/2010 Meier et al.
2010/0121435 A1 5/2010 Subramanian et al.
2010/0121437 A1 5/2010 Subramanian et al.
2010/0130989 A1 5/2010 Bourque et al.
2010/0130992 A1 5/2010 Machold et al.
2010/0152845 A1 6/2010 Bloom et al.
2010/0161043 A1 6/2010 Maisano et al.
2010/0168845 A1 7/2010 Wright
2010/0174358 A1 7/2010 Rabkin et al.
2010/0179574 A1 7/2010 Longoria et al.
2010/0217184 A1 8/2010 Koblish et al.
2010/0217382 A1 8/2010 Chau et al.
2010/0234935 A1 9/2010 Bashiri et al.
2010/0249497 A1 9/2010 Peine et al.
2010/0249908 A1 9/2010 Chau et al.
2010/0249915 A1 9/2010 Zhang
2010/0249920 A1 9/2010 Bolling et al.
2010/0262232 A1 10/2010 Annest
2010/0262233 A1 10/2010 He
2010/0286628 A1 11/2010 Gross
2010/0298929 A1 11/2010 Thornton et al.
2010/0305475 A1 12/2010 Hinchliffe et al.
2010/0324598 A1 12/2010 Anderson
2011/0004210 A1 1/2011 Johnson et al.
2011/0004298 A1 1/2011 Lee et al.
2011/0009956 A1 1/2011 Cartledge et al.
2011/0011917 A1 1/2011 Loulmet
2011/0026208 A1 2/2011 Utsuro et al.
2011/0029066 A1 2/2011 Gilad et al.
2011/0035000 A1 2/2011 Nieminen et al.
2011/0066231 A1 3/2011 Cartledge et al.
2011/0067770 A1 3/2011 Pederson et al.
2011/0071626 A1 3/2011 Wright et al.
2011/0082538 A1 4/2011 Dahlgren et al.
2011/0087146 A1 4/2011 Ryan et al.
2011/0093002 A1 4/2011 Rucker et al.
2011/0118832 A1 5/2011 Punjabi
2011/0137410 A1 6/2011 Hacohen
2011/0144576 A1 6/2011 Rothe et al.
2011/0144703 A1 6/2011 Krause et al.
2011/0202130 A1 8/2011 Cartledge et al.
2011/0208283 A1 8/2011 Rust
2011/0230941 A1 9/2011 Markus
2011/0230961 A1 9/2011 Langer et al.
2011/0238088 A1 9/2011 Bolduc et al.
2011/0257433 A1 10/2011 Walker
2011/0257633 A1 10/2011 Cartledge et al.
2011/0264208 A1 10/2011 Duffy et al.
2011/0276062 A1 11/2011 Bolduc
2011/0288435 A1 11/2011 Christy et al.
2011/0301498 A1 12/2011 Maenhout et al.
2012/0053628 A1 3/2012 Sojka et al.
2012/0053642 A1 3/2012 Lozier et al.
2012/0065464 A1 3/2012 Ellis et al.
2012/0078355 A1 3/2012 Zipory et al.
2012/0078359 A1 3/2012 Li et al.
2012/0089022 A1 4/2012 House et al.
2012/0089125 A1 4/2012 Scheibe et al.
2012/0095552 A1 4/2012 Spence et al.
2012/0109155 A1 5/2012 Robinson et al.
2012/0143226 A1 6/2012 Belson et al.
2012/0143323 A1 6/2012 Hasenkam et al.
2012/0150290 A1 6/2012 Gabbay
2012/0158021 A1 6/2012 Morrill
2012/0158023 A1 6/2012 Mitelberg et al.
2012/0179086 A1 7/2012 Shank et al.
2012/0191182 A1 7/2012 Hauser et al.
2012/0226294 A1 9/2012 Tuval
2012/0226349 A1 9/2012 Tuval et al.
2012/0239142 A1 9/2012 Liu et al.
2012/0245604 A1 9/2012 Tegzes
2012/0271198 A1 10/2012 Whittaker et al.
2012/0296349 A1 11/2012 Smith et al.
2012/0296417 A1* 11/2012 Hill ...................... A61F 2/2445
623/2.11
2012/0310330 A1 12/2012 Buchbinder et al.
2012/0323313 A1 12/2012 Seguin
2013/0030522 A1 1/2013 Rowe et al.
2013/0046373 A1 2/2013 Cartledge et al.
2013/0053884 A1 2/2013 Roorda
2013/0079873 A1 3/2013 Migliazza et al.
2013/0085529 A1 4/2013 Housman
2013/0090724 A1 4/2013 Subramanian et al.
2013/0096673 A1 4/2013 Hill et al.
2013/0116776 A1 5/2013 Gross et al.
2013/0123910 A1 5/2013 Cartledge et al.

(56) References Cited

U.S. PATENT DOCUMENTS

2013/0131791 A1 5/2013 Hlavka et al.
2013/0166017 A1 6/2013 Cartledge et al.
2013/0190863 A1 7/2013 Call et al.
2013/0204361 A1 8/2013 Adams et al.
2013/0218206 A1 8/2013 Gadlage
2013/0226289 A1 8/2013 Shaolian et al.
2013/0226290 A1 8/2013 Yellin et al.
2013/0231701 A1 9/2013 Voss et al.
2013/0268069 A1 10/2013 Zakai et al.
2013/0282059 A1 10/2013 Ketai et al.
2013/0289718 A1 10/2013 Tsukashima et al.
2013/0297013 A1 11/2013 Klima et al.
2013/0304093 A1 11/2013 Serina et al.
2013/0331930 A1 12/2013 Rowe et al.
2014/0067054 A1 3/2014 Chau et al.
2014/0081394 A1 3/2014 Keränen et al.
2014/0088368 A1 3/2014 Park
2014/0088646 A1 3/2014 Wales et al.
2014/0094826 A1 4/2014 Sutherland et al.
2014/0094903 A1 4/2014 Miller et al.
2014/0094906 A1 4/2014 Spence et al.
2014/0114390 A1 4/2014 Tobis et al.
2014/0135799 A1 5/2014 Henderson
2014/0142619 A1 5/2014 Serina et al.
2014/0142695 A1 5/2014 Gross et al.
2014/0148849 A1 5/2014 Serina et al.
2014/0155783 A1 6/2014 Starksen et al.
2014/0163615 A1 6/2014 Gadlage et al.
2014/0163670 A1 6/2014 Alon et al.
2014/0163690 A1 6/2014 White
2014/0188108 A1 7/2014 Goodine et al.
2014/0188140 A1 7/2014 Meier et al.
2014/0188215 A1 7/2014 Hlavka et al.
2014/0194976 A1 7/2014 Starksen et al.
2014/0207231 A1 7/2014 Hacohen et al.
2014/0243859 A1 8/2014 Robinson
2014/0243894 A1 8/2014 Groothuis et al.
2014/0243963 A1 8/2014 Sheps et al.
2014/0251042 A1 9/2014 Asselin et al.
2014/0275757 A1 9/2014 Goodwin et al.
2014/0276648 A1 9/2014 Hammer et al.
2014/0296962 A1 10/2014 Cartledge et al.
2014/0303649 A1 10/2014 Nguyen et al.
2014/0303720 A1 10/2014 Sugimoto et al.
2014/0309661 A1 10/2014 Sheps et al.
2014/0309730 A1 10/2014 Alon et al.
2014/0343668 A1 11/2014 Zipory et al.
2014/0350660 A1 11/2014 Cocks et al.
2014/0379006 A1 12/2014 Sutherland et al.
2015/0018940 A1 1/2015 Quill et al.
2015/0051697 A1 2/2015 Spence et al.
2015/0081014 A1 3/2015 Gross et al.
2015/0094800 A1 4/2015 Chawla
2015/0100116 A1 4/2015 Mohl et al.
2015/0112432 A1 4/2015 Reich et al.
2015/0127097 A1 5/2015 Neumann et al.
2015/0133997 A1 5/2015 Deitch et al.
2015/0182336 A1 7/2015 Zipory et al.
2015/0230919 A1 8/2015 Chau et al.
2015/0272586 A1 10/2015 Herman et al.
2015/0272734 A1 10/2015 Sheps et al.
2015/0282931 A1 10/2015 Brunnett et al.
2015/0351910 A1 12/2015 Gilmore et al.
2016/0008132 A1 1/2016 Cabiri et al.
2016/0029920 A1 2/2016 Kronström et al.
2016/0030034 A1 2/2016 Graul et al.
2016/0038130 A1* 2/2016 Schaller ............ A61B 17/0469 606/139
2016/0058557 A1 3/2016 Reich et al.
2016/0113767 A1 4/2016 Miller et al.
2016/0120642 A1 5/2016 Shaolian et al.
2016/0120645 A1 5/2016 Alon
2016/0158008 A1 6/2016 Miller et al.
2016/0242762 A1 8/2016 Gilmore et al.
2016/0256149 A1 9/2016 Sampson et al.
2016/0256274 A1 9/2016 Hayoz
2016/0262755 A1 9/2016 Zipory et al.
2016/0302917 A1 10/2016 Schewel
2016/0317302 A1 11/2016 Madjarov et al.
2016/0346084 A1 12/2016 Taylor et al.
2016/0361058 A1 12/2016 Bolduc et al.
2016/0361168 A1 12/2016 Gross et al.
2016/0361169 A1 12/2016 Gross et al.
2017/0000609 A1 1/2017 Gross et al.
2017/0042670 A1 2/2017 Shaolian et al.
2017/0100119 A1 4/2017 Baird et al.
2017/0224489 A1 8/2017 Starksen et al.
2017/0245993 A1 8/2017 Gross et al.
2018/0008409 A1 1/2018 Kutzik et al.
2018/0049875 A1 2/2018 Iflah et al.
2018/0140420 A1 5/2018 Hayoz et al.
2018/0168803 A1 6/2018 Pesce et al.
2018/0228608 A1 8/2018 Sheps et al.
2018/0256334 A1 9/2018 Sheps et al.
2018/0280019 A1 10/2018 Azar et al.
2018/0289480 A1 10/2018 D'ambra et al.
2018/0318080 A1 11/2018 Quill et al.
2018/0318083 A1 11/2018 Bolling et al.
2019/0029498 A1 1/2019 Mankowski et al.
2019/0038411 A1 2/2019 Alon
2019/0091445 A1 3/2019 House
2019/0111239 A1 4/2019 Bolduc et al.
2019/0117400 A1 4/2019 Medema et al.
2019/0125325 A1 5/2019 Sheps et al.
2019/0151093 A1 5/2019 Keidar et al.
2019/0159898 A1 5/2019 Kutzik et al.
2019/0175344 A1 6/2019 Khairkhahan
2019/0175345 A1 6/2019 Schaffner et al.
2019/0175346 A1 6/2019 Schaffner et al.
2019/0183648 A1 6/2019 Trapp et al.
2019/0240023 A1 8/2019 Spence et al.
2019/0290260 A1 9/2019 Caffes et al.
2019/0290431 A1 9/2019 Genovese et al.
2019/0321049 A1 10/2019 Herman et al.
2019/0343633 A1 11/2019 Garvin et al.
2020/0015810 A1 1/2020 Piccirillo
2020/0015971 A1 1/2020 Brauon et al.
2020/0178956 A1 6/2020 Mitelberg et al.
2020/0289267 A1 9/2020 Peleg et al.
2020/0337840 A1 10/2020 Reich
2020/0390551 A1 12/2020 McCarthy
2021/0015475 A1 1/2021 Lau
2021/0052387 A1 2/2021 Greenan et al.
2021/0059820 A1 3/2021 Clark et al.
2021/0085461 A1* 3/2021 Neumark .............. A61F 2/2445
2021/0093453 A1 4/2021 Peleg et al.
2021/0145584 A1 5/2021 Kasher et al.
2022/0071620 A1 3/2022 Brauon et al.
2022/0096232 A1 3/2022 Skaro et al.
2022/0110656 A1 4/2022 Azar et al.
2022/0142779 A1 5/2022 Sharon
2022/0176076 A1 6/2022 Keidar
2022/0233316 A1 7/2022 Sheps et al.
2022/0273436 A1 9/2022 Aviv et al.
2022/0313438 A1 10/2022 Chappel-Ram
2022/0323221 A1 10/2022 Sharon et al.
2023/0016867 A1 1/2023 Tennenbaum
2023/0218291 A1 7/2023 Zarbatany et al.
2023/0320856 A1 10/2023 Zarbatany et al.
2024/0008985 A1 1/2024 Yuan et al.
2024/0099736 A1 3/2024 Elsheikh et al.

FOREIGN PATENT DOCUMENTS

EP 0614342 A1 9/1994
EP 1034753 A1 9/2000
EP 3531975 A1 9/2019
JP 2007510525 A 4/2007
JP 2019528888 A 10/2019
WO 1992005093 A1 4/1992
WO 1993010714 A1 6/1993
WO 1996039963 A1 12/1996
WO 1996040344 A1 12/1996
WO 1997001369 A1 1/1997

(56) References Cited

FOREIGN PATENT DOCUMENTS

| | | | |
|---|---|---|---|
| WO | 1998046149 | A1 | 10/1998 |
| WO | 1999033414 | A1 | 7/1999 |
| WO | 1999063907 | A1 | 12/1999 |
| WO | 1999063910 | A1 | 12/1999 |
| WO | 2000009048 | A1 | 2/2000 |
| WO | 2001056457 | A1 | 8/2001 |
| WO | 2002085250 | A2 | 10/2002 |
| WO | 2003047467 | A1 | 6/2003 |
| WO | 2004012583 | A2 | 2/2004 |
| WO | 2005021063 | A2 | 3/2005 |
| WO | 2006116558 | A2 | 11/2006 |
| WO | 2007080595 | A2 | 7/2007 |
| WO | 2007098512 | A1 | 9/2007 |
| WO | 2007136981 | A2 | 11/2007 |
| WO | 2008014144 | A2 | 1/2008 |
| WO | 2009160631 | | 10/2009 |
| WO | 2010000454 | A1 | 1/2010 |
| WO | 2010006905 | A1 | 1/2010 |
| WO | 2010065274 | A1 | 6/2010 |
| WO | 2010128502 | A1 | 11/2010 |
| WO | 2011051942 | A1 | 5/2011 |
| WO | 2011089401 | A1 | 7/2011 |
| WO | 2011089601 | A1 | 7/2011 |
| WO | 2011111047 | A2 | 9/2011 |
| WO | 2011154942 | A2 | 12/2011 |
| WO | 2012011108 | A2 | 1/2012 |
| WO | 2012068541 | A2 | 5/2012 |
| WO | 2012106346 | A1 | 8/2012 |
| WO | 2012176195 | A2 | 12/2012 |
| WO | 2013021375 | A2 | 2/2013 |
| WO | 2013078497 | A1 | 6/2013 |
| WO | 2014064694 | A2 | 5/2014 |
| WO | 2014064964 | A1 | 5/2014 |
| WO | 2014087402 | A1 | 6/2014 |
| WO | 2014108903 | A1 | 7/2014 |
| WO | 2014195786 | A2 | 12/2014 |
| WO | 2015059699 | A2 | 4/2015 |
| WO | 2015193728 | A2 | 12/2015 |
| WO | 2016059639 | A1 | 4/2016 |
| WO | 2016087934 | A1 | 6/2016 |
| WO | 2016174669 | A1 | 11/2016 |
| WO | 2019145941 | A1 | 8/2019 |
| WO | 2019145947 | A1 | 8/2019 |
| WO | 2019182645 | A1 | 9/2019 |
| WO | 2019224814 | A1 | 11/2019 |
| WO | 2020240282 | A2 | 12/2020 |
| WO | 2021014440 | A2 | 1/2021 |
| WO | 2021038559 | A1 | 3/2021 |
| WO | 2021038560 | A1 | 3/2021 |
| WO | WO-2021061945 | A1 | 4/2021 |
| WO | 2022064401 | A2 | 3/2022 |
| WO | 2022090907 | A1 | 5/2022 |
| WO | 2022101817 | A2 | 5/2022 |
| WO | 2022153131 | A1 | 7/2022 |
| WO | 2022157592 | A1 | 7/2022 |
| WO | 2022172108 | A1 | 8/2022 |
| WO | 2022172149 | A1 | 8/2022 |
| WO | 2022200972 | A1 | 9/2022 |
| WO | 2022224071 | A1 | 10/2022 |
| WO | 2022229815 | A1 | 11/2022 |
| WO | 2022250983 | A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation&Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

O'Reilly S et al., "Heart valve surgery pushes the envelope," Medtech Insight 8(3): 73, 99-108 (2006).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

Alfieri et al., "The edge to edge technique," The European Association for Cardio-Thoracic Surgery 14th Annual Meeting Oct. 7-11, Book of Procees. (2000).

Sutton E.E. et al., "Biologically Inspired Catheter for Endovascular Sensing and Navigation", Scientific Reports Journal, vol. 10, 5643, Mar. 27, 2020, DOI https://doi.org/10.1038/s41598-020-62360-w.

* cited by examiner 150
64d
180d
45
150
150
150b
242
150a
22
20
16
63d
82
240
167

180d
45
64d
240
150b
82
210
222
200
224

180d
64d
150
240
82
150b
210
150a

DEVICES AND METHODS FOR AREA REDUCTION AND CLOSURE OF CARDIAC OPENINGS OR CAVITIES

CROSS-REFERENCES TO RELATED APPLICATIONS

The present application is a Continuation of International Patent Application PCT/IB2021/059851 to Spiegel et al., filed Oct. 26, 2021, and entitled "Devices and methods for area reduction and closure of cardiac openings or cavities," which published as WO 2022/090907; which claims priority from U.S. Provisional Patent Application 63/106,324 to Spiegel et al., filed Oct. 27, 2020, and entitled "Devices and methods for area reduction and closure of cardiac openings or cavities."

Each of the above applications is incorporated by reference in its entirety.

BACKGROUND

The heart is a muscular organ which pumps blood through the blood vessels of the circulatory system by contraction and expansion. In a healthy heart, blood flows in a single direction therethrough, facilitated by heart valves preventing the backflow of blood. During a normal heart contraction cycle, while muscle of the heart contracts, the heart valves open and close accordingly. These heart tissues may include various types of cavities and formations.

Various pathologies are associated with structural abnormalities, including abnormalities of opening and cavities, formed within the heart. Dilation of an annulus of a heart valve may occur due to various heart conditions, such as an enlarged heart chamber or a leaking heart valve. An annuloplasty procedure may be necessary to reshape, reinforce or tighten the annulus. Annuloplasty may be done performed by implanting an annuloplasty device to re-shape and/or re-size the annulus, for example, to reduce the size of the annulus.

Similarly, there remains a need for simple, yet effective, systems and methods for remodeling other heart tissues, such as closing the left atrial appendage.

SUMMARY

This summary is meant to provide some examples and is not intended to be limiting of the scope of the disclosure in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

The present disclosure relates to, among other ideas, methods and systems of performing an annuloplasty procedure on a heart of a subject. In some applications, the method comprises using a transluminal (e.g., transfemoral) approach to advance a catheter to the heart of the subject, and implanting a plurality of anchors around an annulus of a valve of the heart. In some applications, the anchors can be threaded onto a tether (e.g., a wire), prior to their advancement, such that implanting the anchors around the annulus disposes a bight of the wire around the annulus, with the ends of the wire disposed outside of the heart, e.g., outside of the subject. Subsequently, the bight is formed into a closed loop that is tightened to contract the annulus, thus reducing valve regurgitation.

In some applications, the catheter is an outer catheter, and the system further comprises an internal catheter. The anchors are implanted into tissue of the annulus while the internal catheter is disposed within a lumen of the outer catheter. The wire can be disposed such that a first portion of the wire extends, from outside of the subject, through the internal catheter, out of the internal catheter at the annulus, and a second portion of the wire extends back through a space defined between the internal catheter and the outer catheter (i.e., in the lumen of the outer catheter, but not inside the internal catheter) and out of the subject, such that both ends of the wire are situated outside of the heart, e.g., outside of the subject. The anchors can be advanced to the annulus while threaded over the wire, such that each anchor is advanced over the wire within the internal catheter, towards the heart, where they are implanted around the annulus. Thus, once the anchors have been implanted around the annulus, the wire extends, from outside of the subject, through the internal catheter, to the heart of the subject, where it forms the bight around the annulus, and back through the space defined between the internal catheter and the outer catheter, and outside of the subject.

Once the anchors are implanted in tissue of the annulus, the internal catheter may be retracted from the outer catheter and the subject, leaving the wire extending, from outside the subject, through the outer catheter, to the annulus, where it is anchored in a bight around the annulus, and back through the outer catheter and out of the subject.

In some applications, in order to facilitate reduction in valve regurgitation, the wire is then fashioned into a closed loop around the annulus, for example, by slidably coupling the ends of the wire to each other, from outside of the subject. In some such applications, in order to slidably couple the ends of the wire to each other, one end of the wire defines a slidable coupling, e.g., an end-portion retainer (e.g., an eyelet, loop, opening, etc.), through which the other end of the wire (henceforth referred to as the free end) is inserted into. In some applications, the end-portion retainer can be an eyelet defined by the end of the wire, which the free end is inserted into, or any other retainer, as described more in detail hereinbelow. The wire is thus arranged into a loop that extends, from the end-portion retainer, through the outer catheter, to the annulus where it is anchored, and back through the outer catheter, and outside of the patient, where the free end is secured in the loop at the end-retainer portion. The free end of the wire (which is secured in the end retainer portion) is then pulled proximally and/or the slidable coupling is pushed distally, reducing the size of the loop, and pulling the loop through the catheter and towards the annulus.

In some applications, subsequently to advancing the closed loop towards the annulus, the first portion of the wire extends, from the heart, where it is coupled to the end-portion retainer, proximally through the outer catheter and out of the subject. In some applications, the wire is then tensioned, in order to reduce the size of the annulus, e.g., such that the tissue anchors move towards each other, further reducing the size of the closed loop. A cutting and locking assembly may be advanced over the first portion, and along the wire, towards the heart. The cutting and locking assembly can be used to cut excess wire extending away from the closed loop, such that the first portion of the wire is cut slightly proximally to the end-portion retainer. The tension within the closed loop may be maintained by a locker delivered by the cutting and locking assembly, in order to maintain the closed loop in the tensioned state.

According to an aspect of the disclosure, there is provided an implant configured to be advanced within a lumen of an internal catheter. The implant comprises a wire (or line, contraction member, or the like) and a plurality of anchors. The wire comprises a first wire portion comprising a proximal free end, and a second wire portion continuously extending from the first wire portion, the second wire portion comprising an end-portion retainer. Each anchor comprises a tissue-engaging element, e.g., a portion that attaches to the tissue. The tissue-engaging element can be configured in a variety of ways, e.g., as or including one or more of a helical portion or helix, hook(s), barb(s), harpoon(s), needle(s), clip(s), adhesive(s), arm(s), extension(s), gripper(s), etc. In some applications, the tissue-engaging element includes a sharpened distal tip and a proximal end defining a helical portion therebetween, wherein said tissue-engaging element is configured to be driven into a tissue of a subject's heart. Each anchor further comprises an eyelet coupled to the proximal end of the tissue-engaging element; the eyelet configured to allow a portion of the wire to extend therethrough.

The end-portion retainer encloses an opening into which the proximal free end can be inserted. The end-portion retainer is slidable over the section of the first wire portion. The end-portion retainer is dimensioned to be larger than the eyelet, so as to prevent it from passing through the eyelet.

According to some applications, the end-portion retainer is a loop.

According to some applications, the end-portion retainer is a terminal clamp comprising a hinged spring-biased gate.

According to some applications, the implant further comprises a clip releasably coupled to the end-portion retainer.

According to some applications, the plurality of anchors comprises between 3 to 30 anchors.

According to some applications, the plurality of anchors comprises between 5 to 25 anchors.

According to some applications, there is provided a system comprising the implant and a handle assembly, an outer catheter, and an internal catheter. The handle assembly comprises an outer catheter handle and an internal catheter handle. The outer catheter extends from the outer catheter handle and has an outer catheter distal end. The internal catheter extends from the internal catheter handle and has an internal catheter distal end, wherein the internal catheter extending through the outer catheter.

In some applications, the first wire portion and the plurality of anchors are configured to be advanced through the internal catheter in a distal direction. At least a first segment of the second wire portion is configured to extend through a plurality of eyelets of a corresponding plurality of anchors, positioned distally to the internal catheter distal end.

According to some applications, at least a second segment of the second wire portion is looped back proximally from the anchors and into an internal space defined between the internal catheter and the outer catheter.

According to some applications, the second wire portion extends proximal to the outer catheter, wherein the end-portion retainer is disposed out of the handle assembly.

According to some applications, the internal catheter and the internal catheter handle are removable from the system, such that upon removal of the internal catheter and the internal catheter handle, the proximal free end is exposed, and sections of both the first wire portion and the second wire portion extend through a lumen of the outer catheter.

According to some applications, the handle assembly further comprises a guide catheter handle, wherein the system further comprises a guide catheter extending from the guide catheter handle and having a guide catheter distal end, and wherein the guide catheter is disposed between the internal catheter and the outer catheter.

According to some applications, at least a second segment of the second wire portion is looped back proximally from the anchors and into an internal space defined between the internal catheter and the guide catheter.

According to some applications, the second wire portion extends proximal to the guide catheter, wherein the end-portion retainer is disposed out of the handle assembly.

According to some applications, the internal catheter and the internal catheter handle are removable from the system, such that upon removal of the internal catheter and the internal catheter handle, the proximal free end is exposed, and sections of both the first wire portion and the second wire portion extend through a lumen of the guide catheter.

According to some applications, the guide catheter and the guide catheter handle are removable from the system, such that upon removal of the internal catheter and the internal catheter handle, and removal of the guide catheter and the guide catheter handle, the proximal free end is exposed, and sections of both the first wire portion and the second wire portion extend through a lumen of the outer catheter.

According to some applications, the system further comprises an anchor driver configured to reversibly engage the anchor and drive it into a tissue.

According to some applications, the internal catheter comprises a lateral slit extending proximally from the internal catheter distal end, such that the lateral slit is continuous with a distal opening of the internal catheter distal end, wherein the lateral slit is configured to allow the wire, but not the anchors, to exit from the internal catheter laterally, proximally from the internal catheter distal end.

According to some applications, there is provided a cinching system comprising the implant, a cinching catheter and a cutting and locking assembly attached to the cinching catheter. The cutting and locking assembly comprises a locker releasable therefrom. The first wire portion extends through the cinching catheter and the cutting and locking assembly. The plurality of anchors, and the first section of the second wire portion extending through the plurality of anchors, are positioned distal to the cutting and locking assembly.

According to some applications, the locker comprises a fastener, configured to transition between an open state and a closed state, wherein the fastener is configured to allow axial movement of the wire through the locker in the open state, and wherein the fastener is configured to restrict movement of the wire with respect to the plurality of anchors in the closed state.

According to some applications, the cutting and locking assembly comprises at least one blade, configured to cut the wire extending therethrough.

According to some applications, sections of both the first wire portion and the second wire portion extend through the cinching catheter and the cutting and locking assembly.

According to another aspect of the disclosure, there is provided a method comprising a step of advancing a plurality of anchors of an implant through an internal catheter and anchoring them in succession into tissues surround an annulus of a heart valve or other tissue region (e.g., an annulus of the mitral valve, an annulus of a tricuspid valve, an appendage, a bulge, a portion of a chamber wall, another tissue opening, etc.), wherein a first wire portion of a wire of the implant extends through the internal catheter and is advanced therethrough, and wherein a second wire portion of the wire extends through the anchored anchors, and is looped back to extend along a space defined between the internal catheter and another catheter disposed over the internal catheter.

The method further comprises a step of retracting the internal catheter and an internal catheter handle thereof, thereby exposing a proximal free end of the first wire portions. The method further comprises a step of inserting the proximal free end into an end-portion retainer at an extracorporeal end of the second wire portion. The method further comprises a step of slidably advancing the end-portion retainer over the first wire portion toward a first anchor of the plurality of anchors. The method further comprises a step of tensioning the wire so as to contract the implant anchored to the annulus or other tissue region. The method further comprises a step of locking the wire of the implant in a tensioned state by a locker advanced toward the implant, wherein the end-portion retainer is positioned distal to the locker.

According to some applications, anchoring of the plurality of anchors in succession is performed such that the anchors are implanted along a path-line that extends at least 270° around the annulus or other tissue region.

According to some applications, anchoring of the plurality of anchors in succession is performed such that the anchors are implanted along a path-line that extends between 270° and 320° around the annulus or other tissue region.

According to some applications, anchoring of the plurality of anchors in succession is performed such that the anchors are implanted along a path-line that extends between 320° and 360° around the annulus or other tissue region.

According to some applications, the other catheter disposed over the internal catheter is a guide catheter.

According to some applications, retracting the internal catheter and an internal catheter handle thereof comprises retracting the internal catheter from the guide catheter, and decoupling the internal catheter handle from a guide catheter handle, such that upon removal of the internal catheter and the internal catheter handle, sections of both the first wire portion and the second wire portion extend through a lumen of the guide catheter, and the proximal free end of the first wire portion is exposed out of the guide catheter handle.

According to some applications, advancing the end-portion retainer comprises pulling the first wire portion in a proximal direction, thereby allowing the end-portion retainer to slide through the lumen of the guide catheter and out of a distal end portion of the guide catheter.

According to some applications, the end-portion retainer is sized so as to allow it to slide through the guide catheter.

According to some applications, an outer catheter is disposed over the guide catheter.

According to some applications, retracting the internal catheter and an internal catheter handle thereof comprises retracting both the internal catheter and the guide catheter from the outer catheter, and decoupling both the internal catheter handle and the guide catheter handle from an outer catheter handle, such that upon removal of these components, sections of both the first wire portion and the second wire portion extend through a lumen of the outer catheter, and the proximal free end of the first wire portion is exposed out of the outer catheter handle.

According to some applications, the another catheter disposed over the internal catheter is an outer catheter, wherein retracting the internal catheter and an internal catheter handle thereof comprises retracting the internal catheter from the outer catheter, and decoupling the internal catheter handle from an outer catheter handle, such that upon removal of the internal catheter and the internal catheter handle, sections of both the first wire portion and the second wire portion extend through a lumen of the outer catheter, and the proximal free end of the first wire portion is exposed out of the outer catheter handle.

According to some applications, advancing the end-portion retainer comprises pulling the first wire portion in a proximal direction, thereby allowing the end-portion retainer to slide through the lumen of the outer catheter and out of a distal end portion of the outer catheter.

According to some applications, the end-portion retainer is sized so as to allow it to slide through the guide catheter.

According to some applications, the end-portion retainer is larger than an eyelet of the first anchor of the plurality of anchors, so as to prevent it from passing through the eyelet.

According to some applications, the end-portion retainer is a loop.

According to some applications, the end-portion retainer is a is a terminal clamp comprising a hinged spring-biased gate.

According to some applications, the method further comprises a step of releasing the end-portion retainer from a clip releasably coupled thereto, prior to the step of insertion of the proximal free end into the end-portion retainer.

According to some applications, the method further comprises a step of advancing a cutting and locking assembly, comprising the locker and attached to a cinching catheter of a cinching system, over the first wire portion inserted thereinto and extending therethrough, and toward the anchors of the implant.

According to some applications, the step of advancing the cutting and locking assembly further facilitates the step of slidably advancing the end-portion retainer, by utilizing the cutting and locking assembly to push against the end-portion retainer toward the anchors of the implant.

According to some applications, the step of tensioning the wire comprises pulling the first wire portion extending through the cutting and locking assembly and the cinching catheter.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing a plurality of anchors of an implant through an internal catheter and anchoring them in succession into tissues surround an annulus of a heart valve or other tissue region, wherein a first wire portion of a wire of the implant extends through the internal catheter and is advanced therethrough, and wherein a second wire portion of the wire extends through the anchored anchors, and is looped back to extend along a space defined between the internal catheter and another catheter disposed over the internal catheter.

The method further comprises a step of retracting the internal catheter and an internal catheter handle thereof. The method further comprises a step of inserting both the first wire portion and the second wire portion into a cutting and locking assembly and a cinching catheter attached thereto. The method further comprises a step of advancing the cutting and locking assembly over both portions of the wire toward the anchors of the implant. The method further comprises a step of tensioning the wire so as to contract the implant anchored to the annulus or other tissue region. The method further comprises a step of locking the wire of the implant in a tensioned state by a locker comprised within the cutting and locking assembly.

According to some applications, anchoring of the plurality of anchors in succession is performed such that the anchors are implanted along a path-line that extends at least 270° around the annulus or other tissue region.

According to some applications, anchoring of the plurality of anchors in succession is performed such that the anchors are implanted along a path-line that extends between 270° and 320° around the annulus or other tissue region.

According to some applications, anchoring of the plurality of anchors in succession is performed such that the anchors are implanted along a path-line that extends between 320° and 360° around the annulus or other tissue region.

According to some applications, the other catheter disposed over the internal catheter is a guide catheter.

According to some applications, retracting the internal catheter and an internal catheter handle thereof comprises retracting the internal catheter from the guide catheter, and decoupling the internal catheter handle from a guide catheter handle, such that upon removal of the internal catheter and the internal catheter handle, sections of both the first wire portion and the second wire portion extend through a lumen of the guide catheter.

According to some applications, an outer catheter is disposed over the guide catheter.

According to some applications, retracting the internal catheter and an internal catheter handle thereof comprises retracting both the internal catheter and the guide catheter from the outer catheter, and decoupling both the internal catheter handle and the guide catheter handle from an outer catheter handle, such that upon removal of these components, sections of both the first wire portion and the second wire portion extend through a lumen of the outer catheter.

According to some applications, the another catheter disposed over the internal catheter is an outer catheter, and wherein retracting the internal catheter and an internal catheter handle thereof comprises retracting the internal catheter from the outer catheter, and decoupling the internal catheter handle from an outer catheter handle, such that upon removal of the internal catheter and the internal catheter handle, sections of both the first wire portion and the second wire portion extend through a lumen of the outer catheter.

According to some applications, the step of tensioning the wire comprises simultaneously pulling both the first wire portion and the second wire portion in a proximal direction.

According to some applications, the step of tensioning the wire comprises applying a pull force to one of the first wire portion or the second wire portion, while the other portion is kept in place, preventing it from sliding in a distal direction while its counterpart wire portion is pulled.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing a first anchor of an implant through an internal catheter, along with the terminal clamp attached to a second wire portion of a wire of the implant, wherein the terminal clamp is coupled to the first anchor via the second wire portion extending through an eyelet of the first anchor. The method further comprises a step of anchoring the first anchor into a tissue of an annulus of a heart valve or other tissue region.

The method further comprises a step of advancing additional anchors through the internal catheter and anchoring them in succession to the tissue of the annulus or other tissue region, wherein a first wire portion of the wire extends through the internal catheter and is advanced therethrough, and wherein the second wire portion of extends through the anchored anchors. The method further comprises a step of maneuvering the internal catheter to approximate a section of the wire extending therefrom to the terminal clamp, and push this wire section against a spring-biased gate of the terminal clamp, thereby inserting it into an internal opening defined by the terminal clamp.

The method further comprises a step of retracting the internal catheter and an internal catheter handle thereof. The method further comprises a step of inserting the first wire portion into a cutting and locking assembly and a cinching catheter attached thereto. The method further comprises a step of advancing the cutting and locking assembly over the first wire portion toward the terminal clamp. The method further comprises a step of tensioning the wire so as to contract the implant anchored to the annulus or other tissue region by applying a pull force to the first wire portion extending through the cutting and locking assembly and the cinching catheter. The method further comprises a step of locking the wire of the implant in a tensioned state by a locker comprised within the cutting and locking assembly.

According to some applications, anchoring of the plurality of anchors in succession is performed such that the anchors are implanted along a path-line that extends at least 270° around the annulus or other tissue region.

According to some applications, anchoring of the plurality of anchors in succession is performed such that the anchors are implanted along a path-line that extends between 270° and 320° around the annulus or other tissue region.

According to some applications, anchoring of the plurality of anchors in succession is performed such that the anchors are implanted along a path-line that extends between 320° and 360° around the annulus or other tissue region.

According to some applications, the terminal clamp is sized so as to allow it to slide through the internal catheter.

According to some applications, the terminal clamp is larger than the eyelet of the first anchor, so as to prevent it from passing through the eyelet.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a locker comprising a housing defining a longitudinal axis, two sliding and locking elements, and a spring. The housing comprises a proximal wire opening formed at a proximal end of the housing, a distal wire opening formed at a distal end of the housing, and two distal actuation openings located on opposite sides of the distal wire opening at the distal end of the housing. The sliding and locking elements can be configured in a variety of different ways. In some applications, the sliding and locking elements are aligned with the distal actuation openings and are movable toward or away from each other. In some applications, the spring is pressed between a wall of the housing and the sliding and locking elements, and is configured to bias the sliding and locking elements distally and toward each other, in the absence of external force applied to the sliding and locking elements.

According to some applications, the locker further comprises two guide elements on opposite sides of the longitudinal axis, wherein each guide element laterally extends between two sidewalls of the housing, and wherein each sliding and locking elements comprises an inclined slot accommodating and movable along a corresponding guide element.

According to some applications, the inclined slots are angled with respect to the longitudinal axis.

According to some applications, the spring is a finger disc spring having at least one spring arm.

According to some applications, the spring comprises two spring arms.

According to some applications, the housing comprises a first housing portion and a second housing portion, attachable to each other.

According to some applications, each sliding locking element further comprises a high friction surface oriented toward the longitudinal axis.

According to some applications, each high friction surface comprises plurality of teeth.

According to some applications, the teeth are oriented at a proximal angle.

According to some applications, the housing comprises inner angled walls, and wherein the sliding and locking elements comprise complementary angled outer surface, facing the inner walls and slidable there-along.

According to some applications, there is provided a system comprising the locker and an actuation assembly. The actuation assembly comprises and actuation element and two pressing arms. The actuation element comprises a hinged portion, positioned proximal to the locker. The pressing arms are hinged to the hinged portion and pivotable around the hinged portion. The pressing arms extend from both sides of the locker, wherein each pressing arm comprises a pin that can be insertable through a corresponding distal actuation opening and may be utilized to apply pressure against a corresponding sliding and locking element.

According to some applications, each pressing arm comprises a proximal arm portion, a longitudinal arm portion, and a distal arm portion. Each proximal arm portion is hinged to the hinged portion and extends away from the longitudinal axis. Each longitudinal arm portion extends between the proximal arm portion and the distal arm portion. Each distal arm portion extends toward the longitudinal axis and comprises the pin extending proximally therefrom.

According to some applications, the length of each longitudinal arm portion is longer than the length of the locker.

According to some applications, each longitudinal arm portion is angled at an obtuse angle with respect to the proximal arm portion.

According to some applications, the actuation element comprises a lumen aligned with the proximal wire opening.

According to another aspect of the disclosure, there is provided a method comprising a step of advancing a sleeve of a sleeved implant toward the LAA ostium. The method further comprises a step of deploying a first anchor from within the sleeve and anchoring it through the sleeve into the LAA ostium. The method further comprises a step of deploying subsequent anchors sleeve and anchoring them through the sleeve around the LAA ostium at subsequent locations, wherein each location is distanced from a previous location by a minimum distance. The method further comprises a step of contracting the sleeve, and thereby contracting the LAA ostium it is anchored to. The method further comprises a step of locking the implant in the contracted state.

According to some applications, the step of contracting the sleeve comprises applying tension to a contraction member extending within sleeve.

According to some applications, the step of deploying subsequent anchors is performed such that the sleeve extends at least 270° around the LAA ostium.

According to some applications, the step of deploying subsequent anchors is performed such that the sleeve extends between 320° and 360° around the LAA ostium.

According to some applications, the minimum distance is at least 1 mm.

According to some applications, the minimum distance is selected from the range of about 3-20 mm.

According to some applications, the minimum distance is selected from the range of about 5-15 mm.

According to some applications, the implant is anchored such that a portion of the sleeve extends over the edge of the LAA ostium.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing a cloth strip and an implant comprising a plurality of anchors and a wire extending through the plurality of anchors, toward the LAA ostium. The method further comprises a step of anchoring a first anchor of the plurality of anchors into the LAA ostium through the cloth strip. The method further comprises a step of anchoring subsequent anchors through subsequent portions of the cloth strip at subsequent locations around the circumference of the LAA ostium, wherein each location is distanced from a previous location by a minimum distance. The method further comprises a step of contracting the wire, thereby approximating the anchors and contracting the LAA ostium they are anchored to. The method further comprises a step of locking the implant in the contracted state.

According to some applications, the step of anchoring subsequent anchors is performed such that the cloth strip extends at least 270° around the LAA ostium.

According to some applications, the anchoring subsequent anchors is performed such that the sleeve cloth strip between 320° and 360° around the LAA ostium.

According to some applications, the minimum distance is at least 1 mm.

According to some applications, the minimum distance is selected from the range of about 3-20 mm.

According to some applications, the minimum distance is selected from the range of about 3-20 mm.

According to some applications, the implant is anchored such that a portion of the cloth strip extends over the edge of the LAA ostium.

According to some applications, the method further comprises a step of advancing a cutting and locking assembly, comprising a locker and attached to a cinching catheter of a cinching system, over the wire inserted thereinto and extending therethrough, and toward the anchors of the implant.

According to some applications, the step of contracting the wire comprises pulling a portion of the wire extending through the cutting and locking assembly and the cinching catheter.

According to some applications, the step of locking is achieved by utilizing the locker through which the wire extends.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing an implant comprising a plurality of anchors and a wire extending through the plurality of anchors, toward the LAA ostium. The method further comprises a step of anchoring a first anchor of the plurality of anchors into the LAA ostium, wherein the first anchor is coupled to a first stopper via the wire. The method further comprises a step of anchoring subsequent anchors at subsequent locations around the circumference of the LAA ostium, wherein each location is distanced from a previous location by a minimum distance. The method further comprises a step of contracting the wire, thereby approximating the anchors and contracting the LAA ostium they are anchored to. The method further comprises a step of locking the implant in the contracted state.

According to some applications, the step of anchoring subsequent anchors is performed such that the implant extends at least 270° around the LAA ostium.

According to some applications, the step of anchoring subsequent anchors is performed such that the implant extends between 320° and 360° around the LAA ostium.

According to some applications, the minimum distance is at least 1 mm.

According to some applications, the minimum distance is selected from the range of about 3-20 mm.

According to some applications, the minimum distance is selected from the range of about 5-15 mm.

According to some applications, the method further comprises a step of advancing a cutting and locking assembly, comprising a locker and attached to a cinching catheter of a cinching system, over the wire inserted thereinto and extending therethrough, and toward the anchors of the implant.

According to some applications, the step of contracting the wire comprises pulling a portion of the wire extending through the cutting and locking assembly and the cinching catheter.

According to some applications, the step of locking is achieved by utilizing the locker through which the wire extends.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), According to another aspect of the disclosure, there is provided a method comprising a step of advancing an implant comprising a plurality of anchors and a wire extending through the plurality of anchors, toward an opening within a patient's body. The method further comprises a step of anchoring a first anchor of the plurality of anchors into bordering tissue of the opening, wherein the first anchor is coupled to a first stopper via the wire. The method further comprises a step of anchoring a second anchor of the plurality of anchors into tissue at an opposite side of the opening. The method further comprises a step of anchoring subsequent anchors at subsequent locations positioned at opposite sides of the tissue of the opening, following a zig-zag formation between the anchors. The method further comprises a step of contracting the wire, thereby approximating the anchors and contracting the opening they are anchored to. The method further comprises a step of locking the implant in the contracted state.

According to some applications, the opening is the LAA ostium.

According to some applications, the method further comprises a step of advancing a cutting and locking assembly, comprising a locker and attached to a cinching catheter of a cinching system, over the wire inserted thereinto and extending therethrough, and toward the anchors of the implant.

According to some applications, the step of contracting the wire comprises pulling a portion of the wire extending through the cutting and locking assembly and the cinching catheter.

According to some applications, the step of locking is achieved by utilizing the locker through which the wire extends.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), According to another aspect of the disclosure, there is provided a method comprising a step of advancing a sleeve of an implant toward an opening within a patient's body. The method further comprises a step of deploying a first anchor from within the sleeve and anchoring it through the sleeve into a bordering tissue of the opening. The method further comprises a step of deploying a second anchor from within the sleeve and anchoring it through the sleeve into tissue at an opposite side of the opening. The method further comprises a step of deploying subsequent anchors sleeve and anchoring them through the sleeve at subsequent locations positioned at opposite sides of the tissue of the opening, following a zig-zag formation between the anchors. The method further comprises a step of contracting the sleeve, and thereby contracting the opening. The method further comprises a step of locking the implant in the contracted state.

According to some applications, the opening is the LAA ostium.

According to some applications, the step of contracting the sleeve comprises applying tension to a contraction member extending within sleeve.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing an implant comprising a plurality of anchors and a wire, having a first extending through the plurality of anchors, toward an opening within a patient's body, wherein the wire comprises a first wire portion extending distally to a first anchor of the plurality of anchors, and a second wire portion configured to extends through the plurality of anchors.

The method further comprises a step of anchoring the first anchor into bordering tissue of the opening. The method further comprises a step of anchoring a second anchor into tissue at an opposite side of the opening. The method further comprises a step of anchoring subsequent anchors at subsequent locations positioned at opposite sides of the tissue of the opening, wherein a second wire portion follows a zig-zag formation. The method further comprises a step of inserting a proximal free end of the first wire portion, through a loop of the second wire portion, and advancing the loop over the first wire portion toward the anchors. The method further comprises a step of contracting the wire, thereby approximating the anchors and contracting the opening they are anchored to. The method further comprises a step of locking the implant in the contracted state.

According to some applications, the opening is the LAA ostium.

According to some applications, the loop is larger than an eyelet of the first anchor, so as to prevent it from passing through the eyelet.

According to some applications, the method further comprises a step of advancing a cutting and locking assembly, comprising a locker and attached to a cinching catheter of a cinching system, over the first wire portion inserted thereinto and extending therethrough, and toward the anchors of the implant.

According to some applications, the step of contracting the wire comprises pulling the first wire portion extending through the cutting and locking assembly and the cinching catheter.

According to some applications, the step of locking is achieved by utilizing the locker through which the wire extends.

According to some applications, the step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing a first implant comprising a plurality of anchors and a wire extending through the plurality of anchors, toward an opening within a patient's body. The method further comprises a step of anchoring a first anchor of the first implant into bordering tissue of the opening, wherein the first anchor is coupled to a first stopper via the wire. The method further comprises a step of anchoring a second anchor of the first implant into tissue at an opposite side of the opening. The method further comprises a step of anchoring subsequent anchors of the first implant at subsequent locations positioned at opposite sides of the tissue of the opening, following a zig-zag formation between the anchors.

In some applications, the method further comprises a step of advancing a second implant comprising a plurality of anchors and a wire extending through the plurality of anchors, toward the opening.

In some applications, the method further comprises a step of anchoring a first anchor of the second implant into the bordering tissue of the opening, wherein the first anchor is coupled to a first stopper via the wire.

In some applications, the method further comprises a step of anchoring a second anchor of the second implant into the tissue at the opposite side of the opening.

In some applications, the method further comprises a step of anchoring subsequent anchors of the second implant at subsequent locations positioned at opposite sides of the tissue of the opening, following a zig-zag formation between the anchors, resulting in a double zig-zag pattern formed by the first implant and the second implant.

In some applications, the method further comprises a step of contracting the wires of the first implant and the second implant, thereby approximating the anchors of both implants and contracting the opening they are anchored to. In some applications, the method further comprises a step of locking the first and the second implants in the contracted state.

According to some applications, the opening is the LAA ostium.

According to some applications, the method further comprises a step of advancing a cutting and locking assembly, comprising a locker and attached to a cinching catheter of a cinching system, over the wires of both the first implant and the second implant inserted thereinto and extending therethrough, and toward the anchors of the implants.

According to some applications, the step of contracting the wire of both implants comprises pulling portions of the wires extending through the cutting and locking assembly and the cinching catheter.

According to some applications, the step of locking is achieved by utilizing the locker through which the wires of both implants extend.

According to some applications, the method further comprises a step of utilizing the cutting and locking assembly to cut the wire portions of both implants extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to both implants.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing an implant comprising a plurality of anchors and a wire extending through the plurality of anchors, toward an opening within a patient's body. The method further comprises a step of anchoring a first anchor of the plurality of anchors into bordering tissue of the opening, wherein the first anchor is coupled to a terminal clamp via the wire. The method further comprises a step of anchoring a second anchor of the plurality of anchors into tissue at an opposite side of the opening.

In some applications, the method further comprises a step of anchoring subsequent anchors at subsequent locations positioned at opposite sides of the tissue of the opening, following a zig-zag formation between the anchors.

According to some applications, the method further comprises a step of approximate a section of the wire extending from a final anchor of the plurality of anchors to the terminal clamp, and push this wire section against a spring-biased gate of the terminal clamp, thereby inserting it into an internal opening defined by the terminal clamp.

According to some applications, the method further comprises a step of contracting the wire, thereby approximating the anchors and contracting the opening they are anchored to. The method further comprises a step of locking the implant in the contracted state.

According to some applications, the opening is the LAA ostium.

According to some applications, the terminal clamp is larger than an eyelet of the first anchor, so as to prevent it from passing through the eyelet.

According to some applications, the method further comprises a step of advancing a cutting and locking assembly, comprising a locker and attached to a cinching catheter of a cinching system, over the wire inserted thereinto and extending therethrough, and toward the terminal clamp.

According to some applications, the step of contracting the wire comprises pulling a portion of the wire extending through the cutting and locking assembly and the cinching catheter.

According to some applications, the step of locking is achieved by utilizing the locker through which the wire extends.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further a step of disconnecting the locker from the cutting and locking assembly, and retrieving the cutting and locking assembly and the cinching catheter from patient's body, leaving the locker attached to implant.

The above method(s) can be performed on a living animal or on a simulation, such as on a cadaver, cadaver heart, simulator (e.g., with the body parts, heart, tissue, etc. being simulated), etc.

According to another aspect of the disclosure, there is provided a method comprising a step of advancing a tissue engaging portion of the helical advancement device, retained within a delivery catheter, toward an opening of a cavity within a patient's body. The method further comprises a step of advancing the tissue engaging portion distally from delivery catheter, thereby allowing it to expand radially outward therefrom.

According to some applications, the method further comprises a step of rotating and advancing the tissue engaging portion via a driving shaft attached thereto, in the distal direction, thereby driving the tissue engaging portion into the internal wall of the cavity.

According to some applications, the method further comprises a step of further driving the tissue engaging portion in a helical form along the length of the internal wall, until a distal tip of the tissue engaging portion penetrates a tissue in the vicinity of a distal inner wall, thereby anchoring a stopper positioned at the distal tip thereto.

According to some applications, the method further comprises a step of rotating and retracting driving shaft in the proximal direction, so as to extract the tissue engaging portion from the internal wall, thereby exposing a wire retained in a lumen of the tissue engaging portion, the wire attached to the stopper and thus is configured to remain anchored in a helical form within the internal wall.

According to some applications, the method further comprises a step of contracting the wire. According to some applications, the method further comprises a step of locking the wire in a contracted state.

According to some applications, the opening is the LAA ostium, and wherein the cavity is the LAA cavity.

According to some applications, the step of advancing toward the opening, comprises further advancing into the cavity.

According to some applications, the stopper has a distal sharp edge and a proximal blunt edge.

According to some applications, the method further comprises a step of re-inserting the tissue engaging portion into the delivery catheter, and retraction thereof, prior to the step of contracting the wire.

According to some applications, the method further comprises a step of advancing a cutting and locking assembly, comprising a locker and attached to a cinching catheter of a cinching system, over the wire inserted thereinto and extending therethrough, and toward the opening.

According to some applications, the step of contracting the wire comprises pulling a portion of the wire extending through the cutting and locking assembly and the cinching catheter.

According to some applications, the step of locking is achieved by utilizing the locker through which the wire extends.

According to some applications, the method further comprises a step of utilizing the cutting and locking assembly to cut the first wire portion extending proximally from the locker.

According to some applications, the step of cutting is performed after the step of locking.

According to some applications, the step of cutting is performed simultaneously with the step of locking.

According to some applications, the method further comprises a step of disconnecting the locker from the cutting and locking assembly, and retrieving the cutting and locking assembly and the cinching catheter from patient's body, leaving the locker attached to wire extending through the internal wall of the cavity.

There is provided, in accordance with some applications, a method for use at a heart of a subject, the method including transluminally advancing a distal end of an internal catheter to the heart of the subject. In some applications, while the internal catheter extends through a lumen of an outer catheter, both (i) a first end of a tether of an implant, and (ii) a second end of the tether of the implant remain disposed outside of the subject.

In some applications, the tether extends distally from the first end of the tether, and into and through the internal catheter, thereby defining a first portion of the tether; out of a distal end of the internal catheter, looping about the distal end of the internal catheter, thereby defining a bight of the tether; and proximally from the distal end of the internal catheter, alongside the internal catheter, thereby defining a second portion of the tether, the second portion of the tether terminating at the second end of the tether.

For some applications, the method further includes subsequently sliding a plurality of anchors distally over and along the first portion of the tether, via the internal catheter, to the distal end of the internal catheter; and securing the bight of the tether to the tissue by anchoring the plurality of anchors to the tissue of the heart.

For some applications, the method further includes subsequently retracting the internal catheter from the outer catheter and the subject, such that the first portion of the tether and the second portion of the tether are disposed side-by-side within the lumen of the outer catheter.

For some applications, the method further includes subsequently, outside of the subject, slidably coupling the first end of the tether to the second end of the tether such that the tether forms a closed loop that extends, from outside of the subject, through the lumen of the outer catheter, to plurality of anchors anchored to the tissue, and back through the lumen of the outer catheter to outside of the subject.

For some applications, the method further includes subsequently sliding the slidable coupling distally through the outer catheter and out of the distal end of the outer catheter, such that the closed loop becomes reduced in size and disposed, within the heart, entirely outside of the distal end of the outer catheter.

In some applications, transluminally advancing the distal end of the internal catheter includes transluminally advancing the distal end of the internal catheter to the heart of the subject, while the second portion of the tether extends proximally from the distal end of the internal catheter, into and through an inner space defined between an inner wall of the outer catheter and an outer wall of the internal catheter.

In some applications, for each tissue anchor of the plurality of tissue anchors, the tissue anchor includes a helical tissue-engaging element, and securing the bight of the tether to the tissue includes screwing the helical tissue-engaging element of each of the anchors to the tissue of the heart.

In some applications, the helical tissue-engaging element defines a helix-lumen therethrough, and sliding the plurality of anchors distally over and along the first portion of the tether includes sliding the plurality of anchors distally over and along the first portion while the tether extends through the helix-lumen.

In some applications, securing the bight of the tether to the tissue by anchoring the plurality of anchors to the tissue of the heart includes anchoring the plurality of anchors to the tissue by rotating the helix in a manner in which (i) the helix becomes anchored into the tissue and (ii) the tether exits the helix-lumen.

In some applications, the method further includes, for each anchor of the plurality of anchors, threading an eyelet of the anchor over the first end of the tether, and, for each anchor of the plurality of anchors, sliding the anchor distally over and along the first portion of the tether includes sliding the anchor distally over and along the first portion of the tether while the eyelet of the anchor remains threaded onto the tether.

In some applications, transluminally advancing the distal end of the internal catheter to the heart of the subject includes transluminally advancing the distal end of the internal catheter to the heart of the subject while an end-portion retainer is disposed at the second end of the tether, and slidably coupling the first end of the tether to the second end of the tether includes slidably coupling the first end of the tether to the end-portion retainer.

In some applications, the end-portion retainer includes an end-loop defined by the second end of the tether, and slidably coupling the first end of the tether to the second end of the tether includes threading the first end through the end-loop.

In some applications, sliding the slidable coupling distally through the outer catheter and out of the distal end of the outer catheter includes sliding the end-loop along the first portion of the wire.

In some applications, sliding the slidable coupling distally through the outer catheter and out of the distal end of the outer catheter includes pulling the first end proximally.

There is provided, in accordance with some applications, a system for use at an annulus of a heart valve of a heart of a subject, the system including a delivery assembly including an outer catheter configured for transluminal advancement towards the heart of the subject, the outer catheter defining a lumen extending therethrough. The delivery assembly can also include an internal catheter configured for extension through the lumen of the outer catheter, the internal catheter defining a lumen extending therethrough. In some applications, the system and/or delivery assembly includes an anchor driver.

In some applications, the system includes a tether having a first end and a second end, disposed proximally from the catheter assembly. In some applications, the tether extends from the first end, distally through the internal catheter, thereby defining a first portion of the tether. In some applications, the tether extends out of a distal end of the internal catheter and loops about the distal end of the internal catheter, thereby defining a bight of the tether. In some applications, the tether extends, from the distal end of the catheter, proximally alongside the internal catheter, thereby defining a second portion of the tether. In some applications, the second portion of the tether terminates at the second end of the tether. In some application, the tether has an end-portion retainer at the second end of the tether.

In some applications, the system includes a plurality of anchors.

In some applications, the delivery assembly is configured to advance the bight of the tether to the annulus, such that both the first end and the second end are disposed outside of the subject, and, while both the first end and the second end remain outside of the subject, to anchor the bight around the annulus. Anchoring the bight to the annulus can be done by, using the anchor driver, for each anchor of the plurality: advancing the anchor, threaded on the tether, distally through the internal catheter over and along the first portion of the tether, towards the annulus, and driving the anchor, threaded on the tether, into tissue of the annulus.

For some applications, the end-portion retainer is configured to slidably couple the second end of the tether to the first end of the tether while the bight remains anchored around the annulus, and the delivery assembly is configured to facilitate distal sliding of the slidable coupling along the first portion, to the bight at the annulus, such that the tether forms a closed loop around the annulus.

In some applications, the second portion of the tether extends proximally from the distal end of the internal catheter, into and through an inner space defined between an inner wall of the outer catheter and an outer wall of the internal catheter.

In some applications, each tissue anchor of the plurality includes a tissue-engaging element. The tissue-engaging element can be the same as or similar to any of the tissue-engaging elements described herein. In some applications, each tissue anchor of the plurality includes a helical tissue-engaging element or tissue-engaging element that includes a helical shape.

In some applications, each anchor of the plurality has a proximal portion that defines an eyelet for receiving the tether therethrough.

In some applications the end-portion retainer includes an end-loop defined by the second end of the tether, and the first end is insertable through the end-loop.

In some applications, the end-loop is slidable along the first portion of the wire.

In some applications, the internal catheter defines a lateral slit extending proximally from the distal end of the internal catheter, and the lateral slit is shaped to allow the tether, but not the anchors, to exit the internal catheter laterally.

In some applications, the internal catheter is retractable from the outer catheter, subsequently to anchoring the bight to the annulus, and prior to distal sliding of the slidable coupling along the first portion.

The above method(s) can be performed on a living animal or on a simulation, such as on a cadaver, cadaver heart, simulator (e.g., with the body parts, heart, tissue, etc. being simulated), etc.

Certain applications of the present disclosure may include some, all, or none of the above advantages. Further advantages may be readily apparent to those skilled in the art from the figures, descriptions, and claims included herein. Aspects and applications of the disclosure are further described in the specification herein below and in the appended claims.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

The following applications and aspects thereof are described and illustrated in conjunction with systems, tools and methods which are meant to be exemplary and illustrative, but not limiting in scope. In various applications, one or more of the above-described problems have been reduced or eliminated, while other applications are directed to other advantages or improvements.

BRIEF DESCRIPTION OF THE FIGURES

Some applications of the disclosure are described herein with reference to the accompanying figures. The description, together with the figures, makes apparent to a person having ordinary skill in the art how some applications may be practiced. The figures are for the purpose of illustrative description and no attempt is made to show structural details of an application in more detail than is necessary for a fundamental understanding of the disclosure. For the sake of clarity, some objects depicted in the figures are not to scale.

In the Figures.

DETAILED DESCRIPTION

Figure 1:
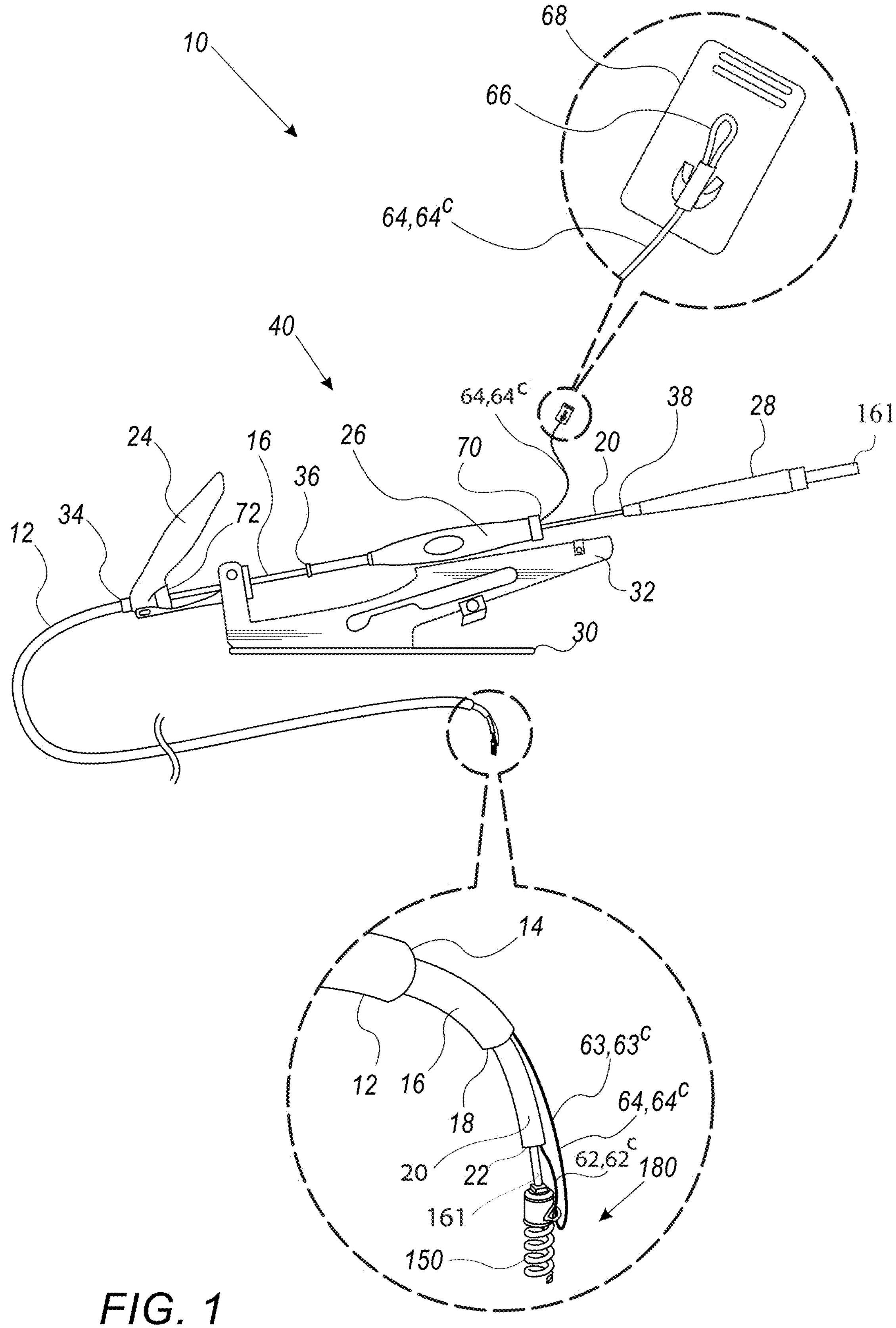
FIG. 1 is a schematic illustration of a multicomponent tubular system providing one or more steerable catheters configured for delivering an implant to a heart of a subject, according to some applications.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Throughout the figures of the drawings, different superscripts for the same reference numerals are used to denote different examples of the same elements. Applications of the disclosed devices and systems can include any combination of different implementations of the same elements. Specifically, any reference to an element without a superscript may refer to another example of the same type of element denoted with a superscript. In order to avoid undue clutter from having too many reference numbers and lead lines on a particular drawing, some components will be introduced via one or more drawings and not explicitly identified in every subsequent drawing that contains that component.

Figure 6A:
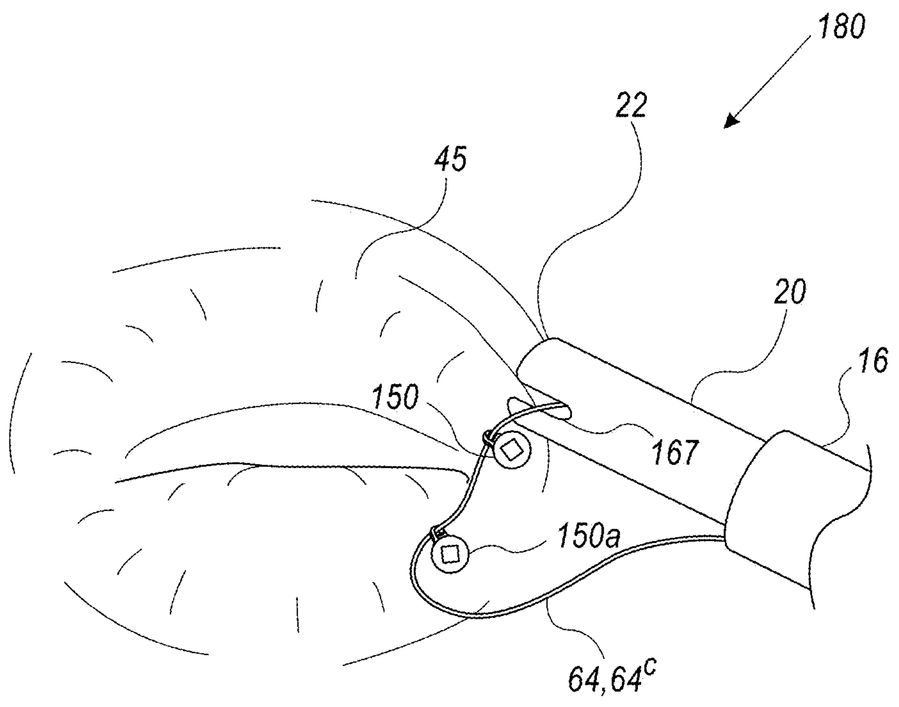
FIGS. 6A-6B are schematic illustrations of example steps of a procedure for anchoring an implant, according to some applications.
Figure 6B:
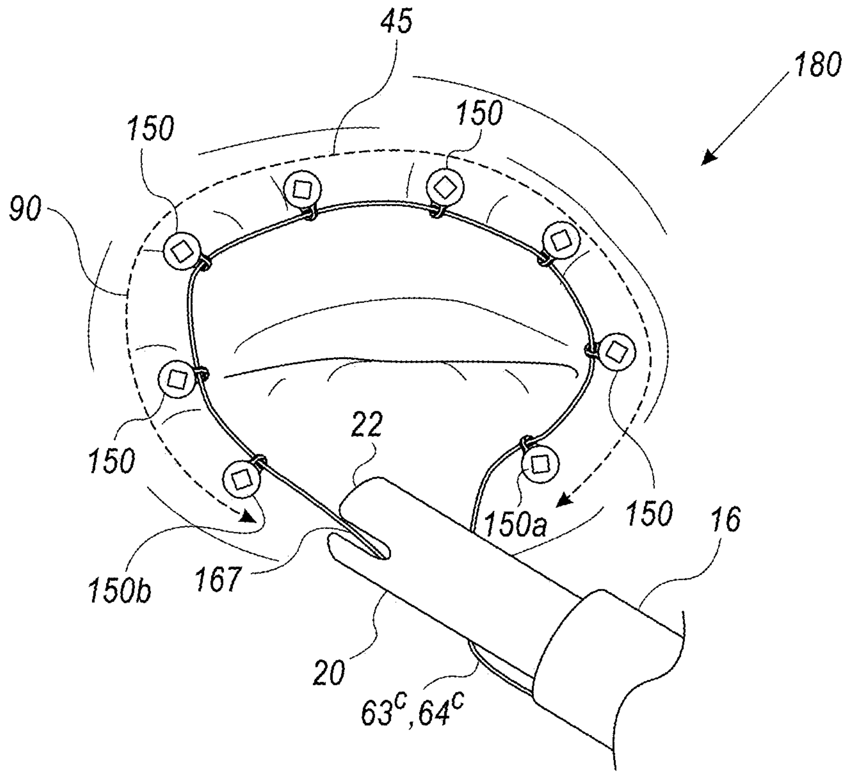

The present disclosure relates to, among other ideas, methods and systems of performing an annuloplasty procedure on a heart of a subject. Some methods comprise using a transluminal (e.g., transfemoral) approach to advance a catheter to the heart of the subject, and implanting a plurality of anchors around an annulus of a valve of the heart, e.g., as is shown in FIGS. 6A-B. The anchors can be threaded onto a wire prior to their advancement, such that implanting the anchors around the annulus disposes a bight of the wire around the annulus (e.g., as shown in FIGS. 6A-B), with the ends of the wire disposed outside of the heart, e.g., outside of the subject, such as for example shown in FIGS. 7A and 8A. Subsequently, as is shown in FIG. 9A, and as will be explained hereinbelow, the ends of the wire are slidably coupled (e.g., as shown in FIGS. 7B and 8B), and the slidable coupling is then advanced towards the annulus and the bight, such that the bight is formed into a closed loop that can be tightened to contract the annulus, thus reducing valve regurgitation, e.g., as shown in FIGS. 9A-B.

In some applications, the catheter is an outer catheter, and the system further comprises an internal catheter. The anchors are implanted into tissue of the annulus while the internal catheter is disposed within a lumen of the outer catheter. As illustrated in FIG. 1, the wire can be disposed such that a first portion of the wire extends, from outside of the subject, through the internal catheter, out of the internal catheter at the annulus, and a second portion of the wire extends back through a space defined between the internal catheter and the outer catheter (i.e., in the lumen of the outer catheter, but not inside the internal catheter) and out of the subject, such that both ends of the wire are situated outside of the heart (FIG. 8A shows both ends extending proximally from out of the catheter), e.g., outside of the subject.

The anchors can be advanced to the annulus while threaded over the wire, such that each anchor is advanced over the wire within the internal catheter, towards the heart, where they are implanted around the annulus. Once the anchors have been implanted around the annulus, the wire can extend, from outside of the subject, through the internal catheter, to the heart of the subject, where it forms the bight around the annulus, and back through the space defined between the internal catheter and the outer catheter, terminating outside of the subject, at the second end of the wire.

Once the anchors are implanted in tissue of the annulus, the internal catheter may be retracted from the outer catheter and the subject, leaving the wire extending, from outside the subject, through the outer catheter, to the annulus, where it is anchored in a bight around the annulus, and back through the outer catheter and out of the subject.

In some applications, in order to facilitate reduction in valve regurgitation, the wire is then fashioned into a closed loop around the annulus, for example, by slidably coupling the ends of the wire to each other, from outside of the subject. In some applications, and as is illustrated by FIGS. 7A-B and 8A-B, in order to slidably couple the ends of the wire to each other, one end of the wire defines a slidable coupling, e.g., an end-portion retainer (e.g., an eyelet), through which the other end of the wire (henceforth referred to as the free end) is inserted into. The end-portion retainer may be an eyelet defined by the end of the wire, or any other retainer, as described more in detail hereinbelow. The wire is thus arranged into a loop that extends, from the annulus where it is anchored, through the catheter (e.g., both the first portion and the second portion extend proximally from the annulus, within the outer catheter), and outside of the patient, where the two ends of the wire are secured in the loop at the end-retainer portion (FIGS. 7B and 8B). The free end of the wire (which is secured in the end retainer portion) is then pulled proximally and/or the slidable coupling is pushed distally, reducing the size of the loop, and pulling the loop through the catheter and towards the annulus.

Subsequently to advancing the closed loop towards the annulus (FIG. 9A), by advancing the end-portion retainer over the first portion of the wire and towards the heart, the first portion of the wire extends, from the heart and the end-portion retainer, proximally through the outer catheter and out of the subject. In some applications, the wire is then tensioned, in order to reduce the size of the annulus, e.g., such that the tissue anchors move towards each other, further reducing the size of the closed loop (e.g., as shown in the transition between FIG. 9A and FIG. 9B, showing the size of the annulus being reduced). A cutting and locking assembly may be advanced over the first portion, and along the wire, towards the heart, as shown in FIG. 9B. The cutting and locking assembly can be used to cut excess wire extending away from the closed loop, such that the first portion of the wire is cut slightly proximally to the end-portion retainer. The tension within the closed loop may be maintained by a locker delivered by the cutting and locking assembly, in order to maintain the closed loop in the tensioned state.

It is to be noted that, whereas an otherwise similar system, in which two lengths of wire extend from the heart out of the subject, may require cutting of both lengths of the wire, it is hypothesized that the annuloplasty procedure described hereinabove advantageously only requires cutting of a single length of wire (i.e., requires only the cutting of the first portion of the wire, and does not require the cutting of the second portion of the wire). For example, this may facilitate the use of smaller and/or simpler tools, and/or may be easier for the operator to perform.

Systems, apparatuses, devices, implants, anchors, tethers (e.g., wires), components, etc. used herein can be the same as or similar to or substituted for, mutatis mutandis, systems, apparatuses, devices, implants, anchors, wires, components thereof, etc. described and used in International Patent Application No. PCT/IB2020/060044, which is incorporated herein by reference in its entirety for all purposes. Further, the methods described herein can be implemented using the systems, apparatuses, devices, implants, anchors, wires, components thereof, etc. described in International Patent Application No. PCT/IB2020/060044 mutatis mutandis. For example, spacers can be disposed between the anchors of the present disclosure (e.g., threaded onto the wire of the present disclosure), e.g., as described in International Patent Application No. PCT/IB2020/060044, mutatis mutandis, in order to distribute force between the anchors and/or to limit the overall contraction of the implant by preventing the anchors from moving too closely together. Such spacers can be threaded onto the tether in an alternating sequence with the anchors, such that an anchor-spacer-anchor sequence ensures adequate force-distribution along the implant, and/or inhibits excessive contraction of the implant around the annulus, by the anchors moving together.

Figure 2:
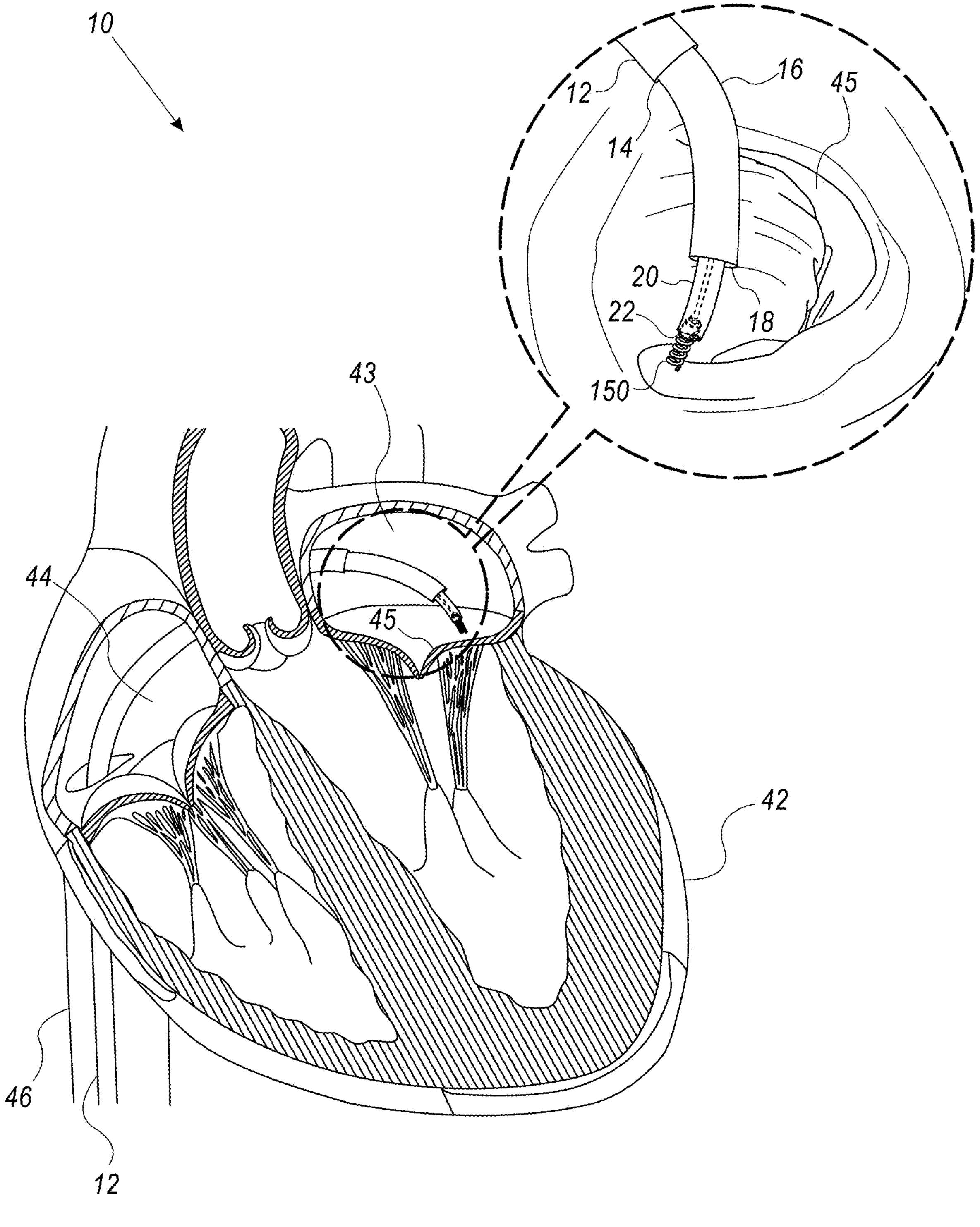
FIGS. 2, and 3A-3B are schematic illustrations of example steps in the implantation of an implant to repair a mitral valve, according to some applications.
Figure 3A:
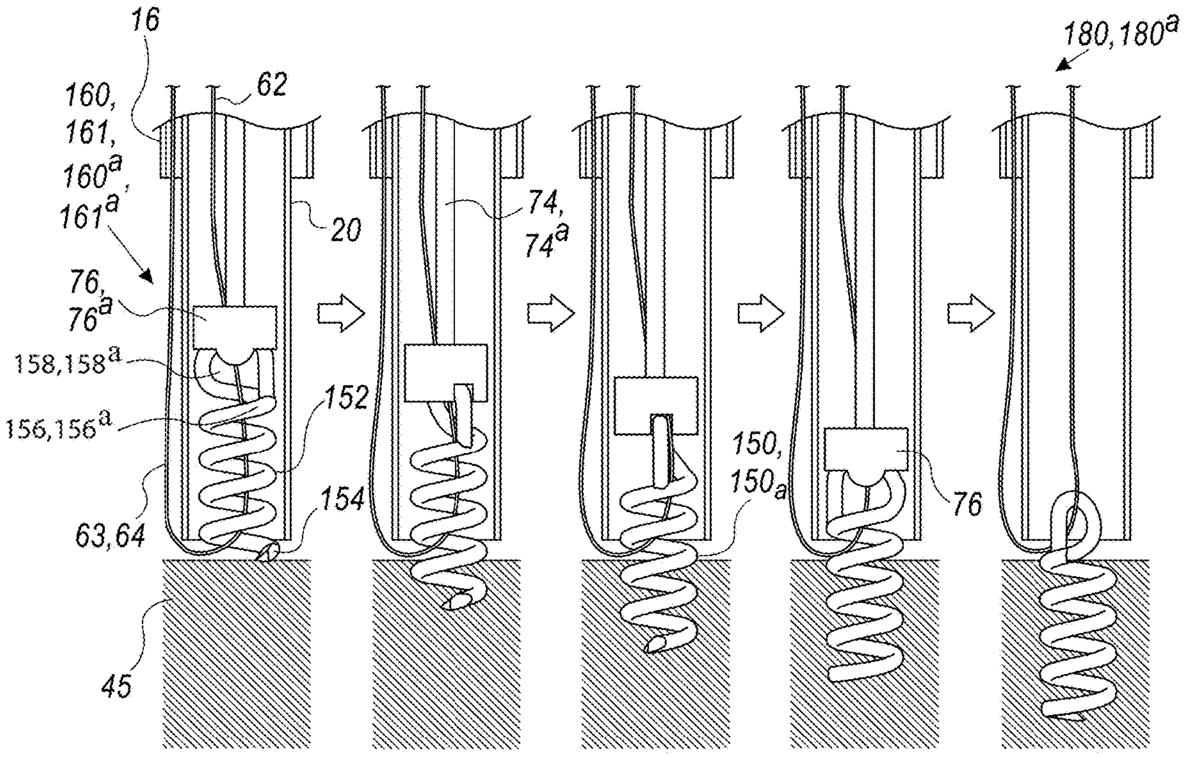
Figure 3B:
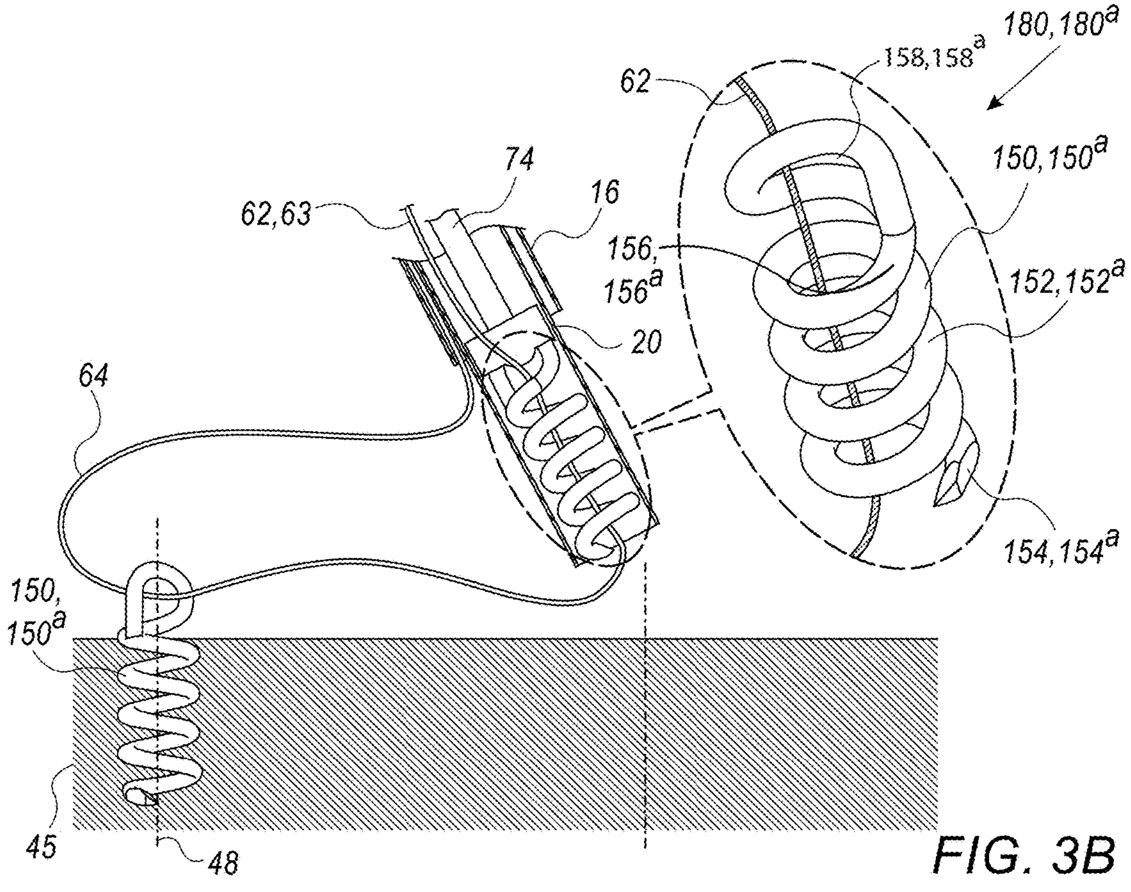

Reference is now made to FIGS. 1-3B. FIG. 1 is a schematic illustration of a multicomponent tubular system 10 providing one or more rotationally-controlled steering catheters configured for delivering an implant to a heart of a subject, according to some applications. FIGS. 2-3B are schematic illustrations of at least some steps in the use of system 10 to implant at an implant 180 to repair a native valve, such as mitral valve 45, according to some applications.

According to some applications, multicomponent tubular system 10 is configured to implant an implant in a heart of a subject. In some applications, system 10 comprises a first, outer catheter 12, configured for transluminal advancement through vasculature of a subject. According to some applications, the outer catheter 12 is configured for advancement through a femoral artery toward an interatrial septum of a heart of a subject. A distal end portion 14 of the outer catheter 12 is configured to pass through the interatrial septum of the subject, and to be oriented in a desired spatial orientation within the left atrium. According to some applications, the distal end portion 14 of the outer catheter 12 is steerable. That is, the distal end portion 14 is deflectable with respect to an immediately more proximal portion of the catheter 12 (e.g., using extracorporeal portions or elements of system 10 to deflect the distal end portion of the catheter).

According to some applications, system 10 further comprises a second catheter, or guide catheter 16, comprising a distal end portion 18 that is configured to pass through outer catheter 12 (i.e., through a primary lumen thereof), to become disposed outside of the distal end portion 14 of the outer catheter 12, and to be oriented in a desired spatial orientation within the left atrium. According to some applications, the distal end portion 18 of the guide catheter 16 is steerable. That is, the distal end portion 18 is deflectable with respect to an immediately more proximal portion of guide catheter 16 (e.g., using extracorporeal portions or elements of system 10 to deflect the distal end portion). The guide catheter 16 is steerable to a desired spatial orientation in order to facilitate advancing and implantation of an implant within a body cavity of the subject.

According to some applications, the system 10 further comprises a third catheter, or internal catheter 20, comprising a distal end portion 22 that is configured to pass through either the guide catheter 16 or the outer catheter 12 (i.e., through primary lumens thereof), to become disposed outside of either the distal end portion 14 of the outer catheter 12 or the distal end portion 18 of the guide catheter 16, and to be oriented in a desired spatial orientation within the left atrium. According to some applications, the distal end portion 22 of the internal catheter 20 is steerable. That is, the distal end portion 22 is deflectable with respect to an immediately more proximal portion of the internal catheter 20 (e.g., by using extracorporeal portions or elements of system 10). The internal catheter 20 is steerable to a desired spatial orientation for advancing and implantation of an implant in a body cavity of the subject.

According to some applications, an extracorporeal handle assembly 40 is used in order to manipulate the catheter(s) within the patient. Handle assembly 40 is supported by a support stand 30 that can include a handle-sliding track 32. The support stand 30 can be moved to control a position of the handle assembly 40, and, in some applications, the position of the entire multi-component system 10. According to some applications, the handle assembly 40 comprises at least one of an outer catheter handle 24, a guide catheter handle 26, and/or an internal catheter handle 28. Outer catheter handle 24 is coupled to an outer catheter proximal end portion 34 of outer catheter 12. Guide catheter handle 26 is coupled to a guide catheter proximal end portion 36 of guide catheter 16. Internal catheter handle 28 is coupled to an internal catheter proximal end portion 38 of internal catheter 20. According to some applications, linear and/or rotational movement of the guide catheter handle 26 with respect to the outer catheter handle 24 moves the guide catheter 16 through the outer catheter 12. According to some applications, linear and/or rotational movement of the internal catheter handle 28 with respect to the outer catheter handle 24 and/or the guide catheter handle 26 moves the internal catheter 20 through the guide catheter 16 and/or through the outer catheter 12.

According to some applications, an implantation procedure begins by advancing a semi-rigid guidewire (not shown) into a right atrium 44 of a heart 42 of the patient. The procedure can be performed with the aid of imaging, such as fluoroscopy, transesophageal echo, and/or echocardiography. The guidewire provides a guide for the subsequent advancement of the outer catheter 12 therealong and into the right atrium 44. Once distal end portion 14 of catheter 12 has entered the right atrium 44, the guidewire can be retracted from the subject's body. While in the right atrium, the system can be used to deliver an implant to the tricuspid valve and/or another portion of the right atrium.

For applications in which system 10 is used to deliver an implant 180 to the mitral valve, LAA, or other tissue in the left atrium of the patient, the outer catheter 12 can be configured for advancement through the patient's vasculature, into the right atrium 44, and the distal end portion 14 of the outer catheter 12 is then advanced into the left atrium 43. The steerable distal end portion 14 of the outer catheter 12 is then steered such that it is positioned in a desired spatial orientation within the left atrium 43. The steering procedure can be performed with the aid of imaging, such as fluoroscopy, transesophageal echo, and/or echocardiography.

According to some applications, the outer catheter 12 is advanced through the vasculature into the right atrium 44 using a suitable point of origin typically determined for a given patient. According to some applications, the outer catheter 12 is introduced into the femoral vein, through the inferior vena cava 46, into the right atrium 44 of heart 42 of the subject, and into the left atrium 43 transseptally, typically through the fossa ovalis, as shown in FIG. 2. According to some applications, the outer catheter 12 is introduced into the basilic vein, through the subclavian vein to the superior vena cava, into the right atrium 44, and into the left atrium 43 transseptally, typically through the fossa ovalis (not shown). According to some applications, the outer catheter 12 is introduced into the external jugular vein, through the subclavian vein to the superior vena cava, into the right atrium 44, and into the left atrium 43 transseptally, typically through the fossa ovalis (not shown). The outer catheter 12 is advanced distally until its distal end portion 14 reaches the interatrial septum, at which point the guidewire is withdrawn.

According to some applications, a resilient needle and a dilator (not shown) are advanced through the outer catheter 12 and into the heart 42. In order to advance the outer catheter 12 transseptally into the left atrium 43, the dilator is advanced to the interatrial septum, and the needle is pushed from within the dilator and punctures the septum to create an opening that facilitates passage of the dilator and subsequently the outer catheter 12 therethrough and into the left atrium 43.

According to some applications, following the steering of the distal end portion 14 of the outer catheter 12, the guide catheter 16 is advanced through the outer catheter 12 in order to facilitate delivery and implantation of an implant 180, for example, along an annulus of the native valve or other tissue region (e.g., an annulus of the mitral valve 45, an annulus of the tricuspid valve, an appendage, a bulge, a portion of a chamber wall, another tissue opening, etc.), or to guide the internal catheter 20 thereto, as illustrated at FIG. 2. According to some applications, the guide catheter 16 is a steerable catheter configured to guide the internal catheter 20 to the heart tissue. During the delivery of the implant, at least a portion of its steerable distal end portion 18 can be exposed from the distal end portion 14 of the outer catheter 12 and thus can be free for steering toward tissues of the heart 42, such as the annulus of the mitral valve 45, an appendage, the chamber wall, etc., as will be further described hereinbelow.

According to some applications, following the steering of the steerable distal end portion 18 of the guide catheter 16, the internal catheter 20 is advanced through the guide catheter 16 in order to facilitate delivery and implantation of implant 180 along the native tissue, e.g., along the native annulus of the mitral valve 45. During the delivery of the implant, at least a portion of the steerable distal end portion 22 of the internal catheter 20 can be exposed from the distal end portion 18 of the guide catheter 16 and thus can be free for steering toward a heart tissue, such as the annulus of the native valve (e.g., mitral valve 45, etc.) or other tissue region, as will be further described hereinbelow.

According to some applications, the system 10 is configured to advance the anchors 150 through the guide catheter 16 and/or internal catheter 20 to a target site within the heart 42 of the patient. According to some applications, the implant 180 comprises a wire 63 having a first wire portion 62 and a second wire portion 64, and a plurality of anchors 150. Although the term "wire" is used in this context, it is to be understood that the wire serves as a tether or line, and thus the terms "wire," "tether," and "line" may alternatively be used for such a component.

An anchor 150 generally includes a tissue-engaging element 152. The tissue-engaging element can be configured in a variety of ways, e.g., as or including one or more of a helical portion or helix, hook(s), barb(s), harpoon(s), needle(s), clip(s), adhesive(s), arm(s), extension(s), gripper(s), etc. In some applications, the tissue a sharpened distal tip 154, and is configured to allow a portion of the wire 63 to extend therethrough, for example through an eyelet 158 thereof.

According to some applications, implant 180$^a$ comprises wire 63 having the first wire portion 62 and the second wire portion 64, and a plurality of anchors 150$^a$ of the type illustrated in FIGS. 3A-3B and described hereinbelow.

According to some applications, each anchor 150$^a$, shown in FIGS. 3A-3B, comprises a tissue-engaging element 152$^a$ and an eyelet 158$^a$. According to some applications, tissue-engaging element 152$^a$ can be the same as or similar to other tissue-engaging elements herein. In some applications, the tissue-engaging element can have a sharpened distal tip 154$^a$, a proximal end 156$^a$, and defines a helical portion therebetween. According to some applications, the eyelet 158$^a$ is coupled to the proximal end 156$^a$ of the tissue-engaging element 152$^a$. According to some applications, the eyelet 158$^a$ spans laterally across the proximal end 156 of the tissue-engaging element 152. Optionally, tissue-engaging element 152$^a$ can be another type of a non-helical tissue-engaging element, such as a dart or a staple.

As described in more detail hereinbelow, according to some applications, anchor 150 (e.g., via eyelet 158$^a$ of an anchor 150$^a$) is configured to facilitate sliding of the anchor along a wire 63 (or sliding of the wire 63 through the anchor) while the anchor is aligned with the wire 63 or oriented orthogonally thereto.

According to some applications, the wire 63 is inserted into the eyelet 158 prior to the insertion of the anchor 150 into the internal catheter 20. According to some applications, implant 180 comprises between 3 to 30 of anchors 150, or 5 to 25 anchors 150, 7 to 13 anchors 150, 5 to 15 anchors 150, 8 to 14 anchors 150, or 6 to 19 anchors 150. Each possibility represents a separate example.

According to some applications, the system 10 further comprises a delivery tool 160 for percutaneous (e.g., transluminal, such as transfemoral) implantation of implant 180. Tool 160$^a$ is configured for use with anchors 150$^a$ and comprises a flexible anchor driver 161$^a$ that is configured to reversibly engage eyelet 158. Driver 161$^a$ can comprise an elongate and flexible shaft 74$^a$, and a driver head 76$^a$ coupled to the distal end of the shaft 74$^a$. Driver head 76$^a$ is the component of anchor driver 161$^a$ that reversibly engages the eyelet 158$^a$. Via this engagement, the driver 161$^a$ is configured to drive tissue-engaging element 152$^a$ into a tissue of heart 42, e.g., by rotating (and distally pushing) anchor 150*a*.

The term "wire", "tether," and "line" as used herein encompasses other elongate structures that can serve a similar function, such as a line, a tether, a cable, a thread, a suture, a braid, contracting member, a ribbon, and other suitable wires in the art. The wire 63 can be formed of at least one material, selected from a metal material, synthetic polymers, natural fibers, and combinations thereof. According to some applications, the wire 63 is formed of a metal material.

At least a portion of the wire 63, such as the first wire portion 62, is disposed within a lumen of the internal catheter 20 as an anchor 150 is advanced over the first wire portion and through the lumen. Thus, once the first anchor 150*a* extends out of the internal catheter 20 and is anchored into the tissue, the first wire portion 62 remains extended through an inner lumen of the internal catheter, from the internal catheter handle 28 to the internal catheter distal end portion 22 and the anchor. The first wire portion 62 is defined as the portion of the wire extending from a proximal end of the wire, to the first anchor 150*a* of a series of anchors 150.

The second wire portion 64 is defined as the remaining portion of the wire 63, continuously extending from the first wire portion 62. In some applications, at least a section of a length of the second wire portion 64 is disposed within an internal space defined between internal catheter 20 (e.g., the outer surface of the internal catheter 20) and the guide catheter 16 (e.g., the inner surface of the guide catheter 16), as illustrated at FIGS. 3A and 3B.

According to some applications, at least a first segment of the second wire portion 64 is configured to extend through a plurality of eyelets 158 of a corresponding plurality of anchors 150, such as through eyelets 158$^a$ of corresponding anchors 150$^a$, such that it forms a bight of wire 63, disposed around the annulus. In some such applications, and as illustrated in FIGS. 3A and 3B, second wire portion 64 then extends, away from the bight and the anchors 150, proximally into the internal space defined between the internal catheter 20 and the guide catheter 16 and can extend out of the guide catheter at a proximal extracorporeal portion thereof. Optionally, the second wire portion 64 can extend out of the guide catheter handle 26, such as from a rear end 70 thereof (see FIG. 1), or through any other opening of the guide catheter handle 26.

As used herein, the term "first wire portion" refers to a portion of the wire 63 that is advanced within the lumen of internal catheter 20 in the distal direction and is defined as the portion of the wire 63 that extends into the patient's body up to the distal end portion of 22 of the internal catheter 20, or the first anchor 150*a* of a plurality of anchors 150, anchored to the tissue at the implantations site.

As used herein, the term "second wire portion" refers to a portion of the wire 63 which continuously extends, from the first wire portion 62, and can extend through at least one anchor 150, (for example, through at least one eyelet 158 thereof), and which loops around the annulus or other body cavity of the patient, and then enters a lumen of either the guide catheter 16 or the outer catheter 12, where it extends proximally alongside (but out of) the internal catheter 20, and toward a component of the handle assembly 40, preferably terminating at a proximal end that is exposed to the external environment.

As used herein, the term "distal direction" refers to the direction pointing towards the human heart of a subject having the heart procedure (e.g., the patient). As used herein, the term "proximal direction" refers to the direction pointing towards the user operating system 10 (e.g., the physician). As used herein, the term "longitudinal direction" refers to the direction pointing towards the heart tissue being treated (e.g., orthogonal to the surface of the heart tissue).

According to some applications, part of the second wire portion 64 is disposed within a space defined between the guide catheter 16 and the outer catheter 12 and extends out of the outer catheter 12 at a proximal extracorporeal portion thereof. Optionally, the second wire portion 64 can extend out of the outer catheter handle 24, such as from a rear end 72 thereof (illustrated, for example, in FIG. 8A), or through any other opening of the outer catheter handle.

Figure 7A:
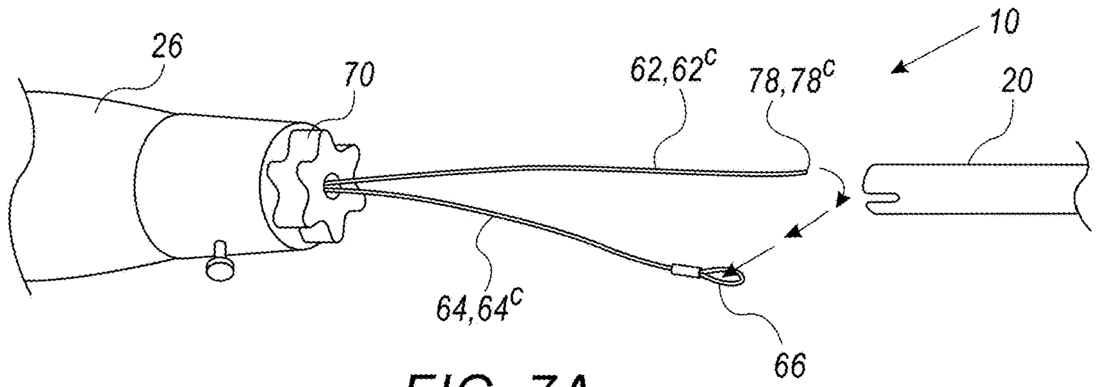
FIGS. 7A-7B are schematic illustrations of example steps performed on extracorporeal components of the system and the implant, according to some applications.
Figure 7B:
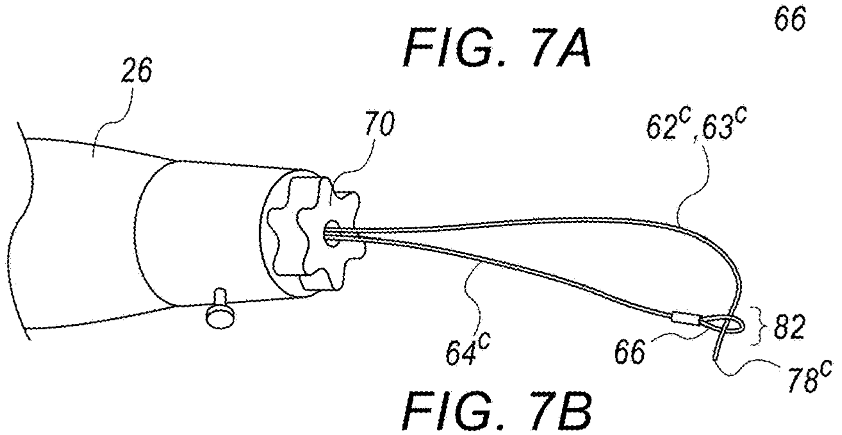
Figure 8A:
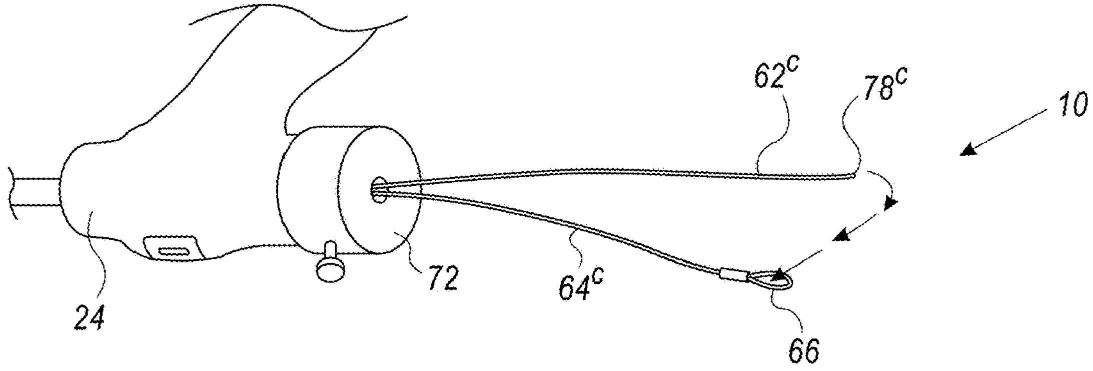
FIGS. 8A-8B are schematic illustrations of example steps performed on extracorporeal components of the system and the implant, according to some applications.
Figure 8B:
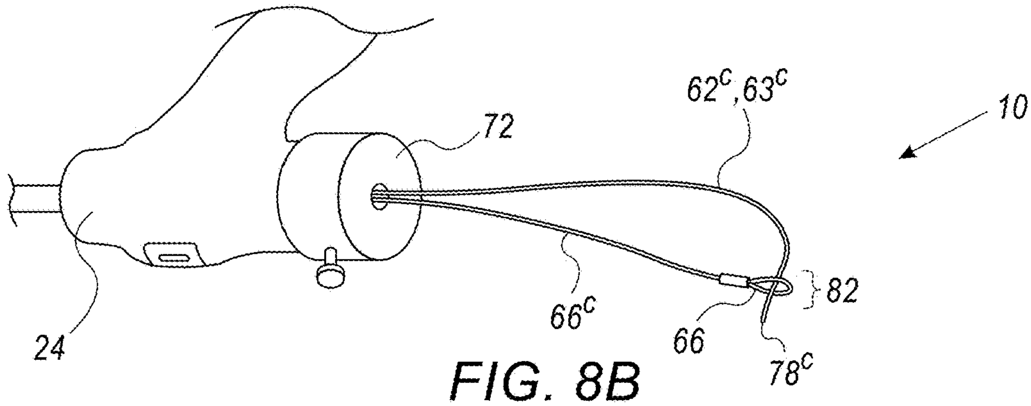
Figure 9A:
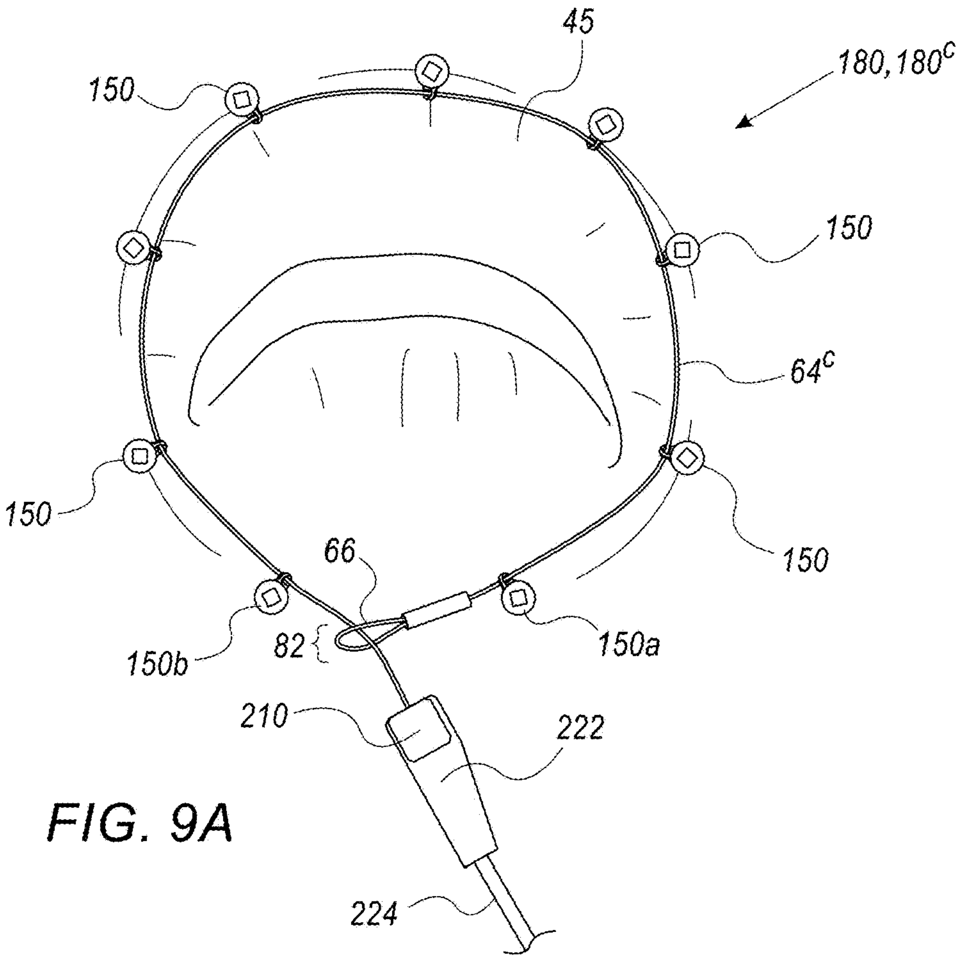
FIGS. 9A-9B are schematic illustrations of example steps of a procedure for tightening an implant equipped with a loop, according to some applications.
Figure 9B:
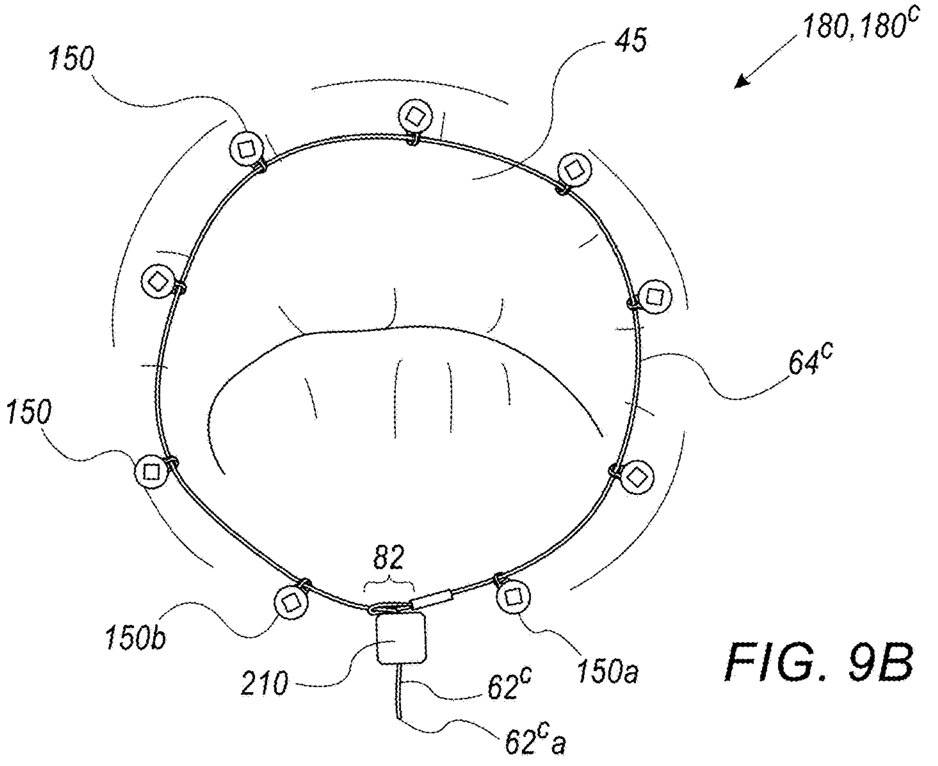

In some applications, the proximal end of second wire portion 64 can comprise a loop 66 (i.e., an end-loop), e.g., as shown in FIGS. 1, 7A-B, 8A-B, and 9A-B. In some applications, immediately following implantation of the anchors, the end-loop 66 can be located extracorporeally and is accessible to the operator. According to some applications, end-loop 66 extends out of the guide catheter handle 26, such as from a rear end 70 thereof, such that the end-loop 66 is exposed and accessible to an operator of the system 10, e.g., as shown in FIGS. 7A-B. Since the size of end-loop 66 may be small relative to an operator's hand, making it difficult to directly grab and manipulate it, the end-loop 66 can be optionally, but not necessarily, releasably coupled to a clip 68 shaped and dimensioned so as to provide the operator with adequate handling (e.g., manual grasping or clutching) of the end-loop 66.

According to some applications, during the delivery of implant 180$^a$, and more specifically, during delivery and anchoring of the anchors 150$^a$ into the tissue of the annulus, anchor driver 161$^a$ reversibly engages eyelets 158$^a$ in succession, while first wire portion 62 extends longitudinally through a lumen of internal catheter 20 such that anchors 150$^a$ are freely slidable along the wire 63 (e.g., as shown in the first left frame of FIG. 3A, and in FIG. 3B). As used herein, the term "longitudinally" refers to generally being parallel with a central longitudinal axis 48 of anchor 150, such as shown for anchor 150$^a$ in FIG. 3B. Although anchor 150$^a$ is described hereinabove as facilitating smooth sliding while the wire 63 is straight and parallel with axis 48, it is to be understood that this is an idealized representation of the wire's orientation, and that in actual use the wire may not be perfectly straight or parallel with axis 48.

According to some applications, during the delivery of implant 180$^a$, rotation of the tissue-engaging element 152$^a$ draws first wire portion 62 proximally along the helical portion of tissue-engaging element 152$^a$ until the wire 63 eventually proximally exits the helical tissue-engaging element and is left threaded through eyelet 158$^a$ of anchor 150$^a$. This is illustrated in FIG. 3A, in which delivery tool 160$^a$ is anchoring anchor 150$^a$ to a tissue of the patient's heart 42, such as a tissue surrounding the annulus of the mitral valve 45 or another valve. By anchoring anchor 150$^a$, tool 160$^a$ transitions the system and/or implant from the delivery state into an implanted state, by rotating the anchor 150$^a$ such that tissue-engaging element 152$^a$ becomes driven into the tissue, and such that wire 63 extends laterally through eyelet 158$^a$ of anchor 150$^a$. As used herein, the term "laterally" refers to generally orthogonal to the central longitudinal axis 48.

According to some applications, once the wire 63 extends laterally through eyelet 158$^a$, the wire 63 can slide smoothly through the eyelet 158$^a$ while being oriented vertically along axis 48. This configuration can be useful for applications in which the wire 63 is tensioned in order to adjust anatomical dimensions, such as during an annuloplasty procedure.

According to some applications, a plurality of anchors 150$^a$ are anchored/implanted at the heart tissue utilizing delivery tool 160$^a$ as described hereinabove. Each anchor 150$^a$ is delivered to the tissue in a delivery state in which the first wire portion 62 extends through eyelet 158$^a$ while generally parallel to axis 48, within the internal catheter 20, as shown in FIGS. 3A and 3B. As anchors 150$^a$ are subsequently anchored around the same tissue at different locations, the second wire portion 64 becomes oriented substantially parallel with the surface of the tissue to which the anchors are anchored.

Figure 4A:
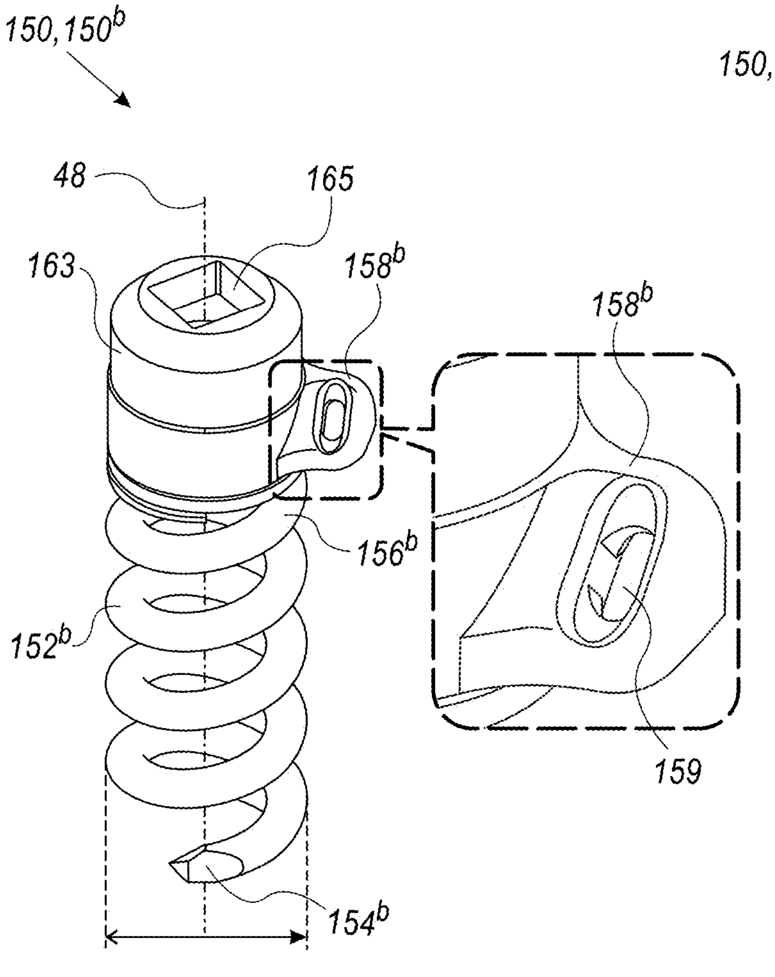
FIGS. 4A-4B and 5 are schematic illustrations of another example of a tissue anchor and an implant comprising such anchors, according to some applications.
Figure 4B:
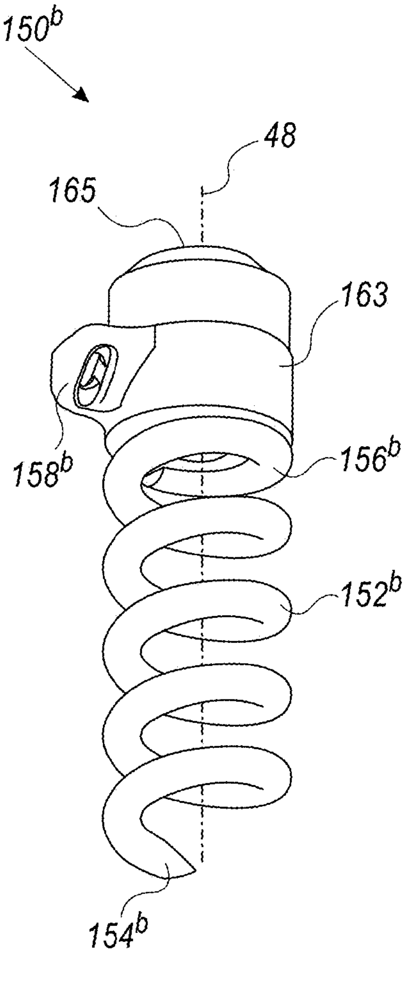
Figure 5:
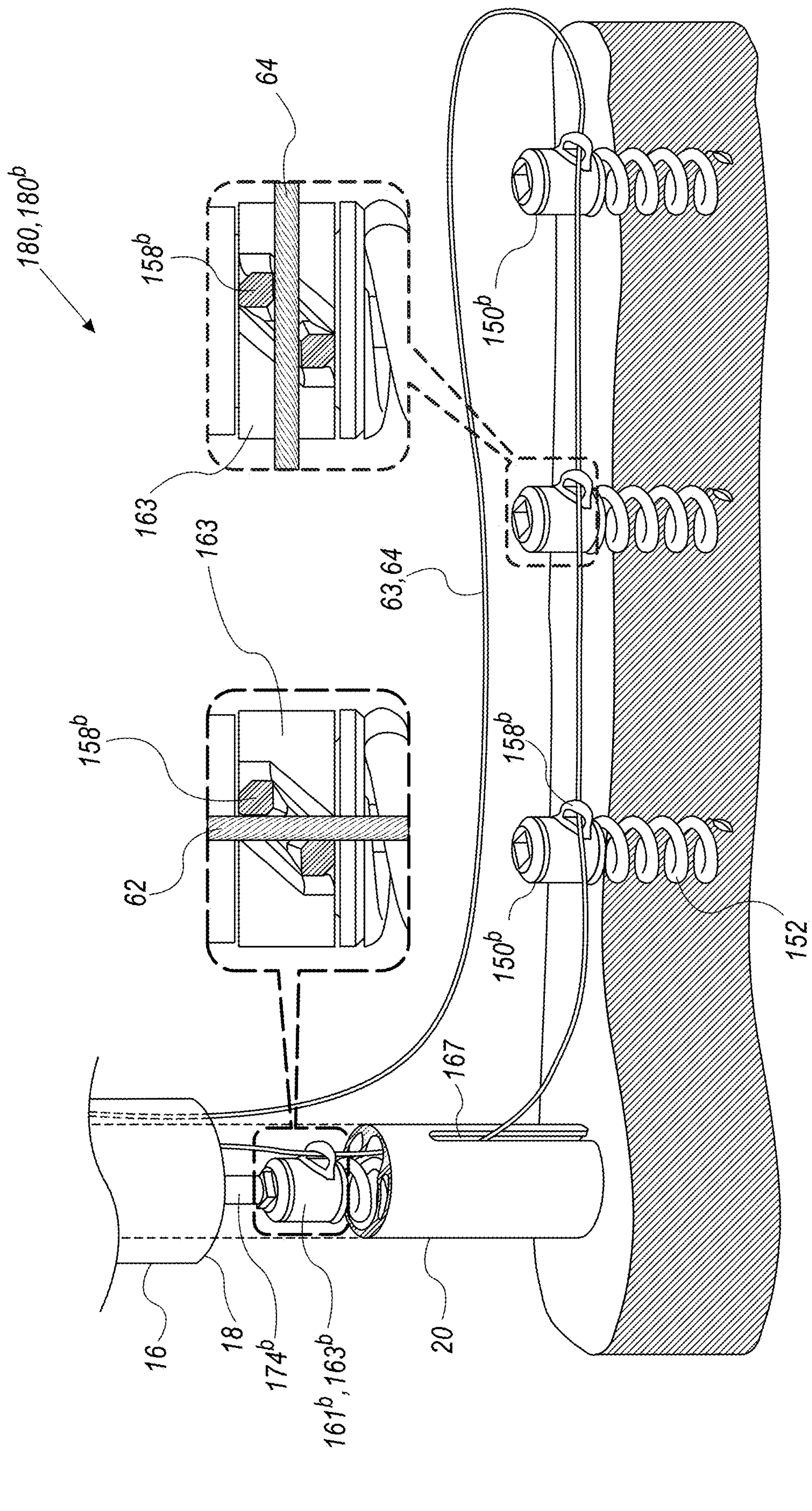

Reference is now made to FIGS. 4A-5, illustrating another type of a tissue anchor 150$^b$ and an implant 180$^b$ comprising such anchors, according to some applications. Anchor 150$^b$ comprises a tissue-engaging element 152$^b$ configured to be driven (e.g., screwed, pushed, etc.) into tissue of the subject. The tissue-engaging element can be the same as or similar to other tissue-engaging elements herein. According to some applications, the tissue-engaging element comprises a proximal end 156$^b$, a sharpened distal tip 154$^b$, and defines a helical portion therebetween, similar to anchor 150$^a$. Optionally, tissue-engaging element 152$^b$ can be another type of a non-helical tissue-engaging element, such as a dart or a staple, and/or the tissue-engaging element 152$^b$ can be configured in a variety of ways, e.g., as a curved tissue-engaging element, as a straight tissue-engaging element, as a barbed tissue-engaging element, a combination of these, etc.

Anchor 150$^b$ further comprises an anchor head 163 coupled to proximal end 156$^b$, wherein anchor head 163 comprises eyelet 158$^b$ and an anchor head interface 165. Anchor head interface 165 is configured to be reversibly engaged by an anchor driver 161$^b$.

In some applications, driver 1616 comprises an elongate and flexible shaft 174$^b$ comprising a distal end of the shaft configured to be reversibly engaged with anchor head interface 165, as illustrated in FIG. 5. Anchor head interface 165 can be rigidly coupled to tissue-engaging element 152$^b$.

According to some applications, anchor head interface 165 is disposed on a proximal top surface of anchor head 163 extending through central longitudinal axis 48, and eyelet 158$^b$ is disposed on a side surface of anchor head 163 extending laterally from axis 48.

According to some applications, anchor 150$^b$ is configured to facilitate sliding of the anchor along the wire 63 (or sliding of the wire 63 through the anchor) while the anchor 150$^b$ is aligned with the wire 63—e.g., while axis 48 is parallel with the wire 63, similarly to anchor 150*a*. As also described in more detail hereinbelow, anchor 150$^b$ is configured to facilitate sliding of the anchor 150$^b$ along the wire 63 (or sliding of the wire 63 through the anchor 150$^b$) while the anchor 150$^b$ is oriented orthogonal to the wire 63, i.e., while axis 48 is orthogonal to the wire 63. This is achieved at least partly due to the shape and dimensions of eyelet 158.

According to some applications, eyelet 158$^b$ defines an aperture 159 and is mounted on anchor head 163 such that the eyelet 1580 and the aperture 159 are slanted at a fixed angle with respect to axis 48 relative to the side surface of anchor head 163.

According to some applications, aperture 159 is shaped as an ellipse (e.g., a noncircular ellipse). According to some applications, eyelet 158$^b$ is shaped to define a first clear straight pathway through aperture 159 along a first line that is parallel to axis 48 (e.g., as shown in FIG. 5 left magnification), and to define a second clear straight pathway through the aperture along a second line that is orthogonal to the first line (e.g., as shown in FIG. 5 right magnification). It is contemplated that the elliptic shape of aperture 159 advantageously allows sliding of the eyelet 158$^b$ along a wire in either of these mutually-orthogonal orientations. It is noted that these pathways are not discrete, and the shape of eyelet 1580 similarly facilitates its sliding along a wire when in an orientation that is partway between these mutually-orthogonal orientations. However, it is to be understood that aperture 159 can be shaped as a circle, square, rectangle, or have any other suitable shape thereof that enables smooth sliding of eyelet 1586 along a wire in either of these orientations (and typically also in a continuum of orientations therebetween).

FIG. 5 shows the delivery and implantation of implant 1806 along heart tissue, such as the annulus of the mitral valve 45 or another valve. During the delivery, at least a portion of the steerable distal end portion 22 of the internal catheter 20 is exposed from the distal end portion 18 of the guide catheter 16 and is thus free for steering toward the heart tissue, as described hereinabove. Anchor 150$^b$ can be advanced longitudinally through the lumen of the internal catheter 20, as described hereinabove. During the delivery, anchor head interface 165 of anchor 150$^b$ is configured to be reversibly engaged by an anchor driver 1616. Via this engagement, driver 161$^b$ can be configured to drive tissue-engaging element 1526 into the heart tissue, e.g., by rotating (and/or distally pushing) anchor 150$^b$.

According to some applications, a plurality of anchors 150$^b$ are anchored/implanted at the heart tissue. Each anchor 150$^b$ is delivered to the tissue in a delivery state in which the first wire portion 62 extends through aperture 159 of eyelet 1580 while generally parallel to axis 48, within the internal catheter 20, as shown in FIG. 5 left magnification. As subsequent anchors 1506 are anchored to the same tissue, the second wire portion 64 assumes a lateral orientation with respect to the anchors 150$^b$, as shown in FIG. 5 right magnification. Due to the configuration of eyelet 158', despite this reorientation of second wire portion 64 around the tissue, the wire 63 can take a direct path through aperture 159 of eyelet 1586. According to some applications, eyelet $158^b$ is mounted to be rotatable around axis 48.

According to some applications, at least a first segment of the second wire portion 64 is configured to extend through a plurality of apertures 159 of eyelets 1586 of a corresponding plurality of anchors $150^b$, and at least a second segment of the second wire portion 64 is configured to be disposed within the internal space defined between the internal catheter 20 and the guide catheter 16 as illustrated at FIG. 5.

To anchor or secure anchor $150^b$, the anchor $150^b$ is advanced out of the distal end portion 22 of the internal catheter 20 while the driver 1610 rotates anchor head interface 165 of anchor $150^b$ (and thereby tissue-engaging element $152^b$) with respect to the internal catheter 20. For some applications, it is advantageous for a distal portion near the distal end portion 22 of the internal catheter 20 to be disposed (or even pressed) against the heart tissue during anchoring of the anchor $150^b$.

For applications in which the internal catheter 20 is used to implant an implant comprising multiple anchors on wire 63, such as implant $180^b$, interference may occur between the wire 63 and the contact between the distal end portion 22 of the internal catheter 20 and the tissue. According to some applications, the internal catheter 20 comprises a lateral slit 167 extending proximally from the distal end portion 22, such that the slit 167 is continuous with a distal opening of distal end portion 22. According to some applications, the slit 167 is configured to allow the second wire portion 64, but not the anchor $150^b$, to exit internal catheter 20 laterally, proximally from the distal end portion 22 thereof. Advantageously, this configuration of distal end portion 22 of internal catheter 20 can facilitate enhanced implantation of implants such as implant $180^b$, comprising multiple anchors $150^b$ coupled to (e.g., threaded on) a wire 63.

Further details regarding implants and system that include an internal catheter, a plurality of anchors, and a wire extending therefrom, including the manner in which such implants are anchored into the tissue, are described in International Patent Application No. PCT/IB2020/060044, which is incorporated herein by reference in its entirety for all purposes.

Reference is now made to FIGS. 6A-6B which are schematic illustrations of steps of a procedure for anchoring an implant 180, according to some applications. It is to be understood that FIGS. 6A-6B are illustrated for a system used for implantation of an implant 180 comprising anchors 150, which can be either an implant $180^a$ with anchors $150^a$, or an implant $180^b$ with anchors $150^b$ (as illustrated).

Throughout the following figures, it is to be understood that any reference to implant 180 may refer to implant $180^a$ or $180^b$, and any reference to 150 may refer to anchors $150^a$ or anchors $150^b$.

According to some applications, implant 180 is configured to be implanted around the annulus of the native valve or other tissue region or opening (e.g., mitral valve 45, an LAA or other appendage, tissue bulge, etc.) so as to span across the entire circumference thereof, as illustrated at FIGS. 6A-6B. It is hypothesized that contraction of a wire that extends along the entire circumference (i.e., that completely circumscribes the entire circumference) of a native annulus or other tissue region or opening, such as the mitral valve 45, etc., may facilitate better and more homogenous size reduction compared to contraction of a similar wire that extends along only part of the circumference. According to some applications, implant 180 is configured to be implanted around the entire circumference the annulus of the mitral valve 45 or other tissue region. As used herein, the term "entire circumference" refers to a pathway extending 360° around a cavity, such as a valve annulus.

According to some applications, a plurality of anchors 150 are configured to be implanted along a path-line 90 (see FIG. 6B) that extends at least 270° around the annulus of a native valve or around another valve or tissue region. According to some applications, a plurality of anchors 150 are implanted along a path-line 90 that extends between 270° and 360° around the annulus of a native valve or around another valve or tissue region.

According to some applications, a plurality of anchors 150 are implanted along a path-line 90 that extends between 270° and 280° around the annulus of a native valve or around another tissue region, between 280° and 290° around the annulus of a native valve or around another tissue region, between 290° and 300° around the annulus of a native valve or around another tissue region, between 310° and 320° around the annulus of a native valve or around another tissue region, between 320° and 330° around the annulus of a native valve or around another tissue region, between 330° and 340° around the annulus of a native valve or around another tissue region, between 340° and 350° around the annulus of a native valve or around another tissue region, between 350° and 360° around the annulus of a native valve or around another tissue region. Each possibility represents another application. According to some applications, a plurality of anchors 150 are implanted along a path-line 90 that extends between 270° and 320° around the annulus of a native valve or around another tissue region. According to some applications, a plurality of anchors 150 are implanted along a path-line 90 that extends between 320° and 360° around the annulus of a native valve or around another tissue region.

FIG. 6A shows a distal portion of the system 10, utilized for anchoring a series of anchors 150 around the annulus of a native valve (e.g., mitral valve 45, etc.) or around another tissue region. In the transitional stage shown in FIG. 6A, a first anchor 150*a* has been anchored into the tissue, and the internal catheter 20, along with a portion of the guide catheter 16 surrounding it, are moved so as to anchor the next anchor 150 into the tissue. As shown, the first wire portion 62 extends, from the internal catheter handle 28, through the lumen of the internal catheter 20, and therefrom out through the lateral slit 167, where it transitions to the second wire portion 64, extending through the anchors 150, and looping back proximally, into the space defined between the lumen of the guide catheter 16 and the internal catheter 20.

FIG. 6B shows a final stage of anchoring, wherein all anchors 150 of implant 180 have been anchored around the annulus of the native valve or other tissue region, wherein the anchors 150 are anchored along the path-line 90 extending circumferentially from the first anchor 150*a* to the last anchor 150*b*. However, as shown, the implant 180 still fails to define a full perimeter surrounding the annulus or other tissue region, since both portions of the wire 63 still extend through the catheters of the system 10 at the region between the first and last anchors 150*a* and 150*b*, respectively. Thus, while the anchors are anchored at this final stage along the perimeter of the annulus or other tissue region, the wire 63 still does not completely circumscribe the annulus or other tissue region so as to extend around the entire circumferential perimeter.

According to some applications, there is provided a wire $63^c$ comprising a first wire portion $62^c$ and a second wire portion $64^c$, wherein the second wire portion $64^c$ comprises a wire loop 66 at an end thereof (see FIG. 1), which can be extracorporeally disposed, and accessible to an operator of the system 10, at the beginning of the implantation procedure.

Reference is now made to FIGS. 7A-7B, which are schematic illustrations of some steps in a procedure for extending the wire 63, and in particular, wire 63$^c$ that includes loop 66, around the entire circumferential perimeter surrounding the annulus or other tissue region, according to some applications. In particular, FIGS. 7A-7B are schematic illustrations of steps performed on extracorporeal components of the system 10 and the implant 180$^c$. Once all of the anchors 150 are implanted along a path-line 90 around the annulus of a native valve or around another tissue region, as illustrated in FIG. 6B, the internal catheter 20 is retracted/extracted from the patient's body, which can include detachment of the internal catheter handle 28 from the guide catheter handle 26, and pulling the internal catheter 20 through the guide catheter, and potentially through the guide catheter handle, thereby removing it from the system 10 as it is no longer required for the following steps of the procedure.

In some implementations, the proximal section of the first wire portion 62 can initially be wound around a drum (e.g., a spool) positioned within the internal catheter handle 28. For such implementations, while or after decoupling the internal catheter handle 28 from the handle assembly 40, and/or pulling away the internal catheter 20, the first wire portion 62 can be unwound from the drum, and pulled out of the internal catheter handle 28, as well as out of the distal end of the internal catheter 20, so as to expose the proximal free end 78 of the first wire portion 62, as shown in FIG. 7A.

Once the internal catheter 20 and the internal catheter handle 28 are removed from the system 10, both ends of the wire 63$^c$, namely the free end 78$^c$ of the first wire portion 62$^c$, and the loop 66 of the second wire portion 64$^c$, can extend from the guide catheter handle 26 (FIG. 7A). Although both portions of the wire 63$^c$ are shown to extend out of a rear end 70 of the guide catheter handle 26 in FIGS. 7A-7B, this is shown by way of illustration and not limitation, and the opening through which the wire 63$^c$ portions extend out of the guide catheter handle 26 can be located elsewhere in other implementations of the handle 26. If the end-loop 66 was retained within clip 68 during implantation of the anchors around the annulus or other body cavity, as shown in FIG. 1, the end-loop can be unclipped to allow an operator of the system 10 to utilize it, as will be elaborated.

Since, during implantation of the anchors, the second wire portion 64$^c$ extended along the space defined between the internal catheter 20 and the guide catheter 16, removal of the internal catheter 20 results in both portions of the wire 63$^c$ extending, side by side, along the same lumen of the guide catheter 16.

According to some applications, the end-loop 66 is sized to enable insertion of the proximal end 78$^c$ of the first wire portion 62$^c$ therethrough, and to be insertable and extendable through a lumen of a catheter of the system 10, such as the lumen of the guide catheter 16 or the lumen of the outer catheter 12.

In general, an end of the second wire portion 64, such as second wire portion 64*c*, can include an end-portion retainer 82, such as end-loop 66, defined as an end-portion of the second wire portion 64 that defines an aperture or eyelet, through which another portion of the wire 63, such as a section of the first wire portion 62, can extend. In some cases, the end-portion retainer 82 can be configured to be slidable over the section of the first wire portion 62 inserted there-into. The end-portion retainer 82 is illustrated and implemented for wire 63$^c$ as a loop formed by the wire material itself. In other implementations, the end-portion retainer can be a ring or an eyelet, attached to the end of the second wire portion 64, and used in the same manner described throughout the current specification for end-loop 66.

According to some applications, in order to advance the end-portion retainer 82 (e.g., the end-loop 66) through guide catheter 16 and toward the anchors 150 of the implant 180 surrounding the annulus of a native valve (or another tissue region) the proximal end 78$^c$ of the first wire portion 62$^c$ can be pulled in the proximal direction, away from guide catheter handle 26, such that the end-portion retainer is pulled into guide catheter 16, and towards the anchors and the bight of the loop. As is shown in the transition from FIG. 9A to FIG. 9B, once the end-portion retainer 82 reaches the anchors 150, and in particular—the first implanted anchor 150*a* (FIG. 9A), wire 63 forms a closed loop around the annulus. The second wire portion 64$^c$ extending through the anchors can then be cinched to reduce the size of the valve annulus, thereby improving coaptation of the valve leaflets, as shown in FIG. 9B.

According to some applications, and as shown in FIG. 7B, the proximal end 78 of the first wire portion 62$^c$ is inserted and extended through the end-loop 66 while both ends of wire 63 are outside of the guide catheter handle 26 and the patient. The proximal end 78$^c$ can then be pulled in a proximally oriented direction through catheter 16, while the end-loop 66 is free to advance distally through the lumen of the guide catheter 16, along the length of the first wire portion 62$^c$, toward the first anchor 150*a*.

In some applications, and as illustrated in FIGS. 8A-B, prior to advancing the end-portion retainer through the catheter and towards the annulus and the anchors, both the internal catheter and, in applications in which the guide catheter was used, the guide catheter can be retrieved out of the patient's body, such that both portions of the wire extend, side by side, along the same lumen of outer catheter 12 (FIG. 8A). According to some examples, and as shown, the internal catheter 20 and the guide catheter 16 are retracted/extracted from within outer catheter 12 through a rear end 72 of outer catheter handle 24. Following said retraction of the internal catheter 20 and the guide catheter 16, at least a segment of first wire portion 62$^c$, which was disposed within the lumen of internal catheter 20, is extracted therefrom and released to the external environment, thereby exposing the proximal end 78$^c$ of first wire portion 62$^c$. According to some applications, following the retraction of the internal catheter 20 and the guide catheter 16 from the outer catheter 12, the first wire portion 62$^c$ extends from the rear end 72 of the outer catheter handle, toward the external environment, next to the end-loop 66 of the second wire portion 64$^c$, as illustrated in FIG. 8A.

The resulting configuration, as shown in FIG. 8A, includes both portions of the wire 63$^c$ extending out of the outer catheter handle 24, in contrast to FIGS. 7A-7B, which illustrate an example in which both end portions of the wire 63 extend out of the guide catheter handle. Although both portions of the wire are shown to extend out of a rear end 72 of the outer catheter handle 24, this is shown by way of illustration and not limitation, and the opening through which the wire portions extend out of the outer catheter handle 24 can be located elsewhere in other implementations of the handle 24.

According to some applications, and as shown in FIG. 8B, the proximal end 78 of the first wire portion 62$^c$ is inserted and extended through the end-loop 66 while both ends of wire 63 are outside of the outer catheter handle 24 and the patient.

According to some applications, the end-loop 66 is then advanced, over the free end 78 and the first portion 62, in a distal direction through catheter 16, until it exits the distal end portion 18 of the guide catheter 16, or the distal end 14 of the outer catheter 12, such that the end-loop 66 becomes disposed at the implantation site around the perimeter of the annulus or other tissue region, between the first and the final anchors 150*a* and 150*b*, respectively, as shown, for example, in FIG. 9A. In some applications, once the end-portion retainer 82 (e.g., end-loop 66) reaches the first anchor 150*a*, the wire extending through the anchors can be tensioned, to reduce the size of the valve annulus, thereby improving coaptation of the valve leaflets (FIG. 9B).

The end-portion retainer 82, such as the end-loop 66, can be dimensioned to be larger than an eyelet 158 of the anchors 150, (e.g., eyelet $\mathbf{158}^a$ of anchor $\mathbf{150}^a$ and/or eyelet $\mathbf{158}^b$ of anchor $\mathbf{150}^b$), so as to prevent the end-loop 66 from passing through the eyelet 158, thus ensuring that the loop is retained between the anchor 150*a* and the anchor 150*b*. Tensioning of the wire 63, as will be further elaborated hereinbelow, may cause end-portion retainer 82 to press against the first anchor 150*a*, and in particular, against eyelet 158*a*, such that the end-portion retainer 82 can provide a counter-force to the tension applied to the opposite end of the wire 63, which, in turn, will cinch the entire implant 180.

Reference is now made to FIGS. 9A-10B, which are schematic illustrations of steps of a procedure for tightening an implant 180, and more specifically, an implant $\mathbf{180}^c$, utilizing a cinching system 200, according to some applications. An implant $\mathbf{180}^c$ is defined as an implant that comprises a wire $\mathbf{63}^c$ having an end-loop 66, and a plurality of anchors 150, that can be implemented as any type of anchors, such as anchors $\mathbf{150}^a$ or $\mathbf{150}^b$.

According to some applications, there is provided a cinching system 200 comprising a cinching catheter 224 extending from a cinching handle (not shown), and a cutting and locking assembly 222 coupled to the distal end of the cinching catheter.

As is illustrated in FIG. 9A, in use, once the anchors 150 have been implanted, for example as shown in FIG. 6B, and the end-loop 66 is advanced distally either through the lumen of the guide catheter 16 or the outer catheter 12, the extracorporeal section of the first wire portion $\mathbf{62}^c$ can be inserted, into the cutting and locking assembly 222, along the cinching catheter 224, and into the handle of the cinching system (not shown). The cutting and locking assembly 222 and the cinching catheter 224 attached thereto, are then advanced toward the site of implantation, over the first wire portion $\mathbf{62}^c$. In some applications, the cutting and locking assembly 222 and the cinching catheter 224 are advanced toward the site of implantation through the lumen of the guide catheter 16 or the outer catheter 12.

The cutting and locking assembly 222 is approximated to the end-loop 66 of the second wire portion $\mathbf{64}^c$ (or any other example of an end-portion retainer 82), in the vicinity of implant $\mathbf{180}^c$, in order to perform annuloplasty or tissue reshaping. The cinching system 200 is configured to facilitate cinching of the wire 63*c*, for example by applying a proximal pull force to the first wire portion $\mathbf{62}^c$, while the end-loop 66 of the second wire portion $\mathbf{64}^c$ is pressed against the first anchor 150*a*, thereby cinching the second wire portion 64 so as to cinch the implant $\mathbf{180}^c$.

As used herein, the term "vicinity" refers to a distance within a radius of less than about 100 mm of a given three-dimensional (3D) space. According to some applications, the term "vicinity" refers to a distance within a radius of less than about 50 mm, less than about 10 mm, less than about 1 mm, or less than about 0.1 mm of a given 3D space.

The cutting and locking assembly 222 comprises a locker 210 configured to lock the wire 63 in position once it is sufficiently cinched, wherein the locker can be released therefrom, and be configured to remain attached to the implant 180 and retain it in a locked state, while the cinching system 200 can be retrieved from the patient's body after completion of the implantation procedure.

While in some implementations, merely applying a pull force on the first wire portion $\mathbf{62}^c$ can be sufficient to advance the end-loop 66 all the way toward the anchors 150, and more specifically, up to the first implant 150*a*. In some circumstances, however, this may not be enough, and additional mechanisms may be required to advance the end-loop 66 through the vasculature and toward the implantation site, such as the annulus of a mitral valve 45 or other tissue region. According to some applications, cutting and locking assembly 222 can be utilized to push against, and thereby advance end-portion retainer 82, such as the end-loop 66, for example through guide catheter 16 or outer catheter 12, to the vicinity of implant $\mathbf{180}^c$, and more specifically, to the vicinity of the first anchor 150*a*.

According to some applications, providing tension to the second wire portion $\mathbf{64}^c$ extending between anchors 150 draws the anchors closer together, thereby contracting the tissue around which the anchors 150 are anchored, in order to perform annuloplasty or tissue reshaping (FIGS. 9A and 9B). This can be facilitated by eyelets 158 providing smooth sliding of the second wire portion $\mathbf{64}^c$ therethrough, for example through apertures 159 if the anchors are implemented as anchors $\mathbf{150}^b$, while the wire is orthogonal to the anchors, as described hereinabove.

According to some applications, providing tension to the second wire portion $\mathbf{64}^c$ is performed by pulling the first wire portion $\mathbf{62}^c$ in the proximal direction, away from any respective catheter handle(s) it can extend into or from, until the wire sufficiently contracts the implant or annuloplasty structure, as described hereinabove. Locker 210 can be placed in the vicinity of the end-portion retainer 82 (e.g., in the vicinity of end-loop 66), and comprise at least one fastening mechanism configured to lock to the wire in a cinched state thereof, as shown in FIG. 9B. The cutting and locking assembly 222 can include a cutting or trimming mechanism, configured to cut the first wire portion 62 extending proximally from the locker 210, after being locked thereby. This cut may result in an excess portion of the wire 63, extending proximally from the locker 210 and terminating at a free cut end 62*a*, as shown for example in FIG. 9B.

Figure 10A:
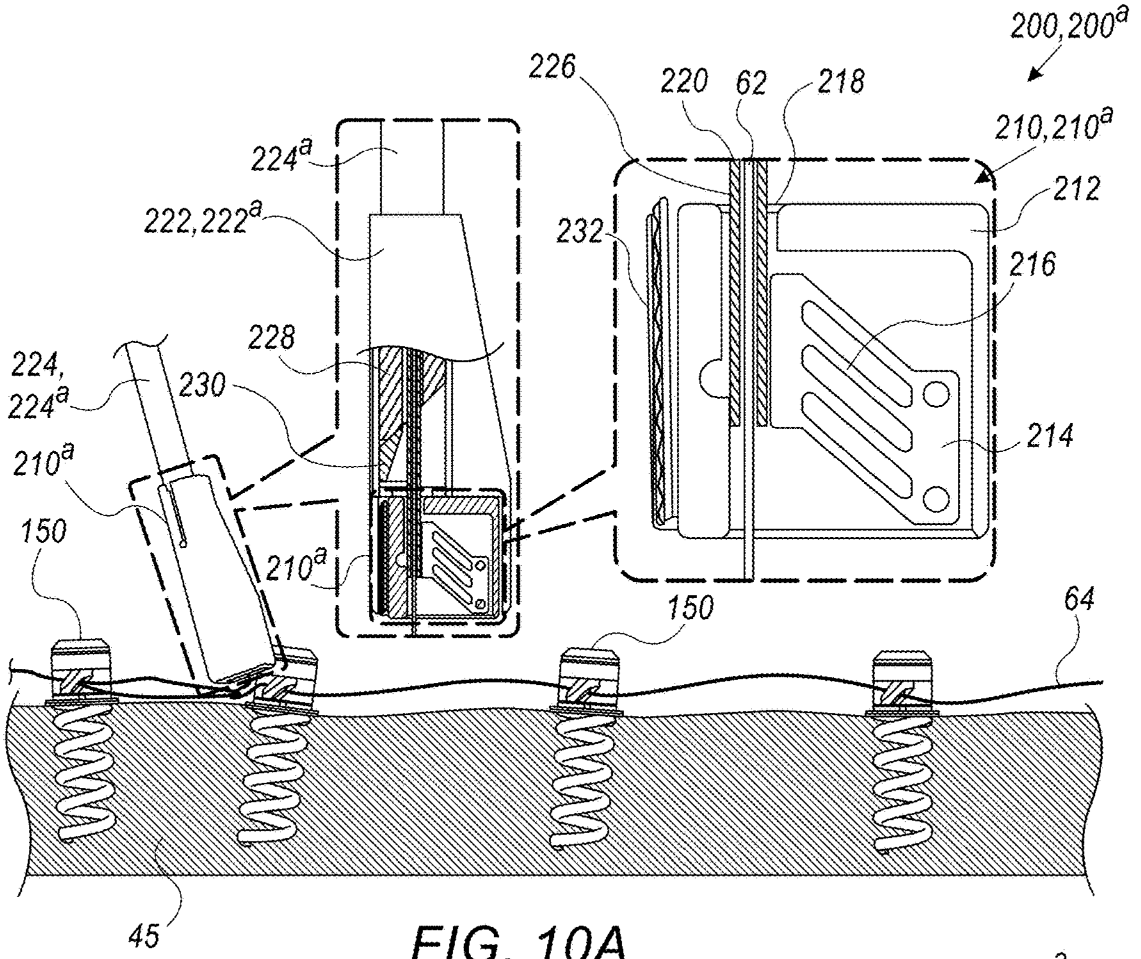
FIGS. 10A-10B show exemplary applications of an example locker comprised within a cutting and locking assembly of a cinching system, according to some applications.
Figure 10B:
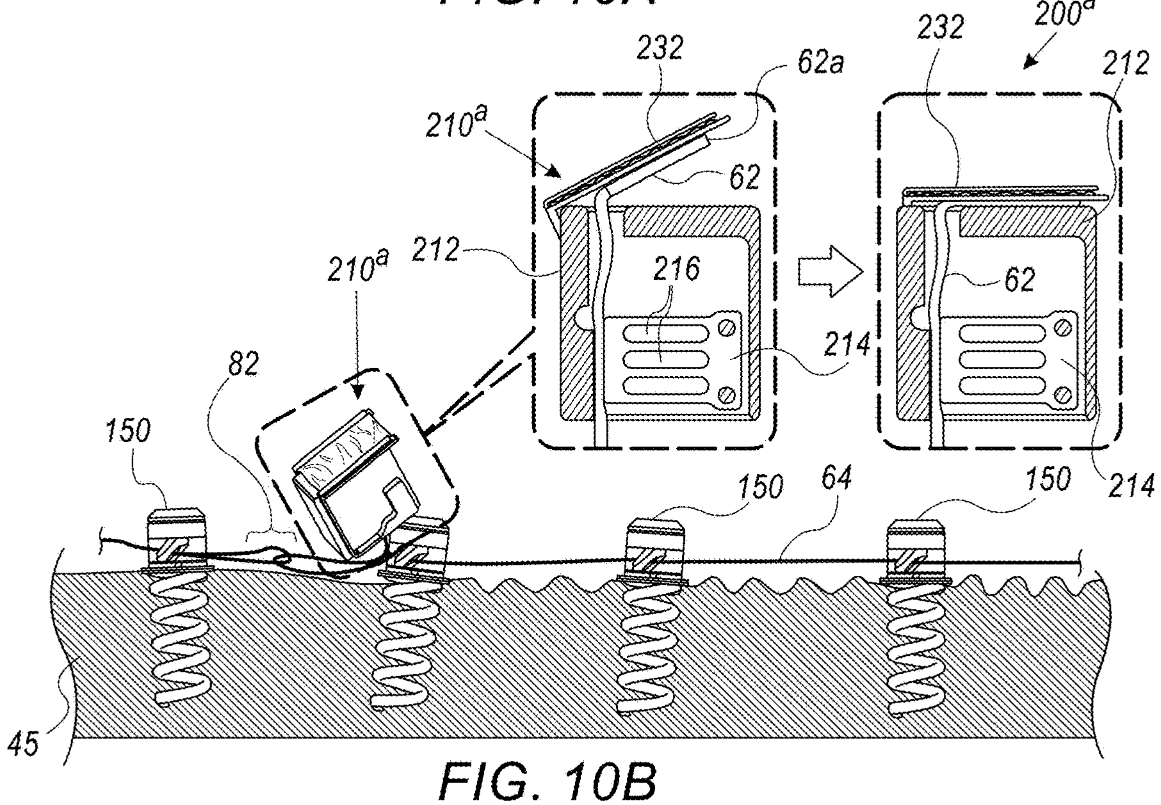

According to some applications, once the first wire portion 62 is clipped or cut following cinching of implant 180 in order to perform annuloplasty or tissue reshaping, it can be advantageous to cover any excess portions of the first wire portion 62, including the free cut end 62*a*, as illustrated at FIG. 10B. According to some applications, the locker 210 is further configured to cover an excess portion of the wire 63, that may terminate at a free cut end 62*a*. Covering of excess portions of first wire portion 62, terminating at free cut end 62*a*, prevents potential damage that may have been otherwise caused, due to exposure of the metal of first wire portion 62 to the tissue. Additionally, covering of excess portions of first wire portion 62, terminating at free cut end 62*a*, prevents additional fibrosis therearound.

FIGS. 10A-10B show examples of a locker $\mathbf{210}^a$, comprised within a cutting and locking assembly $\mathbf{222}^a$ of a cinching system $200^a$. According to some applications, locker $210^a$ comprises a housing 212 which houses a wire fastener 214 which defines the systems' locking mechanism. Fastener 214 is shaped so as to define a generally-rectangular, planar clip comprising a super-elastic material, e.g., nitinol. Fastener 214 comprises a deformable element. The deformable element can be configured in a variety of different ways and shapes. For example, the deformable element can be or comprise one or more of a bendable component, a flexible component, a disk-shaped component or disk, a flat component, an expandable component, (balloon, stent, etc.), a rectangular component, a square, a cubic component, a circular or spherical component, a semi-circular or semi-spherical component, a component with struts, a slitted component, a component with legs and/or arms, a friction-enhanced component, a component with teeth or barbs, etc. In some applications, the deformable element is shaped so as to define a plurality of slits which are surrounded by a plurality of flexible legs 216 which enable the clip to transition between slanted (FIG. 10A) and straight (FIG. 10B) states. In some applications, the wire-engaging surface of the clip is shaped to define a plurality of teeth (not shown for clarity of illustration). For some applications, the teeth are jagged. For some applications, the upper surface of the clip does not comprise teeth and is flat. The teeth are configured to increase friction between the first wire portion 62 and the fastener 214. It is to be noted that fastener 214 is used by way of illustration and not limitation and that any suitable securing means, fastener, clip, etc. can be used.

According to some applications, the fastener 214 comprises a clamping structure that can transition between an open state and a closed state. The clamping structure is naturally biased toward assuming the closed state (FIG. 10B), in which it is configured to clamp onto excess portions of the first wire portion 62 passed therethrough, including free cut end 62*a*. The clamping structure can be flexed to an open state (FIG. 10A) through which the first wire portion 62 can move. In the closed state, the fastener 214 is configured to restrict movement of the first wire portion 62 with respect to the plurality of anchors 150.

According to some applications, the first wire portion 62 extends through an opening 218 of the housing 212 and through a stop 220 (e.g., a holder) that is disposed within an opening of the housing 212 in a vicinity of wire fastener 214. The stop 220 can be shaped so as to define a lumen therethrough for surrounding the first wire portion 62. The stop 220 is engageable by a cutting and locking assembly $222^a$ which is coupled to the cinching catheter $224^a$, and removable from housing 212 via assembly $222^a$. The stop 220 is shaped so as to fit snugly within a channel extending from opening 218 such that it pushes against the wire-engaging surface of the clip and maintains the fastener 214 in a slanted state, i.e., an unlocked state of the fastener 214. In the slanted state shown in FIG. 10A, the clip is deformed and does not push against the first wire portion 62. In the slanted state, the first wire portion 62 is free to move with respect to at least one of: the cinching catheter $224^a$, the locker $210^a$, the fastener 214, the assembly $222^a$, the housing 212, and/or the stop 220, thereby enabling the first wire portion 62 to be pulled until it sufficiently contracts the implant or annuloplasty structure and the end-portion retainer 82 (e.g., loop 66) is in the vicinity of anchors 150 of implant 180.

In FIG. 10B, the stop 220 has been decoupled and removed from housing 212. In the absence of force applied to the contracting-wire-engaging surface of the clip by the stop 220, the clip returns to its resting, straight state and traps the first wire portion 62 between the contracting-wire-engaging surface of the clip and a surface 226 of housing 212, e.g., an inner wall. As such, the fastener 214 is now in a locked state in which the clip locks and crimps the first wire portion 62.

According to some applications, the proximal end 78 of the first wire portion 62 is threaded through any of: the cinching catheter 224, the locker 210, and/or the cutting and locking assembly 222, and the end-portion retainer 82 (e.g., the end-loop 66) is advanced along a lumen of the cinching catheter 224 until it reaches first anchor 150*a* of implant 180. The relative spatial orientation of the components of assembly 222 enable the first wire portion 62 to pass straightly and directly though the lumen of the cinching catheter 224 and along the longitudinal axis of the cinching catheter 224 and the assembly 222 without taking a winding path therethrough. This direct and unwinding path of the wire through the assembly 222 and the cinching catheter 224 reduces friction of the wire as it moves therethrough. This direct path for the wire 63 is enabled due to the orientation of components of the assembly 222.

In some applications, the cutting and locking assembly $222^a$ comprises a static cutting element 228 and a moveable, dynamic cutting element 230, each of the cutting elements 228 and 230 defining a cutting edge. In some applications, the cutting edge can be sharp, but this is not required. In some applications, the dynamic cutting element 230 slides proximally and diagonally with respect to the static cutting element 228. The dynamic cutting element and/or the static cutting element can be configured as one or more of a blade(s), block(s), movable block(s), disk(s), rotating component, razor(s), scissor(s), scissor-like component(s), wire cutter(s), aperture(s), etc.

In some applications, the cutting and locking assembly $222^a$ comprises stop 220 and is configured to facilitate movement of stop 220 proximally in a manner in which the stop 220 is displaced from within the housing 212 through the opening 218. Once the stop 220 is displaced from within the housing 212, the fastener 214 assumes a closed position in order to trap the wire between the clamping surface of the fastener 214 and surface 226 of the housing 212. Such displacement of the stop 220 also enables the stop 220 to push (e.g., by hammering) proximally on dynamic cutting element 230 such that dynamic cutting element 230 slides proximally diagonally along the static cutting element 228 in a manner in which elements 228 and 230 sever and cut the first wire portion 62. Thus, cutting and locking assembly $222^a$ provides a mechanism which enables simultaneous cutting and locking of the first wire portion 62, thereby locking implant 180 in a cinched configuration.

According to some applications, the locker $210^a$ further comprises a flap 232 that is disposed external to the housing 212. The flap 232 is moveable from first, open state in which the flap 232 is distanced from the housing 212, to a second, closed state in which the flap 232 is disposed alongside the housing 212 in a manner in which the flap 232 pushes the excess portions of the first wire portion 62 terminating at the free cut end 62*a*, against an external surface of housing 212, while also covering the excess portions of the first wire portion 62 and free cut end 62*a*.

Additionally, the flap 232 covers the opening 218 of housing 212. The flap 232 is coupled to housing 212 in a manner in which it swivels from the open state in which it is aligned with a first lateral wall of the housing 212, as shown in FIG. 10A, to the closed state in which it is aligned with a second lateral wall of the housing 212, as shown in FIG. 10B. In the second position, the flap 232 traps the excess portion of the wire terminating at free cut end 62$a$ between the flap 232 and the second lateral wall of the housing 212. For some applications, the locker 210$^a$ has a tendency to assume the second, closed position in the absence of force applied thereto.

It is to be understood that the cutting and locking assembly 222$^a$ and locker 210$^a$ described hereinabove with respect to FIGS. 10A-10B merely serve as one example of an assembly that may cut a wire extending therethrough, and a locker configured to lock the portion of the wire extending therethrough in a cinched state of the implant. Further details regarding cinching system, various configurations of lockers configured for locking an implant in a cinched configuration, and potentially cover any slack of a wire formed after cutting it with cutting and locking assemblies, are presented in full detail in International Patent Application No. PCT/IB2020/060044, which is incorporated herein by reference in its entirety for all purposes.

According to some applications, the cinching system 200 is configured to allow locker 210 to simultaneous perform (i) cutting and locking of first wire portion 62 extending therethrough, thereby closing and locking implant 180, and (ii) trap the excess portion of the wire therein. Optionally, but not necessarily, the cinching system 200 can also be utilized to advance end-portion retainer 82. According to some applications, following the trapping of the excess portion of the first wire portion 62 within locker 210, assembly 222 and cinching catheter 224 are disconnected therefrom, and are extracted from within the guide catheter 16 or the outer catheter 12, thereby leaving behind locker 210 attached to implant 180.

According to some applications, there is provided a method for contracting an implant anchored to a native annulus or other tissue region (e.g., an annulus of the mitral valve 45, an appendage, a bulge, a portion of a chamber wall, another tissue opening, etc.) which can comprise an initial step of: (a) providing or obtaining a multicomponent tubular system 10 configured to deliver implant 180 to the vicinity of the tissue surrounding the annulus or other tissue region. In some applications, the system 10 comprises at least one, two, or more of: an outer catheter 12, a guide catheter 16, and an internal catheter 20.

In some applications, the distal end portion 22 of internal catheter 20 is configured to pass through guide catheter 16 or outer catheter 12 (i.e., a primary lumens thereof), to become disposed outside of the distal end portion 14 of the outer catheter 12 and/or distal end portion 18 of guide catheter 16, and to be oriented in a desired spatial orientation within the vicinity of the tissue surrounding the annulus of the mitral valve 45 or other tissue region.

In some applications, the method further comprises a step of: (b) using system 10 to advance and deliver implant 180 to the tissue surrounding the native annulus or other tissue region (e.g., of the mitral valve 45 within the left atrium 43 of subject's heart 42, of another native valve, of an appendage, along a chamber wall, etc.), wherein implant 180 comprises a plurality of anchors 150 and a wire 63$^c$ comprising a first wire portion 62$^c$ which is configured to be advanced within a lumen of internal catheter 20 together with anchors 150. A second wire portion 64$^c$ can be configured to extend outside of distal end portion 22 of internal catheter 20 in a distal direction within the left atrium 43, toward anchors 150 of implant 180, and further extend therebetween, and loop back from the anchors 150 proximally towards the proximal end of the catheter. For example, it can extend through an internal space defined between an internal catheter 20 and either a guide catheter 16 or an outer catheter 12. In some applications, an extracorporeal portion of the second wire portion can be configured to extend through a respective catheter handle(s), such as through outer guide catheter handle 26 or outer catheter handle 24, and/or be exposed to the external environment (e.g., accessible for grasping by an operator's hands outside the patient).

In some applications, the method can further comprise a step of: (c) advancing a plurality of anchors 150 longitudinally through the lumen of catheter 20, and driving/anchoring them in succession into the tissues surrounding the perimeter of the annulus or other tissue region. This can be done by reversibly engaging each anchor of the plurality of anchors with an anchor driver 161 as described herein above. Each anchor 150 is driven into a different location around the perimeter of the annulus of the mitral valve 45 or other tissue region while it is coupled to second wire portion 64$^c$ such that at least a first segment of the second wire portion 64$^c$ extends through the plurality of anchors 150. In some applications, a second segment of the second wire portion 64$^c$ can be configured to be disposed within the internal space defined between internal catheter 20 and guide catheter 16 or outer catheter handle 24.

In some applications, the method can comprise a step of: (d) anchoring implant 180, via the plurality of anchors 150 and wire 64$^c$ extending therebetween thereby connecting the anchors to each other, around the tissues surrounding the perimeter of the annulus of the mitral valve 45 or other tissue region, such that the anchors are implanted along a path-line that extends around the annulus or other tissue region, e.g., 250° to 360° around the annulus or other tissue region, 270° or more around the annulus or other tissue region, etc.

In some applications, the method can further comprise a step of: (e) retracting/extracting the catheter 20 and optionally the guide catheter 16, from or through outer catheter 12, wherein the first wire portion 62$^c$ which was disposed within the internal catheter, extends out of either one of the guide catheter handle 26 or the outer catheter handle 24, exposed to the external environment, enabling positioning thereof next to an end-loop 66 formed at an end portion of second wire portion 64$c$.

In some applications, the method can further comprise a step of: (f) inserting a proximal end 78 of first wire portion 62$^c$ through end-loop 66, or any other type of an end-portion retainer 82. The method can further include inserting the remaining section of wire 62$^c$ into components of a cinching system 200, such as through any of a locker 210, a cutting and locking assembly 222, and a cinching catheter 224, of the cinching system 200.

In some applications, the method can further comprise a step of: (g) advancing the end-portion retainer 82 (e.g., end-loop 66) through guide catheter 16 and/or outer catheter 12, optionally with the aid of cinching system 200, to the vicinity of implant 180, and more specifically, the vicinity of first anchor 150$a$.

In some applications, the method can further comprise a step of: (h) tensioning the wire 63$^c$, for example by proximally pulling the first wire portion 62$^c$ extending through the cinching catheter 224, in order to sufficiently contract the annulus of the native valve and/or contract/reshape the tissue region.

In some applications, the method can further comprise a step of: (i) utilizing locker 210 and the cutting and locking assembly 222 to simultaneously lock the wire 63$^c$ and cutting it proximal to the locker, thereby closing and locking implant 180, and optionally trapping any excess portions of the second wire portion 64$^c$ by the locker, for example by utilizing flap 232 as describe hereinabove.

In some applications, the method can further comprise a step of: (j) decoupling the cutting and locking assembly 222 from the locker 210, and extracting it, along with the cinching catheter coupled thereto, from the patient's body, leaving the locker 210 coupled to the implant 180. This step can include simultaneously extracting the guide catheter 16 and/or the outer catheter 12 therewith, or extracting any of the guide catheter 16 and/or the outer catheter after extraction of the cinching catheter 224 and assembly 222.

The above techniques, methods, steps, etc. can be performed on a living animal or on a simulation, such as on a cadaver, cadaver heart, simulator (e.g., with the body parts, heart, tissue, etc. being simulated), etc.

Figure 11A:
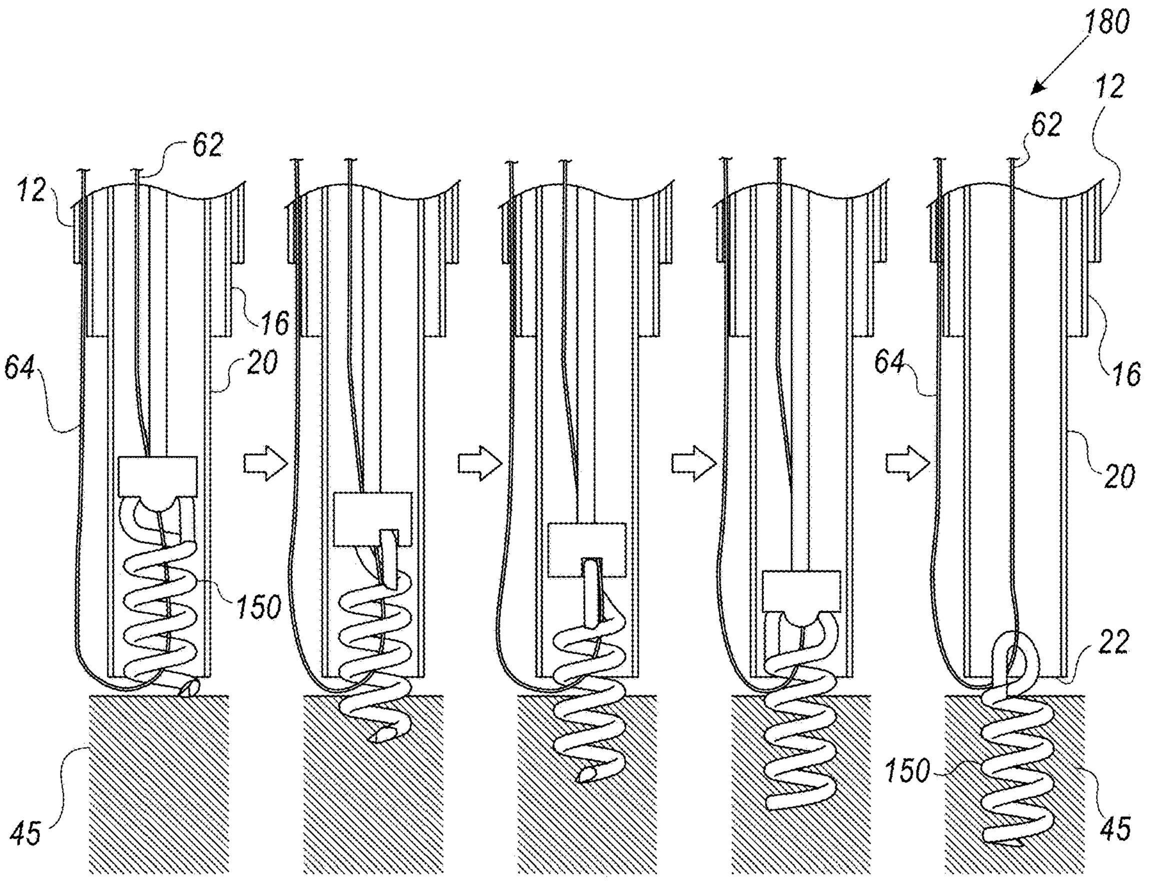
FIGS. 11A-11B are schematic illustrations of example steps in the implantation of an implant to repair mitral valve, according to some applications.
Figure 11B:
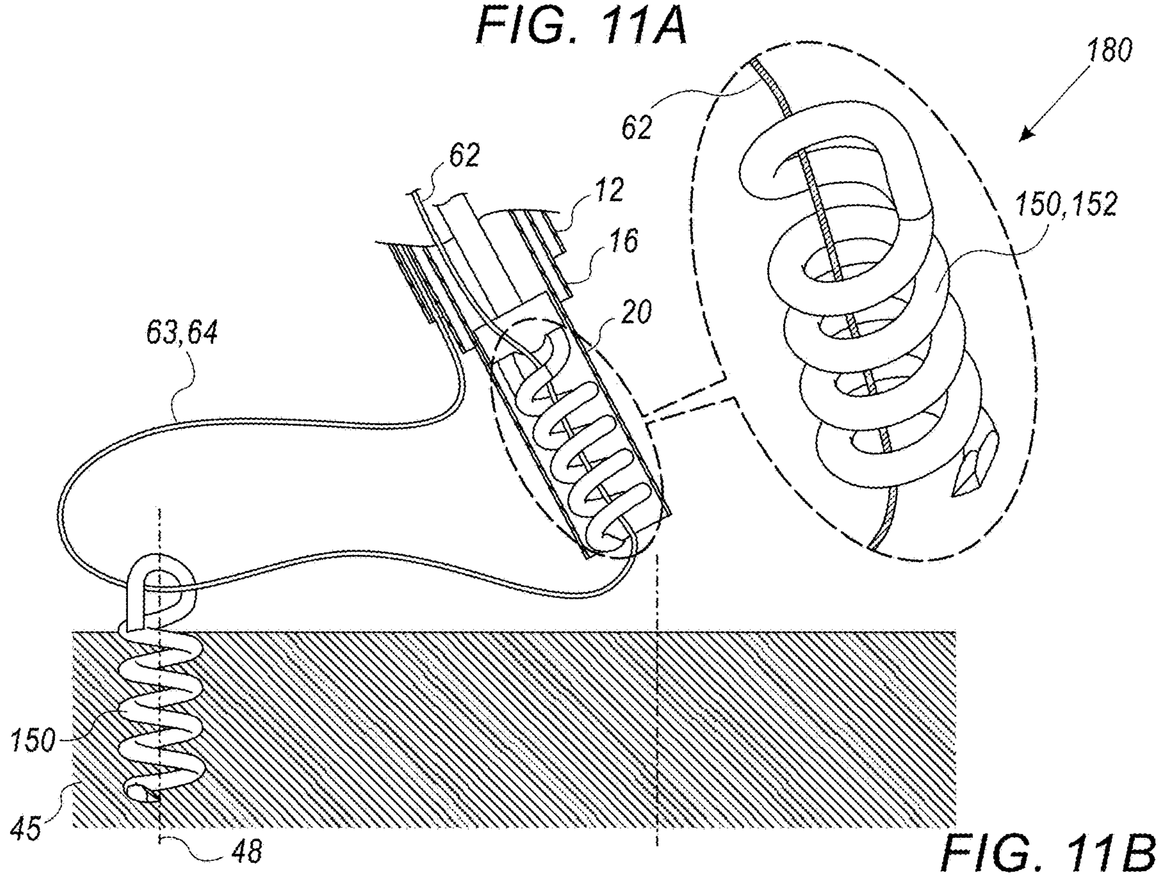
Figure 12:
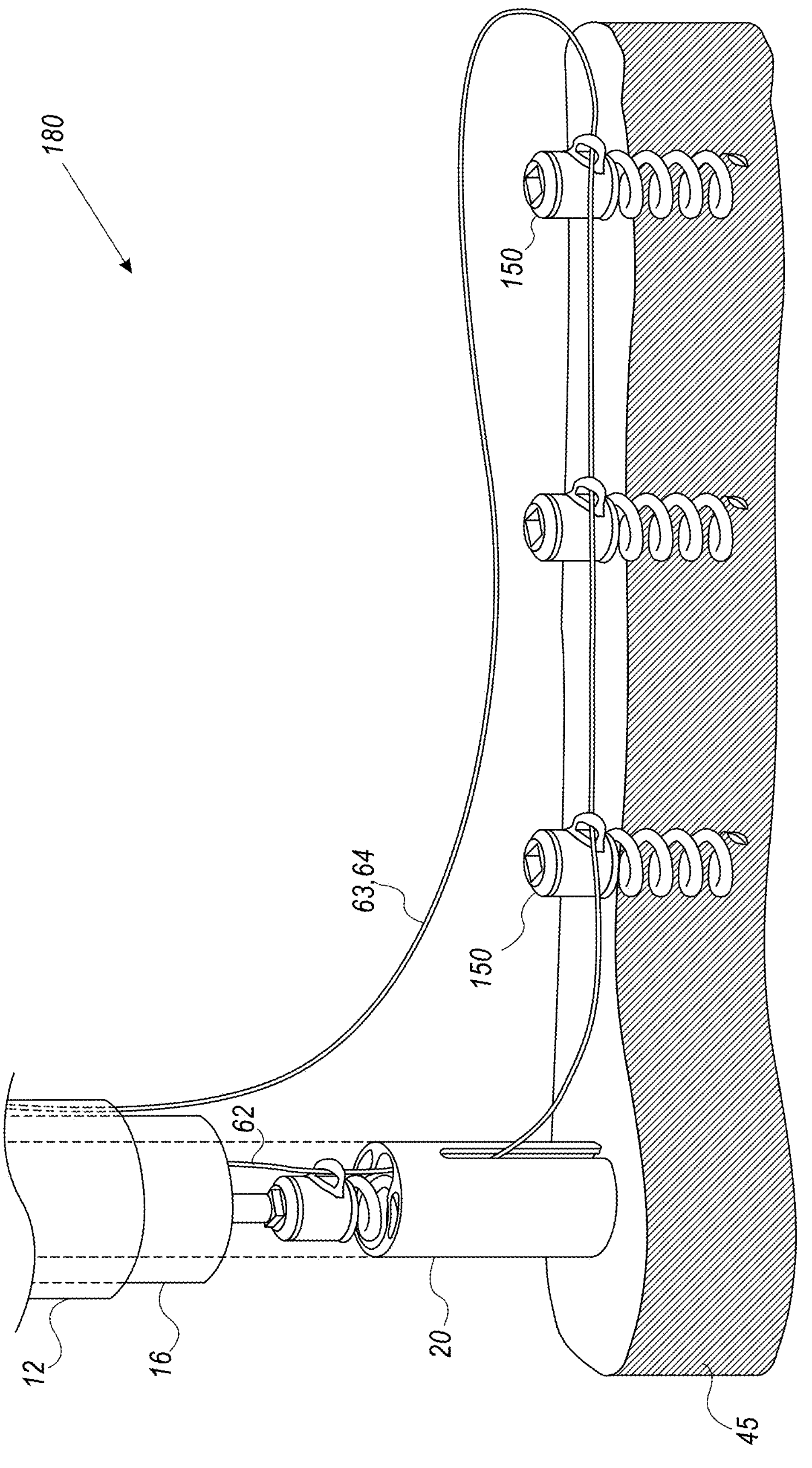
FIG. 12 is a schematic illustration of an example of an implant, according to some applications.

Reference is now made to FIGS. 11A-12. FIGS. 11A and 11B are schematic illustrations of example steps in the implantation of implant 180 to repair mitral valve 45, according to some applications. FIG. 12 is a schematic illustration of an example of an implant 180, according to some applications.

According to some applications, implant 180 as illustrated at FIGS. 11A-11B is identical to implant 180$^a$ as illustrated at FIGS. 3A-3B herein above, except that the second wire portion 64 is extends, during implantation, from the distal end portion 22 of internal catheter 20, or from the first anchor 150$a$, through the plurality of anchors 150, and loops backward to extend along the internal space defined between the guide catheter 16 and the outer catheter 12 toward, into, and out of the outer catheter handle 24. The second wire portion 64 can exit through an opening formed at the rear end 72 of the outer catheter handle 24 (similar to the illustration of FIG. 8A), or any other opening formed in the outer catheter handle 24.

Implant 180 shown FIG. 12 is similar to the configuration shown for implant 180$^b$ in FIG. 5, except that the second wire portion 64 is extends through anchors 150, and loops backward to extend along the internal space defined between the guide catheter 16 and the outer catheter 12 toward, into, and out of the outer catheter handle 24. It is to be understood that implants 150$^b$ are shown in FIG. 12 by way of illustration and not limitation, and that the same configuration can be similarly implemented for a wire 63 extending through a plurality of implant 150$^a$.

The same methods and/or some or all of the same steps of implanting and contracting an implant (e.g., an annuloplasty structure) at a native annulus (e.g., of the mitral valve 45) or other tissue region, described hereinabove, including the methods and/or steps described with respect to contracting an implant 180$^c$ with a wire 63$^c$ having a loop 66, described hereinabove with respect to FIGS. 6A-6B and 9A-9B, can be implemented for an implant 180 mutatis mutandis. This can include, for example, having a second wire portion 64 that extends, during the steps of implantation, along a space defined between an outer catheter 12 and a guide catheter 16. Further, these techniques and methods can be performed on a living animal or on a simulation, such as on a cadaver, cadaver heart, simulator (e.g., with the body parts, heart, tissue, etc. being simulated), In some applications, a system 10 can be provided only with two of the three catheters described above, such as the outer catheter 12 and the internal catheter 20. In such cases, the configuration of the system 10 and the implant 180 can be similar to that shown in FIGS. 11A-12, but without the guide catheter (16), resulting in the second wire portion 64 extend through anchors 150 in a similar manner, but looping backward to extend along the internal space defined between the internal catheter 20 and the outer catheter 12 toward, into, and out of the outer catheter handle 24.

The same or similar methods and/or some or all of the same steps of implanting and contracting an implant (e.g., annuloplasty structure, etc.) at a native annulus (e.g., of the mitral valve 45, etc.) or other tissue region, described hereinabove, including the methods described with respect to contracting an implant 180$^c$ with a wire 63$^c$ having a loop 66, described hereinabove with respect to FIGS. 6A-6B and 9A-9B, can be implemented for an implant 180, mutatis mutandis. As one example, a second wire portion 64 can extend, during the steps of implantation, along a space defined between the outer catheter 12 and the internal catheter 20. In some applications, disconnection of the internal catheter handle 28 from the handle assembly 40 (along with the internal catheter 20 entirely removed from the system 10), can result in the configuration of both portions of the wire 63 extending, side by side, out of the outer catheter handle 24, as shown in FIGS. 8A-8B. These techniques, methods, steps, etc. can be performed on a living animal or on a simulation, such as on a cadaver, cadaver heart, simulator (e.g., with the body parts, heart, tissue, etc. being simulated), etc.

Figure 13A:
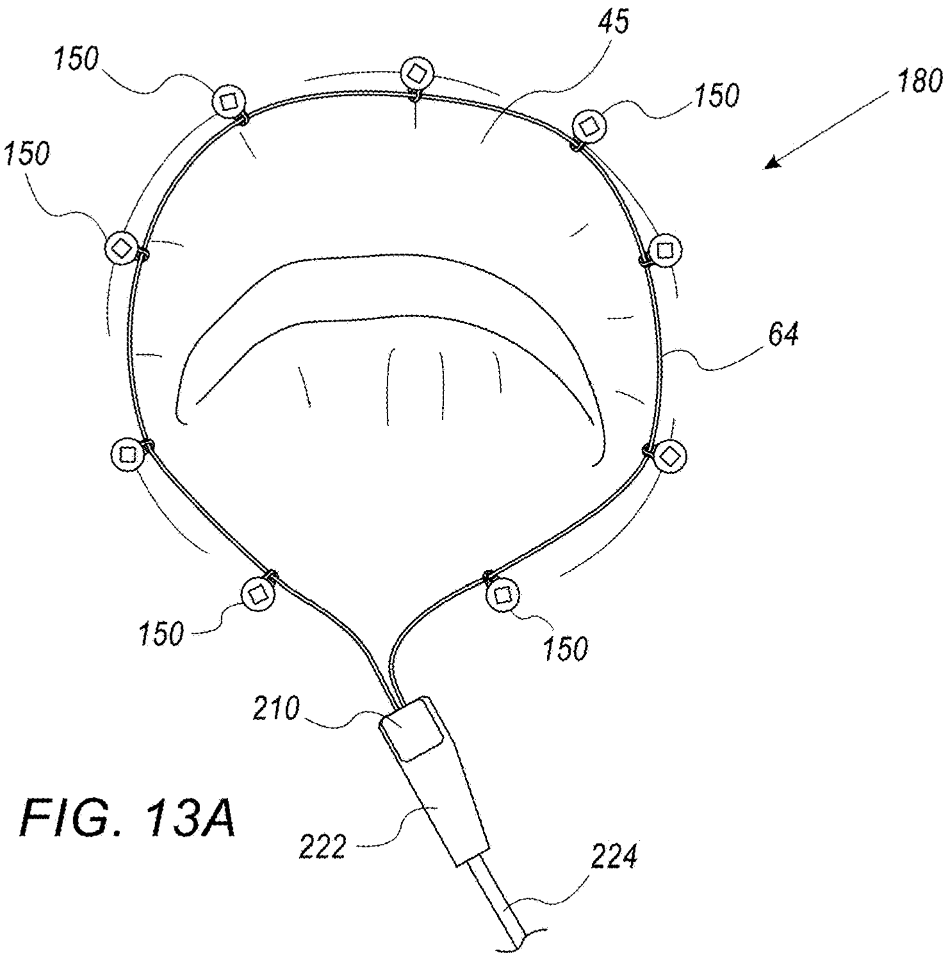
FIGS. 13A-13B are schematic illustrations of example steps of a procedure for tightening an implant utilizing a cinching system, according to some applications.
Figure 13B:
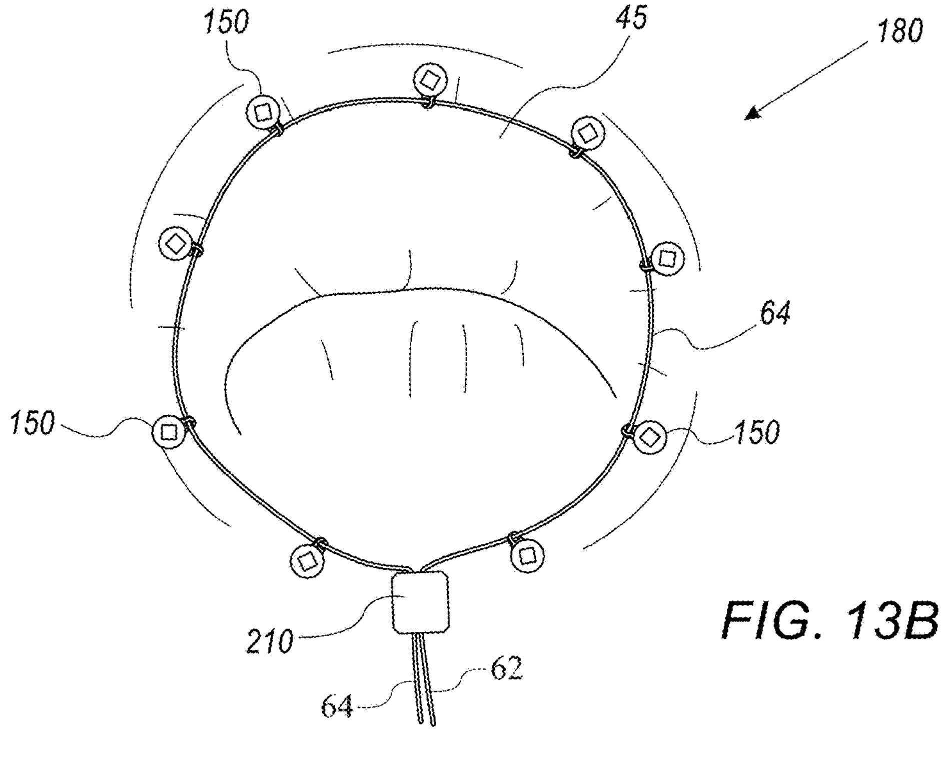

Reference is now made to FIGS. 13A-13B, which are schematic illustrations of examples of tightening procedures of implant 180 equipped with a wire 63 that does not include a loop 66, according to some applications.

According to some applications, implant 180 comprises a plurality of anchors 150 and a wire 63, which is identical to any application of the wire described herein above, including wire 63$^c$, except that it does not necessarily include a loop 66 or any other type of end-portion retainer 82. During implantation of the implant 180, that is-during the steps of anchoring the plurality of anchors 150 around the annulus or other tissue region, both the first wire portion 62 and the second wire portion 64 of the wire 63 extend through the catheters of the system 10, in any of a variety of configurations.

According to some applications, the first wire portion 62 of a wire 63 at least partially extends through the lumen of the internal catheter 20, while the second wire portion 64 at least partially extends through a space defined between the internal catheter 20 and the guide catheter 16, similar to the configurations described hereinabove with respect to FIGS. 3A-3B and 5.

In some applications, the first wire portion 62 of a wire 63 at least partially extends through the lumen of the internal catheter 20, while the second wire portion 64 at least partially extends through a space defined between the outer catheter 12 and the guide catheter 16, similar to the configurations described hereinabove with respect to FIGS. 11A-12.

In other such applications, the first wire portion 62 of a wire 63 at least partially extends through the lumen of the internal catheter 20, while the second wire portion 64 at least partially extends through a space defined between the outer catheter 12 and the internal catheter, similar to the configurations described hereinabove.

In some applications, both the first wire portion 62 and the second wire portion 64 of a wire 63 at least partially extend, optionally side by side, through the lumen of the internal catheter 20. In some such applications, the internal catheter 20 can be a multi-lumen shaft, including at least two lumens, wherein the first wire portion 62 of a wire 63 at least partially extends through one lumen of the internal catheter 20, while the second wire portion 64 at least partially extends through another lumen of the internal catheter 20, thereby reducing risk of entanglement between both wire portions.

The process of extending the catheters of the system 10 toward the site of implantation, such as the annulus of the mitral valve 45, etc., and anchoring a plurality of anchors 150 around the perimeter of the annulus or other tissue region, can be performed in the same manner described hereinabove with respect to FIGS. 2 and 6A-6B. After anchoring the last anchor 150*b*, the internal catheter 20 can be removed from the patient's body, while components of the cinching system 200, such as the assembly 222 and the cinching catheter 224 can be advanced over the wire 63 extending therethrough, toward the implant 80, in a manner similar to that described above, with some modifications as will be elaborated hereinbelow.

As shown in FIG. 13A, both first wire portion 62 and second wire portion 64 extend, for example side by side, through components of the cinching system 200, such as the cinching catheter 224, the cutting and locking assembly 222, and the locker 210 thereof. For example, both first wire portion 62 and second wire portion 64 can extend through opening 218 of the locker 210 and through the lumen of stop 220. According to further applications, the lumen of stop 220 is a double lumen comprising a first stop lumen and a second stop lumen, wherein the first wire portion 62 extends through said first stop lumen, and the second wire portion 64 extends through said second stop lumen.

According to some applications, the cinching catheter 224 is a multi-lumen catheter, such as a double lumen catheter, wherein each of the first wire portion 62 and the second wire portion 64 extend through a different lumen, so as to prevent them from entangling with each other within the cinching catheter 224.

According to some applications, the cutting and locking assembly 222, which includes the locker 210, is configured to advance within a lumen of the guide catheter 16 or the outer catheter 12 toward the vicinity of implant 180, and more specifically, the vicinity of the first anchor 150*a*, as illustrated at FIG. 13A. According to further applications, cinching system 200 is configured to allow both the first wire portion 62 and the second wire portion 64 to be pulled therethrough in order to sufficiently contract the implant or annuloplasty structure (e.g., at the native valve, mitral valve 45, etc.), as illustrated at FIG. 13B. The proximal portions of both first wire portion 62 and second wire portion 64 can extend extracorporeally, for example into a handle of the cinching system 200 (not shown).

In some implementations, contraction of implant 180 is achieved by simultaneously pulling both first wire portion 62 and second wire portion 64 in a proximal direction. In other implementations, contraction of implant 180 is achieved by applying a pull force to one of the first wire portion 62 or second wire portion 64, while the other portion is kept in place, preventing it from sliding in a distal direction while its counterpart wire portion is pulled.

According to some applications, the cutting and locking assembly is configured to lock the wire 63 in the cinched or contracted state of the implant 180, for example by the locker 210, and cut both the first wire portion 62 and the second wire portions 64 extending through the stop lumen or lumens, utilizing cutting fastening and cutting mechanisms in a manner similar to that described hereinabove, mutatis mutandis.

Cutting both wire portions 62 and 64 can result in excess portions thereof, extending proximal to the locker 210, as shown, for example, in FIG. 13B. According to some applications, the locker 210 can be further configured to trap any excess portions of the first wire portion 62 and second wire portion 64 therein, utilizing flap 232 in a similar manner to that described hereinabove, mutatis mutandis.

Figure 14:
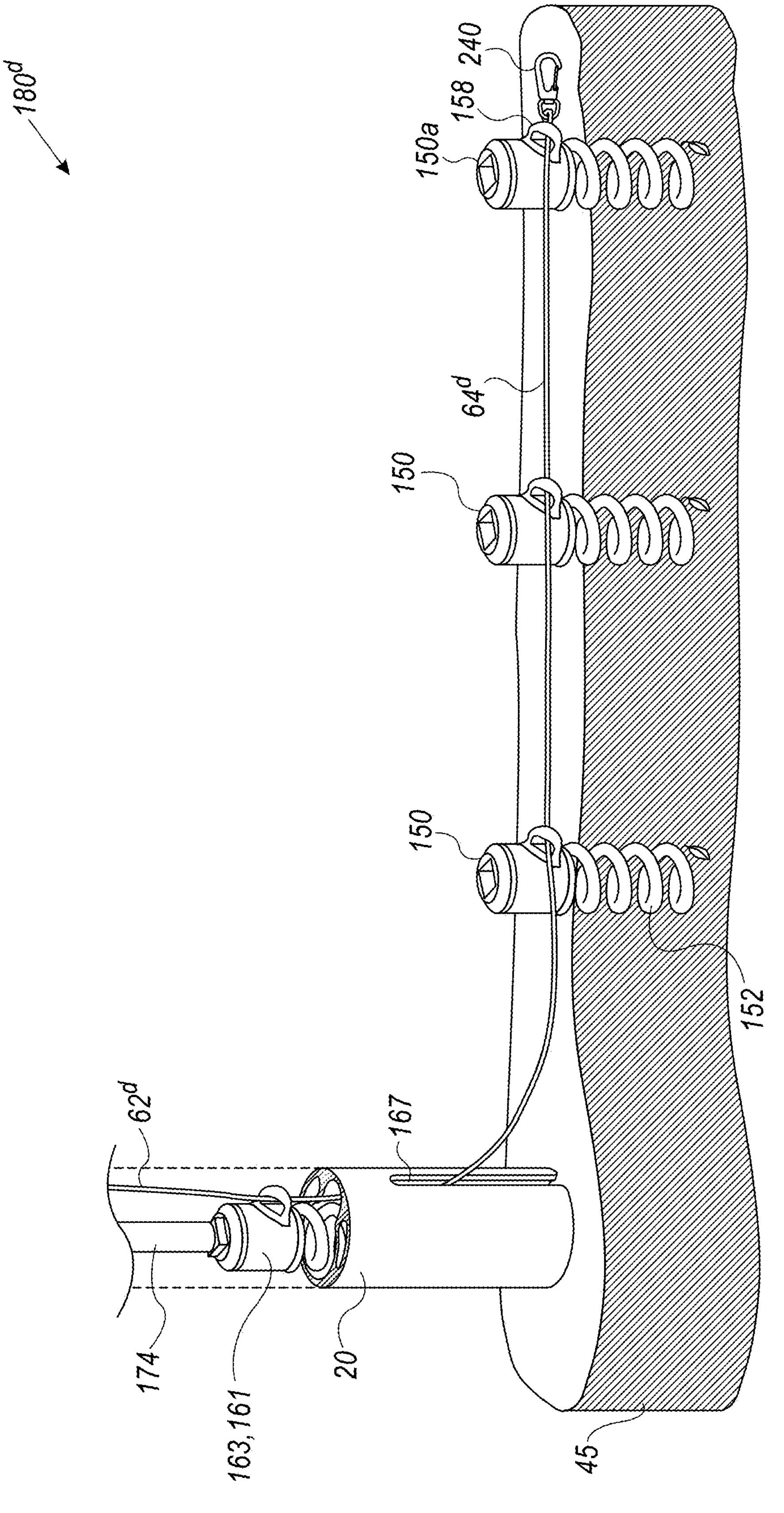
FIGS. 14 and 15A-15C are schematic illustrations of examples of procedures for tightening an implant equipped with a terminal clamp, according to some applications.
Figure 15A:
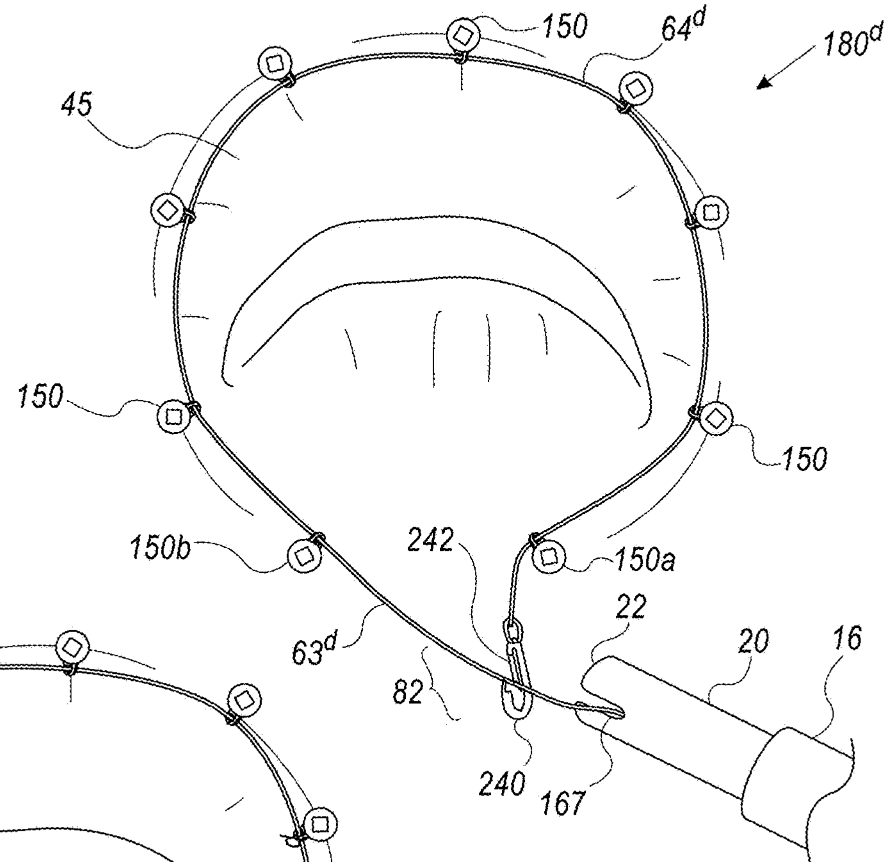
Figure 15B:
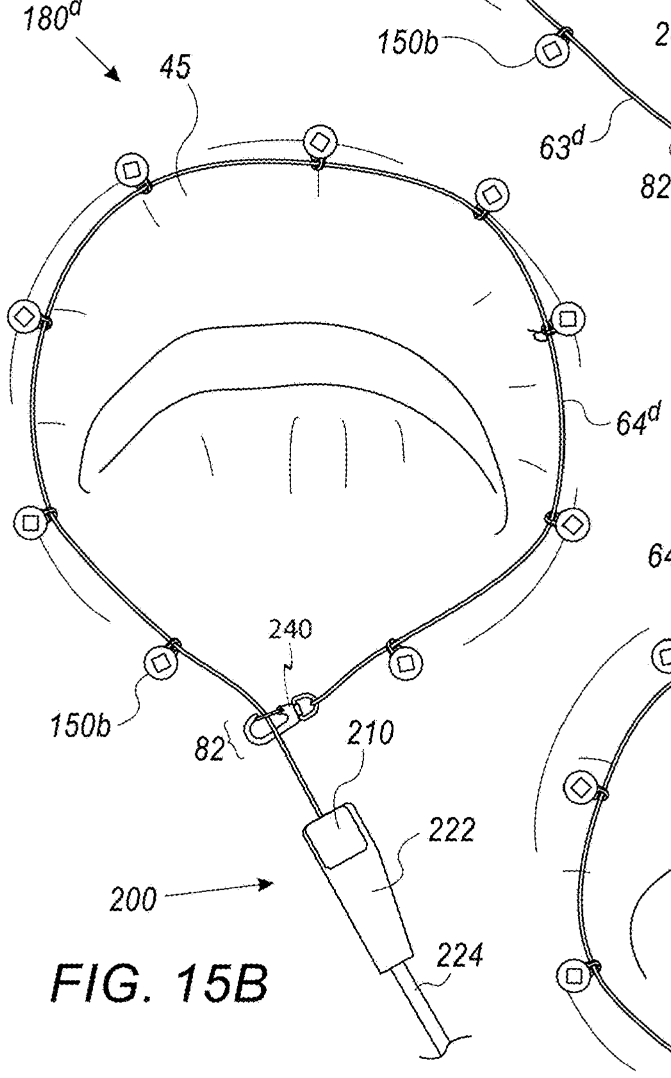
Figure 15C:
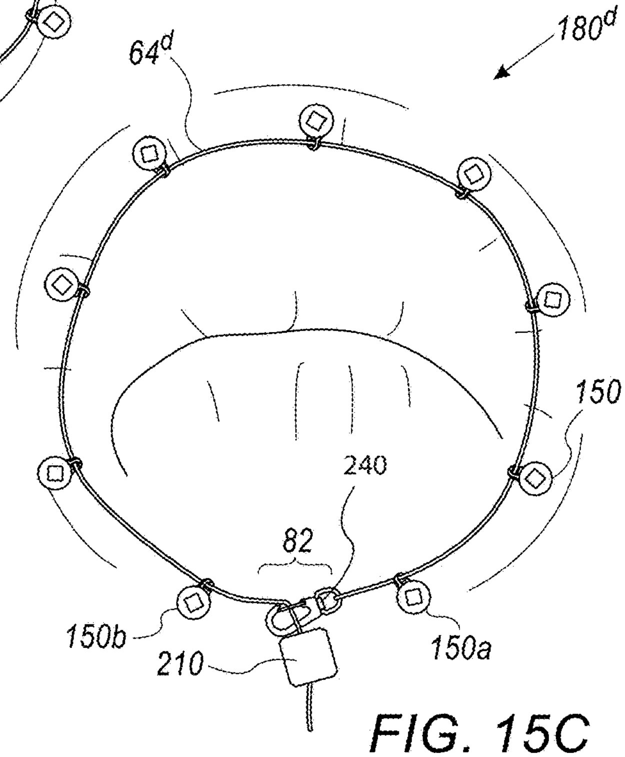

Reference is now made to FIGS. 14-15C, which are schematic illustrations of examples of procedures for tightening an implant 180$^d$ equipped with a wire 63$^d$ having a terminal clamp 240, according to some applications.

An implant 180$^d$ is the same as or similar to implant 180$^c$ described herein above, except that it includes a wire 63$^d$ which comprises an end-portion retainer 82 in the form of a terminal clamp 240 instead of an end-loop 66. The terminal clamp 240 can be in the form of a shackle or a carabiner, including a main body and a spring-biased gate or arm 242 hinged thereto, together enclosing an internal opening in a free state of the clamp 240. The spring biased gate of the clamp is biased in a free state thereof toward an end portion of the main body of the clamp, at an opposite end to the hinge point between the gate and the main body, and can be forced to an open state, biasing it internally, when a force is applied thereto. The terminal clamp 240 can be attached to an end of the second wire portion 64, in the same region described hereinabove with respect to the end-loop 66.

The terminal clamp 240 can be sized to allow it to advance through a lumen of at least one of the catheters of the system 10, such as the lumen of the internal catheter 20, the lumen of the guide catheter 16, and/or the lumen of the outer catheter 12. The terminal clamp 240 is further sized so as to prevent it from passing through an eyelet 158 of an anchor 150, and more specifically, through an eyelet 158 of the first anchor 150*a*. The implant 180$^d$ can include any type of anchors 150. While anchors 150$^b$ are illustrated in FIGS. 14-15C, it is to be understood that this is by way of illustration and not limitation, and that an implant 180$^d$ can include any type of anchors 150, such as anchors 150$^a$ or anchors 150$^b$.

According to some applications, the first anchor 150*a* is advanced toward the implantation site through the internal catheter 20, along with the terminal clamp 240 extending from one side thereof, such as along one side of its eyelet 158. In this manner, as shown in FIG. 14, once the first anchor 150*a* is anchored into the tissue, and subsequent anchors 150 are further anchored along the annulus or other tissue region, the first wire portion 62$^d$ at least partially extends through the internal catheter 20, for example—from an extracorporeal end thereof to the internal catheter distal end portion 22, or to the last anchored anchor 150 of the series of anchors 150. However, as further shown in FIG. 14, the second wire portion 64$^d$ continuously extends from the first wire portion 62$^d$, through the anchors 150, and is not looped back through any of the catheter in this specific configuration, but rather terminates at the terminal clamp 240 disposed next to the first anchor 150*a*.

The system 10 can be utilized to anchor the plurality of anchors 150 around the perimeter of the annulus or other tissue region (e.g., annulus of a native valve, annulus of the mitral valve 45, opening of an appendage, chamber wall area, etc.) in the same manner described hereinabove with respect to FIGS. 6A-6B, for example, mutatis mutandis. This will result in a configuration like that shown in FIG. 15A, wherein the second wire portion 64$^d$ extends between the first anchor 150*a* and the final anchor 150$^b$. As noted above, and throughout the figures and the specification, the first anchor 150*a* is defined the first anchor to be implanted during the implantation procedure of implant 180 around the annulus or tissue region, while a final anchor 150*b* is defined as the final anchor to be implanted.

According to some applications, the terminal clamp 240 comprises a spring biased gate 242 configured to be movable from a closed position to an open position, wherein said open position allows a section of the wire 639, extending between the final anchor 150*d* and the internal catheter distal end portion 22, to be inserted therethrough, thereby closing implant 180.

The term “closing the implant”, as used herein, refers to extending the wire 63 around the entire circumference of the annulus (e.g., the annulus of the mitral valve 45) or other tissue region, into which the anchors 150 of the implant 180 are anchored. In other words, a “closed implant”, as used herein, refers to an implant 180 implanted such that its wire 63 extends 360° in a closed loop around the annulus or tissue region into which the anchors are anchored.

According to further applications, the distal end portion 22 of the internal catheter 20 is steerable so that it can be maneuvered to enable a section of the wire 634, which extends through to the final anchor 150*b*, to be approximated to the terminal clamp 240, and pushed against the spring biased gate 242, followed by insertion thereof into the terminal clamp 240. Once this section of the wire 63$^d$ extends through the terminal clamp 240, the gate 242 is allowed to spring back to its naturally biased closed position, thereby closing the implant 180$^d$.

According to some applications, following the implantation of implant 180$^d$ around the annulus (e.g., of the mitral valve 45) or other tissue region, such that it spans across the entire circumference thereof, the internal catheter 20, and optionally, but not necessarily, the guide catheter 16, are retracted/extracted from the outer catheter 12, and the extracorporeal section of the wire 634, and more specifically, a section of the first wire portion 624, is inserted into components of the cinching system 200 (i.e., locker 210, assembly 222, and cinching catheter 224), in a manner similar to that described hereinabove.

According to some applications, cinching system 200 is configured to enable the section of wire 63$^d$, and more specifically, of first wire portion 62$^d$, to be pulled therethrough in order to apply tension to the second wire portion 64$^d$ which is sufficient to contract the implant or annuloplasty structure around the annulus (e.g., around the mitral valve 45) or tissue region, as illustrated at FIG. 15B. Specifically, as the first wire portion 62$^d$ is pulled in a proximal direction, the terminal clamp 240 is pressed against the first anchor 150*a* to provide a counter force, thereby enabling the second wire portion 64$^d$ extending between the first anchor 150*a* and the final anchor 150$^b$ to reduce in size, and contract the entire implant 180$^d$ therewith.

According to some applications, the cinching system 200 is further configured to enable the assembly 222 to lock and cut the section of wire 63$^d$ extending therethrough, in the same manner described hereinabove, thereby closing and locking implant 1804, as illustrated at FIG. 15C. While an excess portion of the wire 63$^d$ is shown to extend from the locker 210 in FIG. 15C, according to some applications, the locker 210 can be further configured to trap any excess portions of the wire 63$^d$ therein, utilizing a flap 232 as presented hereinabove.

According to some applications, implantation of the implant 180$^d$ does not include advancing the terminal clamp 240 together with the first anchor 150*a* through the internal catheter 20, but rather having the terminal clamp 240 of the second wire portion 64$^d$ positioned outside the patient’s body, and following implantation steps that are identical to those described for an implant 180$^c$ as described above, with the mere modification that the end-loop 66 of the wire 63$^c$ is replaced by the terminal clamp 240 of the wire 634. The implantation procedure, including the steps of anchoring the series of anchors 150 to the tissue, insertion of the free end of the first wire portion 62$^d$ through the terminal clamp 240, and advancing the terminal clamp 240 distally, over the first wire portion 62$^d$, toward the first anchor 150*a*, can be performed according to any example described hereinabove with respect to wire 63$^c$ equipped with an end-loop 66. These steps will result in a configuration of the terminal clamp 240 positioned in the vicinity of the first anchor 150*a* at the site of implantation, as shown in FIG. 15A. Once the terminal clamp 240 is positioned next to the first anchor 150*a*, the rest of the steps of the method for contracting and locking the implant 180$^d$ can be performed in the same manner described hereinabove with respect to FIGS. 15A-15C.

Figure 16:
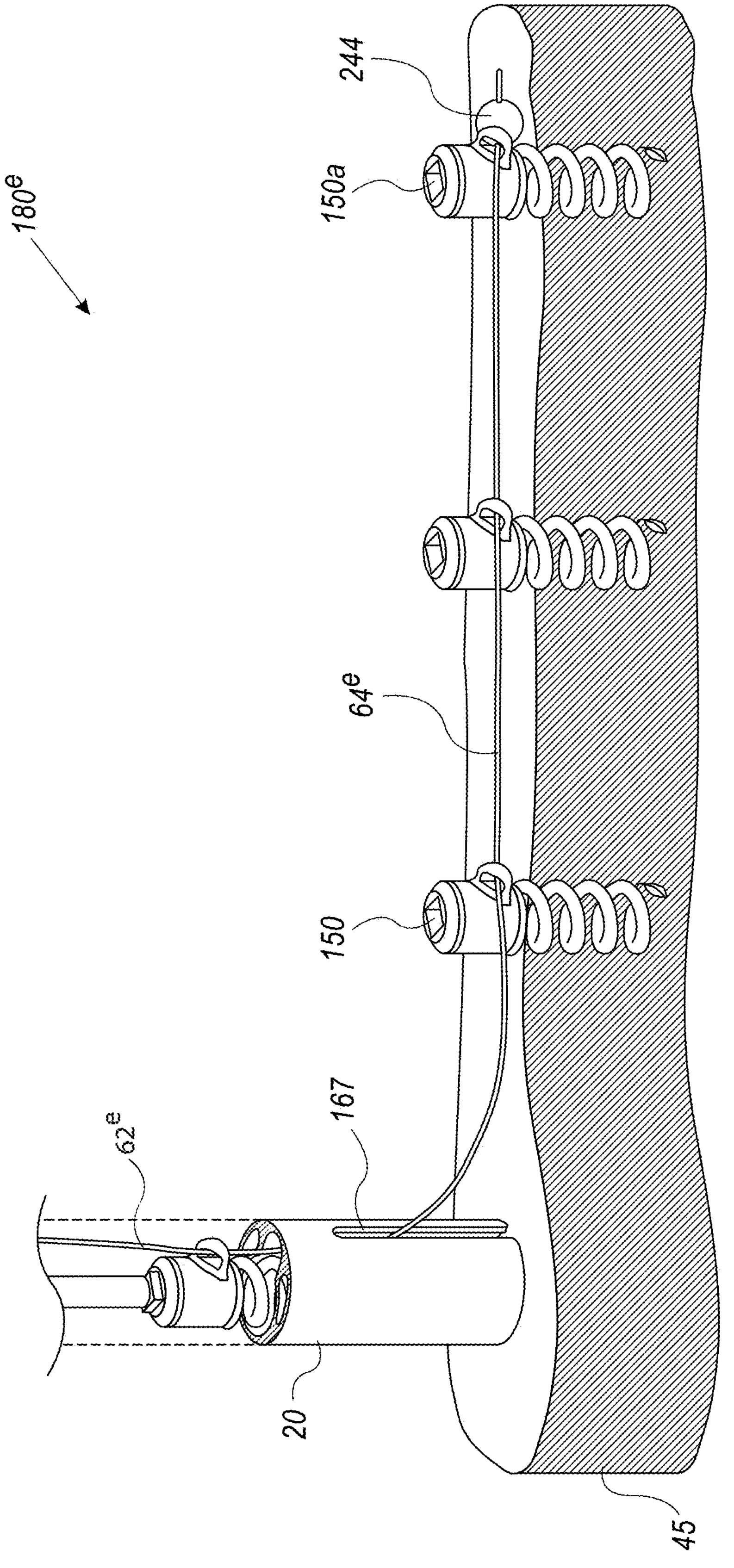
FIGS. 16-17 are schematic illustrations of examples of procedures for tightening an implant equipped with first stopper, according to some applications.
Figure 17:
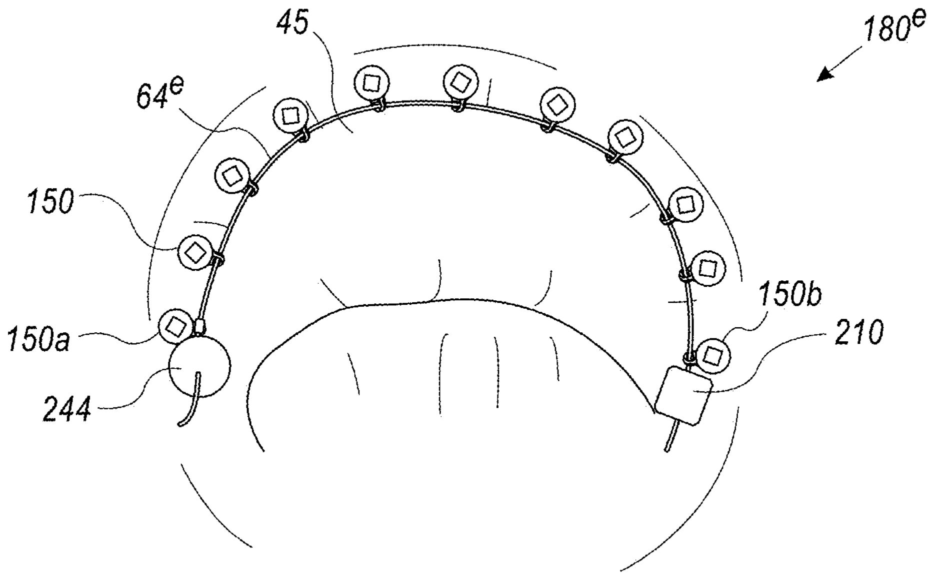

Reference is now made to FIGS. 16 and 17, which are schematic illustrations of examples of procedures for tightening an implant 180$^e$ equipped with a wire 63$^e$ having a first stopper 244, according to some applications. Unlike the configurations of implants 180 configured to extend around the entire circumference of the annulus or tissue region, such as implant 180€ described above and illustrated, for example, in FIGS. 5-9B, implant 180 described herein above and illustrated, for example, in FIGS. 13A-B, and implant 180$^d$ described hereinabove and illustrated, for example, in FIGS. 14-15C, the implant 180$^e$ is not structured to enable it to surround the entire circumference of the annulus or tissue region, but rather to extend along a path-line 90 that is not a full circle (e.g., can be C-shaped, etc.), as shown in FIG. 17.

Implant 180$^e$ can be generally similar to other examples of the implant 180 described hereinabove, such as, for example, implant 1804, except that implant 180$^e$ is equipped with a wire 63$^e$ comprising a first stopper 244 instead of a terminal clamp 240 or any other type of an end-portion retainer 82. The first stopper 244 is attached to the end of the second wire portion 64$^e$, in the same region described hereinabove with respect to end-portion retainers 82. The first stopper 244 can be in the form of a bead or crimp, comprising only a single opening for the end of the second wire portion 64$^e$ to extend through. It is to be understood that while the first stopper 244 is shaped as a sphere in FIG. 16, the first stopper 244 can be shaped as a square, rectangle, or any other suitable polyhedron thereof.

The first stopper 244 can be sized to allow it to advance through the lumen of the internal catheter 20, and at the same time, sized so as to prevent it from passing through an eyelet 158 of an anchor 150, and more specifically, through an eyelet 158 of the first anchor 150*a*. The implant 180$^e$ can include any type of anchors 150. While anchors 150$^b$ are illustrated in FIGS. 16-17, it is to be understood that this is by way of illustration and not limitation, and that an implant 180$^e$ can include any type of anchors 150, such as anchors 150$^a$ or anchors 150$^b$.

According to some applications, the first anchor 150*a* is advanced toward the implantation site through the internal catheter 20, with the first stopper 244 extending alongside the anchor on the wire (e.g., extending from the wire at a distal side of the anchor), such as along a distal side of its eyelet 158. In this manner, as shown in FIG. 16, once the first anchor 150*a* is anchored into the tissue, and subsequent anchors 150 are further anchored along the annulus or other tissue region, the first wire portion 62$^e$ at least partially extends through the internal catheter 20, for example—from an extracorporeal end thereof to the internal catheter distal end portion 22, or to the last anchored anchor 150 of the series of anchors 150. As further shown in FIG. 16, the second wire portion 64$^{e}$ continuously extends from the first wire portion 62$^{e}$, through the anchors 150, and is not looped back through any of the catheter in this specific configuration, but rather terminates at the first stopper 244 disposed next to the first anchor 150*a*.

The system 10 can be utilized to anchor the plurality of anchors 150 around a portion of the perimeter of the annulus of the mitral valve 45 or other tissue region, which does not necessarily span across the entire circumference of the annulus or other tissue region, but rather may be C-shaped, for example (as shown in FIG. 17).

According to some applications, following the implantation of implant 180$^{e}$ around a portion of the annulus (e.g., the mitral valve 45, etc.) or tissue region, the internal catheter 20, and optionally, but not necessarily, the guide catheter 16, are retracted/extracted from the outer catheter 12, and the extracorporeal section of the wire 63$^{e}$, and more specifically, a section of the first wire portion 62$^{e}$, is inserted into components of the cinching system 200 (i.e., locker 210, assembly 222, and cinching catheter 224), in a manner similar to that described hereinabove.

According to some applications, cinching system 200 is configured to enable the section of wire 63$^{e}$, and more specifically, of first wire portion 62$^{e}$, to be pulled therethrough in order to apply tension to the second wire portion 64$^{e}$ which is sufficient to contract the implant (e.g., annuloplasty structure, etc.) surrounding a portion of the perimeter of a native valve (e.g., mitral valve 45, etc.) or other tissue region. Specifically, as the first wire portion 62$^{e}$ is pulled in a proximal direction, the first stopper 244 is pressed against the first anchor 150*a* to provide a counter force, thereby enabling the second wire portion 64$^{e}$ extending between the first anchor 150*a* and the final anchor 150*b* to reduce in size, and contract the entire implant 180$^{e}$ therewith.

According to some applications, the cinching system 200 is further configured to enable the assembly 222 to lock and cut the section of wire 63$^{e}$ extending therethrough, in the same manner described hereinabove, thereby locking implant 180$^{e}$ in a cinched or contracted state, as illustrated at FIG. 17. While an excess portion of the wire 63$^{e}$ is shown to extend from the locker 210 in FIG. 17, according to some applications, the locker 210 can be further configured to trap any excess portions of the wire 63$^{e}$ therein, utilizing a flap 232 as presented hereinabove.

Figure 18:
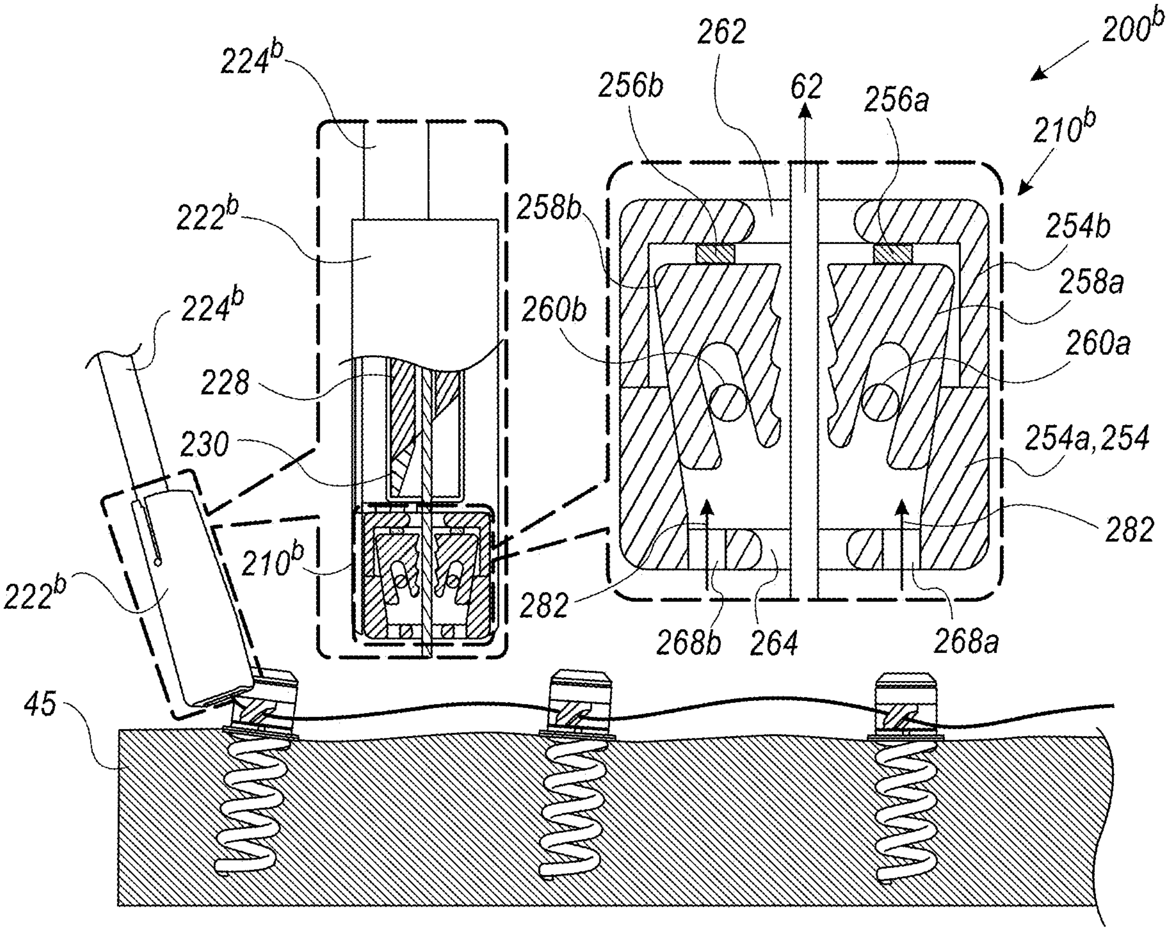
FIG. 18 is a schematic illustration of an example of a locker that can be comprised within a cutting and locking assembly, according to some applications.
Figure 19:
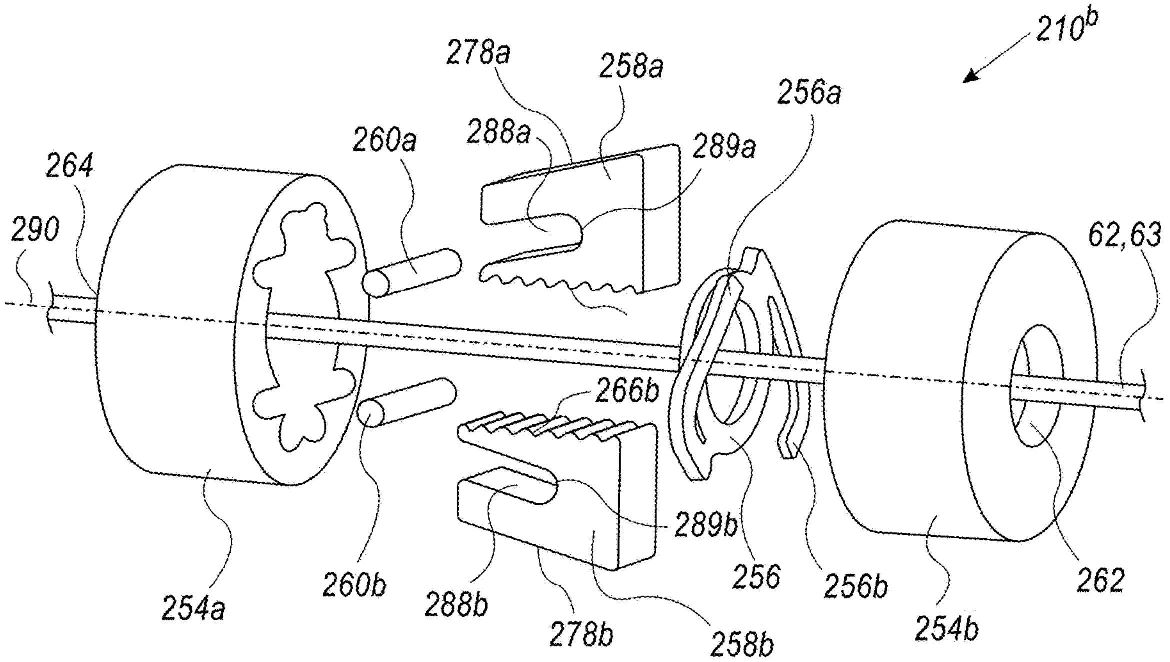
FIG. 19 is an exploded view in perspective of the locker of FIG. 18, according to some applications.
Figure 20A:
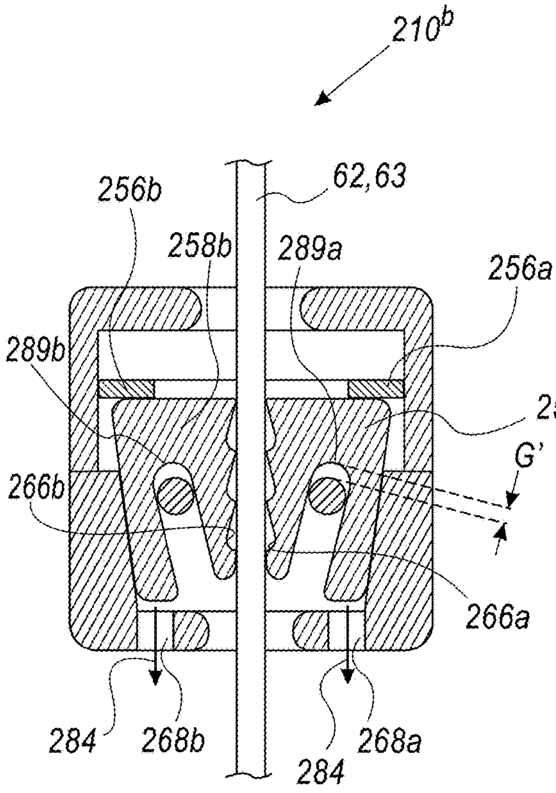
FIGS. 20A-20B are cross sectional view of the locker of FIGS. 18-19 in a locked state and in an unlocked state thereof, according to some applications.
Figure 20B:
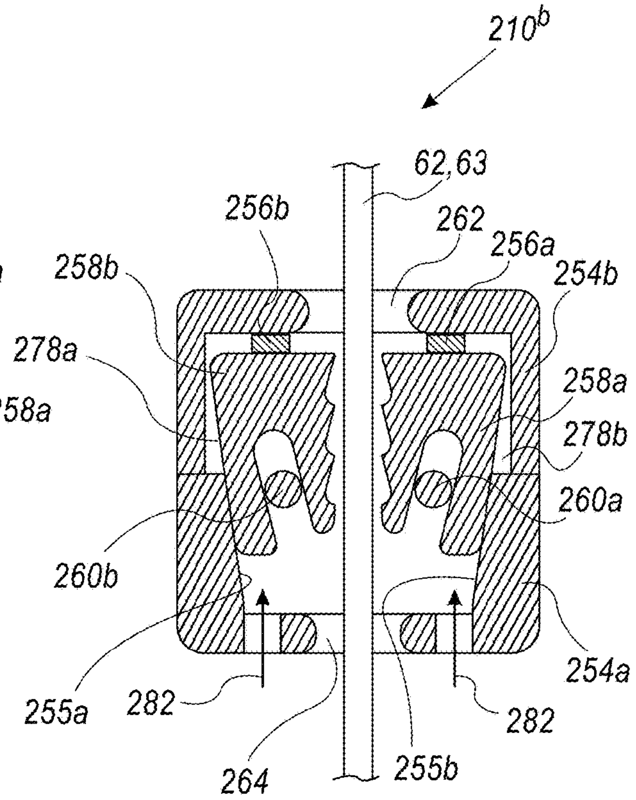
Figure 21A:
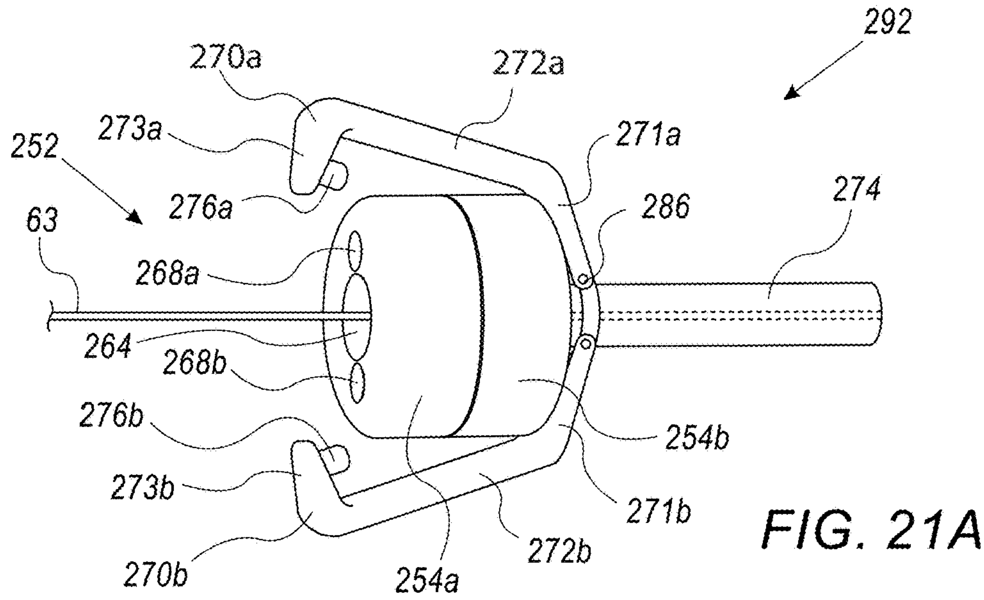
FIGS. 21A-21C are views in perspective of an example actuation assembly useable in combination with the locker of FIGS. 18-20B, at various operational stages thereof, according to some applications.
Figure 21B:
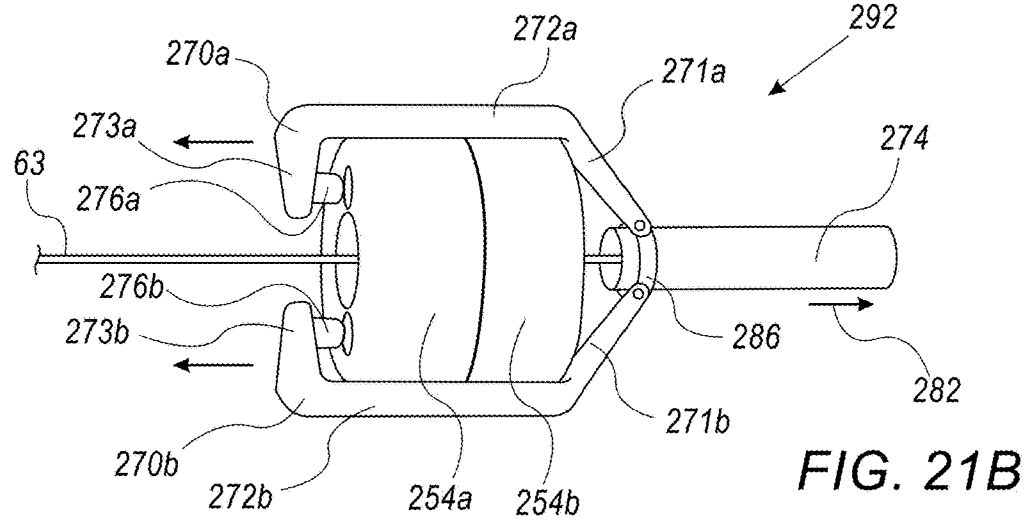
Figure 21C:
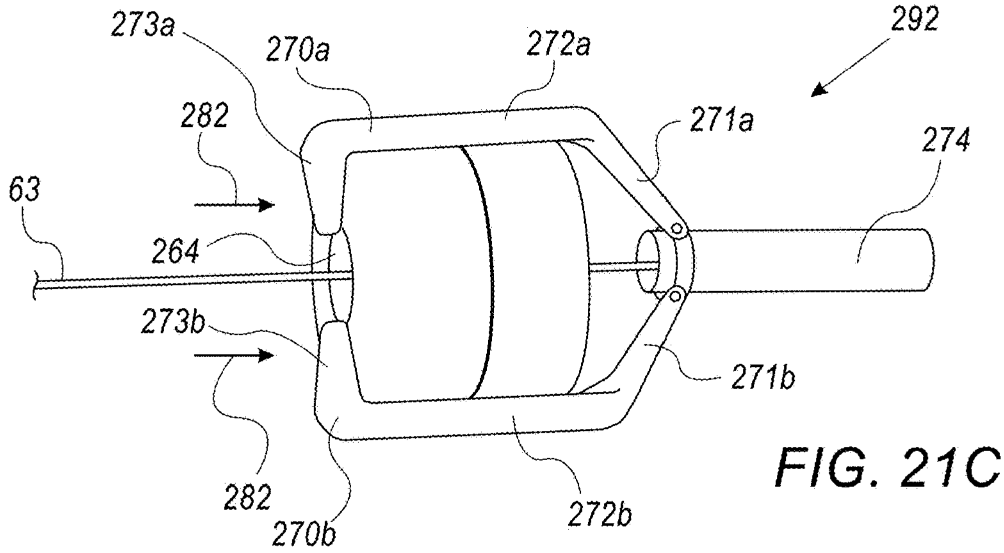

Reference is now made to FIGS. 18-21C, showing a locker 210$^{b}$, according to some applications. FIG. 18 is a schematic illustration of an example of a locker 210$^{b}$, that can be comprised within and or be connected with a cutting and locking assembly 222$^{b}$, according to some applications. FIG. 19 is an exploded view in perspective of locker 210$^{b}$, according to some applications. FIGS. 20A and 20B are cross sections of locker 210$^{b}$ in a locked state and an unlocked state thereof, according to some applications. FIGS. 21A-21C are views in perspective of an actuation assembly 292 used in combination with the locker 210$^{b}$, at various operational stages thereof, according to some applications. The locker can be the same as or similar to other lockers herein.

The cinching system 200$^{b}$ can be the same as or similar to cinching system 200$^{a}$, and can comprise a cinching catheter 224$^{b}$ that can be the same as or similar to cinching catheter 224$^{a}$. It can also comprise a cutting and locking assembly 222$^{b}$ (which can be the same as or similar to other cutting and locking assemblies herein) coupled to the cinching catheter 224$^{b}$, which can include a cutting or trimming mechanism. The cutting or trimming mechanism can be provided with static and dynamic cutting elements 228 and 230 operable to cut a wire 63 extending therethrough. In some applications, this can be configured and done in a manner similar to that described hereinabove for locking assembly 222$^{a}$ with respect to FIGS. 10A-10B. However, cinching mechanism 200$^{b}$ includes a locker 210$^{b}$, which is configured to lock a wire 63 extending therethrough, in a manner which is different than the one shown for locker 210$^{a}$, as will be further elaborated hereinbelow.

According to some applications, locker 210$^{b}$ comprises fasteners and/or a clamping structure which are configured to enable the advancement in the proximal direction of the wire extending through implant 180 in order to perform annuloplasty or tissue reshaping, and afterword to enable the locking thereof, by cutting excess portions of a first wire portion 62, thereby separating an implant 180 from a first wire portion 62 and any other components of cinching system 200$^{b}$ and/or system 10.

In some applications, the locker 210$^{b}$ comprises a housing 254 which houses a spring 256, a first sliding locking element 258*a*, a second sliding locking element 258$^{b}$, a first guide element 260*a*, and a second guide element 260*b*, together defining the systems' locking mechanism or clamping structure. According to some applications, the housing 254 can be integrally formed as a single unit. According to some applications, the housing 254 can be formed of separate portions attachable to each other, comprising a first housing portion 254*a* and a second housing portion 254*b*, wherein the spring 256, the first sliding locking element 258*a*, the second sliding locking element 258*b*, the first guide element 260*a*, and the second guide element 260*b*, are accommodated therebetween in parallel to a longitudinal axis 290 of the locker 210$^{b}$, shown in FIG. 19. Separate portions attachable together to form the housing 254, such as the first housing portion 254*a* and the second housing portion 254*b*, can be utilized to simplify assembly of the locker 210$^{b}$ by allowing placement and attachment of internal components thereof, prior to affixing the first housing portion 254*a* and the second housing portion 254*b* to each other.

According to some applications, a wire, such as wire 63, and in some applications, such as first wire portion 62, can extend through a proximal wire opening 262 formed at a proximal end of the housing 254, such as the proximal end of the second housing portion 254*b*, through or alongside the spring 256, and onward through a distal wire opening 264 formed at a distal end of the housing 254, such as a distal end of the first housing portion 254*a*. According to some applications, a wire, such as the first wire portion 62, extends through the housing 254 between the first sliding locking element 258*a* and the second sliding locking element 258*b*, along longitudinal axis 290. According to some applications, the first housing portion 254*a* further comprises a first distal actuation opening 268*a* and a second distal actuation opening 268*b*, with the distal actuation openings 268*a* and 268*b* located on opposite sides of the distal wire opening 264 at the distal end of the housing 254, each of which is aligned with one of the sliding locking elements.

According to some applications, spring 256 can be any of a finger disc spring, a spring washer, a lift spring, a compression spring, or any other suitable spring. Each option represents a different example. According to some applications, spring 256 is a finger disc spring having at least one spring arm. According to some applications, spring 256 is a finger disc spring having at least two spring arms. According to some applications, spring 256 is a finger disc spring having at least three spring arms. According to some applications, spring 256 is a finger disc spring having a first spring arm 256*a* and a second spring arm 256*b*, as illustrated at FIG. 19. Advantageously, a spring 256 in the form of a finger disc spring can be provided with a relatively small-dimensioned, nearly flat profile, which has a much shorter length compared with compression springs, for example. This may enable size reduction of the locker 210$^b$, which should preferably be provided as a compact, small-dimensioned components, configured to optionally lock a wire in a cinched state, such as a wire 63 of an implant 180, and remain attached to the implant 180 within the patient's body, after completion of the implantation procedure.

According to some applications, the first sliding locking element 258*a* is movable over the first guide element 260*a*, configured to move there-along between open and closed states of the locker 210$^b$. According to some applications, the first spring arm 256*a* is disposed between the first sliding locking element 258*a* and a proximal internal wall of the housing 254, such as a proximal internal wall of the second housing portion 254*b*. The first spring arm 256*a* is configured to press against the first sliding locking element 258*a*, biasing it distally toward a distal internal wall of the housing 254, such as a distal internal wall of the first housing portion 254*a*, in a free closed state. Similarly, according to some applications, the second sliding locking element 258*b* is movable over the second guide element 260*b*, configured to move therealong between open and closed states of the locker 210$^b$. According to some applications, the second spring arm 256*b* is disposed between the second sliding locking element 258*b* and a proximal internal wall of the housing 254, such as a proximal internal wall of the second housing portion 254*b*. The second spring arm 256*b* is configured to press against the second sliding locking element 258*b*, biasing it distally toward a distal internal wall of the housing 254, such as a distal internal wall of the first housing portion 254*a*, in a free, closed state.

The first sliding locking element 258*a* and the second sliding element 258*b* can be configured in a variety of ways with a variety of different shapes and materials. In some applications, the first sliding locking element 258*a* and the second sliding element 258*b* can be two sides or halves of the same sliding component. In some applications, first sliding locking element 258*a* and the second sliding element 258*b* can comprise one or more of a conical shape, a semi-conical shape, a circular shape, a rectangular or cubic shape, opening(s), aperture(s), slot(s), strut(s), arm(s), leg(s), high-friction surfaces, etc. According to some applications, the first sliding locking element 258*a* comprises a high friction first surface 266*a* oriented toward the longitudinal axis 290 of the housing 254, and the second sliding locking element 258*b* comprises a high friction second surface 266*b* oriented toward the longitudinal axis 290 of the housing 254, such that both surfaces 266*a* and 266*b* are facing each other prior to extending a wire there-between, and are facing the wire (e.g., wire 63) when the wire extends through the locker 210$^b$.

In the exemplary illustrations, surfaces 266*a* and 266*b* are disposed at opposite sides of a wire extending there-between, such as first wire portion 62. The high friction surfaces 266*a* and 266*b* are configured to increase friction between a wire extending there-between, such as first wire portion 62, when engaged therewith. In a free state of the locker 210$^b$, the spring 256 is configured to bias both sliding locking elements 258 distally and toward each other, so as to press against, and engage with, the wire extending there-between, thereby locking wire in place in a closed state of the locker 210$^b$.

The high friction surfaces 266 can include surface features or surface treatment, configured to enhance friction thereof against a wire extending there-between. According to some applications, the surfaces 266*a* and 266*b* can be serrated surfaces. According to some applications, surfaces 266*a* and 266*b* comprise plurality of teeth, preferably oriented at a proximal angle to engage the wire 63, so as to prevent spontaneous sliding thereof when retained thereby, as illustrated at FIG. 19.

According to some applications, locker 210$^b$ comprises a clamping structure that is biased toward assuming a closed state (FIG. 20A), and can be flexed to an open state. In the closed state, the clamping structure is configured to clamp onto a wire extending therethrough, such as first wire portion 62. In the open state of the locker 210$^b$, a wire, such as first wire portion 62, can move freely therethrough, thereby enabling the wire to be pulled. For example, a first wire portion 62 can be pulled through a locker 210$^b$ in an open state thereof, until it sufficiently contracts the implant or annuloplasty structure 180, as described hereinabove. In the closed state, the locker 210$^b$ is configured to resist movement of the wire extending therethrough. For example, a first wire portion 62 can be locked within the locker 210$^b$ in the closed state, immovable with respect to the plurality of anchors 150 of implant 180.

According to some applications, in order to transition the locker 210$^b$ to the open state, an external pressure/force is induced on the first and second sliding locking elements 258*a* and 258$^b$, through first and second distal actuation openings 268*a* and 268$^b$ respectively, in a proximal direction 282, thereby pushing the elements 258*a* and 258*a*, respectively, against the spring 256, and optionally against the spring arms 256*a* and 256*b*, toward the rear internal wall of the housing 254, in order to distance the surfaces 266*a* and 266*b* of elements 258*a* and 258*b* away from the wire disposed there-between (e.g., first wire portion 62). This transitions the locker 210$^b$ to the open state, enabling the wire (e.g., first wire portion 62) to move freely through the locker 210$^b$.

According to some applications, each sliding locking element 258 comprises an inclined slot 288 having a proximal end 289, configured to accommodate a corresponding guide element 260, as shown in FIGS. 20A-20B. Each guide element 260 can be configured in a variety of different ways and with a variety of different materials, e.g., comprising one or more pin(s), rod(s), peg(s), ring(s), line(s), wire(s), etc. In some applications, each guide element 260 can be provided in the form of a pin or a rod, laterally extending between two sidewalls of the housing 254.

In some applications, the first sliding locking element 258*a* comprises a first inclined slot 288*a* accommodating the first guide element 260*a* therein, and the second sliding locking element 258*b* comprises a second inclined slot 288*b* accommodating the second guide element 260*b* therein. The guide elements 260 are affixed to the housing 254 and are immovable relative thereto, while each of the inclined slots 288 of the sliding locking elements 258 is slidable over the immovable guide elements 258. Each of the inclined slots 288 is inclined or angled with respect to the longitudinal axis 290 of the housing 254, such that the distal ends of the inclined slots 288 are closer to each other and to the longitudinal axis 290 of the housing 254, and the proximal end of the inclined slots 288 are farther away from each other and from the longitudinal axis 290 of the housing 254.

In some applications, the first sliding locking element 258*a* and the second sliding locking element 258*b* are configured to move over the first and second guide element 260*a* and 26*b*, respectively, along an angular path relative to the longitudinal axis 290, such that when they are pushed proximally in direction 282 from a closed state to an open state of the locker 210*b*, they simultaneously also move away from each other, thereby distancing their surfaces 266*a* and 266*a* away from each other, and/or from a wire extending there-between.

According to some applications, the default state of the locker is the closed state of the locker 210$^b$, whereby no external pressure or external force is induced on the locker 210$^b$, and spring 256 (e.g., first spring arm 256*a* and second spring arm 256*b*) is able to freely engage and press against elements 258*a* and 258*b*, thereby biasing them in a distal direction 284 toward a distal end of the housing 254. As a result, elements 258*a* and 258*b* are able to engage and clamp against a wire extending there-between, such as first wire portion 62, in order to lock it and prevent axial movement thereof. It is to be understood, that unless an external force is induced on the locker 210$^b$ as described herein, the locker 210$^b$ is configured to continuously maintain the closed state, and thereby to prevent any axial movement of a wire extending therethrough.

According to some applications, the housing 254 comprises inner angled walls 255, facing the elements 258, and each element 258 comprises a complementary angled outer surface 278 facing the inner walls of the housing 254, opposite to the high friction surfaces 266. The inner angled walls 255 may taper toward the axis 290 in the distal direction. The elements 258 are dimensioned so as to allow their outer surfaces 278 to contact and slide over the inner walls 255 of the housing 254. The angled orientation of the inner walls 255 and the outer surfaces 278 may advantageously facilitate smoother slidability of the elements 258 in the proximal and/or distal directions. Contrary to the high friction surfaces 266, the outer surfaces 278, as well as the inner walls 255, may be preferably designed with smooth surfaces, so as to enhance slidability thereof relative to each other.

Advantageously, the locker 210$^b$ (e.g., when equipped with a plurality of teeth angled proximally) can be a self-tightening locker, such that upon wire 63 being pulled distally, elements 258 slide further over the guide elements 260, distally and toward each other, thereby applying a stronger gripping force against the wire 63. According to some applications, the inclined slot 288 are dimensioned such that when the locker is in a closed or locked state, as shown in FIG. 20A, having both elements 258 pressing against a wire 63 extending there-between, a space or gap G' remains between the guide elements 260 and the proximal ends 289 of the inclined slots 288. This gap G' allow the elements 258 to move further toward each other and the wire 63 extending there-between, when the wire 63 is pulled distally, thereby enhancing the gripping force there-against.

According to some applications, in order to enable a wire extending through the locker 210$^b$ (e.g., first wire portion 62) to move freely through the locker 210$^b$ in the open state thereof, an external pressure/force is induced on elements 258*a* and 258$^b$, so as to push them in the proximal direction 282, by utilizing an actuation assembly 292, as illustrated at FIGS. 21A-21C. The actuation assembly 292 can be a component of the cinching system 200$^b$.

According to some applications, the actuation assembly 292 comprises an actuation element 274. The actuation element can be configured in a variety of different ways with a variety of different materials, e.g., comprising one or more of wire(s), rod(s), line(s), suture(s), tube(s), etc. In some applications, the actuation element 274 can be coupled to a first pressing arm 270*a* and a second pressing arm 270*b* by a hinged portion 286 located at a distal edge of actuation element 274. The first pressing arm 270*a* and the second pressing arm 270*b* are configured to encompass the locker 2106, e.g., as illustrated by FIGS. 21A-C. Each pressing arm 270 can include a proximal arm portion 271, hinged to the hinged portion 286 and extending away from the longitudinal axis 290 of the locker 210$^b$, a longitudinal arm portion 272, continuously extending from the proximal arm portion in a substantially longitudinal direction, for example—substantially parallel to the longitudinal axis 290 of the locker 210$^b$, and a distal arm portion 273, continuously extending from the longitudinal arm portion 272 toward the longitudinal axis 290 of the locker 210$^b$.

The actuation element 274 extends longitudinally along longitudinal axis 290 of the locker 210$^b$, proximal to the locker 210$^b$, such that the hinged portion 286 and both proximal arm portion 271*a* and 271*b* are positioned proximal to the locker 210$^b$. The length of each longitudinal arm portion 272*a* and 272*b* is longer than the length of the locker 210$^b$, such that the distal arm portions 273*a* and 273*b* are positioned distally with respect to the locker 210$^b$. Each pressing arm 270 comprises a pin 276 extending proximally from its distal arm portions 273. According to some applications, the actuation element 274 is a tube or a shaft having an internal lumen aligned with the proximal wire opening 262, through which the wire 62 can extend toward and through the locker 210$^b$.

In the closed state of the locker 210$^b$, the pressing arms 270 are oriented such that their pins 276 are positioned outside of the housing 254, and in particular, spaced away from the distal actuation openings 268. FIG. 21A shows the locker 210$^b$ in a closed state thereof, wherein the pins 276 are disengaged therefrom. As shown, the actuation element 274 can be positioned in a distal-most position, pressing the hinged portion 286 and the proximal arm portions 271 against the proximal end of the locker 210$^b$, such that both proximal arm portions 271 are oriented substantially perpendicularly to the longitudinal axis 290 of the locker 210$^b$.

According to some applications, each longitudinal arm portion 272 is angled at an obtuse angle with respect to the proximal arm portion 271, such that in the state shown in FIG. 21A, each longitudinal arm portion 272 is angled away from the locker 210$^b$ in the distal direction. Each distal arm portion 273 can be substantially perpendicular to the longitudinal arm portion 272, resulting in both distal arm portions 273, and the pins 276 extending therefrom, oriented away from the distal actuation openings 268.

FIG. 21B shows an intermediate state in a procedure of actuating the actuation assembly 292 to transition the locker 210$^b$ to an open state. As shown, the actuation element 274 is pulled proximally, distancing the hinged portion 286 away from the locker 210$^b$, such that the pressing arms 270 can pivot about the hinged portion 286 until the longitudinal arm portions 272 assume an orientation parallel to the longitudinal axis 290 of the locker 210$^b$, and are optionally pressed over the external surface of the housing 254, as shown in FIG. 21B. In this state, the pins 276*a* and 276*b* are aligned with the distal actuation openings 268*a* and 268*b*, respectively, but have not yet been inserted into the housing 254.

Applying further pull force to pull the actuation element 274 in a proximal direction 282, as shown in FIG. 21C, will facilitate entrance of the pins 276 into the distal actuation openings 268. The length of the pins 276 are chosen such that in this state, they can press against the distal ends of the elements 258 and push them in a proximal direction 282, sufficiently so as to transition the locker 210$^b$ to its open state, as described above with respect to FIG. 20B. Pushing the actuation element 274 in a distal direction, will release the pins 276 and revert the locker 210$^b$ back to the closed state, as shown in FIGS. 21A and 20A.

It is to be understood that the actuation assembly 292 described hereinabove serves as one optional assembly that can be utilized to selectively push the elements 258 in a proximal direction to transition the locker 210$^b$ to an open state, or release such force therefrom to allow the locker 210$^b$ to lock a wire extending therethrough, and that other mechanisms and assemblies, configured to selectively transition the locker 210$^b$ between the open and closed states thereof, can be used in combination therewith.

According to some applications, in order to enable a wire extending through the locker 210$^b$ (e.g., first wire portion 62) to move freely therethrough in the open state thereof, actuation element 274 is pulled in the proximal direction 282, thereby causing pins 276*a* and 276*b* to press elements 258*b* and 258*a*, respectively, in the proximal direction 282, as illustrated at FIG. 21C.

According to some applications, following the implantation of implant 180 around the annulus of the native valve (e.g., mitral valve 45, etc.) or other tissue region as described hereinabove, the internal catheter 20, and optionally, but not necessarily, the guide catheter 16, are retracted/extracted from the outer catheter 12, and the remaining section of wire 62 is inserted into a cinching system 200$^b$. The locker 210$^b$ is coupled to actuation assembly 292 and is configured to be advanced through either guide catheter 16 or outer catheter 12, to the vicinity of implant 180, in order to perform annuloplasty or tissue reshaping. According to some applications, in order to enable the first wire portion 62 to move freely through the locker 210$^b$ in the open state thereof (for annuloplasty or tissue reshaping purposes), the actuation assembly 292 is utilized in order to induce external pressure/force on elements 258 of the locker 210$^b$ as described hereinabove. Once the implant or annuloplasty structure at the native valve (e.g., at the mitral valve 45, etc.) or other tissue region has been sufficiently contracted, the locker 210$^b$ is configured to lock the first wire portion 62 extending therethrough utilizing the closed state thereof.

According to some applications, once the implant or annuloplasty structure at the native valve (e.g., mitral valve 45, etc.) or other tissue region has been sufficiently contracted by implant 180 by pulling the first wire portion 62 in the proximal direction through or along actuation assembly 292 and other components of the cinching system 200$^b$, the actuation element 274 is disengaged, thereby causing pins 276*a* and 276 to cease pressing against elements 258*b* and 258*a*, respectively, and optionally exit from the housing 254, as illustrated at FIG. 21B. Once the external force induced on the elements of the locker 210$^b$ by actuation assembly 292 is ceased, the locker 210$^b$ is configured to continuously maintain the closed state, and thereby lock and prevent any axial movement of the first wire portion 62 therethrough, effectively locking the implant 180 in a cinched or contracted state. Thereafter, the actuation assembly 292 can be decoupled from the locker 210$^b$ and extracted along with the rest of the cinching system 200$^b$.

According to some applications, a cutting and locking assembly 222$^b$ comprising the locker 210' is further configured to simultaneously lock and cut the first wire portion 62 extending therethrough. According to some applications, the locker 210$^b$ can further comprise a flap 232 attached to the housing 254, configured to trap any excess portions of the wire therein, in the same manner described hereinabove for locker 210$^a$, mutatis mutandis.

While shown as part of a cutting and locking assembly 222', it is to be understood that in other applications, the locker 210$^b$ can be used as a stand-alone component, which is not coupled to a cutting and locking assembly 222$^b$. Similarly, while described as a part of a cinching system 200$^b$, it is to be understood that the locker 210$^b$ can be used independently, and as a component of other systems, for locking wires, cables, sutures, and the like, that may extend therethrough.

While described for use in combination with an implant 180, utilized to lock a wire 63, and more specifically, a first wire portion 62 that may extend therethrough, it is to be understood the locker 210$^b$ can be similarly used with any other types of wires, cables, strings, sutures, and the like, that may extend therethrough and need to transition between a free state, in which it can move axially through the locker 210$^b$, and a locked state in which axial movement is inhibited.

It is to be understood that any of the applications described hereinabove, utilizing a locker 210 to lock a wire 63 of an implant 180, such as the wire 63$^c$ of implant 180$^c$, the wire 63 having both portions thereof extending through the locker 210, the wire 634 of the implant 1804, and the wire 63$^e$ of the implant 180$^e$, can be similarly utilized in combination with a locker 210$^b$, mutatis mutandis.

Figure 22:
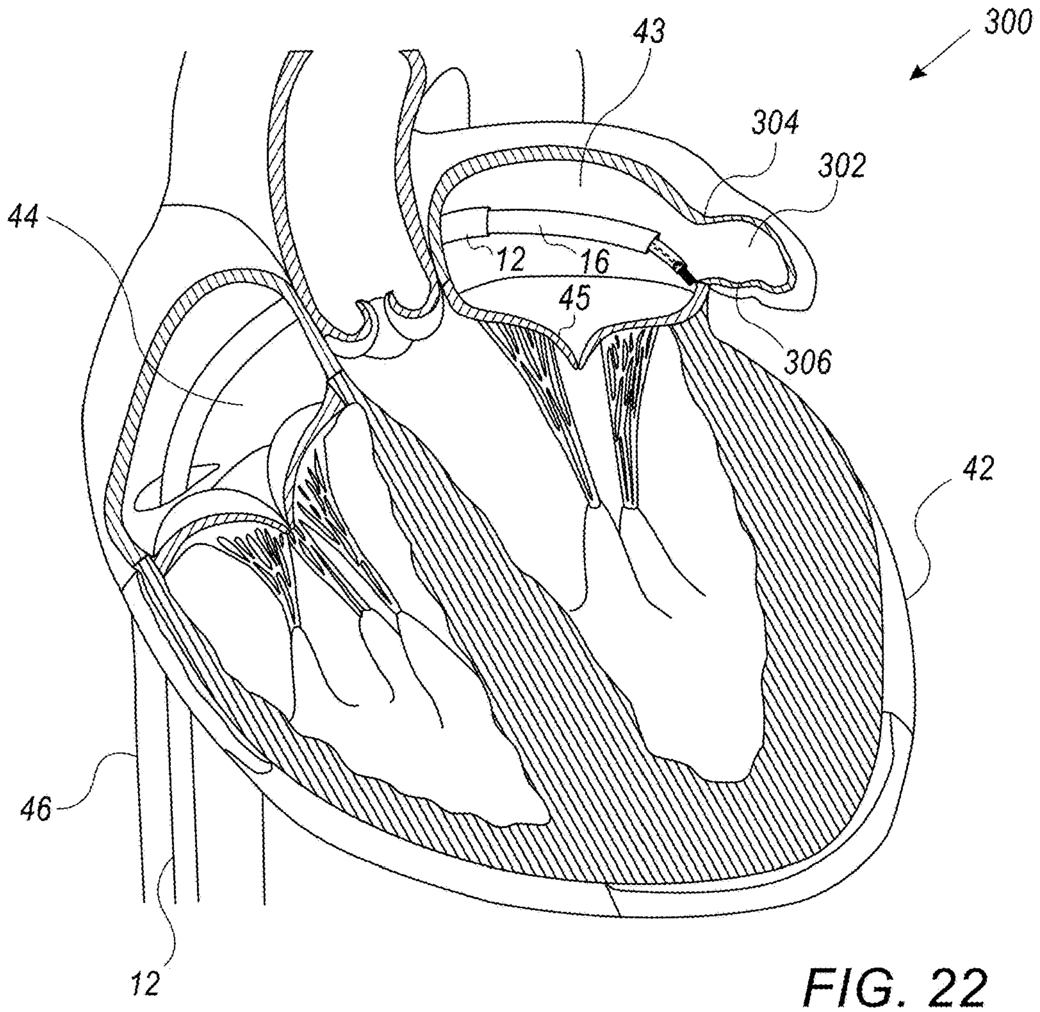
FIG. 22 is a schematic illustration of an example system advanced toward the left atrial appendage (LAA), according to some applications.

Reference is now made to FIGS. 22-30G. FIG. 22 is a schematic illustration of a system advanced toward and used to treat the left atrial appendage (LAA), according to some applications. While these FIGS. 22-30G are discussed with respect to the LAA primarily herein, the same or similar techniques, methods, steps, etc. can be used, mutatis mutandis, with respect to other tissue regions (e.g., another appendage, bulge, chamber wall, opening, gap, etc.).

According to some applications, there are provided herein several methods 300 for closure of the LAA ostium and/or closure of the LAA cavity, in order to prevent thrombus formation therein. These techniques and methods can be performed on a living animal or on a simulation, such as on a cadaver, cadaver heart, simulator (e.g., with the body parts, heart, tissue, LAA, etc. being simulated), etc.

As used herein, the term "closure of the LAA ostium" refers to contracting the ostium of the LAA, for example up to full contact between the borders of the ostium. Closure of the ostium may refer either to full closure of the opening defined by the ostium, thereby preventing fluid flow between the left atrium and the LAA, or to partial closure in a manner that does not necessarily results in full hermetical sealing of the opening defined by the ostium, but may result in narrowing the opening defined by the ostium sufficiently to reduce risks associated therewith, for example resulting in area reduction of the opening defined by the ostium such that large thrombi formed within the cavity of the LAA may be prevented from escaping into the left atrium.

According to some applications, methods 300 as described herein bellow, enable closure of the LAA ostium such that less than about 10%-50% of the ostium's opening area remains open and in fluid communication with the left atrium. According to some applications, methods 300 as described herein below, enable closure of the LAA ostium such that less than about 10% of the ostium's opening area remains open and in fluid communication with the left atrium. According to some applications, methods 300 as described herein bellow, enable closure of the LAA ostium such that less than about 5% of the ostium's opening area remains open and in fluid communication with the left atrium. According to some applications, methods 300 as described herein bellow, enable closure of the LAA ostium such that less than about 1% of the ostium's opening area remains open and in fluid communication with the left atrium.

As used herein, the term "closure of the LAA cavity" refers to contracting the internal surface of the LAA cavity, thereby providing full closure thereof, and preventing fluid flow from the left atrium thereto.

It is to be understood that while methods 300 are described hereinbelow and illustrated in FIGS. 22-30G with respect to closure of an LAA ostium or an LAA cavity, the same methods can be implemented for closure of any other tissue region, opening, or cavity within a patient's body in need thereof, mutatis mutandis. For example, any of the methods 300 described for closure of an LAA ostium can be implemented for closure of openings within the septum of the heart or opening in other organs that need to be closed. Similarly, methods 300 described for closure of an LAA cavity can be implemented for closure of other cavities, such as aneurysms and the like. In some applications, the same or similar techniques, methods, steps, etc. can be used to reshape a chamber wall and/or close off a portion of a heart wall (e.g., to isolate diseased or problematic tissue). In some applications, similar techniques, methods, steps, etc. can be used for reshaping valves, but without entirely closing the valves. These techniques, methods, and steps described herein can be performed on a living animal or on a simulation, such as on a cadaver, cadaver heart, simulator (e.g., with the body parts, heart, tissue, LAA, etc. being simulated), etc.

Reference is now made to FIGS. 22 and 23A-23G. According to some applications, a method 300 comprises method 300*a* for closure of an opening or tissue region within a patient's body, such as the LAA ostium 304, so as to limit or prevent fluid communication between the LAA cavity 302 and the left atrium 43 of a patient's heart 42, according to some applications. It is to be understood that the terms "LAA ostium" and "LAA cavity" can be replaced for "opening", "cavity", and/or "tissue region" for implementation of the method with other openings, cavities, and/or regions.

According to some applications, method 300*a* comprises providing an implant 310 to the vicinity of the LAA ostium 304 within the left atrium 43 of a patient's heart 42 utilizing a multicomponent system 10 that can include an outer catheter 12 and guide catheter 16 as described herein above. It is to be understood that all methods 300 described hereinbelow with respect to FIGS. 22-25C, utilizing a guide catheter 16 extending through an outer catheter 12, can be implemented in the same or similar manner utilizing an internal catheter 20 extending through the outer catheter 12 instead of the guide catheter 16. Thus, any reference to a guide catheter 16 and a distal end portion 18 thereof, can be equally replaced with an internal catheter 20 and a distal end portion thereof 22, respectively. Again, these techniques and methods can be performed on a living animal or on a simulation, such as on a cadaver, cadaver heart, simulator (e.g., with the body parts, heart, tissue, LAA, etc. being simulated), etc.

According to some applications, guide catheter 16, containing implant 310 is advanced through outer catheter 12 into left atrium 43. According to some applications, implant or structure 310 is loaded into guide catheter 16, either prior to, during or after advancing the guide catheter 16 into the left atrium 43. Distal end portion 18 of the guide catheter 16 extends beyond the distal end 14 of outer catheter 12. Distal end portion 18 is then steered (i.e., deflected) in a second steering plane, which can in some examples be perpendicular with respect to the steering plane of outer catheter 12, and further typically toward the LAA ostium 304.

Figure 23A:
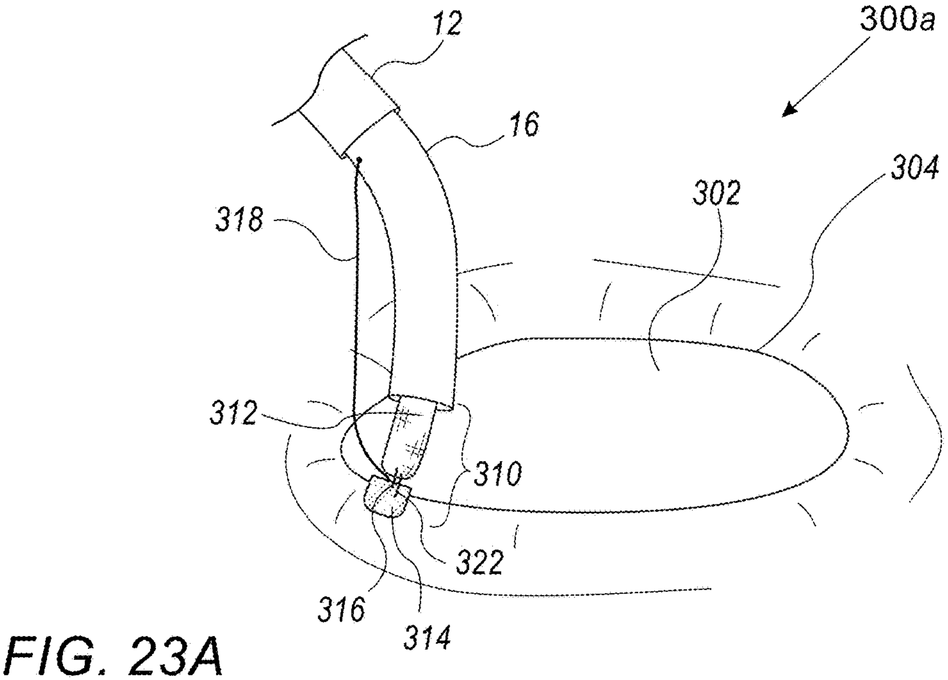
FIGS. 23A-23G are schematic illustration of example steps of a method for closure of an opening (e.g., LAA, or other opening), according to some applications.
Figure 23B:
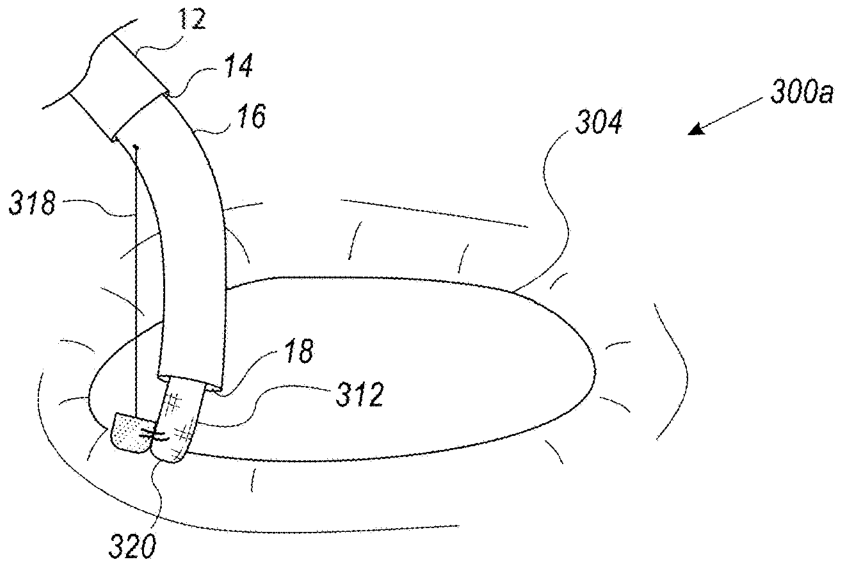

FIG. 23A shows implant 310 comprising a flexible sleeve 312 and an adjustment mechanism 314 having been advanced, via guide catheter 16, to the vicinity of opening the LAA ostium 204. According to some applications, sleeve 312 comprises a braided fabric mesh, e.g., comprising polyethylene terephthalate (such as Dacron™).

Sleeve 312 can be configured to be placed entirely or partially around the LAA ostium 304 and, once anchored in place, to be contracted so as to circumferentially tighten the ostium 304. According to some applications, sleeve 312 comprises a flexible elongated contraction member 322 that extends along sleeve 312. In some applications, elongated contraction member 322 comprises one or more of a wire, a ribbon, a rope, a band, a suture, etc., which can comprise a flexible and/or an elastic material, e.g., nitinol, polyester, stainless steel, or cobalt chrome. According to some applications, the adjustment mechanism 314 is configured to facilitate contracting the LAA ostium 304 so as to facilitate adjusting and tightening the circumferential perimeter thereof.

As is shown in FIG. 23A, during advancement of the implant or sleeved implant 310, the adjustment mechanism 314 is disposed distal to (i.e., in front of) the sleeve 312. The adjustment mechanism 314 can be coupled to the sleeve 312 via one or more connectors 316, such as sutures, which provide flexible and/or articulated coupling. A guide member 318 (e.g., a wire, ribbon, tube, band, suture, etc.), can extend distally from an opening located on the lumen of guide catheter 16 in the vicinity of its distal end portion 18 toward an end wall 320 of sleeve 312, wherein guide member 318 is coupled to the adjustment mechanism 314. The guide member 318 can be identical to wire 63 described hereinabove.

According to some applications, the implant 310 further comprises a plurality of anchors 324. Each one of the anchors 324 can be similar to anchor 150 described hereinabove, and more specifically, to anchor 150$^{a}$, but do not necessarily include an eyelet (158). Nevertheless, in some applications, anchors 324 do include eyelets 158.

According to some applications, the contraction member 322 is a wire that extends through the sleeve, along the sleeve, or is woven into a portion of the sleeve. In some applications, the plurality of anchors 324 are not directly connected to the contraction member 322, but just anchor the sleeve to the tissue, while the contraction member is separately connected to the sleeve (e.g., they are indirectly connected). In some applications, the plurality of anchors are directly connected to the contraction member, e.g., passing through eyelets thereof.

According to some applications, the contraction member 322 is a wire that couples adjustment mechanism 314 to sleeve 312 and/or to the plurality of anchors 324. According to some applications, the contraction member 322 is a wire that is coupled to guide member 318 via adjustment mechanism 314. According to some applications, the contraction member 322 and the guide member 318 are the same wire, extending through adjustment mechanism 314. The contraction member 322 can be identical to wire 63 described hereinabove.

Figure 23C:
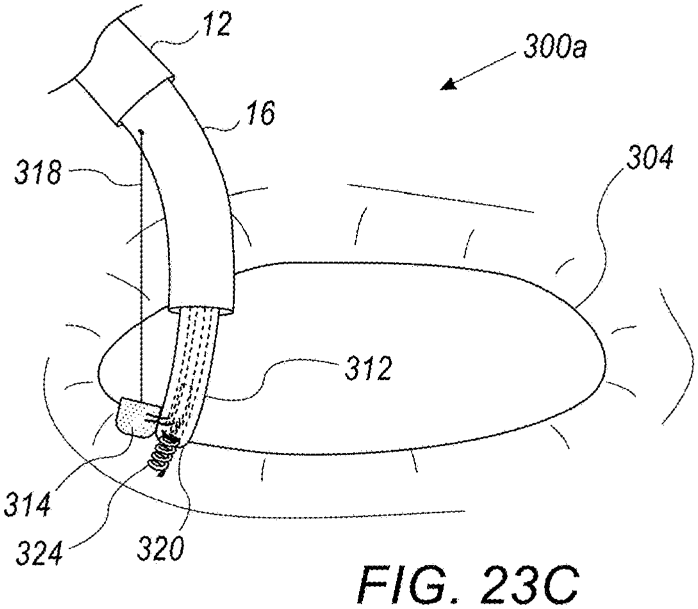
Figure 23D:
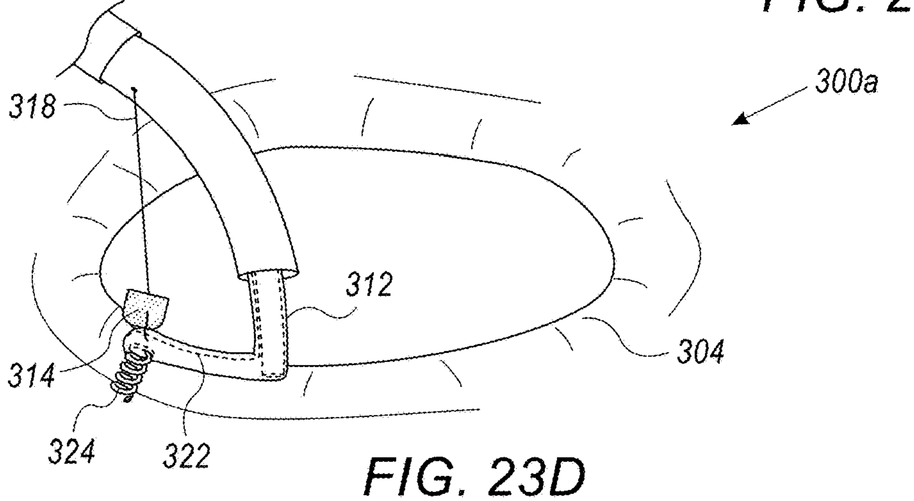

Anchors 324 can be deployed from within sleeve 312 and are anchored/penetrated therethrough around the tissue the LAA ostium 304 as illustrated in FIG. 23C, in order to attach an external surface of sleeve 312 thereto. Anchors 324 can be advanced and deployed from sleeve 312 utilizing a delivery tool such as any example of a delivery tool 160 described hereinabove, or any other suitable advancing and driving mechanism thereof.

Figure 23E:
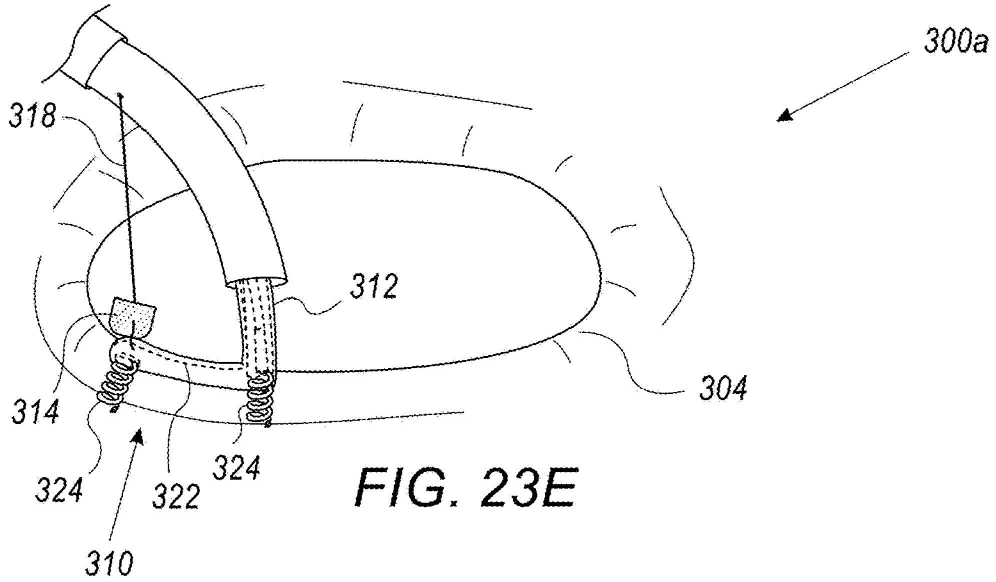

In some applications, the first tissue anchor 324 is deployed most distally in the sleeve 312 (generally at or within a few millimeters of the end wall 320 of sleeve 312), and each subsequent anchor 324 is deployed and anchored more proximally, and around the ostium 304. The already-deployed first one of anchors 324 holds the anchored end of sleeve 312 in place, so that the sleeve 312 is drawn from the site of the first tissue anchor 324 toward the site of the second tissue anchor 324, as illustrated at FIG. 23E, utilizing the steerable distal end portion 18 of the guide catheter 16.

Figure 23F:
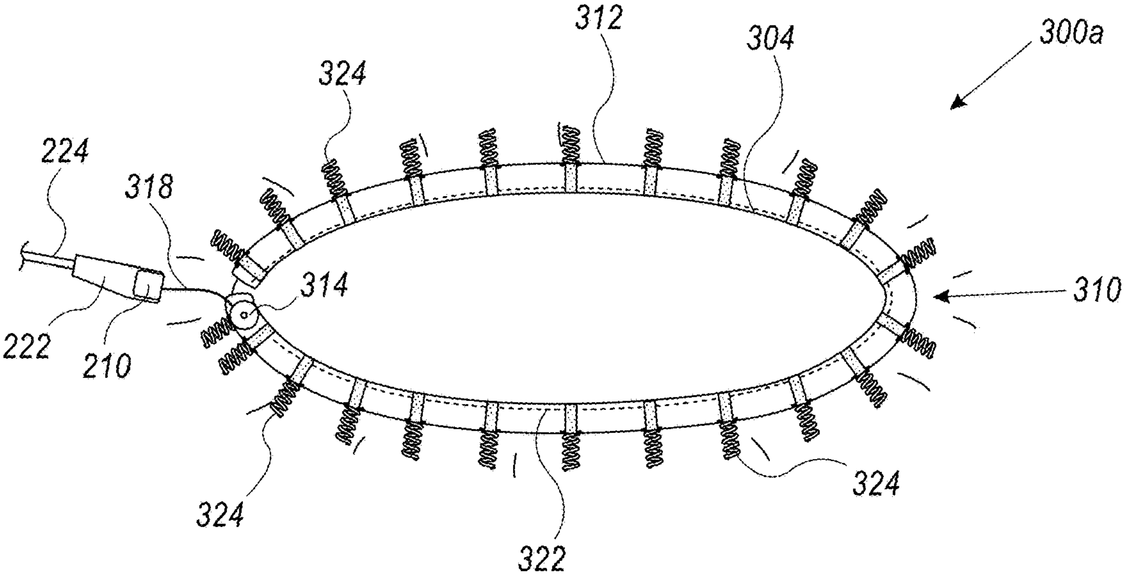

FIG. 23F shows the entire length of sleeve 312 having been anchored around LAA cavity 304, via the anchoring of anchors 324. According to some applications, the implanted sleeve 312 extends at least 270° around the LAA ostium 304. According to some applications, the implanted sleeve 312 extends between 270° and 360° around the LAA ostium 304. According to some applications, the implanted sleeve 312 extends between 270° and 280° around the LAA ostium 304. According to some applications, the implanted sleeve 312 extends between 280° and 290° around the LAA ostium 304. According to some applications, the implanted sleeve 312 extends between 290° and 300° around the LAA ostium 304. According to some applications, the implanted sleeve 312 extends between 300° and 310° around the LAA ostium 304. According to some applications, the implanted sleeve 312 extends between 310° and 320° around the LAA ostium 304. According to some applications, the implanted sleeve 312 extends between 320° and 330° around the LAA ostium 304. According to some applications, the implanted sleeve 312 extends between 330° and 340° around the LAA ostium 304. According to some applications, the implanted sleeve 312 extends between 340° and 350° around the LAA ostium 304. According to some applications, the implanted sleeve 312 extends between 350° and 360° around the LAA ostium 304. According to some applications, the implanted sleeve 312 extends between 270° and 320° around the LAA ostium 304. According to some applications, the implanted sleeve 312 extends between 320° and 360° around the LAA ostium 304.

In some applications, subsequently to anchoring the anchors around the LAA, an adjustment tool (not shown) is threaded over, and advanced along, the guide member 318. In some applications, the actuation mechanism comprises a spool, winch, spindle, etc. that can rotate in one direction to take up a portion of the contraction member, and rotate in the opposite direction to release a portion of the contraction member, thereby increasing or decreasing tension on the implant and thereby on the tissue region. In some applications, the adjustment tool can comprise a rotation tool, which is configured to actuate (e.g., rotate) the adjustment mechanism 314, so as to tension/tighten the contraction member 322 extending within the sleeve 312, and thereby contract the sleeve 312.

In some applications, subsequently to applying the tension to the implant using adjustment mechanism 314, the tension is maintained within the implant. In some applications, adjustment mechanism 314 comprises a locking mechanism that prevents reversing of the tightening (e.g., loosening) of the contraction member 322, thereby maintaining the contraction member 322 that extends within the sleeve 312 tightly tensioned.

Further details regarding sleeved implants, sleeves, adjustment mechanisms, and adjustment tools that can be used herein, including the manner in which such components are operated in order to anchor the implant into the tissue and contract or reshape tissue, are described in greater detail in International Publication Nos. WO 2016/174669 and WO 2020/012481, which are incorporated herein by reference in their entirety for all purposes.

In some applications, a locker 210, that can be similar to examples of the locker 210 described hereinabove, or to lockers that include at least some components of the lockers 210 described hereinabove, such as a flap 232, can be used instead of, or in combination with, an adjustment mechanism 314. For example, following the tightening of LAA ostium 304, the contraction member 322 can be locked, and any excess portions of contraction member 322 can be covered, utilizing a locker 210 as shown in FIG. 23F. Furthermore, in some applications, excess portions of contraction member 322 can be cut utilizing assembly 222, in a similar manner to that described for assemblies 222 hereinabove.

Figure 23G:
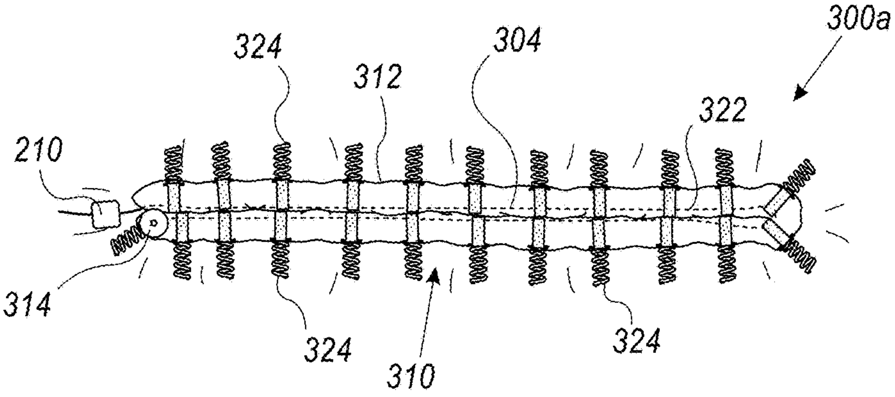

FIG. 23G shows full closure of the LAA ostium 304 utilizing sleeved implant 310 as described hereinabove. The shape of the LAA ostium 304 is, on most occasions, elliptical, such that tightening of the implant 310 may approximate opposite sides of the ostium 304 up to full contact there-between. However, in some instances, tightening of the implant 310 will not necessarily be sufficient to press the ostium borders to fully close the ostium's opening. According to some applications, the implant 310 is anchored such that a portion of the sleeve 312 can extend over the edge of the ostium 304. Advantageously, this configuration enables the portions of the sleeve 312 which extend inward over the edge of the ostium 304 to approximate each other, and potentially contact each other even of the tissue borders of the ostium 304 are not contacting each other, thereby forming a physical barrier over the gap between the borders of the ostium 304, which can facilitate sealing thereof.

Thus, according to some applications, a method **300*a* for closure or reduction of an opening within a patient's body, such as the LAA ostium 304, comprises a step of (a) providing an implant 310 as described hereinabove, wherein the implant 310 comprises: a flexible sleeve 312, an adjustment mechanism 314, a flexible elongated contraction member 322 that extends along sleeve 312, a guide member 318, and a plurality of anchors 324**. It is to be understood that the terms "LAA ostium" and "LAA cavity" can be replaced with "opening", "cavity", or "tissue region" for implementation of the method with other openings, cavities, and/or tissue regions.

According to some applications, the method further comprises a step of (b) advancing the implant 310 to vicinity of the LAA ostium 304 within the left atrium 43 of a patient's heart 42, utilizing outer catheter 12 and guide catheter 16, and/or internal catheter 20, of a system 10, as described hereinabove.

According to some applications, the method further comprises a step of (c) deploying a first anchor 324 from within the sleeve 312 and anchoring/penetrating it through the sleeve 312 into the tissue of the LAA ostium 304 at a first location.

According to some applications, the method further comprises a step of (d) deploying subsequent anchors 324 around the LAA ostium 304 at subsequent locations, wherein each location is distanced from a previous location by a minimum distance, thereby anchoring the entire length of the sleeve 312, via the plurality of anchors 324, around the LAA ostium 304, such that the sleeve 312 extends at least 270° around the LAA ostium 304, as described hereinabove.

According to some applications, the method further comprises a step of (e) applying tension to the contraction member 322 extending within sleeve 312, thereby contracting the LAA ostium 304, potentially closing it thereby.

According to some applications, the method further comprises a step of (f) locking any excess portions of contraction member 322 and optionally cutting it.

According to some applications, the minimum distance between anchor locations is at least about 0.1 mm. According to some applications, the minimum distance is at least about 1 mm. According to some applications, the minimum distance is selected from the range of about 1-100 mm. According to some applications, the minimum distance is selected from the range of about 1-50 mm. According to some applications, the minimum distance is selected from the range of about 1-30 mm. According to some applications, the minimum distance is selected from the range of about 3-20 mm. According to some applications, the minimum distance is selected from the range of about 5-15 mm. According to some applications, the minimum distance is selected from the range of about 7-12 mm.

Reference is now made to FIGS. 24A-24G. According to some applications, method 300 comprises method 300*b* for closure of the LAA ostium 304 utilizing a cloth 326, the method 300*b* comprising (a) providing multicomponent tubular system 10 configured to provide implant 180 to the vicinity of the LAA ostium 304, wherein system 10 comprises one, two, or more of: outer catheter 12, guide catheter 16, and internal catheter 20. The distal end portion 22 of the internal catheter 20 can be configured to pass through the guide catheter 16 or the outer catheter 12 (i.e., primary lumens thereof), to become disposed outside of the distal end portion 14 of the outer catheter 12 or the distal end portion 18 of the guide catheter 16, and to be oriented in a desired spatial orientation within the vicinity of the LAA ostium 304.

According to some applications, the method further comprises a step of (b) using system 10 to advance and deliver implant 180 to the tissue surrounding LAA ostium 304 within the left atrium 43 of patient's heart 42, wherein the implant 180 comprises: a plurality of anchors 150; a wire 63 comprising a first wire portion 62 which is configured to be advanced within a lumen of internal catheter 20 together with anchors 150, and a second wire portion 64 which is configured to extend between the anchors 150, and a cloth strip 326 which is advanced within either the internal catheter 20 or the guide catheter 16.

Figure 24A:
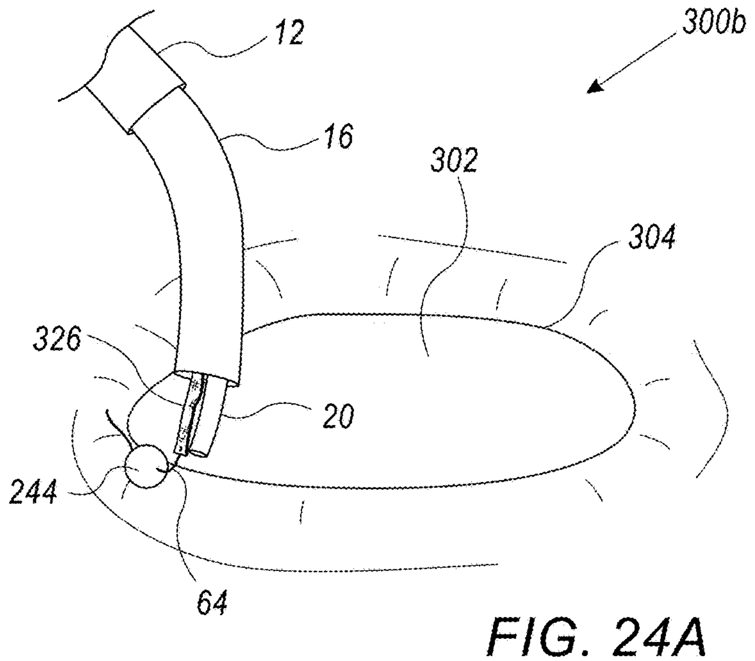
FIGS. 24A-24G are schematic illustration of example steps of a method for closure of an opening (e.g., LAA, or other opening), according to some applications.
Figure 24B:
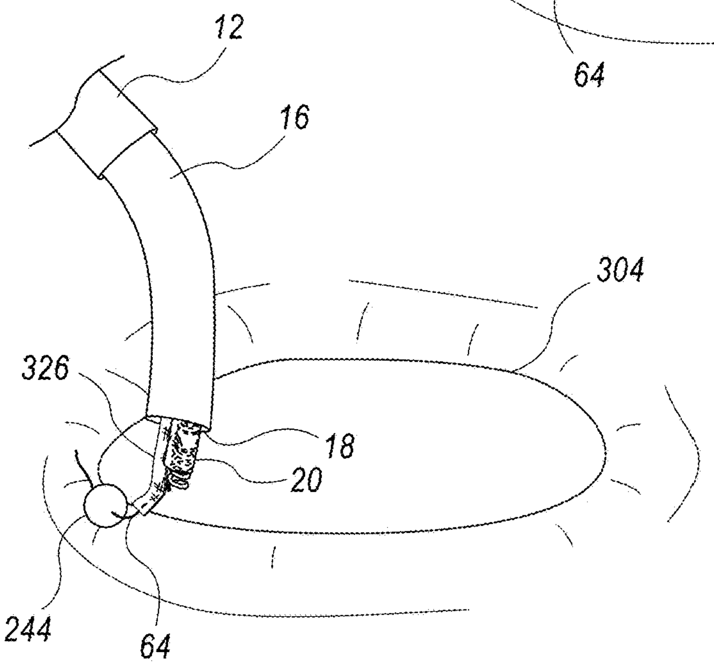
Figure 24C:
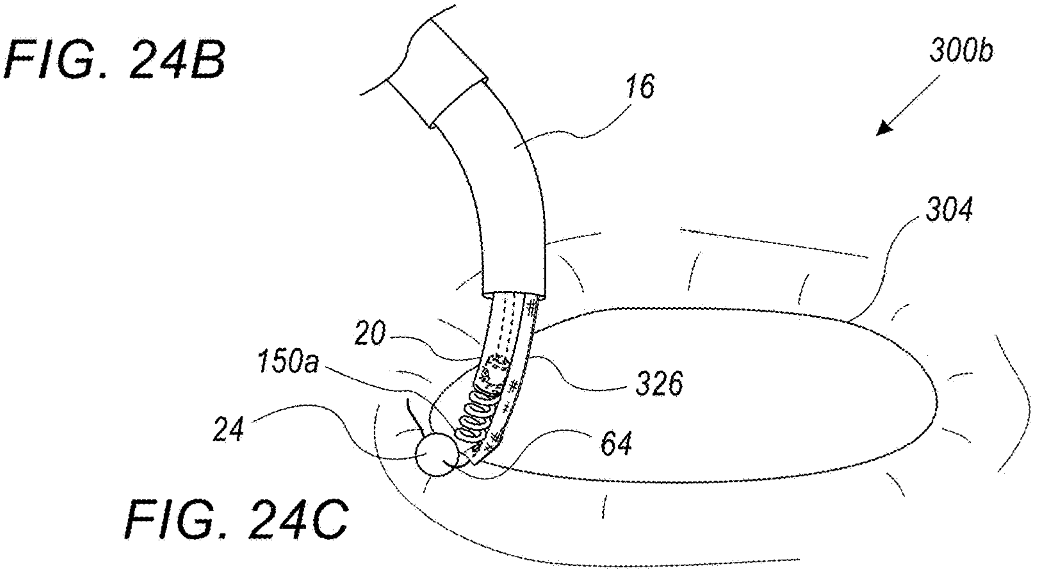

According to some applications, the method further comprises a step of (c) inserting and advancing the cloth strip 326 longitudinally through the lumen of either the internal catheter 20 or the guide catheter 16, and extracting it from distal end portion 22 of the internal catheter 20, or the distal end portion 18 of the guide catheter 16, respectively, in the distal direction within the left atrium 43 towards the LAA ostium 304, wherein at least a portion of the cloth strip 326 is positioned between distal end portion 22 of internal catheter 20 and a location along the tissue of opening 304 of LAA cavity 302 in which a first anchor 150*a* is to be anchored/driven through, as illustrated at FIGS. 24B and 24C.

According to some applications, the cloth strip 326 is attached, at a distal end thereof, to the first anchor 150*a*, and is advanced therewith through the internal catheter 20 toward the LAA ostium 304.

According to some applications, the method further comprises a step of (d) advancing a first anchor 150*a* longitudinally through the lumen of internal catheter 20 and driving it through the cloth strip 326 and into the tissue of the LAA ostium 304 at a first location by being reversibly engaged by anchor driver 161 as described hereinabove.

According to some applications, the cloth strip 326 is attached, at a distal end thereof, to the first anchor 150*a*, and is advanced therewith through the internal catheter 20 toward the LAA ostium 304, such that step (d) can include advancing a first anchor 150*a* carrying an end of a cloth strip 326 attached thereto through the lumen of internal catheter 20, and driving it into the tissue of the LAA ostium 304 at a first location by being reversibly engaged by anchor driver 161 as described hereinabove.

Figure 24D:
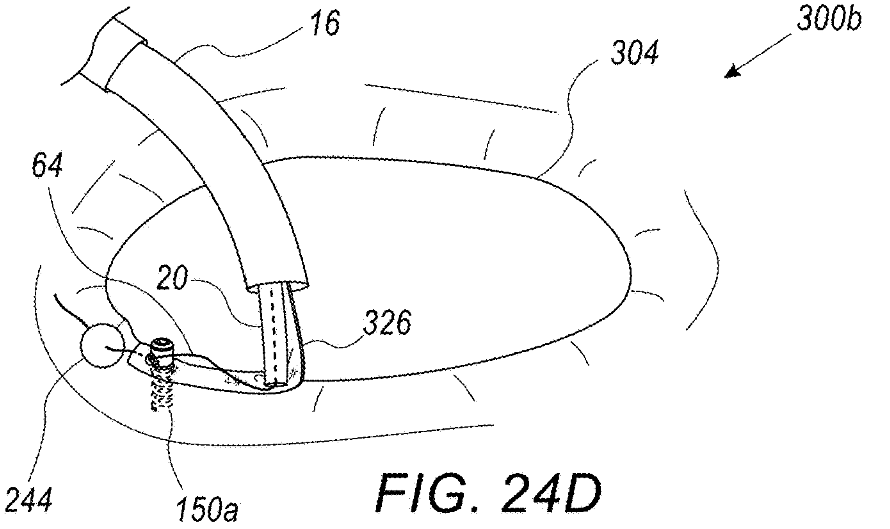
Figure 24E:
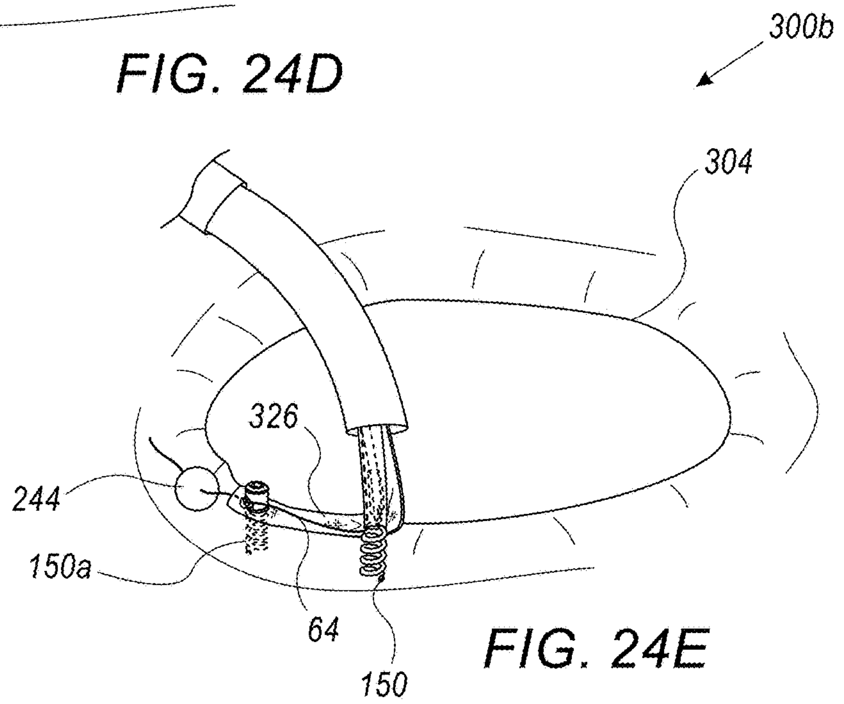
Figure 24F:
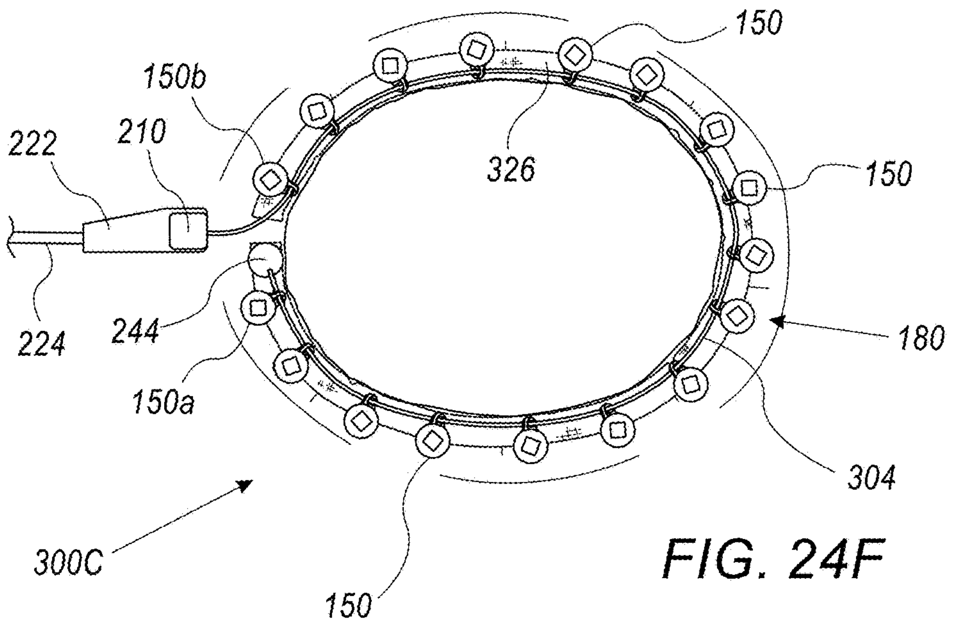

According to some applications, the first anchor 150*a* is coupled to a first stopper 244 via the second wire portion 64, as illustrated at FIG. 24D, thereby securing at least a portion of cloth strip 326 to the LAA ostium 304 at the first location;

According to some applications, the method further comprises a step of (e) deploying/driving subsequent anchors 150 through subsequent portions of cloth strip 326 at subsequent locations around the circumference of the LAA ostium 304, wherein each location is distanced from a previous location by the minimum distance, thereby anchoring implant 180 through cloth strip 326, via the plurality of anchors 150 and a wire 63 extending therebetween, such that the cloth strip 326 extends at least 270° around the LAA ostium 304, as illustrated in FIG. 24F, or extending around the LAA ostium 304 according to any examples described above with respect to a sleeve 312 extending around the ostium 304.

According to some applications, the method further comprises a step of (f) retracting/extracting the internal catheter 20, and optionally the guide catheter 16, from the outer catheter 12, and insertion of the remaining section of wire 63 which was disposed therein into a cinching system 200, wherein said system 200 comprises a locker 210, a cutting and locking assembly 222, and a cinching catheter 224, as illustrated in FIG. 24F.

Figure 24G:
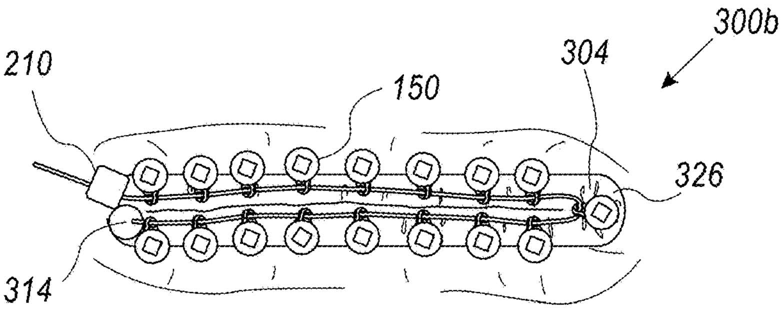

According to some applications, the method further comprises a step of (g) applying tension to the section of the wire 63 which was inserted into the system 200 during step (f) in the proximal direction through cinching catheter 224, in order to sufficiently contract the LAA ostium 304 for the purpose of closure thereof, as illustrated in FIG. 24G;

According to some applications, the method further comprises a step of (h) utilizing locker 210 and assembly 222 to cut and lock, potentially in a simultaneous manner, the section of wire 63 extending from final anchor 150*b* and passing therethrough, as described herein above, thereby locking implant 180, and optionally trapping any excess portions of the wire 63 therein, for example by utilizing a flap 232 as described hereinabove.

According to some applications, the method further comprises a step of (i) decoupling the assembly 222 from the locker 210, and extracting the assembly 222, along with the cinching catheter 224 connected thereto, from either the guide catheter 16 or the outer catheter 12, thereby leaving behind locker 210 attached to the implant 180.

It is to be understood that the multicomponent system 10 and the cinching system utilized for the method 300*b* described above, can be implemented according to any examples of the systems 10 and 200 described elsewhere within the current specification. It will be understood that an implant 180, comprising a plurality of anchors 150 and a wire 63, utilized for the method 300*b* described above, can be similar to other implants 180 described hereinabove, and in particular to implant 180$^e$ described hereinabove with respect to FIGS. 16-17.

FIG. 24G shows full closure of the LAA ostium 304 utilizing implant 180 and cloth strip 326 as described hereinabove with respect to method 300*b*. According to some applications, the cloth strip 326 is anchored such that a portion thereof can extend over the edge of the ostium 204. Advantageously, this configuration enables the portions of the cloth strip 326 which extend inward over the edge of the ostium 304 to approximate each other, and potentially contact each other or partially overlap each other, even if the tissue borders of the ostium 304 are not contacting each other after contraction of the implant 180, thereby forming a physical barrier over the gap between the borders of the ostium 304, which can facilitate sealing thereof.

According to some applications, cloth strip 326 is shaped as an elongated strip having dimensions suitable to be advanced within the lumen of either the internal catheter 20 of the guide catheter 16, and having a length suitable to surround at least 270° around the LAA ostium 304, at least 300° around the LAA ostium 304, at least 330° around the LAA ostium 304, at least 360° around the LAA ostium 304. Each possibility is a separate example.

According to some applications, cloth strip 326 comprises a biocompatible polymer such as polyethylene terephthalate (PET). Further examples of suitable polymers include, but are not limited to, copolymers of dimethylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes and polyurethane elastomers, polybutadiene, polyisoprene, poly(methacrylate), polymethyl methacrylate, styrene-butadiene-styrene block copolymers, poly(hydroxyethyl-methacrylate) (pHEMA), polyvinyl chloride, polyvinyl acetate, polyethers, polyacrylonitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, and combinations and variations thereof. Each possibility is a separate example.

Figure 25A:
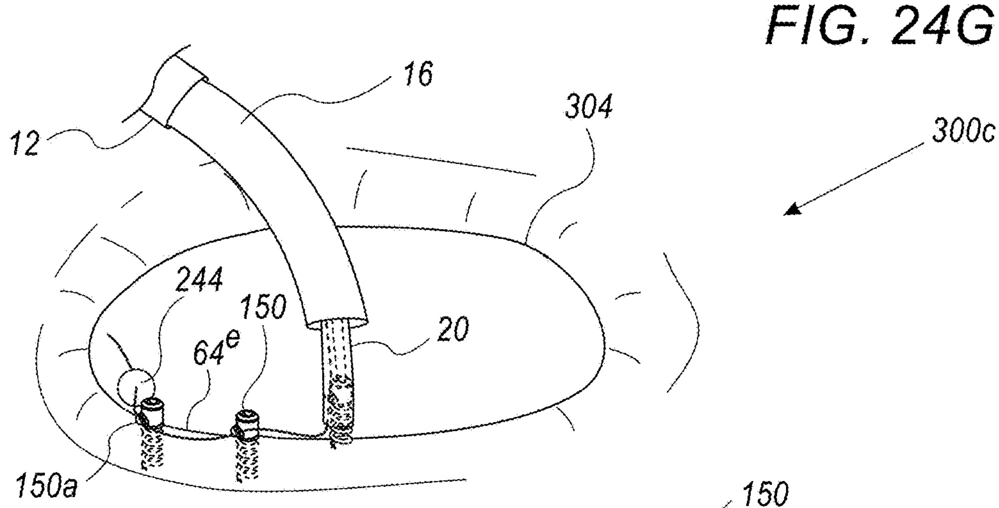
FIGS. 25A-25C are schematic illustration of example steps of a method for closure of an opening (e.g., LAA, or other opening), according to some applications.
Figure 25B:
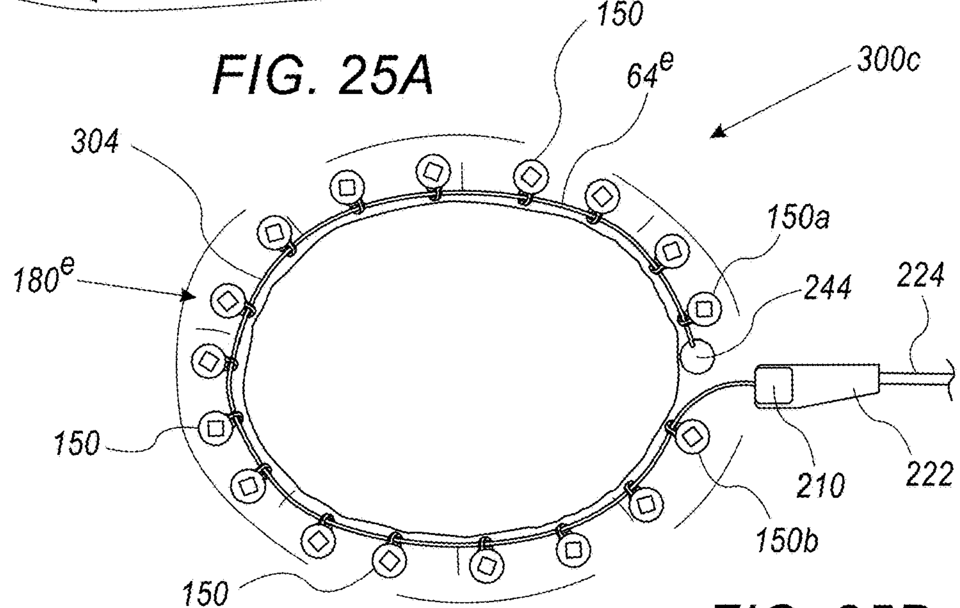
Figure 25C:
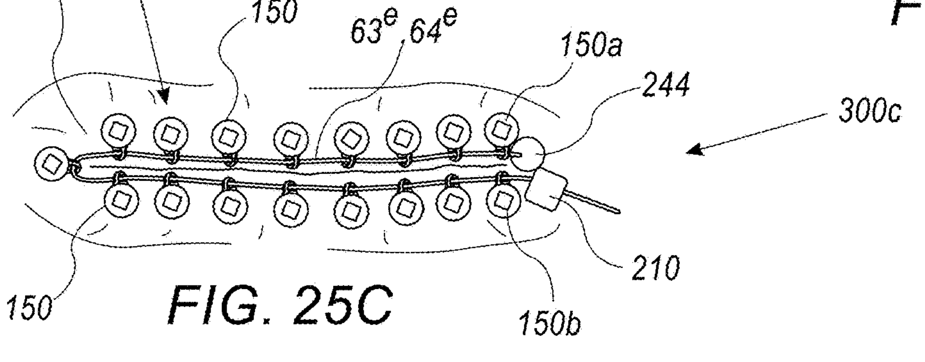

Reference is now made to FIGS. 25A-25C. According to some applications, method 300 comprises method 300*c* for closure of an opening or reshaping a tissue region within a patient's body, such as the LAA ostium 304 utilizing an implant 180$^e$, in combination with systems 10 and 200, as described hereinabove with respect to FIGS. 16-17.

According to some applications, the method 300*c* comprises the step of (a) providing multicomponent tubular system 10 configured to deliver implant 180$^e$ to the vicinity of the LAA ostium 304, wherein the system 10 comprises at least one, two, or more of: outer catheter 12, guide catheter 16, and internal catheter 20. According to some applications, the distal end portion 22 of the internal catheter 20 is configured to pass through the guide catheter 16 or the outer catheter 12 (i.e., primary lumens thereof), to become disposed outside of the distal end portion 14 of the outer catheter 12 or the distal end portion 18 of the guide catheter 16, and to be oriented in a desired spatial orientation within the vicinity of the LAA ostium 304. It is to be understood that the terms "LAA ostium" and "LAA cavity" can be replaced with "opening", "cavity", or "tissue region" for implementation of the method with other openings, cavities, and/or tissue regions.

According to some applications, the method further comprises a step of (b) using the system 10 to advance and deliver implant 180$^e$ to the tissue surrounding the LAA ostium 304 within the left atrium 43 of patient's heart 42, wherein implant 180$^e$ comprise a plurality of anchors 150 and a wire 63$^e$ comprising a first wire portion 62$^e$ which is configured to be advanced within a lumen of internal catheter 20, and along which anchors 150 are delivered, within the lumen of the internal catheter, to the heart, and a second wire portion 64$^e$ which is configured to extend between the anchors 150.

According to some applications, the method further comprises a step of (c) advancing a first anchor 150*a* longitudinally through the lumen of the internal catheter 20 and driving it into the tissue of LAA ostium 304 at a first location, using an anchor driver 161 that is reversibly engaged with the anchor, as described hereinabove, wherein the first anchor 150*a* is coupled to a first stopper 244 via second wire portion 64$^e$, as illustrated in FIG. 25A and further described hereinabove with respect to FIGS. 16-17.

According to some applications, the method further comprises a step of (d) deploying subsequent anchors 150 around the LAA ostium 304 at subsequent locations, wherein each location is distanced from a previous location by a minimum distance, thereby anchoring implant 180$^e$, via the plurality of anchors 150 and wire 63$^e$ extending therebetween, such that the implant 180$^e$ extends at least 270° around the LAA ostium 304, as illustrated in FIG. 25B, or extending around the LAA ostium 304 according to any examples described above with respect to a sleeve 312 extending around the ostium 304.

According to some applications, the minimum distance between anchor locations is at least about 0.1 mm. According to some applications, the minimum distance is at least about 1 mm. According to some applications, the minimum distance is selected from the range of about 1-100 mm. According to some applications, the minimum distance is selected from the range of about 1-50 mm. According to some applications, the minimum distance is selected from the range of about 1-30 mm. According to some applications, the minimum distance is selected from the range of about 3-20 mm. According to some applications, the minimum distance is selected from the range of about 5-15 mm. According to some applications, the minimum distance is selected from the range of about 7-12 mm.

According to some applications, the method further comprises a step of (e) retracting/extracting the internal catheter 20, and optionally the guide catheter 16, from the outer catheter 12, and insertion of the remaining section of wire 63$^e$ which was disposed therein into a cinching system 200, wherein said system 200 comprises a locker 210, a cutting and locking assembly 222, and a cinching catheter 224, as illustrated in FIG. 25B.

According to some applications, the method further comprises a step of (f) applying tension to the section of the wire 63$^e$ which was inserted into the system 200 during step (e) in the proximal direction through cinching catheter 224, in order to sufficiently contract the LAA ostium 304 for the purpose of closure thereof, as illustrated in FIG. 25C;

According to some applications, the method further comprises a step of (g) utilizing locker 210 and assembly 222 to cut and lock, potentially in a simultaneous manner, the section of wire 63$^e$ extending from final anchor 150*b* and passing therethrough, as described herein above, thereby locking implant 180, and optionally trapping any excess portions of the wire 63$^e$ therein, for example by utilizing a flap 232 as described hereinabove;

According to some applications, the method further comprises a step of (h) decoupling the assembly 222 from the locker 210, and extracting the assembly 222, along with the cinching catheter 224 connected thereto, from either the guide catheter 16 or the outer catheter 12, thereby leaving behind locker 210 attached to the implant 180$^e$.

While described and illustrated in combination with an implant 180$^e$, it is to be understood that in some applications, the method 300_c_ can be performed in a similar manner in combination with implants 180 described hereinabove so as to surround the entire perimeter of the LAA ostium 304, mutatis mutandis. For example, any of: the implant 180$^c$ described with respect to FIGS. 9A-9B, the implant 180 having both portions thereof pulled and locked within a locker as described with respect to FIGS. 13A-13B, and the implant 180$^d$ described with respect to FIGS. 15A-15C, can be utilized according to the steps of method 300_c_ and the required modifications, to anchor the above-mentioned implants and contract them around the LAA ostium 304 or another appendage or bulge instead of an annulus of a native valve.

Reference is now made to FIGS. 26A-26E. According to some applications, method 300 comprises method 300_d_ for closure of an opening or reshaping a tissue region within a patient's body, such as the LAA ostium 304, utilizing an implant 180$^e$, in combination with systems 10 and 200, as described hereinabove with respect to FIGS. 16-17. It is to be understood that the terms "LAA ostium" and "LAA cavity" can be replaced with "opening", "cavity", or "tissue region" for implementation of the method with other openings, cavities, and/or tissue regions.

According to some applications, the method 300_d_ comprises the step of (a) providing multicomponent tubular system 10 configured to deliver implant 180$^e$ to the vicinity of the LAA ostium 304, wherein the system 10 comprises at least one, two, or more of: outer catheter 12, guide catheter 16, and internal catheter 20. According to some applications, the distal end portion 22 of the internal catheter 20 is configured to pass through the guide catheter 16 or the outer catheter 12 (i.e., primary lumens thereof), to become disposed outside of the distal end portion 14 of the outer catheter 12 or the distal end portion 18 of the guide catheter 16, and to be oriented in a desired spatial orientation within the vicinity of the LAA ostium 304.

According to some applications, the method further comprises a step of (b) using the system 10 to advance and deliver implant 180$^e$ to the tissue surrounding the LAA ostium 304 within the left atrium 43 of patient's heart 42, wherein implant 180$^e$ comprise a plurality of anchors 150 and a wire 63$^e$ comprising a first wire portion 62$^e$ which is configured to extend within a lumen of internal catheter 20, and a second wire portion 64$^e$ which is configured to extend between the anchors 150.

Figure 26A:
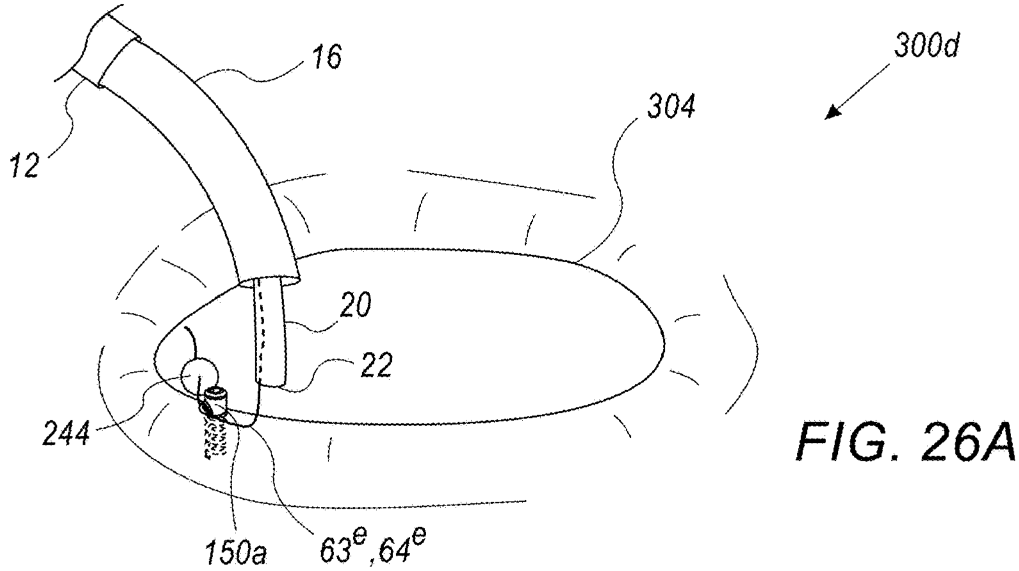
FIGS. 26A-26E are schematic illustration of example steps of a method for closure of an opening (e.g., LAA, or other opening), according to some applications.

According to some applications, the method further comprises a step of (c) advancing a first anchor 150_a_ longitudinally through the lumen of the internal catheter 20, while threaded onto first wire portion 62$^e$, and driving it into the tissue of LAA ostium 304 at a first location, by being reversibly engaged, using anchor driver 161 as described hereinabove, wherein the first anchor 150_a_ is coupled to a first stopper 244 via second wire portion 64$^e$, as illustrated in FIG. 26A and further described hereinabove with respect to FIGS. 16-17.

Figure 26B:
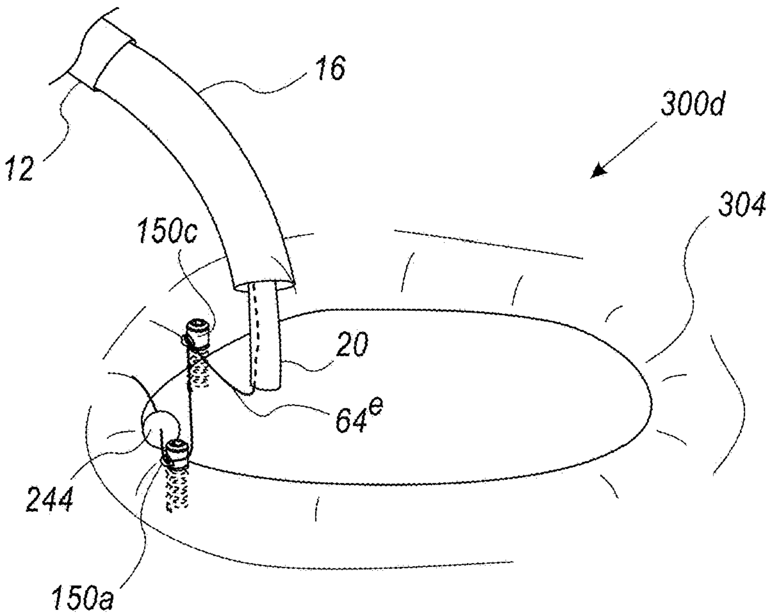
Figure 26C:
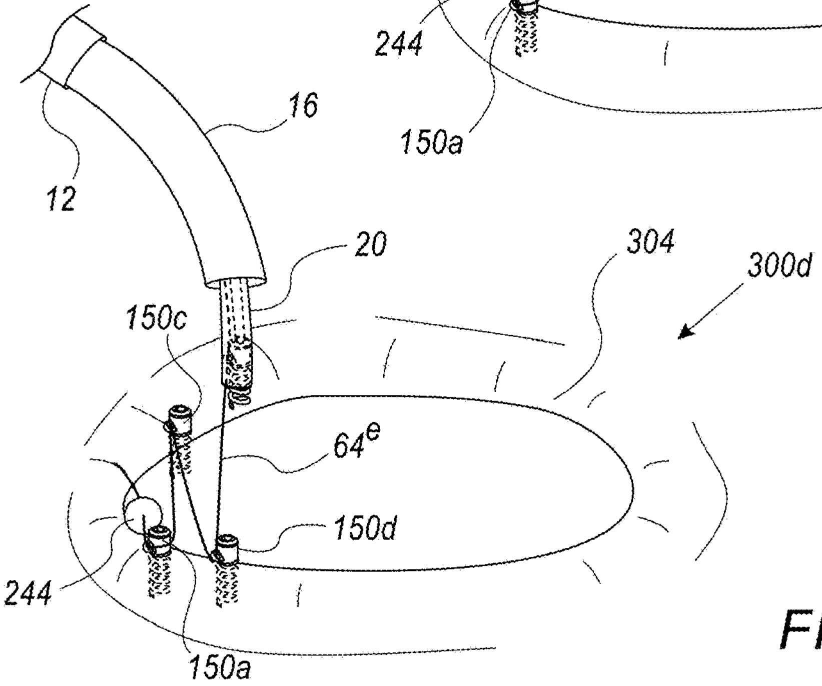

According to some applications, the method further comprises a step of (d) advancing a second anchor 150_c_ longitudinally through the lumen of internal catheter 20, while threaded onto first wire portion 62$^e$, and driving it into an opposite side of the LAA ostium 304 at a second location, using anchor driver 161 as presented herein above, wherein the second location is located at ostium 304 such that the first location and the second location are located on opposite sides thereof across the opening defined by the ostium 304, as illustrated in FIG. 26B;

According to some applications, the method further comprises a step of (e) advancing a third anchor 150_d_ longitudinally through the lumen of internal catheter 20 and driving it into the LAA ostium 304 at a third location, by being reversibly engaged by anchor driver 161 as presented herein above, wherein the third location is located at the ostium 304 such that the first location and the third location are located at the same side of the ostium 304 and are distanced from one another by the minimum distance, and the third location and the second location are located at opposite side of the ostium 304, as illustrated in FIG. 26C, the second wire portion 64$^e$, extending between anchors 150, thereby forming a an alternating pattern (i.e., zig-zag formation).

According to some applications, the method further comprises a step of (f) deploying subsequent anchors 150 at subsequent locations positioned at alternating sides of the tissue of LAA ostium 304, thereby anchoring implant 180$^e$, via the plurality of anchors 150 and wire 63$^e$ extending therebetween, around the ostium 304. The anchors are thus connected to each other, over the ostium 304, in a zig-zag formation between the first anchor 150_a_ and the final anchor 150_b_, as illustrated in FIG. 26D.

Figure 26D:
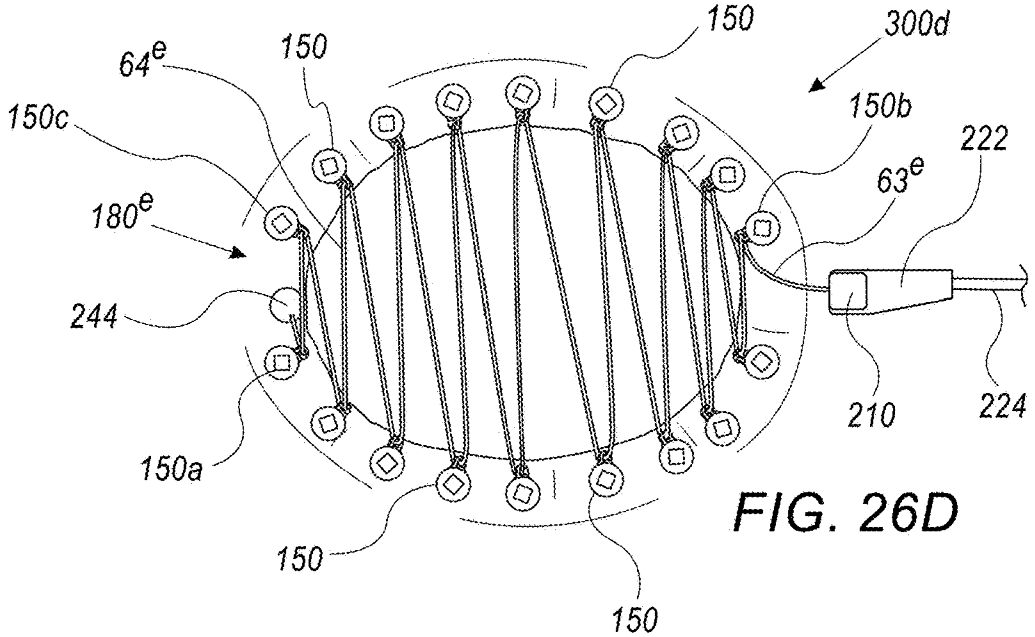

According to some applications, the method further comprises a step of (g) retracting/extracting the internal catheter 20, and optionally the guide catheter 16, from the outer catheter 12, and insertion of the remaining section of wire 63$^e$ which was disposed therein into a cinching system 200, wherein said system 200 comprises a locker 210, a cutting and locking assembly 222, and a cinching catheter 224, as shown in FIG. 26D.

Figure 26E:
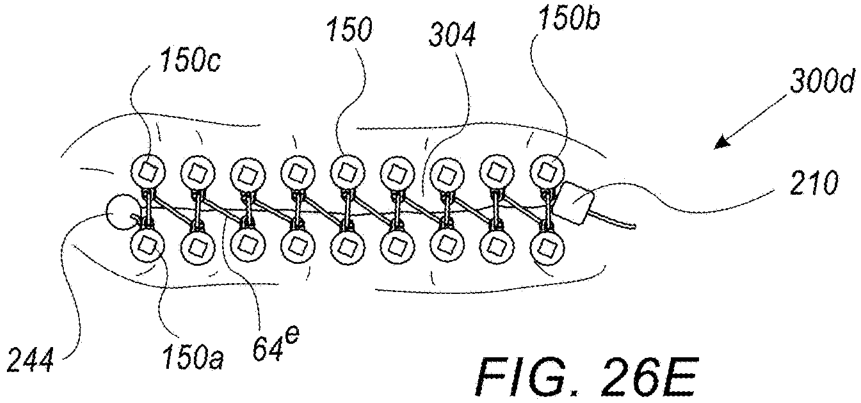

According to some applications, the method further comprises a step of (h) applying tension to the section of the wire 63$^e$ which was inserted into the system 200 during step (g) in the proximal direction through cinching catheter 224, in order to sufficiently contract the LAA ostium 304 for the purpose of closure thereof, as illustrated in FIG. 26E;

According to some applications, the method further comprises a step of (i) utilizing locker 210 and assembly 222 to cut and lock, potentially in a simultaneous manner, the section of wire 63$^e$ extending from final anchor 150_b_ and passing therethrough, as described herein above, thereby locking implant 180, and optionally trapping any excess portions of the wire portion 63$^e$ therein, for example by utilizing a flap 232 as described hereinabove.

According to some applications, the method further comprises a step of (j) decoupling the assembly 222 from the locker 210, and extracting the assembly 222, along with the cinching catheter 224 connected thereto, from either the guide catheter 16 or the outer catheter 12, thereby leaving behind locker 210 attached to the implant 180$^e$.

Reference is now made to FIGS. 23A-23G and FIGS. 26A-26E. It is to be understood that method 300_d_ described above with respect to FIGS. 26A-26E can be modified to extend an implant 310 described above, with respect to FIGS. 23A-23G, instead of the implant 180$^e$ having the wire 63$^e$. Thus, an implant 310 will be implanted so as to define an alternating pattern (i.e., zig-zag formation) across the LAA ostium 304 (or any other bodily opening), similar to that shown in FIG. 26D, mutatis mutandis. Advantageously, the additional contact area formed by the external surface of the sleeve 312 may provide additional material for covering and sealing the LAA ostium 304.

Reference is now made to FIGS. 27A-27D. According to some applications, methods 300 comprises method 300*e* for closure of an opening within a patient's body, such as the LAA ostium 304 utilizing an implant 180*c*, in combination with systems 10 and 200, as described hereinabove with respect to FIGS. 5-10B. It is to be understood that the terms "LAA ostium" and "LAA cavity" can be replaced with "opening", "cavity", and "tissue region" for implementation of the method with other openings, cavities, and/or tissue regions.

According to some applications, the method 300*e* comprises a step of (a) providing multicomponent tubular system 10 configured to deliver implant 180*c* to the vicinity of the LAA ostium 304, wherein the system 10 comprises at least two of: outer catheter 12, guide catheter 16, and internal catheter 20, wherein the distal end portion 22 of the internal catheter 20 is configured to pass through the guide catheter 16 or the outer catheter 12 (i.e., primary lumens thereof), to become disposed outside of the distal end portion 14 of the outer catheter 12 or the distal end portion 18 of the guide catheter 16, and to be oriented in a desired spatial orientation within the vicinity of the LAA ostium 304.

According to some applications, the method further comprises a step of (b) using the system 10 to advance and deliver implant 180*c* to the tissue surrounding the LAA ostium 304 within the left atrium 43 of patient's heart 42, wherein implant 180*e* comprise a plurality of anchors 150 and a wire 63*c* comprising a first wire portion 62*c* which is configured to extend within a lumen of internal catheter 20, and a second wire portion 64*c* which is configured to extend between the anchors 150, loop backward and extend through the internal space defined between the internal catheter 20 and either the guide catheter 16 or the outer catheter 12, in the proximal direction, further extending into, and potentially through, a respective catheter handle(s) to be exposed to outer environment.

Figure 27A:
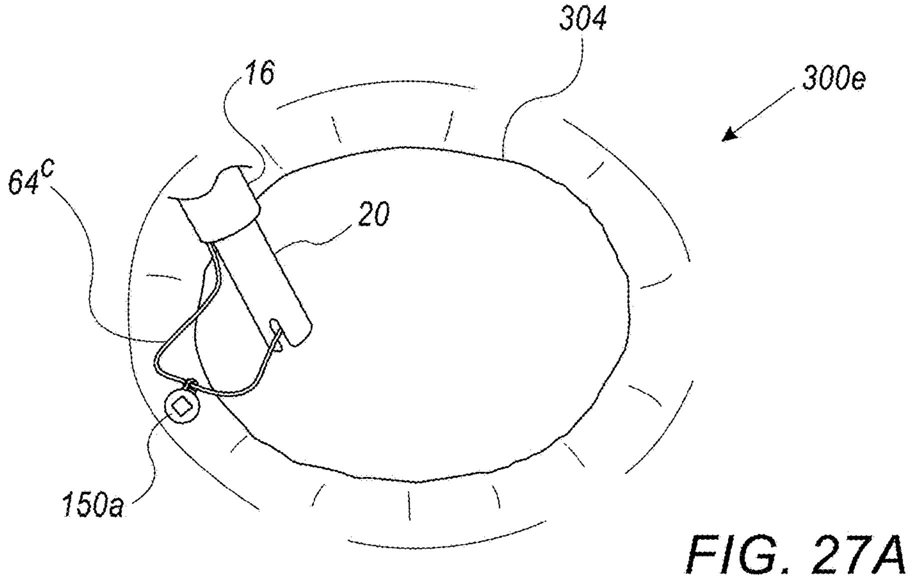
FIGS. 27A-27D are schematic illustration of example steps of a method for closure of an opening (e.g., LAA, or other opening), according to some applications.

According to some applications, the method further comprises a step of (c) advancing a first anchor 150*a* longitudinally through the lumen of the internal catheter 20, over first wire portion 62*c*, and driving it into the tissue of LAA ostium 304 at a first location, using anchor driver 161, as described hereinabove, wherein first anchor 150*a* is coupled to the second wire portion 64*c* such that at least a first segment of the second wire portion 64*c* is configured to extend through a plurality of anchors 150, and at least a second segment of the second wire portion 64*c* is configured to be disposed within the internal space defined between internal catheter 20 and either the guide catheter 16, as illustrated in FIG. 27A, or the outer catheter 12.

Figure 27B:
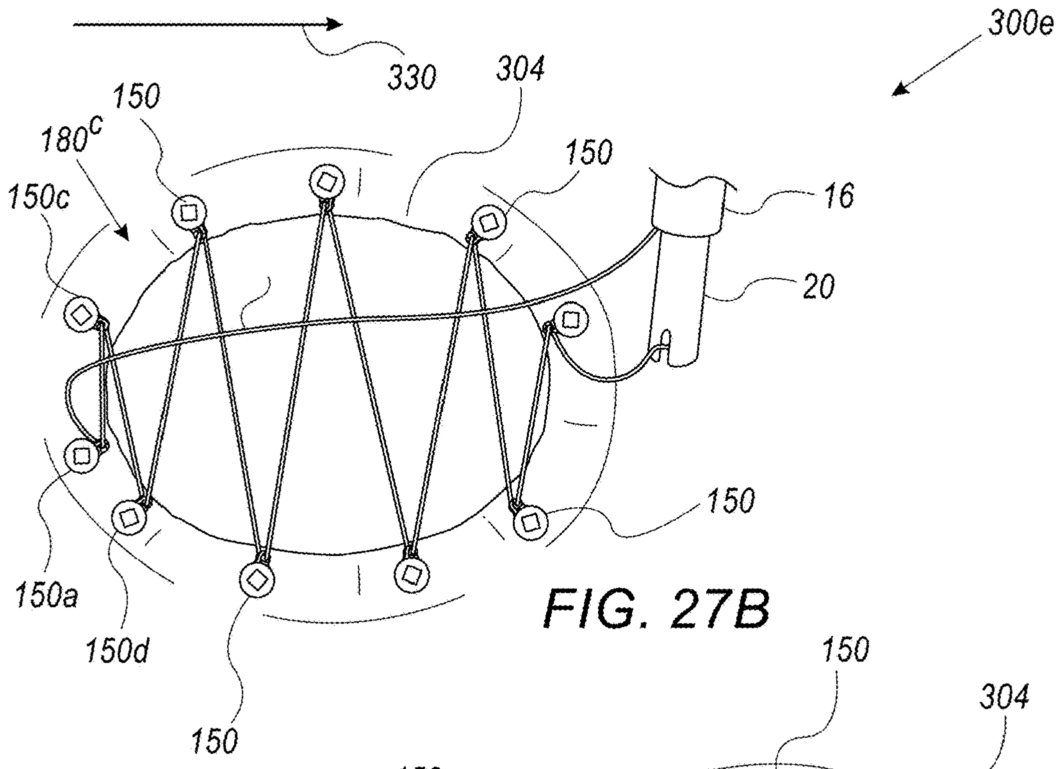

According to some applications, the method further comprises a step of (d) advancing a second anchor 150*c* longitudinally through the lumen of internal catheter 20 and driving it into an opposite side of the LAA ostium 304 at a second location, while being reversibly engaged by anchor driver 161 as presented herein above, wherein the second location is located at ostium 304 such that the first location and the second location are located on opposite sides thereof across the opening defined by the ostium 304, as illustrated in FIG. 27B;

According to some applications, the method further comprises a step of (e) advancing a third anchor 150*d* longitudinally through the lumen of internal catheter 20 and driving it into the LAA ostium 304 at a third location, while being reversibly engaged by anchor driver 161 as presented herein above, wherein the third location is located at the ostium 304 such that the first location and the third location are located at the same side of the ostium 304 and are distanced from one another by the minimum distance, and the third location and the second location are located at opposite side of the ostium 304, thereby forming a an alternating pattern (i.e., zig-zag formation) of the second wire portion 64*c* extending between anchors 150.

According to some applications, the method further comprises a step of (f) deploying subsequent anchors 150 at subsequent locations positioned at opposite sides of the tissue of LAA ostium 304, thereby anchoring implant 180*c*, via the plurality of anchors 150 and wire 63*c* extending therebetween, and connecting the anchors to each other over the ostium 304 following a zig-zag formation between the first anchor 150*a* and the final anchor 150*b*.

Figure 27C:
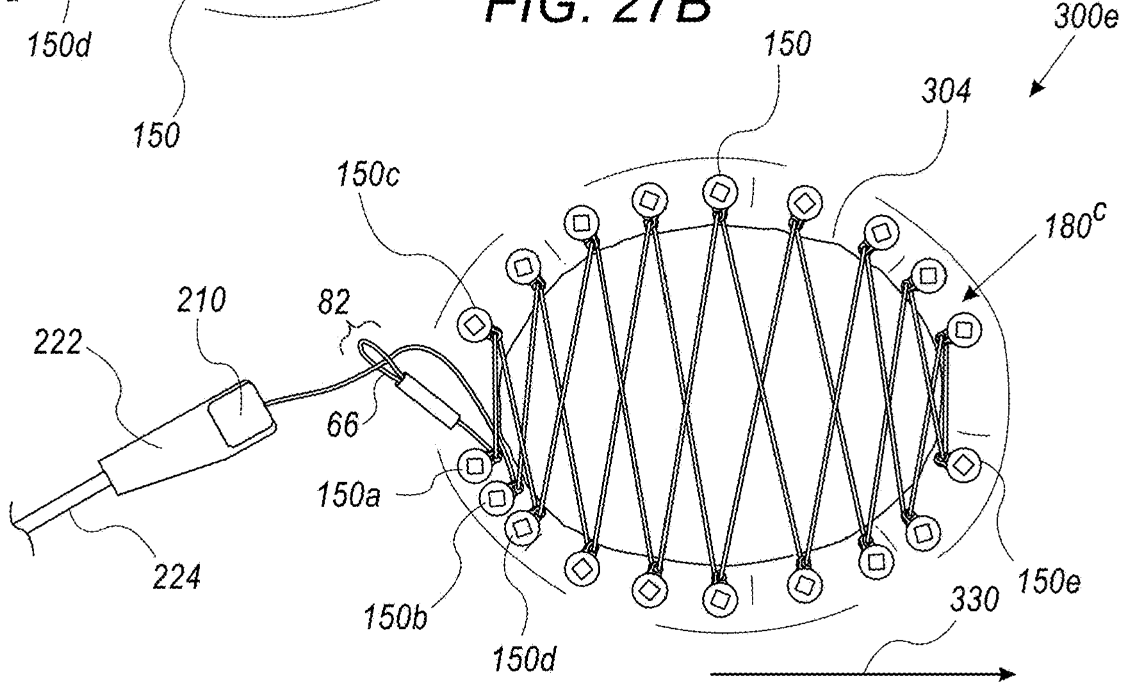

According to some applications, the method further comprises a step of (g) advancing in an opposite direction to longitudinal direction 330, shown as a direction parallel to the longer diameter of the LAA ostium 304, and deploying subsequent anchors 150 at subsequent locations positioned at opposite sides of the ostium 304, in order to form a double zig-zag formation over the ostium 304, wherein a final anchor 150*b* is implanted in the vicinity of first anchor 150*a*, as illustrated in FIG. 27C.

According to some applications, the method further comprises a step of (h) retracting/extracting the internal catheter 20, and optionally the guide catheter 16, from the outer catheter 12, such that an extracorporeal end of the first wire portion 62*c* is exposed to the external environment, and wherein both the first wire portion 62*c* and the second wire portion 64*c* extend through a single catheter, such as the guide catheter 16 or the outer catheter 12, optionally side by side.

According to some applications, the method further comprises a step of (i) inserting a proximal free end 78 of the first wire portion 62*c* through end-loop 66, or any other type of an end-portion retainer 82, optionally advancing the end-loop 66 toward the first anchor 150*a*, for example, and inserting the remaining section of the first wire portion 62*c* into a cinching system 200, wherein said system 200 comprises a locker 210, a cutting and locking assembly 222, and a cinching catheter 224.

According to some applications, the end-portion retainer 82 (e.g., loop 66) can be advanced through the guide catheter 16 and/or the outer catheter 12 toward the first anchor 150*a*, either by pulling the first wire portion 62*c* as described herein above, or with the aid of the assembly 222 pushing it distally through the respective catheter.

Figure 27D:
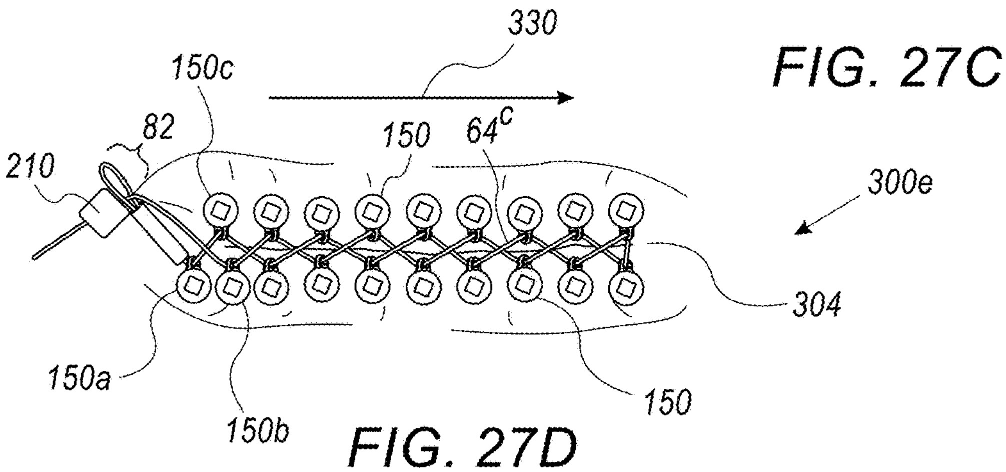

According to some applications, the method further comprises a step of (j) applying tension to the section of the wire 63*c* which was inserted into the system 200 during step (i) in the proximal direction through cinching catheter 224, in order to sufficiently contract the LAA ostium 304 for the purpose of closure thereof, as illustrated in FIG. 27D.

According to some applications, the method further comprises a step of (k) utilizing locker 210 and assembly 222 to cut and lock, potentially in a simultaneous manner, the section of wire 63*c* extending from the end-portion retainer 82 and passing therethrough, as described herein above, thereby locking implant 180, and optionally trapping any excess portions of the wire portion 63*c* therein, for example by utilizing a flap 232 as described hereinabove.

According to some applications, the method further comprises a step of (1) decoupling the assembly 222 from the locker 210, and extracting the assembly 222, along with the cinching catheter 224 connected thereto, from either the guide catheter 16 or the outer catheter 12, thereby leaving behind locker 210 attached to the implant $180^e$.

According to some applications, method 300*e* comprises implanting implant $180^c$ so as to surround the perimeter of the LAA cavity 304, similarly to the pattern of the implant $180^c$ surrounding an annulus described above with respect to FIGS. 9A-9B, instead of a zig-zag formation illustrated in FIGS. 27B-27D.

Figure 28A:
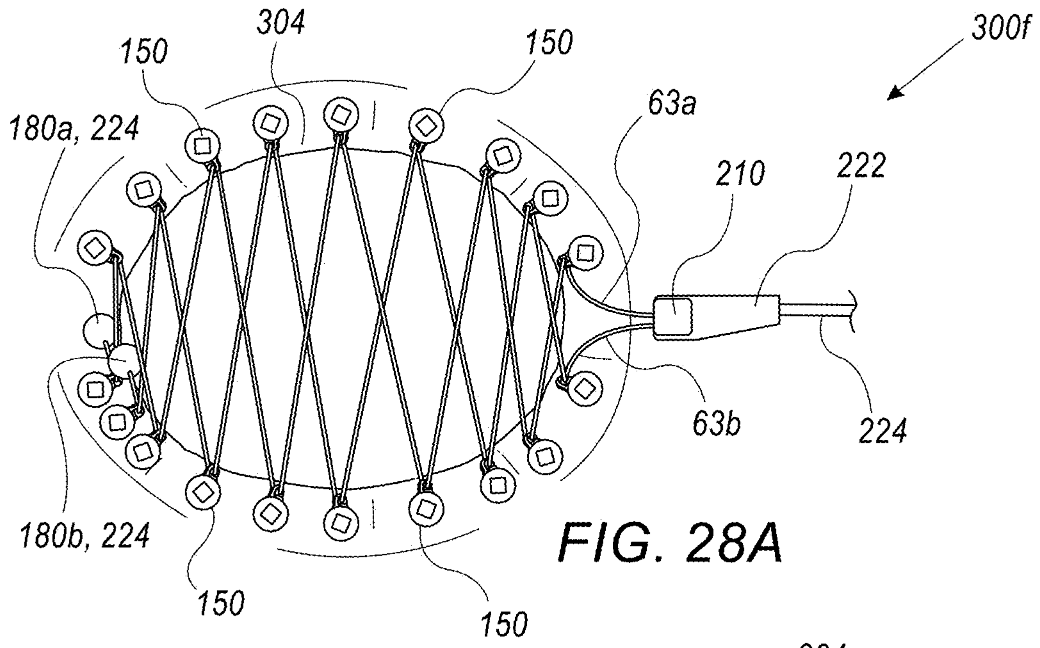
FIGS. 28A-28B are schematic illustration of example steps of a method for closure of an opening (e.g., LAA, or other opening), according to some applications.
Figure 28B:
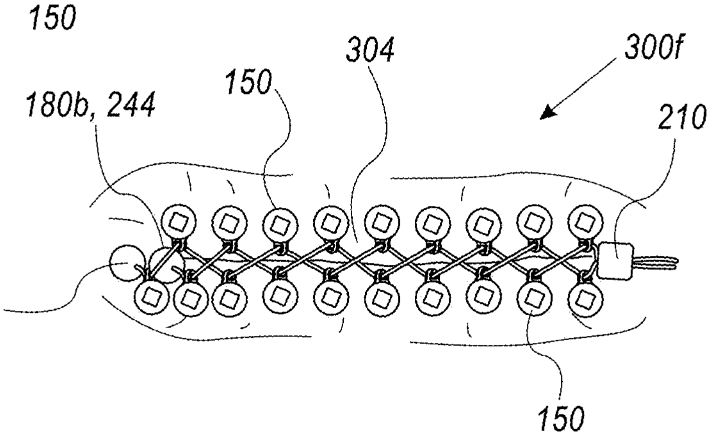

Reference is now made to FIGS. 28A-28B. According to some applications, methods 300 comprises method 300*f* for closure of an opening within a patient's body, such as the LAA ostium 304 utilizing an implant 180, in combination with systems 10 and 200, as described hereinabove with respect to FIGS. 13A-13B. It is to be understood that the terms "LAA ostium" and "LAA cavity" can be replaced with "opening", "cavity", and "tissue region" for implementation of the method with other openings, cavities, and/or tissue regions.

According to some applications, the method 300*f* can comprise steps that are similar to the steps of method 300*d* described above with respect to FIGS. 26A-26E described herein above. According to some applications, the method 300*f* comprises a step of (k) performing one, some, or all of steps (a)-(f) of method 300*d* described hereinabove, in order to anchor a first implant 180*a*, via the plurality of anchors 150 and a wire 63*a* extending therebetween, over the LAA ostium 304 forming a first zig-zag formation.

According to some applications, the method further comprises a step of (1) repeating steps (a)-(f) of method 300*d* as described hereinabove, in order to anchor a second implant 180*b*, via the plurality of anchors 150 and a wire 63*b* extending therebetween, over the LAA ostium 304 forming a second zig-zag formation, together forming a double zig-zag formation over the ostium 304 via implants 180*a* and 180*b*.

According to some applications, the method further comprises a step of (m) retracting/extracting the internal catheter 20, and optionally the guide catheter 16, from the outer catheter 12, wherein the remaining sections of a wire 63*a* of first implant 180*a* and a wire 63*b* of second implant 180*b* are inserted into cinching system 200. In some applications, the locker 210 of the system 200 comprises a double lumen configured to allow wire 63*a* of the first implant 180*a* and wire 63*b* of the second implant 180*b* to extend therethrough, in a manner similar to that described above with respect to FIGS. 13A-13B.

According to some applications, the method further comprises a step of (n) applying tension to the sections of wire 63*a* of the first implant 180*a* and wire 63*b* of the second implant 180*b* which were inserted into system 200 during step (m) in the proximal direction through cinching catheter 224, in order to sufficiently contract the LAA ostium 304 for the purpose of closure thereof, as illustrated in FIG. 28B;

According to some applications, the method further comprises a step of (o) utilizing locker 210 and assembly 222 to cut and lock, potentially in a simultaneous manner, the sections of wires 63*a* and 63*b* extending from the final anchors of implants 180*a* and 180*b*, respectively, thereby locking implant 180, and optionally trapping any excess portions of the wires 64*a* and 64*b* therein, for example by utilizing a flap 232 as described hereinabove.

According to some applications, the method further comprises a step of (p) decoupling the assembly 222 from the locker 210, and extracting the assembly 222, along with the cinching catheter 224 connected thereto, from either the guide catheter 16 or the outer catheter 12, thereby leaving behind locker 210 attached to implants 180*a* and 180*b*.

Reference is now made to FIGS. 29A-29E. According to some applications, methods 300 comprises method 300*g* for closure of an opening within a patient's body, such as the LAA ostium 304 utilizing an implant 1804, in combination with systems 10 and 200, as described hereinabove with respect to FIGS. 14-15C. It is to be understood that the terms "LAA ostium" and "LAA cavity" can be replaced with "opening", "cavity", or "tissue region" for implementation of the method with other openings, cavities, and/or tissue regions.

According to some applications, the method 300*g* comprises a step of (a) providing multicomponent tubular system 10 configured to deliver implant $180^c$ to the vicinity of the LAA ostium 304, wherein the system 10 comprises at least one, two, or more of: outer catheter 12, guide catheter 16, and internal catheter 20. According to some applications, the distal end portion 22 of the internal catheter 20 is configured to pass through the guide catheter 16 or the outer catheter 12 (i.e., primary lumens thereof), to become disposed outside of the distal end portion 14 of the outer catheter 12 or the distal end portion 18 of the guide catheter 16, and to be oriented in a desired spatial orientation within the vicinity of the LAA ostium 304.

According to some applications, the method further comprises a step of (b) using the system 10 to advance and deliver implant 180*d* to the tissue surrounding the LAA ostium 304 within the left atrium 43 of patient's heart 42, wherein implant $180^d$ comprise a plurality of anchors 150 and a wire 63*d* comprising a first wire portion $62^d$ which is configured to extend within a lumen of internal catheter 20, and a second wire portion $64^d$ which is configured to extend between the anchors 150.

According to some applications, the second wire portion $64^d$ further loops backward and extends through the internal space defined between the internal catheter 20 and either the guide catheter 16 or the outer catheter 12, in the proximal direction, further extending into, and potentially through, a respective catheter handle(s) to be exposed to outer environment, wherein the extracorporeal end of the second wire portion $64^d$ comprises a terminal clamp 240. In some applications, the terminal clamp 240 is coupled to the first anchor 150*a* via second wire portion $64^d$, ready to be advanced therewith toward the tissue. Further details of both applications are elaborated above with respect to FIGS. 14-15C.

According to some applications, the method further comprises a step of (c) advancing a first anchor 150*a* longitudinally through the lumen of the internal catheter 20, while threaded over first wire portion $62^d$, and driving it into the tissue of the LAA ostium 304 at a first location, using anchor driver 161, as described hereinabove.

Figure 29A:
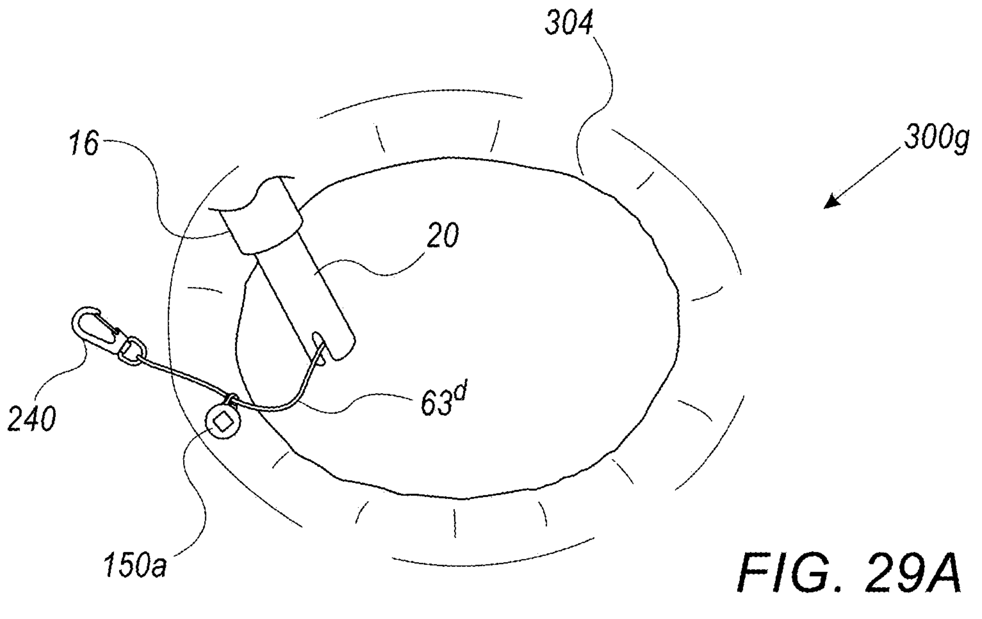
FIGS. 29A-29E are schematic illustration of example steps of a method for closure of an opening (e.g., LAA, or other opening), according to some applications.

According to some applications, wherein the terminal clamp 240 is coupled to the first anchor 150*a*, it is advanced therewith toward the LAA ostium, as illustrated in FIG. 29A.

Figure 29B:
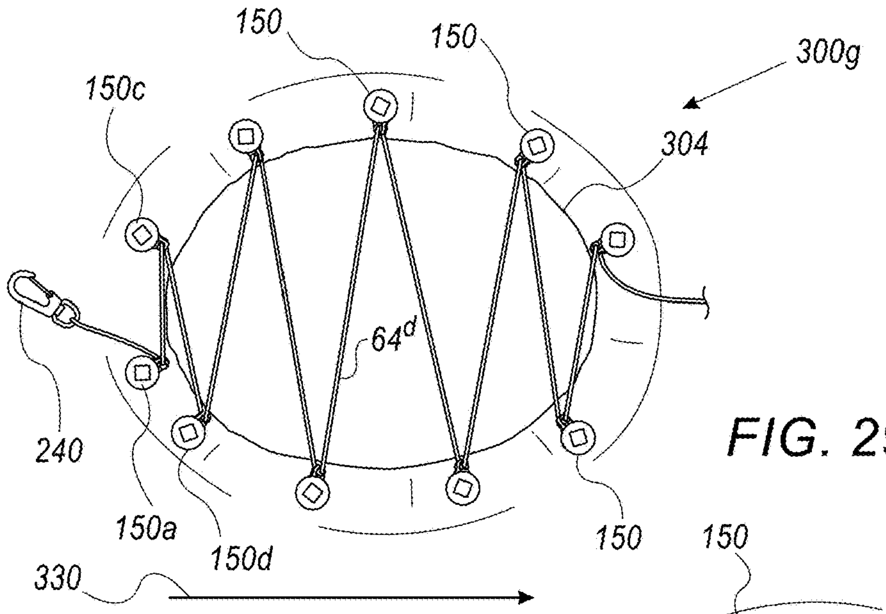

According to some applications, the method further comprises a step of (d) advancing a second anchor 150*c* longitudinally through the lumen of internal catheter 20 and driving it into an opposite side of the LAA ostium 304 at a second location, while being reversibly engaged by anchor driver 161 as presented herein above, wherein the second location is located at ostium 304 such that the first location and the second location are located on opposite sides thereof across the opening defined by the ostium 304, as illustrated in FIG. 29B;

According to some applications, the method further comprises a step of (e) advancing a third anchor 150*d* longitudinally through the lumen of internal catheter 20 and driving it into the LAA ostium 304 at a third location, by being reversibly engaged by anchor driver 161 as presented herein above, wherein the third location is located at the ostium 304 such that the first location and the third location are located at the same side of the ostium 304 and are distanced from one another by the minimum distance, and the third location and the second location are located at opposite side of the ostium 304, thereby forming a an alternating pattern (i.e., zig-zag formation) of the second wire portion $64^d$ extending between anchors 150.

According to some applications, the method further comprises a step of (f) advancing along the longitudinal direction 330 and deploying subsequent anchors 150 at subsequent locations positioned at alternating sides of the ostium 304 of LAA, thereby anchoring implant $180^d$, via the plurality of anchors 150 and wire $63^d$ extending therebetween, over the ostium 304 along a zig-zag formation as illustrated in FIG. 29B. According to some applications, a halfway anchor 150*e* shown in FIG. 29B, distanced on an opposite end of the ostium 304 at the longitudinal direction 330 from the first anchors 150*a*, is the last anchor to be implanted during the current step.

Figure 29C:
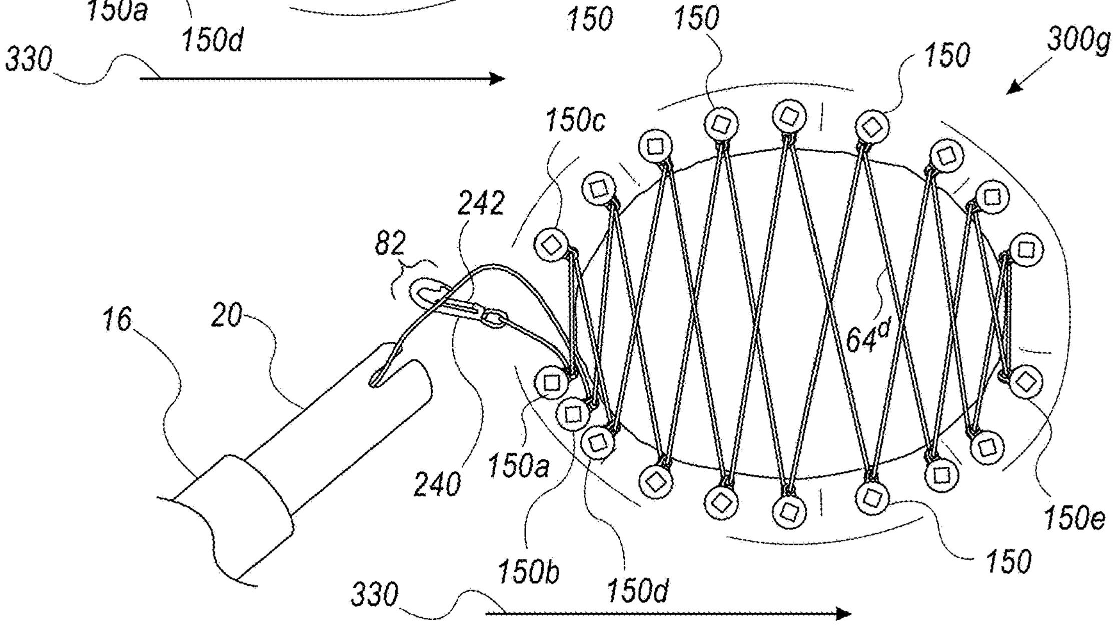

According to some applications, the method further comprises a step of (g) advancing in an opposite direction to longitudinal direction 330 and deploying subsequent anchors 150 at subsequent locations positioned at opposite sides of the tissue of ostium 304, in order to form a double zig-zag formation over the ostium 304, wherein a final anchor 150*b* is implanted in the vicinity of first anchor 150*a*, as illustrated in FIG. 29C.

According to some applications, wherein the terminal clamp 240 is disposed next to the first anchor 150*a*, the method further comprises a step of (h) steering/maneuvering the distal end portion 22 of the internal catheter 20 to enable a section of the wire 634, which extends from the final anchor 150*b*, to be inserted into terminal clamp 240 through a spring biased gate 242 attached thereto, as illustrated at FIG. 29C.

According to some applications, the method further comprises a step of (i) retracting/extracting the internal catheter 20, and optionally the guide catheter 16, from the outer catheter 12.

Not all steps are required, and the steps can be performed in different orders. For example, according to some applications, wherein the terminal clamp 240 was disposed out of the patient's body instead of in the vicinity of the first anchor 150*a*, the step (i) is performed after step (g), and includes inserting a proximal end 78 of the first wire portion $62^d$ through the terminal clamp 240, and advancing the terminal clamp 240 toward the first anchor 150*c*, for example.

Figure 29D:
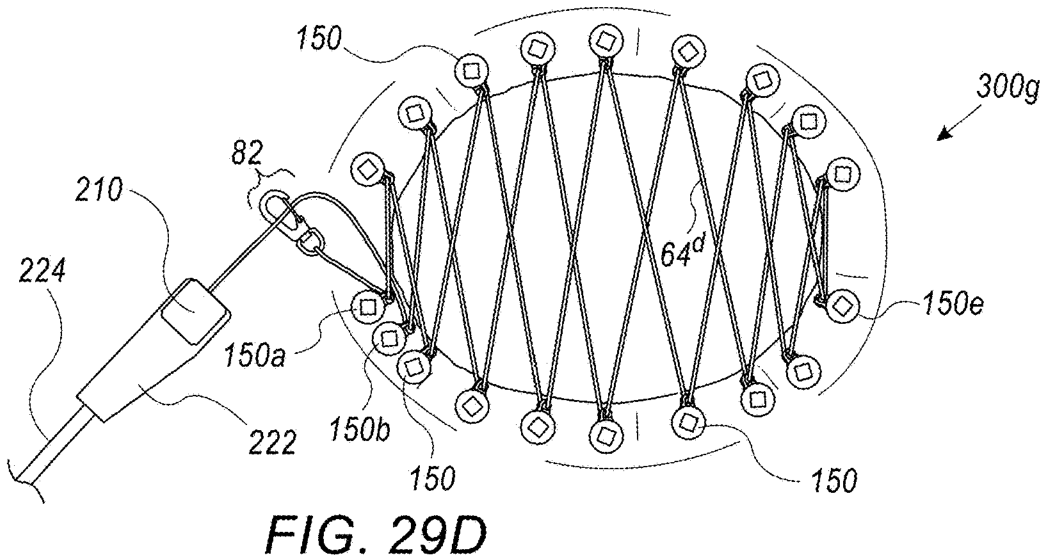

According to some applications, the step (i), whether performed after step (g) or after step (h), includes and inserting the remaining section of the first wire portion $62^d$ into a cinching system 200, wherein said system 200 comprises a locker 210, a cutting and locking assembly 222, and a cinching catheter 224, as illustrated in FIG. 29D.

Figure 29E:
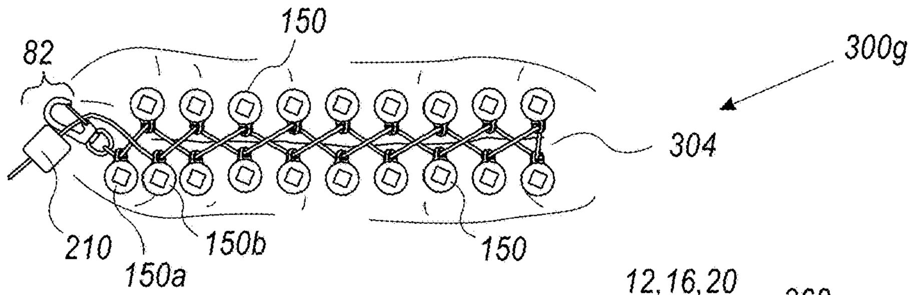

According to some applications, the method further comprises a step of (j) applying tension to the section of the wire $63^c$ which was inserted into the system 200 during step (i) in the proximal direction through cinching catheter 224, in order to sufficiently contract the LAA ostium 304 for the purpose of closure thereof, as illustrated in FIG. 29E.

According to some applications, the method further comprises a step of (k) utilizing locker 210 and assembly 222 to cut and lock, potentially in a simultaneous manner, the section of wire $63^d$ extending from the terminal clamp 240 and passing therethrough, as described herein above, thereby locking implant 180, and optionally trapping any excess portions of the wire portion $63^d$ therein, for example by utilizing a flap 232 as described hereinabove.

According to some applications, the method further comprises a step of (l) decoupling the assembly 222 from the locker 210, and extracting the assembly 222, along with the cinching catheter 224 connected thereto, from either the guide catheter 16 or the outer catheter 12, thereby leaving behind locker 210 attached to the implant $180^d$.

According to some applications, method 300*g* comprises implanting implant $180^d$ so as to surround the perimeter of the LAA cavity 304, similarly to the pattern of the implant $180^d$ surrounding an annulus described above with respect to FIGS. 15A-15B, instead of a zig-zag formation illustrated in FIGS. 29B-29E. Further, these techniques and methods can be performed on a living animal or on a simulation, such as on a cadaver, cadaver heart, simulator (e.g., with the body parts, heart, tissue, LAA, etc. being simulated), etc.

Reference is now made to FIGS. 30A-30G. According to some applications, there is provided an advancement device or helical advancement device 350, configured to facilitate closure of a cavity within a patient's body, such as the LAA cavity 302, for example by contracting the internal wall 306 of the cavity 302. The helical advancement device 350 comprises a tissue engaging portion 352 having a sharpened distal tip 354, wherein said tip 354 is coupled to a stopper 356. It is to be understood that the terms "LAA ostium" and "LAA cavity" can be replaced with "opening", "cavity", or "tissue region" for implementation of the method with other openings and/or cavities.

According to some applications, tissue engaging portion 352 is a helical coil or a spring having a plurality of spaced windings. According to some applications, stopper 356 comprises a sharpened distal tip 362 configured to be flush with sharpened distal tip 354 or otherwise form a continuous sharpened edge therewith, and a stopper proximal surface 358 which is oriented orthogonally with respect to the surface of a winding of the tissue engaging portion 352, as shown in the zoomed in section of FIG. 30B. Stopper proximal surface 358 is attached to a wire 360, wherein said wire 360 is disposed within and through the windings of the tissue engaging portion 352. According to some applications, tissue engaging portion 352 comprises a hollow lumen within the windings thereof, the lumen accommodating a wire 360 extending therethrough. Wire 360 can be identical to wire 63.

According to some applications, advancement device or helical advancement device 350 is configured to be advanced to the vicinity of the LAA ostium 304, or further advanced into the LAA cavity 302, utilizing a multicomponent tubular system, which can be similar or different than the multicomponent system 10 described above with respect to FIG. 1.

According to some applications, the advancement device or helical advancement device 350 is attached to a distal end portion 22 of internal catheter 20 and is configured to be advanced within the lumen of an outer catheter 12 or a guide catheter 16, utilizing the internal catheter 20.

According to other applications, the advancement device or helical advancement device 350 further comprises a driving shaft 364 attached to the tissue engaging portion 352 at a proximal end 368 of tissue engaging portion 352. According to some applications, tissue engaging portion 352 extends from proximal end 368 to distal tip 354. According to some applications, driving shaft 364 comprises a hollow lumen accommodating a wire 360 extending therethrough.

Figure 30A:
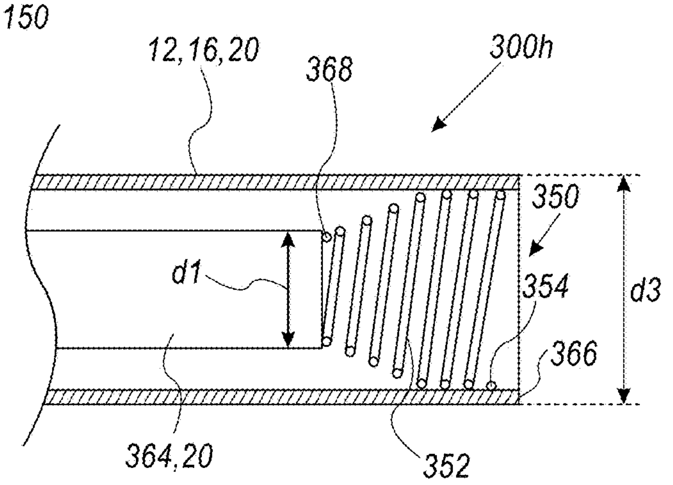
FIG. 30A is a cross sectional view of an example advancement device, according to some applications.

According to some applications, the helical advancement device 350 is configured to be advanced within the lumen of a delivery catheter selected from: outer catheter 12, guide catheter 16, or internal catheter 20, wherein tissue engaging portion 352 is retained along its entire length within said delivery catheter, such that the distal tip 354 is positioned at the level of or proximal to the delivery catheter distal lip 366, as illustrated in FIG. 30A. The delivery catheter distal lip 366 can be selected from: distal end portion 14 of outer catheter 12, distal end portion 18 of guide catheter 16, or distal end portion 22 of internal catheter 20, depending on the type of delivery catheter device 350 which is advanced therein. According to some applications, driving shaft 364 is configured to enable the advancement of tissue engaging portion 352 within the lumen of the delivery catheter.

According to some applications, the most distal winding of tissue engaging portion 352, terminating with the distal tip 354, has an outer diameter d2 which is larger than the diameter d1 of the driving shaft 364.

According to some applications, the delivery catheter has a diameter d3, which is larger than d1. It is contemplated that during the advancement of tissue engaging portion 352 within the lumen of the delivery catheter, tissue engaging portion 352 is in a compressed-spring state, in which tissue engaging portion 352 is subjected to external forces provided by the inner walls of delivery catheter. Thus, the maximal diameter of the distal most winding of the tissue engaging portion 352 is constricted by the internal wall of the delivery catheter, when the tissue engaging portion 352 is retained therein during delivery toward the LAA ostium 304 or the LAA cavity 302.

According to some applications, once the tissue engaging portion 352 is advanced distally with respect to the delivery catheter, for example by the driving shaft 364, to exit through and beyond the delivery catheter distal lip 366, the tissue engaging portion 352 is free to expand to a free-spring state thereof. According to some applications, each subsequent, adjacent winding, from the proximal end 368 of tissue engaging portion 352 to distal tip 354, increases in diameter in the free-spring state, such that d2 is larger than d3 in the free-spring state.

Figure 30B:
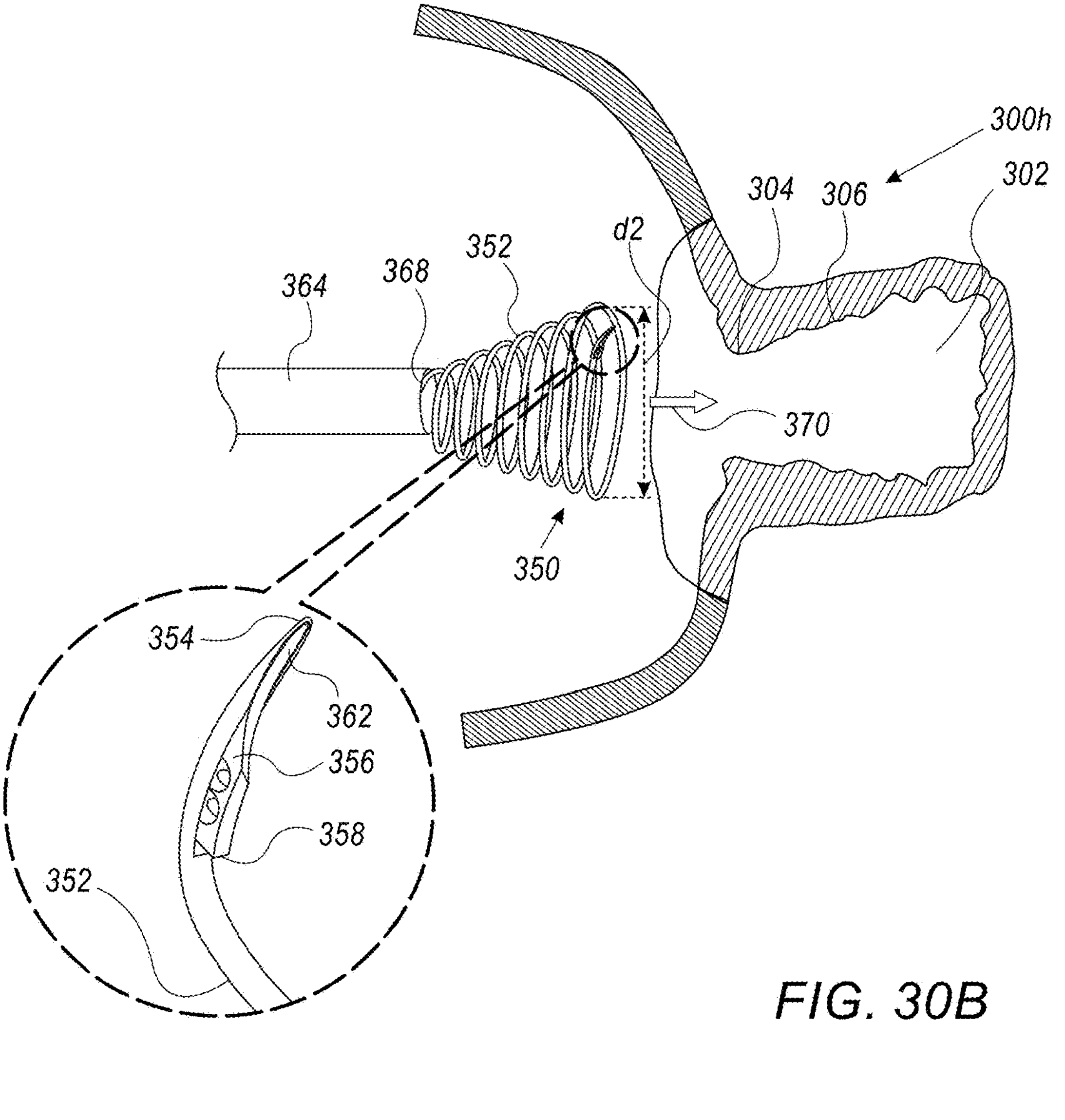
FIGS. 30B-30G are schematic illustration of example steps of a method for closure of an opening (e.g., LAA, or other opening), according to some applications.

FIG. 30B shows the tissue engaging portion 352 completely extended beyond the delivery catheter distal lip 366, allowing its windings to expand to their spring-free state. As mentioned, this can be facilitated by advancing the driving shaft 364 in a distal direction 370 relative to the delivery catheter lip 366. According to some applications, tissue engaging portion 352 comprises internal flexibility such that it is spring-biased radially outwards during the spring-free state, and can be pushed radially inwards by a force exerted thereon during the compressed-spring state. When no external force is applied to the windings of the tissue engaging portion 352 during the spring-free state, the windings expand radially away from each other.

According to some applications, tissue engaging portion 352 is configured to transition between an unexpanded (or contracted) state of its windings when retained and within the lumen of the delivery catheter and advance thereby to the target site, maintained in a compressed-spring state, and an expanded state in which the windings extend radially outward when advanced distally from delivery catheter lip 366, transitioning to a spring-free state, as illustrated in FIGS. 30A-30B. According to some applications, during the spring-free state, the shape of the expanded state of the tissue engaging portion 352 is configured to anatomically match an inner shape of an internal wall 306 of the LAA cavity 302. According to some applications, the diameter d2 is configured to be larger than an average diameter of the LAA ostium 304, and/or an average diameter of the LAA cavity 302.

According to some applications, tissue engaging portion 352 is configured to be inserted and advanced by driving shaft 364 within the lumen of a delivery catheter selected from: outer catheter 12, guide catheter 16, or internal catheter 20, toward the vicinity of the LAA ostium 304 or into the LAA cavity 302, and when advanced distally from delivery catheter lip 366, to switch from compressed-spring state to spring-free state, thereby expanding radially outward therefrom.

According to some applications, tissue engaging portion 352 is configured to be inserted and advanced by driving shaft 364 within the lumen of outer catheter 12 towards the vicinity of the LAA ostium 304 or into the LAA cavity 302, and when advanced distally from the distal end portion 14 of the outer catheter 12, to transition from compressed-spring state to spring-free state, thereby expanding radially outwards therefrom.

According to some applications, tissue engaging portion 352 is configured to be inserted and advanced by driving shaft 364 within the lumen of a guide catheter 16 towards the vicinity of the LAA ostium 304 or into the LAA cavity 302, and when advanced distally from the distal end portion 18 of the guide catheter 16, switch from compressed-spring state to spring-free state, thereby expanding radially outwards therefrom.

According to some applications, tissue engaging portion 352 is configured to be inserted and advanced by driving shaft 364 within the lumen of an internal catheter 20 towards the vicinity of the LAA ostium 304 or into the LAA cavity 302, and when advanced distally from the distal end portion 22 of the internal catheter 20, switch from compressed-spring state to spring-free state, thereby expanding radially outwards therefrom.

Figure 30C:
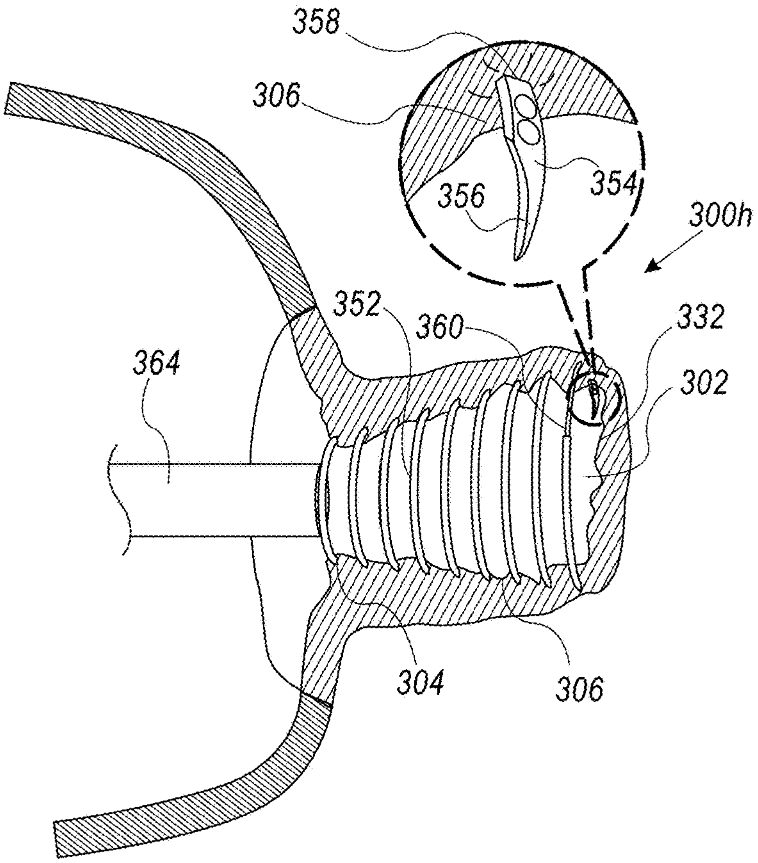

According to some applications, tissue engaging portion 352 is configured to penetrate/puncture the tissue surrounding the LAA ostium 304 utilizing sharpened distal tip 354. According to some applications, driving shaft 364 is configured to be rotated and advanced in the distal direction 370 from the delivery catheter lip 366 of the delivery catheter, thereby driving the tissue engaging portion 352 into the tissue surrounding the LAA ostium 304 and onwards into the tissue of the internal wall 306 of the LAA cavity 302 in a helical advancement pattern, along the length of the internal wall 306 as illustrated in FIG. 30C, until distal tip 354 penetrates/punctures a tissue in the vicinity of a distal inner wall 332 of the internal wall 306. According to some applications, during the advancement of driving shaft 364 in the distal direction 370, the tissue engaging portion 352 is configured to be advanced within the tissue of the internal wall 306 of LAA cavity 302 in a threaded advancement form.

Following the penetration of said tissue, stopper 356 is configured to be anchored thereto, by attaching stopper proximal surface 358 to the tissue surrounding it. According to some applications, stopper proximal surface 358 is a high friction surface configured to increase friction between itself and the tissue surrounding it. Stopper proximal surface 358 can comprise a seared surface, a plurality of teeth, or have any other shape or texture enabling the formation of high friction. Advantageously, stopper proximal surface 358 is shaped and positioned in a manner which enables stopper 356 to become anchored or fixed in its position within the tissue surrounding it.

According to some applications, following the anchoring of stopper 356, driving shaft 364 is further configured to be rotated and retracted in the opposite direction to the distal direction 370 towards the delivery catheter, thereby extracting the tissue engaging portion 352 out of the tissue of the internal wall 306 of LAA cavity 302 in a helical form. During the retraction of the driving shaft 364, tissue engaging portion 352 is threaded out of the internal wall 306 of LAA cavity 302, while the stopper remains at the distal-most original penetration point, having its relatively flat surface 358 pressed against the inner wall 306.

Figure 30D:
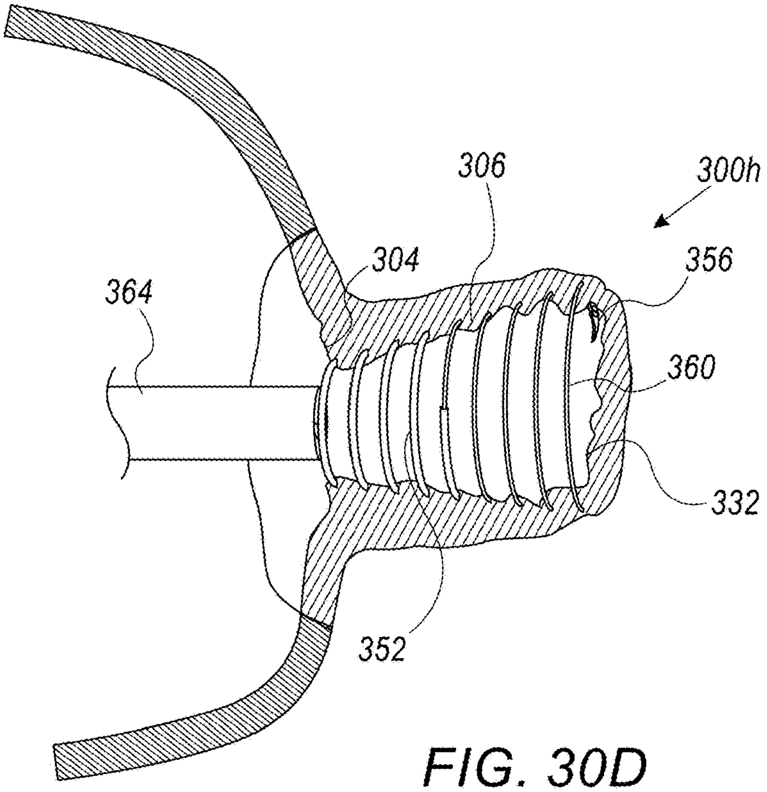

During the extraction of tissue engaging portion 352 from the tissue of the internal wall 306, wire 360 is configured to be exposed/extracted out of the lumen thereof, thereby remaining anchored in a helical/threaded form within the tissue of the internal wall 306 of LAA cavity 302 due to stopper 356 retained at the distal position, pressed against the tissue, so as to provide a counter force to pull the wire 360 out of the lumen of the tissue engaging portion 352, as illustrated in FIG. 30D. Advantageously, the stopper proximal surface 358 is shaped and positioned in a manner which enables the stopper 356 to become anchored or fixed in its position within the tissue surrounding it, thereby enabling the wire 360 to remain anchored in a helical/threaded form within the tissue of internal wall 306 of LAA cavity 302 during the extraction of the tissue engaging portion 352 therefrom.

Figure 30E:
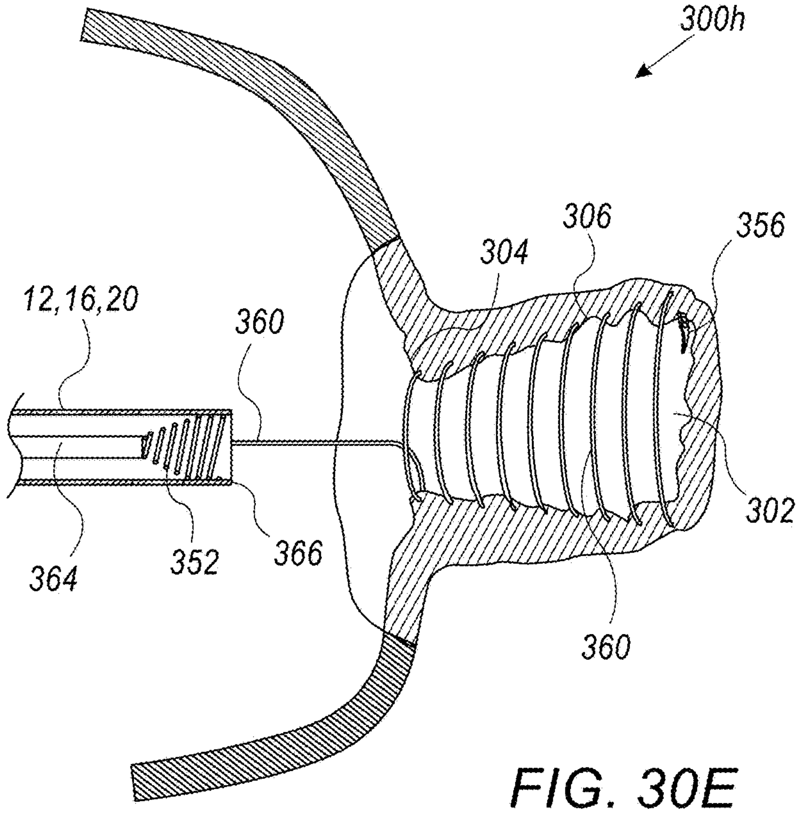

Following the full or complete extraction of tissue engaging portion 352 from the tissue of the internal wall 306, tissue engaging portion 352 is configured re-enter into the lumen of the delivery catheter through the delivery catheter lip 366, and to be proximally pulled and extracted therefrom, thereby leaving the wire 360 anchored in a helical form around the tissue of the internal wall 306 of LAA cavity 302 in a threaded formation, as illustrated at FIG. 30E.

Figure 30F:
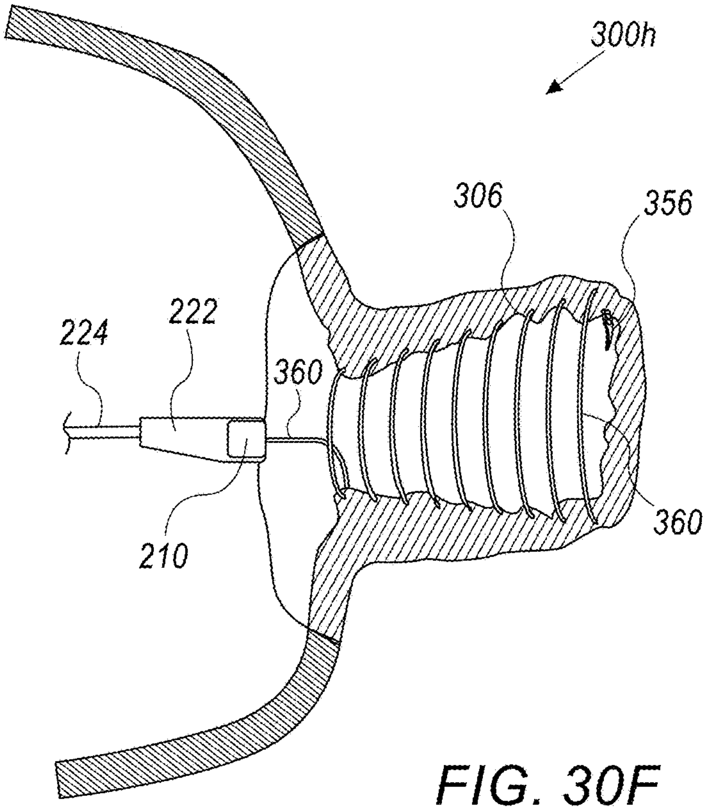
Figure 30G:
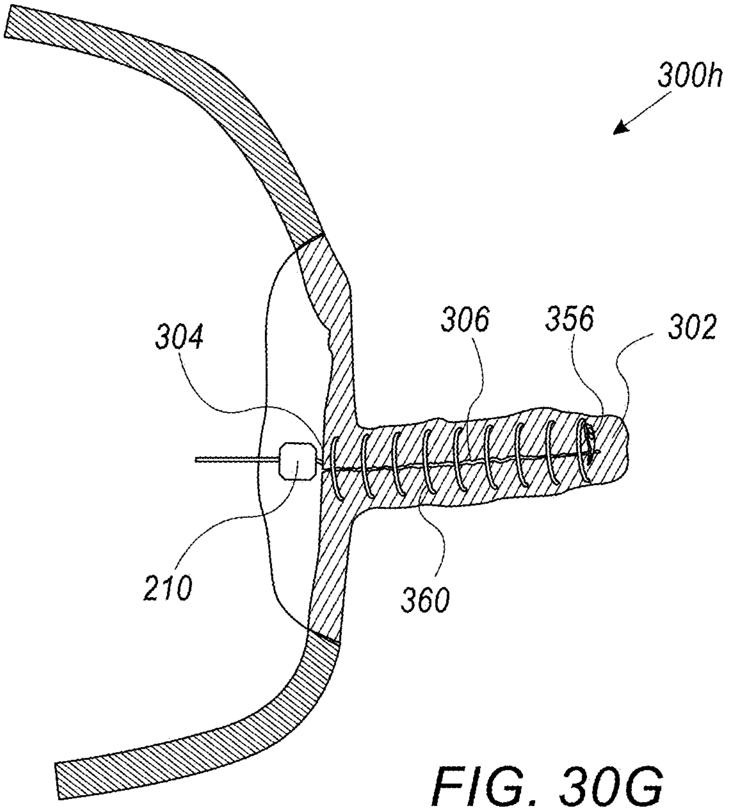

According to some applications, a cinching system 200 is threaded over the wire 360, as illustrated at FIG. 30F. The cinching system 200 comprises locker 210, a cutting and locking assembly 222, and cinching catheter 224, as described hereinabove and throughout the current specification. According to some applications, cinching system 200 is utilized in order to provide tension to the section of wire 360 which was inserted thereto, for example by pulling it in the proximal direction through cinching catheter 224, in order to sufficiently contract the internal wall 306 of the LAA cavity 302, for the purpose of closure thereof, as illustrated at FIG. 30G. According to some applications, locker 210 and assembly 222 are configured to lock and cut the section of wire 360 extending therethrough, potentially in a simultaneous manner, as described hereinabove, thereby locking the wire 360 extending through the internal wall 306 of the LAA cavity 302 in its tensioned or cinched state, and optionally trapping any excess portions of the wire 360 therein, for example utilizing flap 232 as described hereinabove.

According to other applications, the tissue engaging portion 352 is configured to be inserted and advanced by the driving shaft 364 within the lumen of the delivery catheter, wherein the delivery catheter is configured to be inserted at least partially into the LAA cavity 302, beyond the LAA ostium 304. According to some applications, the tissue engaging portion 352 is configured to be advanced distally from delivery catheter lip 366 of the delivery catheter and switch from a compressed-spring state to a spring-free state within the LAA cavity 302. According to some applications, the tissue engaging portion 352 is configured to penetrate and be advanced within the tissue of the internal wall 306 of the LAA cavity 302 in a threaded advancement form, as described hereinabove, for the purpose of closure thereof.

According to some applications, method 300 comprises method 300*h* for closure of the LAA cavity 302, the method comprising a step of (a) providing multicomponent tubular system (e.g., system 10) configured to deliver helical advancement device 350 as described hereinabove, to the vicinity of the LAA ostium 304 of LAA, or optionally, into the LAA cavity 302, wherein the system (10) comprises at least one delivery catheter selected from: an outer catheter 12, a guide catheter 16, an internal catheter 20, or any combination thereof.

According to some applications, the method further comprises a step of (b) inserting and advancing a tissue engaging portion 352 of the helical advancement device 350 coupled to a driving shaft 364, both of which are positioned within the lumen of the delivery catheter from step (a), toward the vicinity of the LAA ostium 304, or optionally into the LAA cavity 302.

According to some applications, the method further comprises a step of (c) advancing the tissue engaging portion 352 distally from delivery catheter lip 366, thereby allowing it to transition from a compressed-spring state to spring-free state and expand radially outward therefrom;

According to some applications, the method further comprises a step of (d) rotating and advancing the driving shaft 364 in the distal direction 370 relative to the delivery catheter lip 366 of the delivery catheter, thereby driving the tissue engaging portion 352 into the internal wall 306 of the LAA cavity 302. Rotation in a first direction to advance the tissue engaging portion 352 distally through the tissue, can be either clockwise or counterclockwise.

According to some applications, driving the tissue engaging portion 352 into the internal wall 306, as described in step (d), is achieved by driving the tissue engaging portion 352 into tissue surrounding the LAA ostium 304 and onward into the tissue of the internal wall 306 of the LAA cavity 302 in a helical form therefrom.

According to some applications in which the tissue engaging portion 352 transitions towards the spring-free state when already positioned within the LAA cavity 302, driving the tissue engaging portion 352 into the internal wall 306, as described in step (d), is achieved by simply rotating it within the cavity 302, wherein its distal tip 354, which is biased toward the wall 306, is urged to penetrate it.

According to some applications, the method further comprises a step of (e) further driving the tissue engaging portion 352 into the tissue of the internal wall 306 of the LAA cavity 302 in a helical form therefrom along the length of the internal wall 306, until the distal tip 354 penetrate a tissue in the vicinity of a distal inner wall 332 of the internal wall 306, thereby anchoring the stopper 356 therethrough;

According to some applications, the method further comprises a step of (f) rotating and retracting driving shaft 364 in the opposite, proximal direction, toward the delivery catheter, in order to extract the tissue engaging portion 352 out of the tissue of the internal wall 306 of LAA cavity 302, thereby exposing wire 360 which is configured to remain anchored in a helical form within the tissue of internal wall 306 of LAA cavity 302 due to stopper 356 held in place at the distal location against the tissue. Rotation in step (f) is performed in a second direction, which is opposite to the first direction of rotation of steps (d) and (e).

According to some applications, the method further comprises a step of (g) re-inserting the tissue engaging portion 352 into the lumen of the delivery catheter through the delivery catheter lip 366, and optionally extracting it therefrom.

According to some applications, the method further comprises a step of (h) inserting a proximal section of wire 360 into a cinching system 200, wherein the cinching system 200 comprises a locker 210, a cutting and locking assembly 222, and a cinching catheter 224, as described hereinabove, and advancing the system 200 within the lumen of the delivery catheter to the vicinity of the LAA ostium 304.

According to some applications, the method further comprises a step of (i) applying tension to the section of wire 360 which was inserted into the cinching system 200 during step (h) in the proximal direction through cinching catheter 224, in order to sufficiently contract the internal wall 306 of the LAA cavity 302, for the purpose of closure thereof.

According to some applications, the method further comprises a step of (j) utilizing locker 210 and assembly 222 to cut and lock, potentially in a simultaneous manner, the section of wire 360 extending therethrough, as described hereinabove, thereby locking the wire 360 extending through the internal wall 306 of the LAA cavity 302 in its tensioned or cinched state, and optionally trapping any excess portions of the wire 360 therein, for example by utilizing a flap 232 as described hereinabove.

According to some applications, the method further comprises a step of (k) decoupling the assembly 222 from the locker 210, and extracting the assembly 222, along with the cinching catheter 224 connected thereto, from the delivery catheter, thereby leaving behind locker 210 attached to wire 360 in its tensioned state, threaded through the internal wall 306 of the LAA cavity 302. Further, these techniques and methods can be performed on a living animal or on a simulation, such as on a cadaver, cadaver heart, simulator (e.g., with the body parts, heart, tissue, etc. being simulated), etc.

The term "plurality", as used herein, means more than one.

The term "about", as used herein, when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to the disclosed devices, systems and/or methods.

It is appreciated that certain features of the disclosure, which are, for clarity, described in the context of separate examples, may also be provided in combination in a single application. Conversely, various features of the disclosure, which are, for brevity, described in the context of a single example, may also be provided separately or in any suitable sub-combination or as suitable in any other described application of the disclosure. No feature described in the context of an example is to be considered an essential feature of that example, unless explicitly specified as such.

Although the disclosure is described in conjunction with specific examples thereof, it is evident that numerous alternatives, modifications, and variations that are apparent to those skilled in the art may exist. It is to be understood that the disclosure is not necessarily limited in its application to the details of construction and the arrangement of the components and/or methods set forth herein. Other applications may be practiced, and an application may be carried out in various ways. Methods described herein do not require all the steps described and the steps can be performed in a different order than that presented. Accordingly, the disclosure embraces all such alternatives, modifications and variations that fall within the scope of the appended claims. Further, the various techniques, methods, operations, steps, etc. described or suggested anywhere herein can be performed on a living animal or on a non-living simulation, such as on a cadaver, cadaver heart, simulator (e.g., with the body parts, tissue, etc. being simulated), etc.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use at a heart of a subject, the method comprising:

transluminally sliding multiple anchors distally over and along a first portion of a tether to the heart while, for each anchor, an eyelet of the anchor is threaded on the tether, and anchoring the multiple anchors to tissue of the heart, such that:

the first portion of the tether extends transluminally to the heart, within the heart, a bight of the tether extends from the first portion and is secured to the tissue by the anchors, and a second portion of the tether extends from the bight to a second end of the tether;

subsequently, slidably coupling the first portion of the tether to an end-portion retainer that is disposed at the second end of the tether such that the tether forms a closed loop, the end-portion retainer being larger than the eyelet of at least one of the anchors; and subsequently, reducing a size of the loop by sliding the first portion through the slidable coupling until the end-portion retainer abuts the eyelet of the at least one anchor.

2. The method according to claim 1, wherein reducing the size of the loop comprises reshaping the tissue by reducing the size of the loop.

3. The method according to claim 1, wherein slidably coupling the first portion of the tether to the end-portion retainer comprises slidably coupling the first portion of the tether to the end-portion retainer within the heart.

4. The method according to claim 1, wherein slidably coupling the first portion of the tether to the end-portion retainer comprises slidably coupling the first portion of the tether to the end-portion retainer outside of the heart.

5. The method according to claim 4, wherein slidably coupling the first portion of the tether to the end-portion retainer comprises slidably coupling the first portion of the tether to the end-portion retainer outside of the subject.

6. The method according to claim 4, wherein reducing the size of the loop comprises sliding the end-portion retainer distally over and along the first portion to the heart.

7. The method according to claim 1, wherein transluminally sliding the anchors distally over and along the first portion comprises transluminally sliding the anchors distally over and along the first portion, while:

the first portion extends distally through a catheter, the bight extends out of a distal end of the catheter and loops about the distal end of the catheter, and the second portion extends proximally, from the distal end of the catheter, alongside an exterior of the catheter, terminating at the second end.

8. The method according to claim 7, wherein:

the catheter is an internal catheter, and extends through an outer catheter, transluminally sliding the anchors distally over and along the first portion while the first portion extends through the catheter comprises transluminally sliding the anchors distally over and along the first portion while:

the first portion extends distally through the internal catheter, and the second portion extends proximally through an inner space defined between an inner wall of the outer catheter and an outer wall of the internal catheter, and the method further comprises, prior to reducing the size of the loop, retracting the internal catheter from the outer catheter, such that the first portion of the tether and the second portion of the tether become disposed side-by-side within the outer catheter.

9. The method according to claim 1, wherein sliding the first portion through the end-portion retainer comprises sliding the first portion by pulling the first portion proximally.

10. The method according to claim 1, wherein for each of the anchors, the anchor includes a helical tissue-engaging element, and wherein securing the bight of the tether to the tissue comprises screwing the helical tissue-engaging element of each of the anchors to the tissue.

11. The method according to claim 1, wherein:

the end-portion retainer comprises an end-loop defined by the second end of the tether, and slidably coupling the first portion of the tether to the end-portion retainer of the tether comprises threading the first portion through the end-loop.

12. The method according to claim 1, wherein the end-portion retainer is a terminal clamp comprising a hinged spring-biased gate, and wherein slidably coupling the first portion of the tether to the end-portion retainer comprises slidably coupling the first portion of the tether to the terminal clamp.

13. The method according to claim 1, wherein anchoring the multiple anchors to the tissue comprises anchoring the multiple anchors to the tissue such that the bight is secured around an annulus of a valve of the heart.

14. The method according to claim 1, wherein anchoring the multiple anchors to the tissue comprises anchoring the multiple anchors to the tissue such that the bight is secured around an ostium of a Left Atrial Appendage of the heart.

15. The method according to claim 1, the method further comprising locking the tether in the closed loop by intracardially locking a locker to the tether.

16. The method according to claim 15, wherein sliding the end-portion retainer over and along the first portion comprises pushing the end-portion retainer over and along the first portion using the locker.

17. The method according to claim 15, further comprising, subsequently to locking the tether in the closed loop, trimming a part of the first portion that extends, out from the locker, and away from the closed loop.

18. The method according to claim 15, wherein locking the locker to the tether comprises locking, to the tether, a locker that includes:

a housing defining a longitudinal axis, the housing including:

a proximal wire opening formed at a proximal end of the housing, a distal wire opening formed at a distal end of the housing, and two distal actuation openings located on opposite sides of the distal wire opening at the distal end of the housing;

two sliding and locking elements, aligned with the distal actuation openings, and movable toward or away from each other; and a spring pressed between a wall of the housing and the sliding and locking elements, configured to bias the sliding and locking elements distally and toward each other, in the absence of external force applied to the sliding and locking elements.

19. A method for use at a heart of a subject, the method comprising:

transluminally sliding multiple anchors distally over and along a first portion of a tether to the heart, and anchoring the multiple anchors to tissue of the heart, such that:

the first portion of the tether extends transluminally to the heart, within the heart, a bight of the tether extends from the first portion and is secured to the tissue by the anchors, and a second portion of the tether extends from the bight to a second end of the tether;

subsequently, slidably coupling the first portion of the tether to an end-portion retainer that is disposed at the second end of the tether such that the tether forms a closed loop; and subsequently, reducing a size of the loop by sliding the first portion through the slidable coupling, wherein the end-portion retainer is a terminal clamp comprising a hinged spring-biased gate, and wherein slidably coupling the first portion of the tether to the end-portion retainer comprises slidably coupling the first portion of the tether to the terminal clamp.

20. A method for use at a heart of a subject, the method comprising:

transluminally sliding multiple anchors distally over and along a first portion of a tether to the heart, and anchoring the multiple anchors to tissue of the heart, such that:

the first portion of the tether extends transluminally to the heart, within the heart, a bight of the tether extends from the first portion and is secured to the tissue by the anchors, and a second portion of the tether extends from the bight to a second end of the tether;

subsequently, slidably coupling the first portion of the tether to the second end of the tether such that the tether forms a closed loop;

subsequently, reducing a size of the loop by sliding the first portion through the slidable coupling; and locking the tether in the closed loop by intracardially locking a locker to the tether, wherein the locker includes:

a housing defining a longitudinal axis, the housing including:

a proximal wire opening formed at a proximal end of the housing, a distal wire opening formed at a distal end of the housing, and two distal actuation openings located on opposite sides of the distal wire opening at the distal end of the housing;

two sliding and locking elements, aligned with the distal actuation openings, and movable toward or away from each other; and a spring pressed between a wall of the housing and the sliding and locking elements, configured to bias the sliding and locking elements distally and toward each other, in the absence of external force applied to the sliding and locking elements.

* * * * *